US012571019B2

(12) United States Patent (10) Patent No.: US 12,571,019 B2
Jensen et al. (45) Date of Patent: Mar. 10, 2026

(54) NISIN-PERMEABILIZED MICROBIAL CELL CATALYSTS

(71) Applicant: DANMARKS TEKNISKE UNIVERSITET, Kongens Lyngby (DK)

(72) Inventors: Peter Ruhdal Jensen, Kongens Lyngby (DK); Christian Solem, Kongens Lyngby (DK); Jianming Liu, Kongens Lyngby (DK); Robin Dorau, Kongens Lyngby (DK); Qi Wang, Kongens Lyngby (DK); Ge Zhao, Kongens Lyngby (DK)

(73) Assignee: DANMARKS TEKNISKE UNIVERSITET, Kongens Lyngby (DK)

( * ) Notice: Subject to any disclaimer, the term of this patent is extended or adjusted under 35 U.S.C. 154(b) by 601 days.

(21) Appl. No.: 17/795,983

(22) PCT Filed: Feb. 12, 2021

(86) PCT No.: PCT/EP2021/053505
§ 371 (c)(1),
(2) Date: Jul. 28, 2022

(87) PCT Pub. No.: WO2021/160832
PCT Pub. Date: Aug. 19, 2021

(65) Prior Publication Data
US 2023/0051156 A1 Feb. 16, 2023

(30) Foreign Application Priority Data
Feb. 13, 2020 (EP) ..................................... 20157131

(51) Int. Cl.
*C12P 21/02* (2006.01)
*A23C 9/12* (2006.01)
*C12N 9/38* (2006.01)

(52) U.S. Cl.
CPC ............ *C12P 21/02* (2013.01); *A23C 9/1206* (2013.01); *C12N 9/2471* (2013.01); *C12Y 302/01023* (2013.01); *A23V 2400/231* (2023.08); *A23V 2400/249* (2023.08)

(58) Field of Classification Search
CPC ..... C12P 21/02; A23C 9/1206; C12N 9/2471; C12Y 302/01023; A23V 2400/231; A23V 2400/249
USPC ......................................................... 536/125
See application file for complete search history.

(56) References Cited

U.S. PATENT DOCUMENTS 6,833,260 B1 12/2004 Ruch

FOREIGN PATENT DOCUMENTS

EP 0137869 A2 4/1985

OTHER PUBLICATIONS

Zhang et al. D-Tagatose production by Lactococcus lactis NZ9000 Cells Harboring Lactobacillus plantarum L-arabinose Isomerase. Indian Journal of Pharmaceutical Education and Research 51(2):288-294, 2017. (Year: 2017).*
Wanarska et al. A method for the production of D-tagatose using a recombinant Pichia pastoris strain secreting β-D-galactosidase from Arthrobacter chlorophenolicus and a recombinant L-arabinose. Microbial Cell Factories 2012, 11:113, p. 1-15. (Year: 2012).*
De Ruyter et al. Controlled Gene Expression Systems for Lactococcus lactis with the Food-Grade Inducer Nisin. Applied and Environmental Microbiology, Oct. 1996, vol. 62, No. 10, p. 3662-3667. (Year: 1996).*
*Lactococcus lactis* subsp. cremoris NZ9000, complete genome. GenBank Accession: CP002094, Jan. 30, 2014 (Year: 2014).*
Terzaghi et al. Improved Medium for Lactic Streptococci and Their Bacteriophages. Applied Microbiology, Jun. 1975, vol. 29, No. 6, p. 807-813. (Year: 1975).*
NCBI Blast SEQ ID No. 11 (Rid: 3XXJETXV016), performed in Jun. 2025.. (Year: 2025).*
NCBI Blast SEQ ID No. 4 (Rid: 3XW5UBH2016), performed in Jun. 2025. (Year: 2025).*
Chang et al. The Study of Food-Grade Induced Expression and Enzymatic Properties of L-Arabinose Isomerase from Lactobacillus plantarum WU14 with High D-Tagatose Yield. Food and Nutrition Sciences, 2016, 7, 320-337. (Year: 2016).*
Noriko Imoto et al: "Permeabilization induced by lipid II-targeting lantibiotic nisin and its effect on the bioconversion of vitamin D3 to 25-hydroxyvitamin D3 by Rhodococcus erythropolis". Biochemical and Biophysical Research Communications. vol. 405, No. 3. Feb. 18, 2011 (Feb. 18, 2011). pp. 393-398. XP028145480.
Parmjit S Panesar et al: "Microbial production. immobilization and applications of [beta]-D-galactosidase". Journal of Chemical Technology and Biotechnology. vol. 81, No. 4. Jan. 1, 2006 (Jan. 1, 2006). pp. 530-543. XP055721570.
Dorau Robin et al: "Complete Genome Sequence of *Lactococcus lactis* subsp. lactis bv. diacetylactis SD96", Microbiology Resource Announcements. vol. 9, No. 3, article No. e01140-19. Jan. 16, 2020 (Jan. 16, 2020). pp. 1-2. XP055799081, DOI: 10.1128/MRA.01140-19 Retrieved from the Internet: URL:https://www.ncbi.nlm.nih.gov/pmcjartic les/PMC6965574/pdf/MRA.01140-19.pdf>.
(Continued)

*Primary Examiner* — Yih-Horng Shiao
(74) *Attorney, Agent, or Firm* — Lisa Mueller; Casimir Jones SC

(57) ABSTRACT

A method and use of nisin-permeabilized microbial cells as whole-cell catalysts for reducing the amount of a target substrate in a sample to one of more product are provided. Specifically, a method of reducing the amount of lactose in a dairy sample using nisin-permeabilized lactic acid bacterial cell catalysts, which have been permeabilized by incubating with a nisin producing microbial cell and/or culture medium derived thereof. Further provided is a nisin producing microbial cell, derived from parent strain *Lactococcus lactis* subsp. *lactis* bv. diacetylactis SD96 (NCBI accession No. SRX6686433).

16 Claims, 10 Drawing Sheets
Specification includes a Sequence Listing.

(56) References Cited

OTHER PUBLICATIONS

Wang Q, et al., No more cleaning up—Efficient lactic acid bacteria cell catalysts as a cost-efficient alternative to purified lactase enzymes. Appl Microbiol Biotechnol. Jul. 2020;104(14):6315-6323.

Somkuti, G., et al., Sensitivity of *Streptococcus thermophilus* to Chemical Permeabilization . Curr Microbiol 32, 101-105 (1996). https://doi.org/10.1007/s002849900018, Issue date, Feb. 1996.

Somkuti, G., et al., Permeabilization of *Streptococcus thermophilus* and *Lactobacillus delbrueckii* subsp. bulgaricus with Ethanol. Curr Microbiol 36, 202-206 (1998). https://doi.org/10.1007/s002849900294, Issue date, Apr. 1998.

Broadbent, J. R., et al., 1995. Characteristics of Tn5307 exchange and intergeneric transfer of genes associated with nisin production. Appl. Microbiol. Biotechnol. 44:139-146; https://doi.org/10.1007/BF00164493; Issue date—Dec. 1995.

Broadbent JR, et al., Genetic construction of nisin-producing *Lactococcus lactis* subsp. cremoris and analysis of a rapid method for conjugation. Appl Environ Microbiol. Feb. 1991;57(2):517-24. doi: 10.1128/aem.57.2.517-524.1991.

Zhang YF, et al., Genome shuffling of *Lactococcus lactis* subspecies lactis YF11 for improving nisin Z production and comparative analysis. J Dairy Sci. May 2014;97(5):2528-41. doi: 10.3168/jds. 2013-7238. Epub Mar. 5, 2014.

Liu C, et al., Effects of nutrient supplements on simultaneous fermentation of nisin and lactic acid from cull potatoes. Appl Biochem Biotechnol. 2005 Spring; 121-124:475-83. doi: 10.1385/abab:122:1-3:0475.

Kaneko T, et al., Acetoin Fermentation by Citrate-Positive *Lactococcus lactis* subsp. lactis 3022 Grown Aerobically in the Presence of Hemin or Cu. Appl Environ Microbiol. Sep. 1990;56(9):2644-9. doi: 10.1128/aem.56.9.2644-2649.1990.

* cited by examiner

NISIN-PERMEABILIZED MICROBIAL CELL CATALYSTS

CROSS REFERENCE TO RELATED APPLICATIONS

This application is a national stage application of PCT/EP2021/053505, filed Feb. 12, 2021, which claims priority to European Application No. 20157131.2, filed Feb. 13, 2020, each of which are hereby incorporated by reference in their entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 237,889 Byte ASCII (Text) file named "41149_251_ST25.TXT," created on Jul. 28, 2022.

FIELD OF THE INVENTION

The present invention relates to use of nisin-permeabilized microbial cells as whole-cell catalysts for conversion (partial or full) of a target substrate(s) to one or more products. More specifically, the invention relates to a method for reducing the amount of lactose in a dairy sample, wherein a microbial cell catalyst comprising beta-galactosidase is first prepared by nisin-permeabilization by incubating with a nisin producing microbial cell or a culture medium thereof, prior to incubating with said dairy sample for hydrolyzing said lactose. The invention further relates to a nisin producing microbial cell for producing a microbial cell catalyst.

BACKGROUND OF THE INVENTION

Many microbial enzymes with a potential for industrial application are retained within the microbial cells in which they are produced, which makes recovery and subsequent purification difficult.

Further, enzymes, while inside cells, are in a protected environment and are often more stable than when isolated. But for use of such enzyme(s) inside the cells, the substrate(s) must be able to cross the cell envelope to reach the enzyme(s), which may decrease the reaction rate obtained with such cells when compared to the corresponding isolated enzyme. One way to circumvent substrate transfer limitations involves the permeabilization of the cell wall and membranes by a chemical (e.g. by adding detergents or solvents) or physical (e.g. temperature shock) treatment. However, these procedures may interfere with the manufacturing and downstream processes, besides damaging the cells.

These problems are illustrated by the enzyme beta-galactosidase of *Streptococcus thermophilus* which, because of its food-grade classification, has attractive possibilities for application in the production of low-lactose foods. Since beta-galactosidase in *S. thermophilus* is a cytoplasmic enzyme, its isolation and use as a catalyst may only be achieved through the perturbation of cell integrity, either by sonic disruption or by chemical treatment such as using solvent mixtures. Sonication of the cells results in the release of beta-galactosidase, whereas permeabilization with organic solvents allows the passage of lactose to the cell interior while the beta-galactosidase is retained within the cell. Permeabilized cells may be used in place of purified beta-galactosidase in the production of low-lactose foods. Somkuti et al., 1996 found that several detergents and the commercial bile salt preparation Oxgall were effective in disrupting membrane structures in *S. thermophilus* to allow lactose influx but without causing enzyme leakage or denaturation. However, naturally a concern must be addressed in relation to the use of such chemicals in relation to food products, as residual permeabilizing agents may remain associated with the concentrated cell preparations intended for food applications (even after washing the cells).

The main concern when using chemical permeabilization of microbial cultures in the preparation of foods or beverages is solvent or detergent residues remaining associated with treated cells and ending up in finished food or beverage products. E.g. organic solvents such as toluene or acetone-toluene mixtures are excellent permeabilizing agents, but their residues would surely find objection when used in foods. In this regard, ethanol may be a better solvent choice, since it is already present in trace amounts in many fermented dairy foods consumed by humans. Somkuti et al., 1998 found that ethanol is efficient as a permeabilizing agent for increasing the level of measurable beta-galactosidase activity.

However, traces of any solvent, even ethanol, in a food or beverage, due to their treatment with permeabilized cells during manufacture, is considered undesirable and hence there remains a need to provide food grade microbial cell catalysts that avoid these problems.

SUMMARY OF THE INVENTION

In a first aspect, the present invention provides a method for reducing the amount of lactose in a first dairy sample, said method comprising the steps of:

- a) providing one or more non-GMO microbial cells comprising an intracellular beta-galactosidase enzyme for catalyzing conversion of lactose into glucose and galactose,
- b) incubating said non-GMO microbial cells with a nisin producing microbial cell culture and/or a culture medium derived thereof,
- c) optionally harvesting permeabilized non-GMO microbial cell catalysts obtained in step (b),
- d) incubating permeabilized non-GMO microbial cell catalysts obtained in step (b) or harvested non-GMO microbial cell catalysts harvested in step (c) with said first dairy sample comprising lactose;

wherein said non-GMO microbial cell is a lactic acid bacterium

In a second aspect, the invention provides a nisin producing microbial cell derived from parent strain *Lactococcus lactis* subsp. *lactis* bv. diacetylactis SD96 (NCBI accession No. SRX6686433) by virtue of inserting transposon Tn5307 (SEQ ID NO. 4) comprising a nisin biosynthesis gene cluster and genes needed for metabolizing sucrose into the genome of the parent strain.

In a third aspect, the invention provides nisin producing microbial cell Ge001 for producing a microbial cell catalyst.

In a fourth aspect, the invention provides the use of a nisin producing microbial cell of the invention for producing a microbial cell catalyst, preferably a non-GMO microbial cell comprising an intracellular beta-galactosidase enzyme.

DESCRIPTION OF THE INVENTION

Brief Description of the Figures

(FIG. 26) for 10 min using a nisin concentration of 2.5 μg/ml. Hydrolysis was subsequently performed using 100 mg/l dry weight of permeabilized cells in a POM buffer solution comprising 5% lactose, incubated at temperatures ranging 20-60° C.

ABBREVIATIONS, TERMS, AND DEFINITIONS

Figure 1:
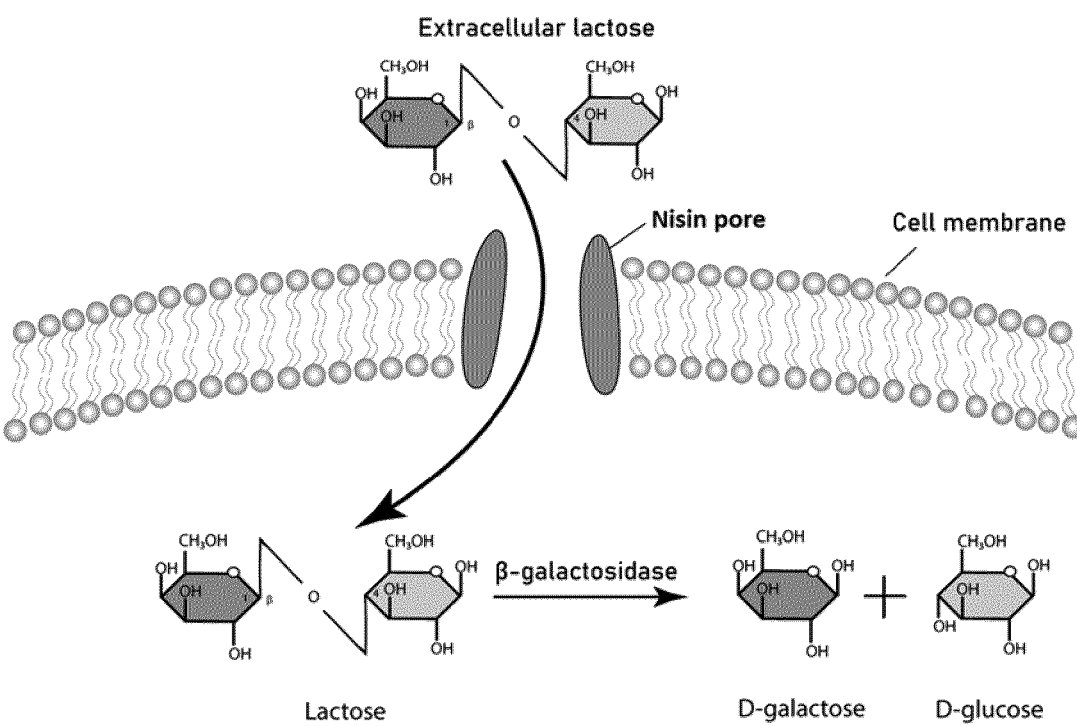
FIG. 1: Illustration of lactose hydrolysis by nisin-permeabilized cell.

Nisin-permeabilized cells are cells which have been treated with nisin whereby pores have formed in the membrane through which a target substrate can transit while enzymes that catalyze the conversion of the substrate are retained within the cells.

Susceptible to nisin-permeabilization defines a property of a cell that on interaction with nisin, allows nisin to form a pore in its cell membrane through which target substrates can transit while enzymes which catalyze the conversion of the target substrates are retained within the cell; such cell being defined as susceptible to nisin-permeabilization.

Class A lantibiotics are bacteriocins that disrupt bacterial cell walls by pore formation. Class A lantibiotics include nisin, bisin, subtilin, epidermin, gallidermin, and mutacin.

DETAILED DESCRIPTION OF THE INVENTION

I. Nisin-Permeabilized Microbial Cell Catalysts

The microbial cell according to the invention is a cell which is susceptible to nisin-permeabilization—in other words, a cell with which nisin interacts to form a pore in the cell's cell membrane.

The microbial cell of the invention is preferably a bacterium, such as a Gram-positive or Gram-negative bacterium. A non-exhaustive list of suitable bacteria is given as follows: a species belonging to the genus selected from among *Escherichia, Streptococcus, Lactobacillus, Lactococcus, Lactovum, Pediococcus, Leuconostoc, Fructobacillus, Weissella, Oenococcus, Corynebacterium, Brevibacterium, Bacillus, Sporolactobacillus, Geobacillus, Halobacillus, Halolactibacillus, Tetragenococcus, Acetobacter, Acinetobacter*, Proprionibacterium, and *Bifidobacterium*.

In one embodiment, the microbial cell of the invention is selected from lactic acid bacteria, such as from the group consisting of species of the genera *Streptococcus, Lactobacillus, Lactococcus Abiotrophia, Aerococcus, Carnobacterium, Enterococcus, Leuconostoc, Oenococcus, Pediococcus, Tetragenococcus, Vagococcus*, and *Weissella*. Even more preferably, in one embodiment, the microbial cell of the invention is selected from *Streptococcus thermophilus, Lactobacillus casei, Lactobacillus plantarum, Lactobacillus helveticus, Lactobacillus delbrueckii, Lactobacillus acidophilus*, and *Lactococcus lactis*.

While not wishing to be bound to theory, the action mechanism of nisin consists in the adsorption of nisin on the target cell surface and destabilization of the cytoplasmic membrane structure through the insertion of nisin in the lipid cell membrane leading to its permeabilization. The cells become "leaky" as a result of the nisin treatment, and release of e.g. essential cytoplasm components, and/or cell lysis, eventually results in the bacterium death.

The present invention is based on the novel idea of exploiting the ability of nisin to puncture holes (pores off approx. 2-2.5 nm in diameter) in the cytoplasmic cell membrane of microbial cells, in order to create non-growing cells (non-viable) that can find a new use as whole cell catalysts.

The nisin-permeabilized microbial cell is used as a per-meabilized whole-cell catalyst, where substrate can enter the nisin-permeabilized cells though the nisin pores and undergo enzymatic catalysis by a suitable enzyme within the cell, and products of the enzymatic reaction can then optionally also exit the cell through the nisin pores. Small molecules thereby transit though the nisin pores, while larger molecules (such as intracellular enzymes) are retained. The enzyme is thus kept within a stabilizing cell bag, which can easily be recovered from a solution by simple filtration.

II. Methods for Preparing Nisin-Permeabilized Microbial Whole-Cell Catalysts

In preparing nisin-permeabilized cells, microbial cells of the invention are simply brought in contact with nisin, such as nisin being added to a suspension of the microbial cells. Nisin will insert into the lipid cell membrane and lead to its permeabilization by formation of a pore in the membrane.
II.i Providing Nisin for Permeabilizing Cells In one embodiment of the invention, nisin for permeabilizing cells of the invention is provided in purified form, such as commercially available nisin: e.g. Nisaplin® from Dupont Nutrition & Biosciences, Delvo®Nis from DSM, Niseen® from Siveele B. V., Galacin® from Galactic, Nisin from Shandong Freda Biotechnology Co., Ltd., Nisin from Zhejiang Silver-Elephant Bio-Engineering Co., Ltd., and NisinPro from Chihon Biotechnology Co., Ltd.

In another embodiment, nisin is provided in the form of a nisin producing microbial strain or a culture medium derived from a nisin producing strain. The strain may be genetically modified to produce nisin or be a natural producer of nisin. Nisin is for example naturally produced by certain *Lactococcus* species, which may be used in the present invention for providing nisin. In one embodiment, nisin-producing *Lactococcus* species or culture media derived therefrom are used as a source of nisin. In a preferred embodiment, a nisin-producing *Lactococcus lactis* strain or culture media derived therefrom is used as a source of nisin.

In a preferred embodiment of the invention, the nisin producing microbial strain is a strain modified to produce nisin by classical mutagenic methods, hence a non-GMO strain. Such classical mutagenic methods may involve adaptive laboratory evolution, chemical mutagenesis and/or conjugation. Such strains are considered "natural" and thus can be applied in e.g. dairy fermentation without any restrictions. However, the strain can also be obtained by genetic engineering using gene recombination methods to introduce the desired genetic modifications using known in the art, including CRISPR.

In one embodiment, the nisin producing strain comprises a nisin gene encoding a nisin polypeptide having at least 80, 82, 84, 86, 88, 90, 92, 94, 96, or 98% amino acid sequence identity to SEQ ID No. 2.

A nisin gene cluster encoding nisin as well as genes for sucrose metabolism are located on a conjugative transposon in *L. lactis* (Broadbent et al 1995); this transposon can 'jump' from one strain and 'insert' itself into another strain by conjugal transfer. In one embodiment, the nisin producing microbial strain is prepared by transposon conjugation. In a preferred embodiment, the nisin producing microbial strain is obtained by transferring the nisin gene cluster of *L. lactis* ATCC 11454 (SEQ ID No. 3), by conjugation, into a lactate dehydrogenase (LDH) deficient strain as specified above.

In a preferred embodiment, the nisin producing microbial strain comprises a nucleic acid sequence having at least 80, 82, 84, 86, 88, 90, 92, 94, 96, or 98% nucleic acid sequence identity to transposon Tn5307 (SEQ ID No. 4).

In one embodiment, the nisin producing strain is additionally characterized in having reduced lactate dehydrogenase (LDH) activity when compared to the parent strain from which it was derived. Reduced LDH activity can block the main metabolic flux from pyruvate to lactate and thus reduce acid production. Such strain having reduced lactate dehydrogenase activity can be grown to high cell densities without pH control.

In a preferred embodiment, the ldh gene encoding lactate dehydrogenase enzyme having at least 80, 82, 84, 86, 88, 90, 92, 94, 96, or 98% amino acid sequence identity with SEQ ID NO. 6 is disrupted in the nisin producing strain, such as by one or more mutations in the ldh gene, by deletion of the ldh gene or parts thereof, by insertion of one or more nucleic acids into the ldh gene leading to a translated peptide which does not have LDH activity, or by other means of gene disruption as recognized by a person skilled in the art.

In one embodiment, the ldh gene is disrupted by insertion of one or more nucleotides in the ldh gene. In a specific embodiment, the nisin producing strain is a lactic acid bacterium comprising the nucleotides CCGTCAAG inserted between nucleotide T464 and C465 in the CDS region of the parent ldh gene (SEQ ID No. 5), hence resulting in a frameshift change.

In a one embodiment, the nisin producing strain is a strain derivable from the parent strain lactic acid bacterium *Lactococcus lactis* subsp. *lactis* bv. diacetylactis SD96 (NCBI accession No SRX6686433), characterized by the ability to produces nisin and being devoid of lactate dehydrogenase activity, by virtue of the following genetic modification in the genome when compared to the genome of the parent strain:

I. a transposon Tn5307 (SEQ ID NO. 4) comprising nisin biosynthesis gene cluster and genes needed for metabolizing sucrose is inserted into the parent genome,
II. nucleic acid sequence CCGTCAAG is inserted between nucleotide T464 and C465 in the CDS region of the parent ldh gene (SEQ ID No. 5) encoding lactate dehydrogenase, In a further embodiment, the nisin producing microbial strain is capable of growing in milk and/or stream derived from milk processing. Milk may be any kind of milk, such as skimmed milk, regular milk, whole milk, including ultra-high temperature (UHT) treated milk and pasteurized milk. Milk derived streams may be any stream derived from milk production, such as a waste stream, for example a stream comprising whey, e.g. whey mother liquor. In a preferred embodiment, the nisin producing strain is a lactic acid bacterium adapted to grow in milk and/or a stream derived from milk.

The dairy industry generates significant volumes of low-value side-streams, i.e. dairy waste. One of these is whey mother liquor (ML), which is a remaining product of whey processing and which mainly contains lactose along with citrate and different salts. Worldwide whey production is estimated to be around 1.8 to $1.9 \times 10^8$ ton/year, and quite large amounts of ML are available worldwide. These whey side-streams are often challenging to dispose of, due to their high organic load, and the Chemical Oxygen Demand (COD) can be as high as 100,000 mg $O_2$ $L^{-1}$. There is a great potential in transforming these waste materials into high value-added products.

In one embodiment, the nisin producing microbial strain is capable of growing in milk and/or a stream derived from milk at elevated temperatures, such as temperatures at least up to 40° C. In one embodiment, the nisin producing microbial strain is capable of growing at temperatures up to 30, 31, 32, 33, 34, 35, 36, 37, 38, 39, or even 40° C.

In one embodiment, the nisin producing strain is a lactic acid bacterium that is derivable from *Lactococcus lactis* subsp. *lactis* bv. diacetylactis SD96, and is characterized by the ability to produce nisin as well as the ability to grow in milk, preferably at elevated temperatures. The acquisition of these characteristics may be achieved by targeted mutation (CRISPR editing) or for example by adaptive evolution.

Accordingly, in one embodiment, the nisin producing strain is a strain derivable from the parent strain lactic acid bacterium *Lactococcus lactis* subsp. *lactis* bv. diacetylactis SD96 (NCBI accession No SRX6686433), that is characterized by the ability to produce nisin and grow in milk at elevated temperatures (such as at least up to 40° C.), by virtue of the following genetic modifications in the genome when compared to the genome of the parent strain:

I. a transposon Tn5307 (SEQ ID NO. 4) comprising the nisin biosynthesis gene cluster and genes needed for metabolizing sucrose is inserted into the parent genome, II. a parent gene encoding UDP-N-acetylmuramate-L-alanine ligase of SEQ ID No. 8 is modified to encode said amino acid sequence having substitution F68L, III. a parent gene encoding GTP pyrophosphokinase (RelA) of SEQ ID No. 10 is modified to encode said amino acid having substitution V469L, IV. base pairs 1,823,878-1,897,135 (SEQ ID No. 11) in the parent genome are deleted, and V. a tandem repeat ((A)6 to (A)5) upstream of the CodY transcription regulator (SEQ ID No. 12) in the parent genome is deleted.

In a preferred embodiment, the nisin producing strain is a strain derivable from the parent strain lactic acid bacterium *Lactococcus lactis* subsp. *lactis* bv. diacetylactis SD96 (NCBI accession No SRX6686433), characterized by:

(i) the ability to produces nisin by virtue of the following genetic modification in the genome when compared to the genome of the parent strain:

I. a transposon Tn5307 (SEQ ID NO. 4) comprising nisin biosynthesis gene cluster and genes needed for metabolizing sucrose is inserted into the patent genome, (ii) the ability to grow in milk at elevated temperatures (such as at least up to 40° C.), by virtue of the following genetic modifications in the genome when compared to the genome of the parent strain:

II. a parent gene encoding UDP-N-acetylmuramate-L-alanine ligase of SEQ ID No. 8 is modified to encode said amino acid sequence having substitution F68L, III. a parent gene encoding GTP pyrophosphokinase (RelA) of SEQ ID No. 10 is modified to encode said amino acid having substitution V469L, IV. base pairs 1,823,878-1,897,135 (SEQ ID No. 11) in the parent genome are deleted, and V. a tandem repeat ((A)6 to (A)5) upstream of the CodY transcription regulator (SEQ ID No. 12) in the parent genome is deleted, and (iii) being devoid of lactate dehydrogenase activity by virtue of the following genetic modification in the genome when compared to the genome of the parent strain:

VI. nucleic acid sequence CCGTCAAG is inserted into the CDS region of the parent ldh gene (SEQ ID No. 5) encoding lactate dehydrogenase between nucleotides T464 and C465, As mentioned above, the ability of the nisin producing strain to produce nisin is preferably obtained by classical mutagenic methods, hence a non-GMO strain.

In a much preferred embodiment, the nisin-producing microbial strain is Ge001, deposited with depository institution DSMZ German collection of microorganism and cell cultures, Inhoffenstraβe 7B, 38124 Braunschweig, GERMANY, under the Budapest Treaty having Deposit Number XXX. Ge001 produces nisin and is deficient in lactate dehydrogenase activity, and can therefore be grown to high cell densities without pH control. Ge001 is further especially preferred due to its ability to grow in milk and milk derived streams, such as illustrated in examples 8-10.

II.ii Permeabilization Conditions

Permeabilization may be performed within a wide temperature range—such as demonstrated in Example 4. It is preferred to avoid temperatures that are sufficiently high that they compromise cell and enzyme stability, rather than using a temperature that is optimal for nisin permeabilization as such. Permeabilization temperature for mesophilic organisms is therefore preferably lower than 60° C., such as lower than 55° C., preferably even lower than 54, 53, 52, 51, of 50° C. Meanwhile for thermophilic organisms the permeabilization temperatures may be relatively higher, depending on the specific microorganism.

Without being bound by theory, the nisin permeabilization reaction happens as soon as the cells are brought in contact with the nisin. In other words, in a well-mixed nisin saturated solution, the cells will quickly become permeabilized, and extended permeabilization reaction time is not needed. This is, for example, demonstrated in Example 4, where 30 minutes permeabilization time showed no significant improvement compared to 10 minutes. In one embodiment, the permeabilization time may be 5, 10, 15, 20, 25, 30, 35, 40, 45, 50, 55, or 60 seconds, In one embodiment, permeabilization time may be 1-60 minutes, such as 1-45 minutes, 1-30 minutes, 1-20 minutes; or even 1-10 minutes permeabilization time may suffice.

The amount/concentration of nisin applied for sufficient permeabilization of cells may depend on permeabilization conditions, such as the type of microbial cell to be permeabilized, concentration of cells, permeabilization time, and other medium conditions.

As an illustrative example, when 100 mg/l *S. thermophilus* cells are to be permeabilized: the examples provided herein show that 2.5 μg/ml nisin in POM buffer efficiently permeabilizes the cells within merely 10 minutes. Increasing the cell concentration may require increased nisin concentration to obtain efficient permeabilization within the same time period. Meanwhile, if the cell concentration is increased, but nisin concentration is maintained, then the permeabilization time can be increased to obtain sufficient permeabilization. A person skilled in the art would know how to adjust/optimize these different parameters to obtain optimal permeabilization for a given organism at a desired cell concentration.

In one embodiment, a nisin concentration of 2-250 μg nisin per mg cells is used in permeabilization of the cells, such as a nisin concentration of 10-150 μg nisin per mg cells, such as a nisin concentration of 10-100 μg nisin per mg cells, such as a nisin concentration of 20-50 μg nisin per mg cells, such as preferably around 25 μg nisin per mg cells.

In a preferred embodiment, 0.1 g/l cells are treated with around 2.5 μg/ml nisin for around 10 minutes.

After nisin-treatment, the cells may be used directly as permeabilized whole-cell catalysts, or they may preferably first be purified prior to use. A person skilled in the art would know how to perform such cell purification. Purification may simply be performed by pelleting the cells by centrifugation and removing the top liquid portion; or such as by simple filtration. The cells may further be washed, if needed, prior to their intended application. Any excess nisin left in the permeabilization medium may after harvesting the permeabilized cells be used in the subsequent permeabilization treatments of other cells.

In one embodiment, the nisin-permeabilized cells may be prepared as described above and further treated by a method ensuring preservation and possible storage of the cells prior to use. Methods of preservation, such as drying, freezing, or preparing liquid stocks of the microbial cells are known by a person skilled in the art and include, for example, glycerol stocks, or freezing concentrated cell slurries in liquid nitrogen, freeze-drying, spray drying, vacuum drying, etc.

II.iii Nisin-Permeabilized Microbial Whole-Cell Catalysts

One aspect of the present invention relates to a whole-cell catalyst comprising nisin-permeabilized microbial cells; wherein the nisin-permeabilized cells comprise at least one intracellular enzyme for catalyzing conversion of a target substrate; and wherein the nisin-permeabilized cells are in a frozen or dried state.

Such whole-cell catalysts may be provided in bags, ampoules, tubes, vial, or the like depending on consumer preference.

The whole-cell catalyst may comprise any microbial cell susceptible to nisin-permeabilization comprising an enzyme capable of catalyzing the conversion of a substrate, provided that (i) the size/shape/conformation of the enzyme ensures it being retained within the cell (not transiting though the nisin pores), and (ii) the size/shape/conformation of the substrate allows for the substrate to transit through nisin pores of the cell membrane.

In one embodiment, the whole-cell catalyst comprises frozen or dried preparations of nisin-permeabilized lactic acid bacteria comprising beta-galactosidase EC 3.2.1.23 for catalyzing conversion of lactose to glucose and galactose.

In one embodiment, the whole-cell catalyst comprises frozen or dried preparations of nisin-permeabilized bacteria comprising arabinose isomerase EC. 5.3.1.4 for isomerization of galactose to tagatose.

In one embodiment, the whole-cell catalyst comprises frozen or dried preparations of nisin-permeabilized bacteria comprising xylose (glucose) isomerase EC 5.3.1.5 for isomerization of glucose to fructose.

In one embodiment, the whole-cell catalyst comprises frozen or dried preparations of nisin-permeabilized bacteria comprising alpha-acetolactate decarboxylase EC 4.1.1.5 for conversion of alpha-acetolactate into acetoin.

In one embodiment, the whole-cell catalyst comprises frozen or dried preparations of nisin-permeabilized bacteria comprising alpha-acetolactate synthase EC 2.2.1.6 for conversion of pyruvate into alpha-acetolactate.

III. Method for Reducing the Content of a Substrate in a Sample Using Permeabilized Microbial Cell Catalysts One aspect of the present invention relates to a method for reducing the content of a substrate in a sample, said method comprising the steps of:
- a. providing microbial cells comprising an intracellular enzyme for catalyzing conversion of said substrate into one or more products,
- b. incubating said microbial cells with nisin,
- c. optionally harvesting permeabilized cells obtained in step (b),
- d. incubating permeabilized cells obtained in step (b) or harvested cells obtained in step (c) with said sample comprising said substrate;
  - wherein said microbial cells are susceptible to nisin-permeabilization, and wherein the substrate can transit through nisin pores of the permeabilized cells.

Nisin-permeabilized microbial cells are hereby used as a whole-cell catalyst. Whereas prior art has only used nisin as a means for killing cells—such as to avoid food spoilage by contaminating microbes, the present invention surprisingly reveals that nisin-permeabilized cells are excellent whole-cell catalysts as the cells function as a porous "bag" retaining and protecting the enzymes while substrates can freely transit across the cell membrane via the nisin pores to be hydrolyzed within the cell. The products of the enzymes reaction may transit out through the nisin pores into the medium or be consumed by the cell such as used by the cells metabolic machinery.

Depending on the application, it may be desirable to harvest the nisin-permeabilized cells prior to use to either be able to re-use excess nisin or to simply avoid having nisin carry-over in the catalytic reaction by the nisin-treated cell catalysts. In other embodiments, the presence of nisin in the catalytic reaction by the nisin-treated cell catalysts is of no concern, and nisin treatment (step b) and incubation with the substrate (step d) may therefore occur simultaneously, rather than as separate steps.

Numerous different applications exist for the method of the present invention. Any microbial cell susceptible to nisin-permeabilization may be used in the present method for conversion (reducing the amount) of a target substrate in a sample, provided that the cell comprises an enzyme capable of catalyzing the conversion of the substrate and that the size/shape/conformation of the substrate allows for the substrate to transit through nisin pores in the cell membrane, while the size/shape/conformation of the enzyme ensures it being retained within the cell (not transiting though the nisin pores). The nisin pores are expected to have an approximate size of 2-2.5 nm.

In one embodiment, suitable applications of the present invention involves an enzyme catalyst having its smallest dimension being at least 1, 1.5, 2, 2.5, 3, 3.5, 4, 4.5, or 5 nm, for the enzyme to be retained within the cell, while the largest dimension of the substrate of the catalyst correspondingly does not exceed 1, 1.5, 2, 2.5, 3, 3.5, 4, 4.5, or 5 nm, for the substrate to be able to transit through the nisin pores into the cell.

Embodiments of such applications of the invention may comprise hydrolysis of lactose by bacteria comprising beta-galactosidase; isomerization of galactose to tagatose using a bacterium comprising arabinose isomerase; isomerization of glucose to fructose using a bacterium comprising xylose (glucose) isomerase; conversion of alpha-acetolactate into acetoin using a bacterium comprising alpha-acetolactate decarboxylase; conversion of pyruvate into alpha-acetolactate using a bacterium comprising alpha-acetolactate synthase; etc.

The above applications are merely illustrative—as mentioned previously, the method has very broad application since the use of whole-cell catalysts of the invention for catalysis avoids the problems associated with enzyme secretion or purification. Furthermore, the enzymes in the whole cell catalysts of the invention are better protected and thus more active than secreted or isolated intracellular enzymes. The microorganisms applied in the method may naturally comprise the needed enzyme(s) for conversion of a target substrate, or they may be genetically modified by standard methods known in the art to express the required enzyme(s).

In a preferred embodiment, the application of the method of the present invention is within food industries, such as where the substrate of the invention is a food or beverage. Natural, non-GMO microbes are preferred for such application.

In one embodiment, the present method is suitable for reducing the lactose content of a dairy product—such as for producing lactose-reduced milk, yoghurt (and yoghurt like products, e.g. Gaio®, Cultura®), Skyr, Quark, Greek yoghurt, butter milk, cream, butter, whey, and other dairy products.

Specifically, such method of the present invention for reducing the lactose content of a dairy product comprises the steps of:

a. providing lactic acid bacteria comprising beta-galacto-sidase EC 3.2.1.23. for catalyzing conversion of lactose to galactose and glucose, b. incubating said bacteria with nisin, c. optionally harvesting permeabilized bacteria obtained in step (b), d. incubating permeabilized bacteria obtained in step (b) or (c) with said dairy product.

In a preferred embodiment, the method of the present invention for reducing the amount of lactose in a dairy sample comprising the steps of:

a) providing one or more non-GMO microbial cells comprising an intracellular beta-galactosidase enzyme for catalyzing conversion of lactose into glucose and galactose, b) incubating said non-GMO microbial cell with a nisin producing second microbial cell culture and/or a culture medium derived thereof, c) optionally harvesting permeabilized non-GMO microbial cell catalysts obtained in step (b), d) incubating permeabilized non-GMO microbial cell catalysts obtained in step (b) or harvested non-GMO microbial cell catalysts harvested in step (c) with said first dairy sample comprising lactose;

wherein said first microbial cell is a lactic acid bacterium

In one embodiment, the nisin producing microbial cell culture is obtained by culturing a nisin producing microbial cell in a second dairy sample, prior to incubating with the second microbial cell in step (b).

In one embodiment, the second dairy product is milk and/or streams derived from milk processing. Milk may be any kind of milk, such as skimmed milk, regular milk, whole milk, including ultrahigh temperature (UHT) treated milk and pasteurized milk. As mentioned previously, the dairy industry generates significant volumes of low-value side-streams, i.e. dairy waste. There is a great potential in transforming these waste materials into high value-added products. Milk derived streams may be any stream derived from milk production, such as a waste stream, for example a stream comprising whey, e.g. whey mother liquor.

Lactose is converted to glucose and galactose by the beta-galactosidase EC 3.2.1.23 enzyme. Several different bacteria naturally produce beta-galactosidase. When the method is used for reducing the lactose content in a dairy product, from a commercial/regulatory point of view, it is favorable to apply the method using a beta-galactosidase producing lactic acid bacterium, since lactic acid bacteria are naturally found in dairy products. Example 2 illustrates the performance of a selection of different nisin-permeabilized lactic acid strains comprising beta-galactosidase in hydrolyzing lactose. In one embodiment, the lactic acid bacterium comprising beta-galactosidase EC 3.2.1.23 may be selected from *Streptococcus thermophilus, Lactobacillus casei, Lactobacillus plantarum, Lactobacillus helveticus, Lactobacillus delbrueckii, Lactobacillus acidophilus*, and *Lactococcus lactis*. Preferably, the lactic acid bacterium is a *S. thermophilus* strain.

The lactic acid bacterium is incubated with nisin, such as with a nisin producing microbial cell culture and/or a culture medium derived thereof, under conditions easily optimized by a person skilled in the art by testing different combinations of temperature, time, cell concentration, etc. With their intended use in processing of a dairy product, the permeabilized cells are preferably harvested after nisin-treatment prior to adding them to the dairy product, and further optionally washed before adding them to the dairy product. Once added to the dairy product, the beta-galactosidase enzymes inside the cells will facilitate hydrolysis of lactose in a dairy product into glucose and galactose, yielding a lactose-reduced dairy product (see FIG. 1).

In one embodiment, the dairy product is a milk product, such as selected from skimmed milk, regular milk, whole milk, etc. Example 3 illustrates efficient hydrolysis of lactose in milk.

In one embodiment, the original lactose content of the dairy product is reduced by at least 50%, such as 55%, 60%, 65%, or even up to 70%. In one embodiment, 70% of the original lactose content of the dairy product is hydrolyzed by the nisin-permeabilized cells comprising beta-galactosidase, such as 75%, 80%, 85%, 90%, or even 95% or above is hydrolyzed.

In another embodiment, the method of the present invention is suitable for preparing yoghurt (or yoghurt-like products) having a reduced lactose content. The method described above for preparing a dairy product having reduced lactose content may in this regard be followed by the addition of a step:

e. culturing yoghurt starter bacteria in the product obtained in step (d), wherein said starting dairy product is milk.

The added yoghurt starter bacteria will thereby facilitate conversion of the lactose-reduced milk to lactose-reduced yoghurt.

Specifically, the steps for making a yoghurt product having a low lactose content may be performed by the method of the present invention comprising the steps of:

a. providing lactic acid bacteria comprising beta-galacto-sidase EC 3.2.1.23 for catalyzing conversion of lactose to galactose and glucose, b. incubating said bacteria with nisin, c. optionally harvesting permeabilized bacteria obtained in step (b),

d. incubating permeabilized bacteria obtained in step (b) or (c) with milk, e. culturing yoghurt starter bacteria in the hydrolyzed milk product obtained in step (d).

Yoghurt starter bacteria are commonly known in the art, and for example may be selected from *Streptococcus thermophilus* and *Lactobacillus* delbruckii subsp. *bulgaricus*. In preparing lactose-reduced yoghurt, in one embodiment, the permeabilized cells comprising beta-galactosidase may hydrolyze between 50-100% of the lactose in milk, such as between 70-100% of the lactose. In another embodiment, the permeabilized cell catalyst may hydrolyze merely 50%, 55%, 60%, 65%, 70%, 75%, or 80% of the lactose prior to addition of the yoghurt starter culture, where after the remaining lactose content may be removed (utilized) by the yoghurt starter culture in combination with further hydrolysis by the permeabilized cell catalyst.

In a further embodiment, the method of the present invention may be applied to increase the sweetness of a lactose product. As a non-limiting example, partially hydrolyzed lactose may be used as a sweetener, as the presence of several types of sugars has a synergistic effect on sweetness. Thus the method can be used in all types of lactose-comprising products, such as yoghurts or even chocolates, to increase sweetness, and at the same time allow for reducing the overall added-sugar content.

In a further embodiment of the invention, value-added compounds may be produced. One such example is tagatose and fructose from the isomerization of galactose and glucose, respectively. This may be facilitated by microbial cells comprising arabinose isomerase EC 5.3.1.4 (for conversion of galactose to tagatose) and/or xylose isomerase EC 5.3.1.5 (for conversion of glucose to fructose).

In one embodiment, the method of the invention comprises treating a microbial cell with nisin as described herein, wherein the cell comprises (i) xylose isomerase EC 5.3.1.5 for conversion of glucose to fructose and/or (ii) arabinose isomerase EC 5.3.1.4 for conversion of galactose to tagatose; and wherein the substrate is glucose and/or galactose, respectively.

A microbial cell comprising arabinose isomerase EC. 5.3.1.4 and/or xylose isomerase EC 5.3.1.5 may in a preferred embodiment be selected from the group of lactic acid bacteria. These microbial cells may be added to a lactose-reduced milk product produced by the method of the invention. In a preferred embodiment, the microbial cell comprising arabinose isomerase EC 5.3.1.4 and/or xylose isomerase EC 5.3.1.5 is nisin-permeabilized, such as by methods described in section II for more efficient isomerization of the sugars.

In a further embodiment of the invention, the method may be applied to prepare a nisin-permeabilized bacterium comprising alpha-acetolactate decarboxylase EC 4.1.1.5 to be used for efficient conversion of alpha-acetolactate into acetoin.

In yet a further embodiment of the invention, the method may be applied to prepare a nisin-permeabilized bacterium comprising alpha-acetolactate synthase EC 2.2.1.6 to be used for efficient conversion of pyruvate into alpha-acetolactate—such as demonstrated in example 6.

In a further embodiment of the invention, microbial cells are treated with a combination of nisin and monolaurin for obtaining a further improved catalyst—such as demonstrate in example 7. More specifically, in step b of the method of the present invention, incubation of the microbial cell with nisin in combination with monolaurin may be beneficial.

Hence, the present invention also concerns a method for reducing the amount of a substrate in a sample, said method comprising the steps of:

a. providing microbial cells comprising at least one intracellular enzyme for catalyzing conversion of said substrate into one or more products, b. incubating said microbial cells with nisin and monolaurin, c. optionally harvesting permeabilized cells obtained in step (b), d. incubating permeabilized cells obtained in step (b) or harvested cells obtained in step (c) with said sample comprising said substrate;

wherein said microbial cells are susceptible to nisin-permeabilization, and wherein the substrate can transit through nisin pores of the permeabilized cells.

IV. A Composition Comprising Nisin-Permeabilised Microbial Cells

One aspect of the present invention relates to a composition comprising (i) nisin-permeabilised microbial cells comprising an intracellular enzyme and (ii) substrate(s) and product(s) of a reaction catalyzed by said enzyme—as defined in previous sections of the present application.

In one embodiment, the composition comprises (i) nisin-permeabilized lactic acid bacteria comprising beta-galactosidase EC 3.2.1.23, and (ii) a dairy product comprising lactose and glucose and galactose.

In another embodiment, the composition comprises (i) nisin-permeabilized lactic acid bacteria comprising beta-galactosidase and a nisin-permeabilized microbial cell comprising arabinose isomerase EC 5.3.1.4 and/or xylose isomerase EC 5.3.1.5 and (ii) a dairy product comprising one or more of lactose, glucose, galactose, tagatose, and sucrose.

V. A Nisin Producing Microbial Cell

One aspect of the present invention relates to a nisin producing microbial cell.

In one embodiment, the nisin producing microbial cell is derived from parent strain *Lactococcus lactis* subsp. *lactis* bv. diacetylactis SD96 (NCBI accession No. SRX6686433) by virtue of inserting transposon Tn5307 (SEQ ID NO. 4) comprising nisin biosynthesis gene cluster and genes needed for metabolizing sucrose into the genome of the parent strain.

In a further embodiment, the nisin producing microbial cell is phenotypically devoid of lactate dehydrogenase activity.

In a further embodiment, the nisin producing microbial cell is further characterized by the ability to grow in milk at a temperature of 40° C., by virtue of the following genetic modifications in the genome when compared to the genome of the parent strain:

I. a parent gene encoding UDP-N-acetylmuramate-L-alanine ligase of SEQ ID No. 8 is modified to encode said amino acid sequence having substitution F68L, II. a parent gene encoding GTP pyrophosphokinase (RelA) of SEQ ID No. 10 is modified to encode said amino acid having substitution V469L, III. base pairs 1,823,878-1,897,135 (SEQ ID No. 11) in the parent genome are deleted, and IV. a tandem repeat ((A)6 to (A)5) upstream of the CodY transcription regulator (SEQ ID No. 12) in the parent genome is deleted, In a preferred embodiment, the nisin producing microbial cell of the invention for producing a microbial cell catalyst is strain Ge001.

VI. Use of Nisin-Permeabilized Cells as Whole-Cell Catalyst

One aspect of the present invention concerns the use of nisin-permeabilized microbial cells comprising an intracellular enzyme as whole-cell catalyst in an enzyme reaction. An essential prerequisite of the invention is that the substrate(s) of the enzyme reaction catalyzed by the intracellular enzyme of the nisin-permeabilized microbial cells has a size/shape/conformation that allows their transit through nisin pores of the nisin-permeabilized microbial cells.

Any given organism susceptible to nisin-permeabilization comprising an intracellular enzyme having a substrate small enough to travel through the nisin pore may be of use in the present invention—the enzyme and its substrate being defined in greater detail in previous sections of the present application.

In one embodiment, the nisin-permeabilized microbial cells are lactic acid bacteria comprising beta-galactosidase for hydrolysis of lactose. The nisin-permeabilized cells are thereby used as whole-cell catalysts for lactose hydrolysis in e.g. dairy products. The beta-galactosidase of *S. thermophilus* or other lactic acid bacteria naturally contributes to the partial hydrolysis of lactose in dairy foods such as yogurt during product manufacture and again during the passage through the gastrointestinal tract, as the result of permeabilization by bile acids. Therefore, fortification of milk with permeabilized *S. thermophilus* prior to direct consumption or incorporation into milk-based products as a source of beta-galactosidase thereby provides a close to "natural process", wherein the beta-galactosidase of inherently safe and edible *S. thermophilus* needs no further purification or isolation to qualify for food-grade status.

In one embodiment, the invention concerns the use of a nisin producing microbial cell as described herein for producing a microbial cell catalyst, preferably comprising an intracellular beta-galactosidase enzyme. In a preferred embodiment, the nisin producing microbical cell is derived from parent strain *Lactococcus lactis* subsp. *lactis* bv. diacetylactis SD96 (NCBI accession No. SRX6686433) by virtue of inserting a copy of transposon Tn5307 (SEQ ID NO. 4) comprising nisin biosynthesis gene cluster and genes needed for metabolizing sucrose into the genome of the parent strain. In a further preferred embodiment, the nisin producing microbical cell is further characterized by being devoid of lactate dehydrogenase activity. In a further preferred embodiment, the nisin producing microbial cell is further characterized by the ability to grow in milk at a temperature of 40° C., by virtue of the following genetic modifications in the genome when compared to the genome of the parent strain: (I) a parent gene encoding UDP-N-acetylmuramate-L-alanine ligase of SEQ ID No. 8 is modified to encode said amino acid sequence having substitution F68L, (II) a parent gene encoding GTP pyrophosphokinase (RelA) of SEQ ID No. 10 is modified to encode said amino acid having substitution V469L, (III) base pairs 1,823,878-1,897,135 (SEQ ID No. 11) in the parent genome are deleted, and (IV) a tandem repeat ((A)6 to (A)5) upstream of the CodY transcription regulator (SEQ ID No. 12) in the parent genome is deleted. In a most preferred embodiment, the nisin producing microbial cell is strain Ge001.

In another embodiment, nisin-permeabilized cells may be used as whole-cell catalyst in producing value-added compounds. One example is a nisin-permeabilized microbial cell capable of conversion of glucose and galactose to fructose and tagatose.

VII. A Method of Detecting Products Produced by the Nisin-Permeabilized Cells Methods for detecting and quantifying products, such as sugars, produced by a microbial cell of the invention include high performance liquid chromatography (HPLC) combined with refractive index detection to identify and quantify the products compared to standards, as one ordinary skilled in the art would be familiar with. Example 1 comprises the outline of one method of detection and quantification of sugars.

VIII. Advantages and Commercial Application

Nisin was first identified in 1928 in fermented milk cultures and commercially marketed in England in 1953 as an antimicrobial agent. In 1969, nisin was approved by the Joint Food and Agriculture Organization/World Health Organization (FAO/WHO) as a safe food additive. In the United States, nisin was approved by the Food and Drug Administration in 1988 and was given a generally regarded as safe (GRAS) designation for use in processed cheeses.

Nisin therefore represents an excellent choice as a permeabilizing agent—especially within the food industry as it is a natural compound, which is food approved and easy to handle. Further, in the present invention, only a very low concentration of nisin is required for permeabilizing the cells.

Using nisin-permeabilized cells as a substitute for commercial purified 3-galactosidases has many advantages such as low cost, low resource utilization, and possibility for clean-label status of lactose-free dairy products. Also of importance, is that it provides a more natural process when compared to commercial lactase solutions, where lactases are often derived from GMO's (engineered microorganisms).

Somkuti et al. 1998, have previously demonstrated that ethanol-permeabilized lactic acid bacteria can be used as lactase, however, using ethanol has some obvious drawbacks, such as in terms of handling the ethanol, as large amounts of ethanol are involved and some ethanol could end up in the final product. Kosher/Halal status of dairy products is increasingly important, and using ethanol as a permeabilizing agent may raise issues in this respect, as small amounts of ethanol could be introduced, with the cells, into the product. Furthermore, it was demonstrated in Example 5 that ethanol compromised the stability of the whole-cell catalyst, hence more cells will be needed to achieve a satisfactory degree of hydrolysis within a certain time limit. Meanwhile, nisin-treated cells showed a higher stability. Summarized, Example 5 clearly shows that nisin-treated cells perform better as whole-cell catalysts than ethanol-treated cells.

Further, the high stability of nisin-permeabilized cells supports the re-use of them as cell catalyst. The cells may simply be harvested after use and re-used, which could further lower the cost of use compared to e.g. conventional purified enzymes that cannot simply be collected and reused.

In all of the above embodiments, nisin may be substituted by any pore forming lantibiotic, such as Class A lantibiotics including bisin, subtilin, epidermin, gallidermin, and mutacin.

Hence, the present invention concerns a method for reducing the amount of a substrate in a sample, said method comprising the steps of:

a. providing microbial cells comprising at least one intracellular enzyme for catalyzing conversion of said substrate into one or more products, b. incubating said microbial cells with a Class A lantibiotic, c. optionally harvesting permeabilized cells obtained in step (b), d. incubating permeabilized cells obtained in step (b) or harvested cells obtained in step (c) with said sample comprising said substrate;

wherein said microbial cells are susceptible to nisin-permeabilization, and wherein the substrate can transit through nisin pores of the permeabilized cells.

The present invention further concerns a whole-cell catalyst comprising Class A lantibiotic-permeabilized microbial cells; wherein the permeabilized cells comprise at least one intracellular enzyme for catalyzing conversion of a target substrate; and wherein the permeabilized cells are in a frozen or dried state.

The present invention further concerns a composition comprising (i) Class A lantibiotic-permeabilised microbial cells comprising at least one intracellular enzyme and (ii) substrate(s) and product(s) of a reaction catalyzed by said at least one enzyme.

The present invention further concerns use of Class A lantibiotic-permeabilized microbial cells comprising at least one intracellular enzyme as whole-cell catalyst in an enzyme reaction, wherein substrate(s) and product(s) of said reaction can transit through Class A lantibiotic-pores of the permeabilized microbial cells.

EXAMPLES

Example 1: Nisin-Permeabilized S. thermophilus can Hydrolyze Lactose 1.1. Microbial Strains Streptococcus thermophilus (S. thermophilus) strain CS1980 was isolated from a Danish yoghurt. Other S. thermophilus strains were isolated from starter cultures kindly provided by Sacco Srl. Italy (ST057, ST022).

1.2 Growth Media

S. thermophilus was grown at 37° C. in LM17 medium (Sigma-Aldrich, Darmstadt, Germany) further comprising 20% whey mother liquor (ML) and 10% HFI-110 in 10 ml test tubes, without agitation. ML is the concentrated residue remaining after extraction of lactose from whey. HFI-110 is a whey protein hydrolysate prepared by Arla Foods Ingredients.

1.3 Cell Permeabilization Using Nisin A

S. thermophilus CS1980 was grown in 500-ml Erlenmeyer flasks containing 200 ml of medium at 37° C. for 16 h without agitation. As inoculum, 2 ml of a 24 hour, outgrown culture was used. Cells were collected by centrifugation at 10,000 g for 10 min at 4° C., washed once with sterile POM buffer (50 mM K2HPO4/KH2PO4, 1 mM MgCl2, pH 7.4) and finally re-suspended in POM buffer to an optical density (600 nm) of 0.33, corresponding to approximately 100 mg/l dry cell weight. The cell suspension was kept on ice until use. For permeabilization, cell suspensions were dispensed into sterile tubes (1 ml per tube) and centrifuged in a microcentrifuge at top speed for 5 min at 4° C. After decanting supernatants and draining tubes on sterile paper towels, pellets were re-suspended in 1 ml nisin A (2.5

µg/ml, Sigma-Aldrich, Darmstadt, Germany) in POM buffer and held for 10 min at 28 or 37° C. cells were collected as before and kept on ice for later use. Controls included non-nisin treated cells.

1.4 Lactose Hydrolysis by Nisin-Permeabilized Cells

The nisin-permeabilized S. thermophilus cells (100 mg/l dry cell weight) were added to a 50 g/l lactose solution (POM buffer) and incubated at different temperatures for 72 hours. Samples were withdrawn at different time points, and conversion of lactose (formation of glucose and galactose) was determined by HPLC analysis.

1.5 Analysis of Sugar Products

The concentrations of sugars (carbohydrate monomers and dimers) were determined using an Ultimate 3000 high-pressure liquid chromatography system (Dionex, Sunnyvale, CA) equipped with an Aminex HPX-87H column (Bio-Rad, Hercules, CA) and a Shodex RI-101 detector (Showa Denko KK, Tokyo, Japan). The column oven temperature was set to 30° C., and the mobile phase consisted of 5 mM H2SO4 with a flowrate of 0.5 ml/min.

1.6 Hydrolysis Results

The cell catalyst was tested at different temperatures (20, 30, 40, 50, and 60° C.). It was found that the initial hydrolysis rate was fast at 60° C., but already after approx. 2 hours, the catalyst was inactivated. At lower temperatures, the catalyst was more stable. At 50° C., 95% of the lactose had been hydrolyzed within 24 hours (FIG. 2).

Figure 2A:
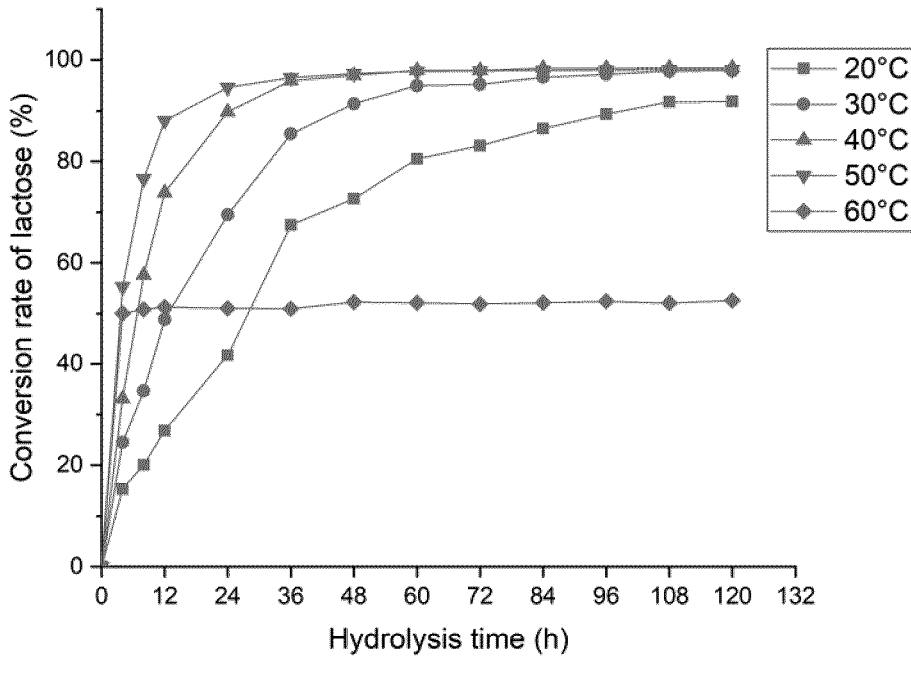
(FIG. 2A) or 37° C.
Figure 2B:
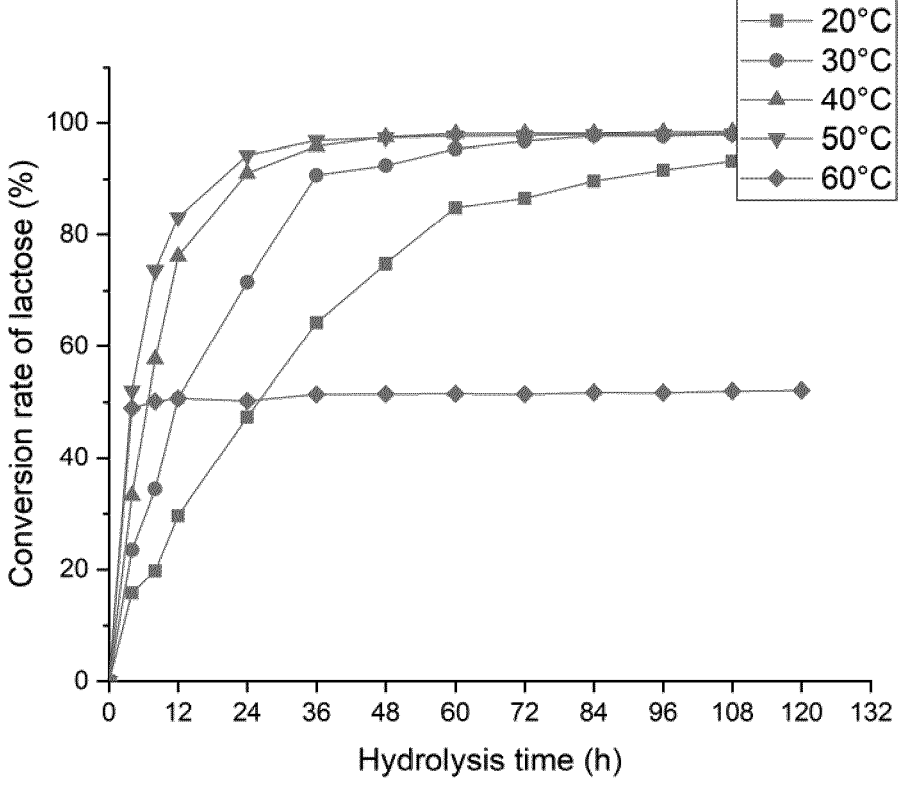
FIG. 2: Lactose hydrolysis by *S. thermophilus* CS1980. Cells (100 mg/l) were permeabilized at 28° C.

Comparing FIGS. 2A and 2B, it is seen that permeabilization may be performed within a wide temperature range: permeabilization at 28° C. and 37° C. seem to be equally efficient—it does not affect the final lactose conversion. Rather, it is the enzyme's stability that is challenged at the higher temperatures, resulting in the lower conversion at high hydrolysis temperature. Example 4 provides more examples demonstrating the influence of permeabilization temperature.

Example 2: Comparison of Performance of Different Nisin-Permeabilized S. thermophilus Whole-Cell Catalysts 2.1. Microbial Strains, Nisin-Permeabilization and Lactose Hydrolysis Streptococcus thermophilus (S. thermophilus) strain CS1980 was isolated from a Danish yoghurt (same as used in example 1). Additional S. thermophilus strains were isolated from starter cultures kindly provided by Sacco Srl. Italy (ST057, ST022).

The different S. thermophilus strains were nisin permeabilized, and tested for their ability to serve as whole-cell catalyst (lactase source) in lactose hydrolysis as described in example 1. Permeabilization of the cells was achieved using 2.5 µg/ml nisin in POM buffer for 10 minutes at 28° C. Hydrolysis was performed at 50° C.

2.1 Results

Figure 3:
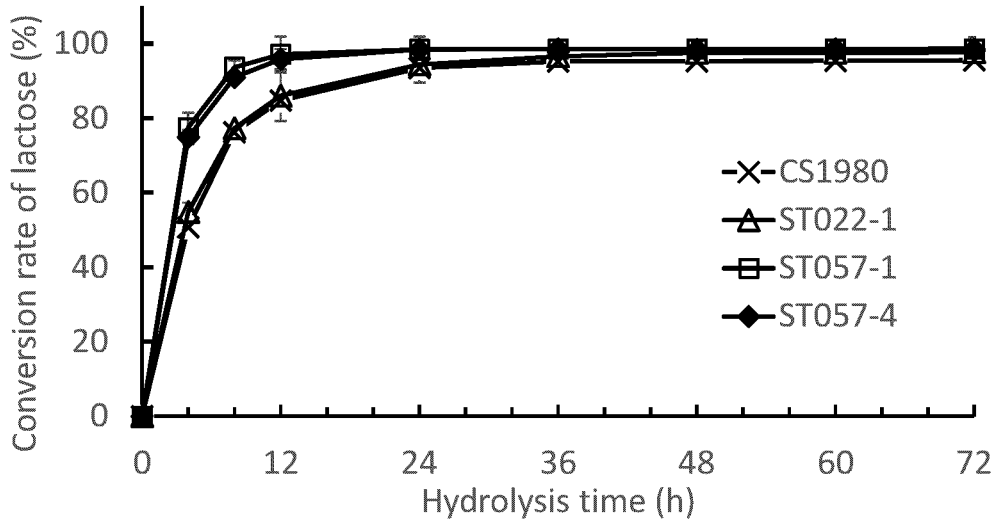
FIG. 3: Lactose hydrolysis by different *S. thermophilus* strains. Cells (100 mg/l) were permeabilized at 28° C. for 10 min using a nisin concentration of 2.5 μg/ml. Hydrolysis was subsequently performed at 50° C., using 100 mg/l dry weight of permeabilized cells in POM buffer solution comprising 5% lactose.

All isolates were able to hydrolyze lactose by the method of the present invention, see FIG. 3. The two strains from starter culture ST057 were almost twice as efficient as the other strains, facilitating >90% conversion of the lactose in less than half of the time.

Example 3: Nisin-Permeabilized S. thermophilus can Hydrolyze Lactose in Milk Above, the performance of the cell catalyst in buffered lactose solution has been tested, however, since the obvious substrate is milk or lactose-containing feedstocks derived from milk processing, it is relevant to characterize its performance in milk as well.

3.1. Microbial Strains, Nisin-Permeabilization and Lactose Hydrolysis

Nisin-treated *S. thermophilus* ST057-1 was applied in hydrolysis of lactose in milk, at cell concentration of approximately 100 mg/l or 1 g/l. Permeabilization of the cells was achieved using 2.5 µg/ml nisin in POM buffer for 10 minutes at 28° C. The starting concentration of lactose in the milk used was 52 g/l. Hydrolysis took place at 50° C.

3.2 Results

Figure 4:
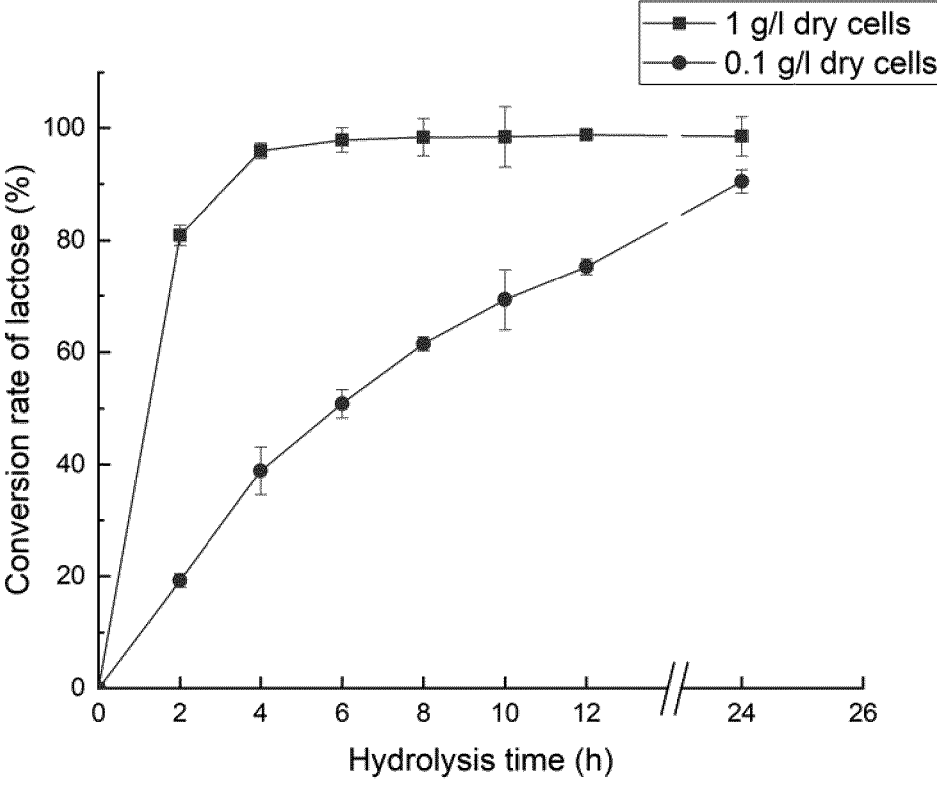
FIG. 4: Hydrolysis of lactose in milk by *S. thermophilus* ST057-1 cells using different cell concentrations: either 100 mg/l or 1 g/l. Permeabilization was performed at 37° C. for 10 min using a nisin concentration of 2.5 μg/ml. Hydrolysis of milk-lactose was subsequently performed at 50° C.

Hydrolysis of lactose in milk occurs slower than in POM buffer (FIG. 3 compared to FIG. 4): using 100 mg/l whole-cell catalyst concentration, 80% hydrolysis can be reached in within 4 hours POM buffer, whereas more than 12 hours is needed in milk.

Though milk can generally tolerate elevated temperatures (such as 50° C.) for an extended period of time without affecting its quality, a more rapid hydrolysis is preferred. Increasing the whole-cell catalyst concentration, the conversion rate was significantly increased (FIG. 4), reaching conversion levels as seen in the buffered samples.

Example 4: Nisin-Permeabilization is Efficient Over a Broad Temperature Range 4.1. Microbial Strains, Nisin-Permeabilization and Lactose Hydrolysis

*S. thermophilus* CS1980 was nisin-permeabilized using 2.5 µg/ml nisin in POM buffer for 10 or 30 minutes at 28, 50 and 55° C. Controls were prepared without addition of nisin in the permeabilization step. Hydrolysis of 50 g/l lactose in POM using nisin-treated cells was carried out at a cell concentration of approximately 100 mg/l. Hydrolysis took place at 50° C.

*S. thermophilus* ST057-1 was nisin-permeabilized using 2.5 µg/ml nisin in POM buffer for 10 minutes at 28° C. or 37° C. Hydrolysis of lactose in milk (52 g/l lactose) using nisin-treated cells was carried out at a cell concentration of approximately 1 g/l. Hydrolysis took place at 50° C.

4.2. Results

Figure 5A:
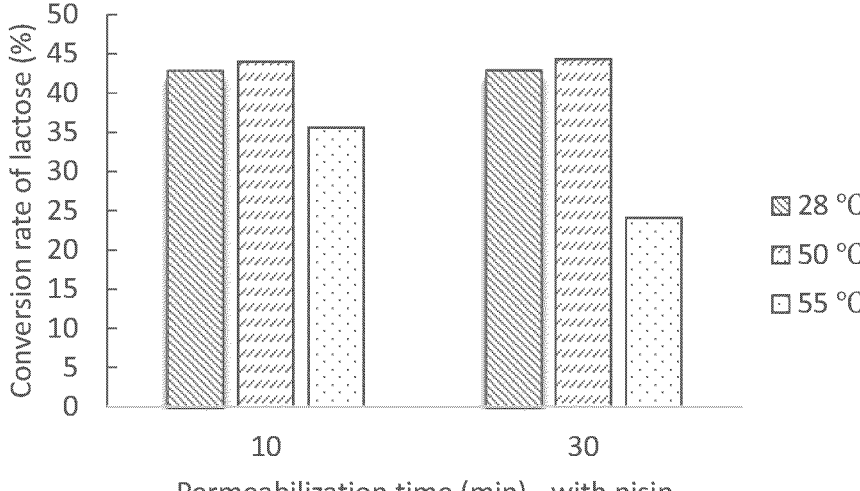
FIG. 5: Hydrolysis of lactose by *S. thermophilus* CS1980 using different permeabilization temperatures: 28, 50, and 55° C. Nisin-permeabilization was performed using 2.5 μg/ml nisin in POM buffer for 10 minutes. Hydrolysis of lactose in POM was performed at 50° C., using nisin-treated cells (FIG. 5A) or non-nisin-treated cells (FIG. 56) at a cell concentration of approximately 100 mg/l (dry cell weight).
Figure 5B:
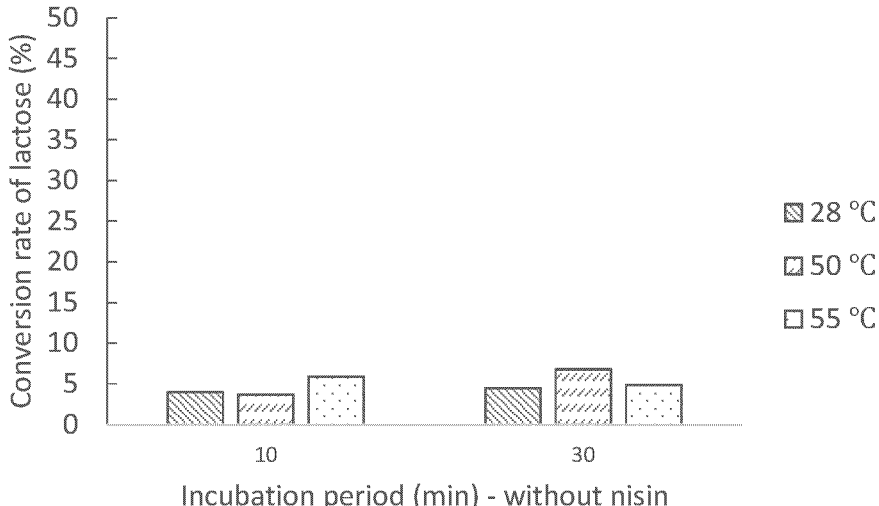

As seen in FIG. 5A, a broad range of permeabilization temperatures: 28-50° C., were found to be equally efficient. Temperatures as high as 50° C. may be applied, but at 55° C. the cell stability (and likely also the enzyme stability, especially at the longer permeabilization time) seemed to be compromised, hence for this particular strain and enzyme combination it is undesirable to use such high temperatures for the permeabilization. The control, where nisin was not added in the permeabilization step, showed only some very limited conversion (FIG. 5B); it is thereby clear that the temperature treatment itself is not the contributing cause of the substrate conversions reported herein. The nisin treatment is essential.

Figure 6:
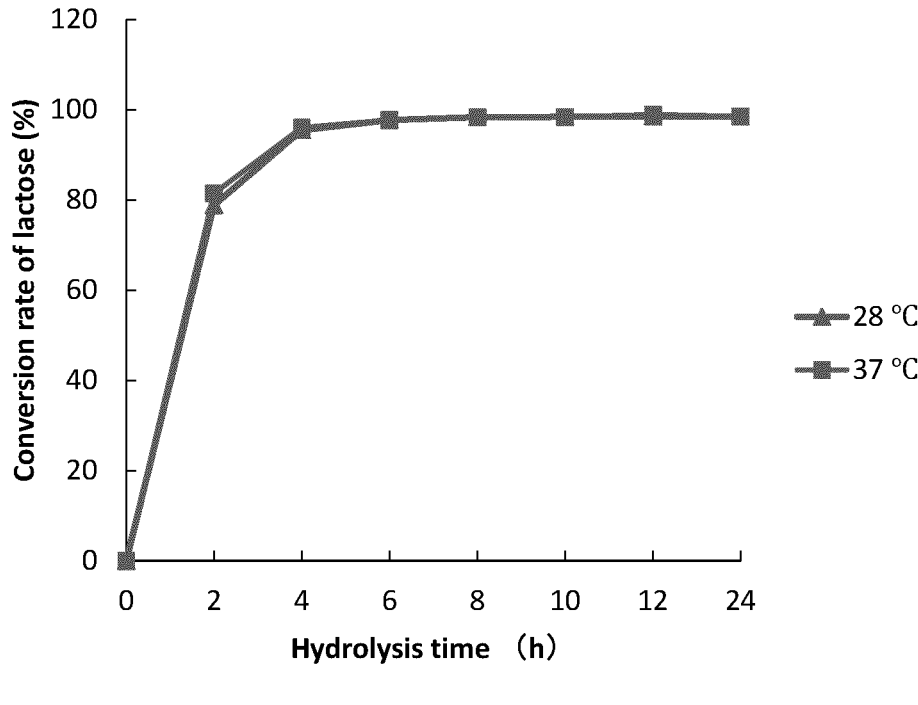
FIG. 6: Hydrolysis of lactose in milk by *S. thermophilus* ST057-1 using different permeabilization temperature: 28° C. or 37° C. Nisin-permeabilization was performed using 2.5 μg/ml nisin in POM buffer for 10 minutes at 28° C. or 37° C. Hydrolysis of lactose in milk was performed at 50° C., using nisin-treated cells at a cell concentration of approximately 1 g/l.

Further, as seen in FIG. 6, the different permeabilization temperature (28° C. vs 37° C.) provided nisin-permeabilized cells which performed equally well in terms of lactose conversion in milk samples.

FIG. 5A also demonstrates that prolonged nisin treatment (30 minutes vs 10 minutes) does not give better results. The nisin reaction is essentially instantaneous as long as the contraction of nisin is well-matched with the cell concentration.

Example 5: Nisin-Permeabilized Cells Perform Better than Ethanol-Permeabilized Cells Somkuti et al. 1998, previously demonstrated that ethanol-permeabilized lactic acid bacteria can be used as a source of lactase activity. The present example compared the present invention to the current state of the art.

5.1. Microbial Strains, Permeabilization and Lactose Hydrolysis

*S. thermophilus* CS1980 was permeabilized for 10 minutes at 28° C. using (i) 2.5 µg/ml nisin in POM buffer or (ii) 45% (v/v) ethanol for 10 minutes, or (iii) not permeabilized (control). Hydrolysis of lactose in POM buffer (50 g/l lactose) at 50° C. was carried out at a cell concentration of approximately 100 mg/l.

5.2. Results

Figure 7:
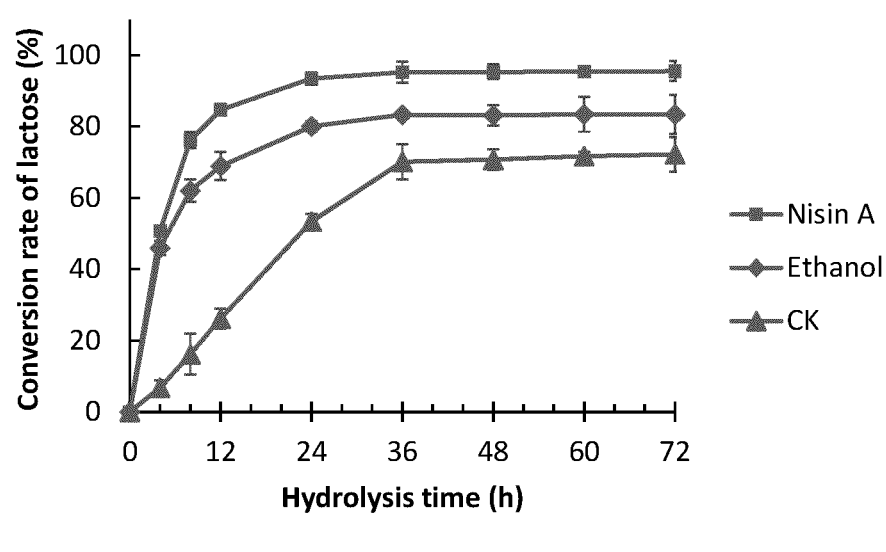
FIG. 7: Hydrolysis of lactose by *S. thermophilus* CS1980 where the cells have been permeabilized for 10 minutes at 28° C. using (i) 2.5 μg/ml nisin in POM buffer or (ii) 45% (v/v) aqueous ethanol, or (iii) have not been permeabilized (control). Hydrolysis of lactose in POM buffer (50 g/l lactose) at 50° C. was carried out at a cell concentration of approximately 100 mg/l.

As seen in FIG. 7, nisin-permeabilized cells perform better than the control as well as the ethanol-permeabilized cells in terms of lactose conversion. Ethanol is generally known to affect the stability of enzymes, which is supported by the data in FIG. 7: it was found that ethanol compromised the stability of the whole-cell catalyst, which is unfavorable in terms of cost, as more cells will be needed to achieve a satisfactory degree of hydrolysis within a certain time limit.

Example 6: Nisin-Permeabilized *L. lactis* Catalyst for Conversion of Pyruvate to Alpha-Acetolactate A modified *L. lactis* strain MG1363 lacking alpha-acetolactate decarboxylase activities was used in the present experiment. More specifically, the strain RD04 was *L. lactis* strain MG1363 ΔldhB ΔldhX Δpta ΔadhE ΔbutBA ΔaldB, while harboring an expression vector for overexpressing native alpha-acetolactate synthase (Als). RD04 was nisin-treated and tested for alpha-acetolactate synthase acticity in the present study as follows:

Cells were harvest in stationary phase (overnight culture), resuspended to OD(600 nm)=1.0 in POM buffer containing 100 µg/ml nisin, permeabilized by incubating for 15 min at 37° C., supernatant was removed, cells were resuspended to OD(600 nm)=1 (0.36 g cells/l dry weight basis) in reaction solution (200 mM sodium pyruvate, 100 mM KPO$_4$ pH 6.0, 20 mM MgCl$_2$, 2 mM thiamine pyrophosphate).

Figure 8:
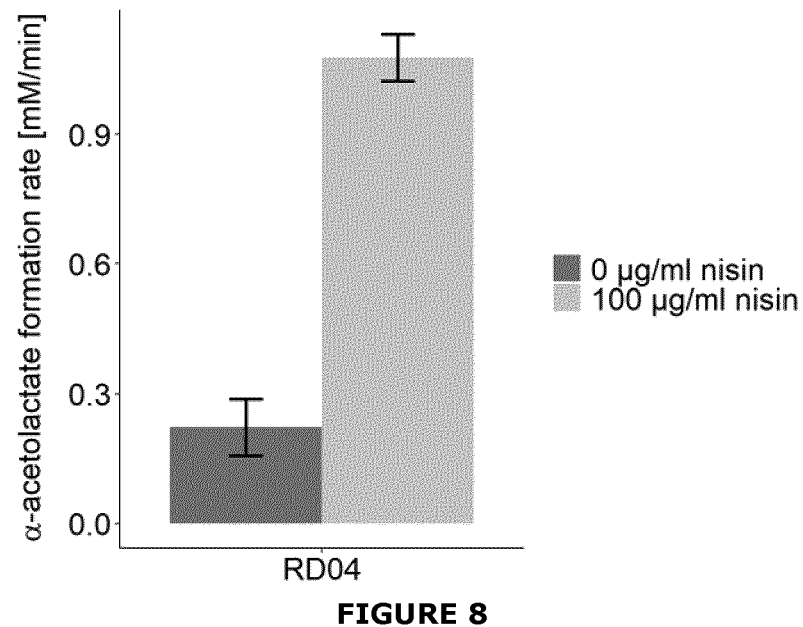
FIG. 8: Alpha-acetolactate synthase activity of nisin-permeabilized *L. lactis* strain MG1363 ΔldhB ΔldhX Δpta ΔadhE ΔbutBA ΔaldB, harboring an expression vector for overexpressing native alpha-acetolactate synthase; compared to activity of non-permeabilized cells.

Alpha-acetolactate synthase activity was determined by investigating the conversion rate of pyruvate to alpha-acetolactate, using HPLC measurements of alpha-acetolactate formation. The results are reported in FIG. 8, showing that nisin permeabilized cells performed much better than non-permeabilized cells in conversion of pyruvate to alpha-acetolactate.

Example 7: Nisin in Combination with Monolaurin Provides an Improved Catalyst 5.1. Microbial Strains, Permeabilization and Lactose Hydrolysis

*S. thermophilus* CS1980 (approximately 100 mg/l) was permeabilized in POM buffer pH 7.4 for 10 minutes at 28° C. using (i) 0.25 µg/ml nisin, (ii) 0.25 µg/ml nisin+10 µg/ml monolaurin, or (iii) not permeabilized (control—no addition of nisin or monolaurin). Hydrolysis of lactose (50 g/l) was carried out in POM buffer at 50° C.

5.2. Results

Figure 9:
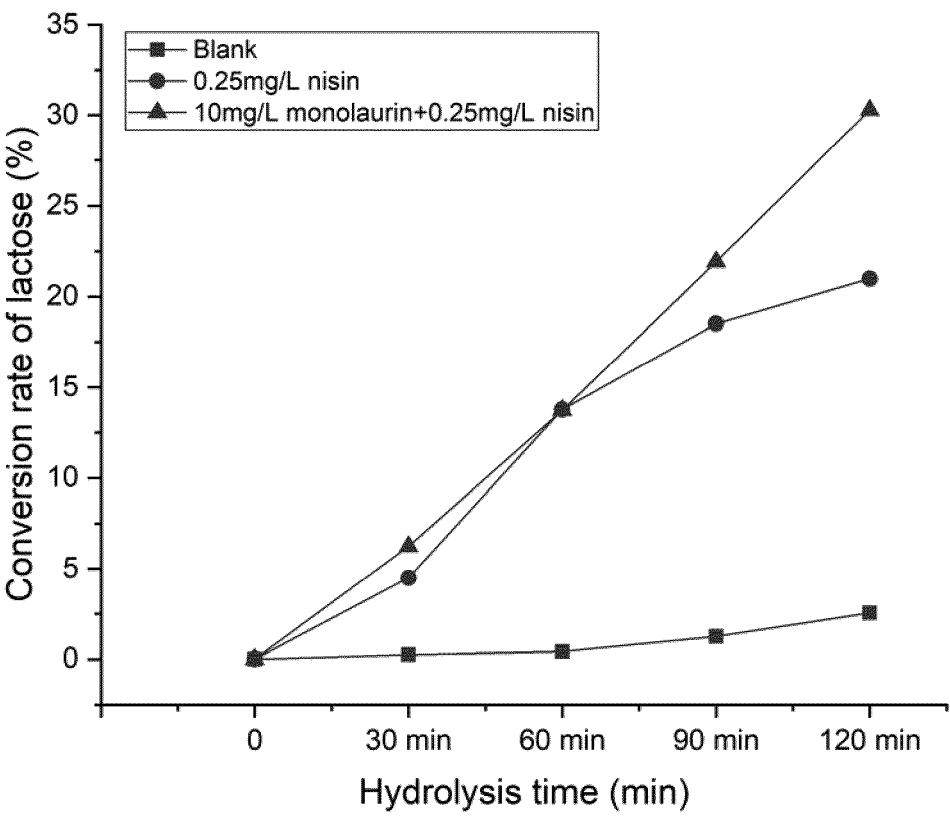
FIG. 9: Hydrolysis of lactose by *S. thermophilus* CS1980 where the cells have been permeabilized in POM buffer pH 7.4 for 10 minutes at 28° C. using (i) 0.25 μg/ml nisin, (ii) 0.25 μg/ml nisin+10 μg/ml monolaurin, or (iii) not permeabilized (control—no addition of nisin or monolaurin).

As seen in FIG. 9, nisin treatment in combination with monolaurin gives improved conversion rates of lactose compared to using nisin alone.

Example 8: Nisin-Producing Microbial Strain Ge001

Parent strain: dairy isolate *L. lactis* subsp. *lactis* biovar diacetylactis SD96, which grows well in milk, and is generally insensitive to phage attack (Dorau et al 2020). A natural (non-engineered) approach using a combination of adaptive laboratory evolution (ALE) in milk at high temperatures, random mutagenesis using proflavine as mutagen, and finally conjugation for transfer of the nisin gene cluster, was applied.

L. lactis subsp. lactis biovar diacetylactis SD96 was cultivated on M17 agar supplemented with 0.5% lactose (LM17), and a single colony was used to start two separate cultures in 9 ml UHT milk. Generally, when the milk was coagulated, the culture was considered fully grown with approximately $10^{10}$ cells. Fully-grown cultures were homogenized by shaking and propagated in 9 ml fresh UHT milk. Then the procedure was repeated. Every week, the culture was saved by mixing a fully-grown culture with 50% glycerol 1:1 and storing at −80° C.

The culture was kept continuously at high temperatures. For avoiding a long time between propagation steps, the coagulated, fully grown culture was propagated by diluting 10-fold into 9 ml fresh UHT-milk, which corresponds to 3.32 generations per propagation step. Initially, SD96 was grown at 39° C., and the coagulation of the UHT milk was observable after approximately 48 h. 20 propagation steps were conducted until coagulation was observable after ca. 24 h, then the temperature was increased to 40° C., again resulting in coagulation after ca. 48 h. After 25 propagation steps at 40° C. (45 propagation steps in total, 150 generations), coagulation was observable after 24 h.

A first mutant strain was isolated after these 150 generations, approximately five months after the ALE was started. This first mutant strain was able to grow in milk and had improved thermotolerance compared to strain SD96.

A single colony of this first mutant stain grown on LM17-Agar was inoculated into 5 mL of M17 with 1% lactose (LM17) in a 20 mL test tube, put in a 45° angled test tube rack, and cultivated at 30° C. and 220 rpm shaking. The overnight culture was diluted with fresh LM17 medium supplemented with 10 mg/L of proflavine to a final cell density (OD600) of 0.1. After 18 h incubation at 30° C. with shaking, the cells were harvested by centrifugation (5000 g for 2 min) and washed three times with 0.9% NaCl. The cells were then resuspended in fresh LM17 medium and incubated at 30° C. with shaking for 1 h. After appropriate dilution in 0.9% NaCl, the cells were plated on TTC medium to obtain single colonies.

TTC (2,3,5-triphenyltetrazolium chloride) is reduced to the red compound triphenylformazan under non-acidic conditions, and colonies which do not form acid (here lactate) appear as dark red on such plates.

By screening a large number of colonies on this TTC medium a second mutant with reduced LDH (lactate dehydrogenase) activity was obtained.

Finally, Ge001 was obtained after transferring a nisin gene cluster from the donor L. lactis ATCC 11454, by conjugation, into the lactate dehydrogenase (LDH) deficient second mutant.

The nisin gene cluster as well as the sucrose fermentation genes are located on a conjugative transposon (SEQ ID No. 4) in L. lactis (Broadbent et al 1995); this transposon can 'jump' from one strain and 'insert' itself into other L. lactis strains by conjugal transfer.

Solid-surface conjugation between donor ATCC 11454 and the mutant recipient was conducted using the method described by Broadbent et al 1991.

L. lactis is more resistant to nisin after introducing the nisin immunity gene (nisI), which is part of the nisin biosynthesis gene cluster. Nisin was therefore used to select for the desired transconjugant, in combination with the fact that only the mutant (not ATCC 11454) can grow on lactose.

Cells from solid surface milk agar were harvested in 1 ml of 0.85% saline and then 0.1 mL volumes were plated onto SA selective agar plates with 25 μg/mL nisin, 0.1% TTC (2,3,5-triphenyltetrazolium chloride) and 0.5% lactose, and incubated at 30° C. for 48 h. Plates were examined for red colonies.

SA medium: 1% (wt/vol) nonfat milk, 0.25% milk protein-hydrolysate peptone, 0.5% dextrose, and 1.5% agar. The pH was adjusted to 6.6, the agar medium was sterilized, and tempered at 45° C. after sterilization. Two solutions, one containing 10% potassium ferricyanide and one containing 1 g of ferric citrate and 1 g of sodium citrate in 40 ml of water, were steamed (100° C.) for 30 min. Ten milliliters of each solution was added to 1 liter of agar medium, and the agar was swirled gently and poured. Plates were dried in the dark for 24 h at 300 C.

Transconjugant Ge001 was picked up from the SA selective agar plates and analyzed. Sequencing revealed that a single copy of Tn5307, with a size of 66040 bp, was present in the genome of Ge001.

Of high relevance to the present invention, Ge001 is phenotypically characterized as follows: (i) grows well in milk, even at elevated temperatures up to 40° C., (ii) is deficient in lactate dehydrogenase activity, and (iii) both produces and tolerates nisin.

Genotype of Ge001:

With regards to the genetic alterations related to good growth in milk at elevated temperatures, compared to the parent strain Lactococcus lactis subsp. lactis bv. diacetylactis SD96 (NCBI accession No SRX6686433), the genotype of Ge001 was found to comprise the following changes:

I. the parent gene encoding UDP-N-acetylmuramate-L-alanine ligase (SEQ ID No. 8) is modified to encode the amino acid sequence substitution F68L, II. the parent gene encoding GTP pyrophosphokinase (RelA) (SEQ ID No. 10) is modified to encode the amino acid substitution V469L, III. base pairs 1,823,878-1,897,135 (SEQ ID No. 11) in the parent genome are deleted, and IV. the tandem repeat ((A)6 to (A)5) upstream of the CodY transcription regulator (SEQ ID No. 12) in the parent genome is deleted, Further, sequencing revealed that the lactate dehydrogenase gene of Ge001 was disrupted by insertion of eight nucleotides in the ldh gene; more specifically insertion of CCGTCAAG (SEQ ID No. 7) in the CDS region of the ldh gene encoding lactate dehydrogenase (SEQ ID No. 5) between nucleotides T464 and C465

And finally, as specified above, the nisin gene cluster was introduced as a single copy of transposon Tn5307 (SEQ ID No. 4) in the genome of Ge001.

Example 9: Ge001 Produces Nisin Using Dairy Waste as Fermentation Substrate

The ability of Ge001 to produce nisin was tested using dairy waste as fermentation substrate, where biomass accumulation, lactose consumption, citrate consumption, lactate formation, pH, and nisin production were monitored over time. Cell density was determined by measuring the optical density (OD) at a wavelength of 600 nm using UV-1600PC spectrophotometer (VWR, Denmark). The pH change during the growth was measured using a pH meter (Lab845, SI Analytics, Denmark). Nisin production was assayed using the bioassay agar plate diffusion method described below.

Quantification of lactose, lactate, citrate was done using high-performance liquid chromatography.

Nisin activity assay: To precisely estimate the nisin activity in the fermentation broth, the hot extraction method described by Zhang et al 2014 was used. The nisin activity was determined using the bioassay agar plate diffusion method and *Micrococcus luteus* ATCC 10240 as indicator strain as described by Thunyarat [33]. Briefly, a series of standard solutions containing 10-1,000 IU mL-1 were prepared by diluting a stock solution with 0.02 N HCl, and these were used to prepare a standard curve. Subsequently, the autoclaved NB agar medium was cooled to 40° C., and inoculated with 1% of *M. luteus* ATCC 10240 with OD600 2.0 (diluted using NB broth). The 25 mL medium was then poured into a sterile Petri dish and five 6 mm diameter wells were introduced after solidification. Eighty microliters of standard solution and test solutions were added to the wells. First, the agar plates were stored at 4° C. for 12 h to allow nisin to diffuse, and then the plates were transferred to a 30° C. incubator and kept there for 24 h. The diameters of the inhibition zones were measured horizontally and vertically using a digital caliper. The assay was done in triplicates.

Whey Mother liquor (ML), the residue obtained after lactose crystallization from concentrated whey permeate, was provided by Arla Food Ingredients (Viby J, Denmark), and its composition is described in Liu et al 2005. ML in combination with yeast extract can serve as a complete fermentation medium for *L. lactis*. Specifically, the nisin-producing strain Ge001 was streaked on an LM17-TTC plate, and incubated overnight at 30° C. A red single colony was inoculated into 25 mL of medium consisting of 10% ML and 1% yeast extract (YE) in a 250 mL shake flask and cultivated to early exponential phase. The 10% (v/v) seed-culture was inoculated into 25 mL of the same medium in a 250 mL shake flask culture.

Figure 10:
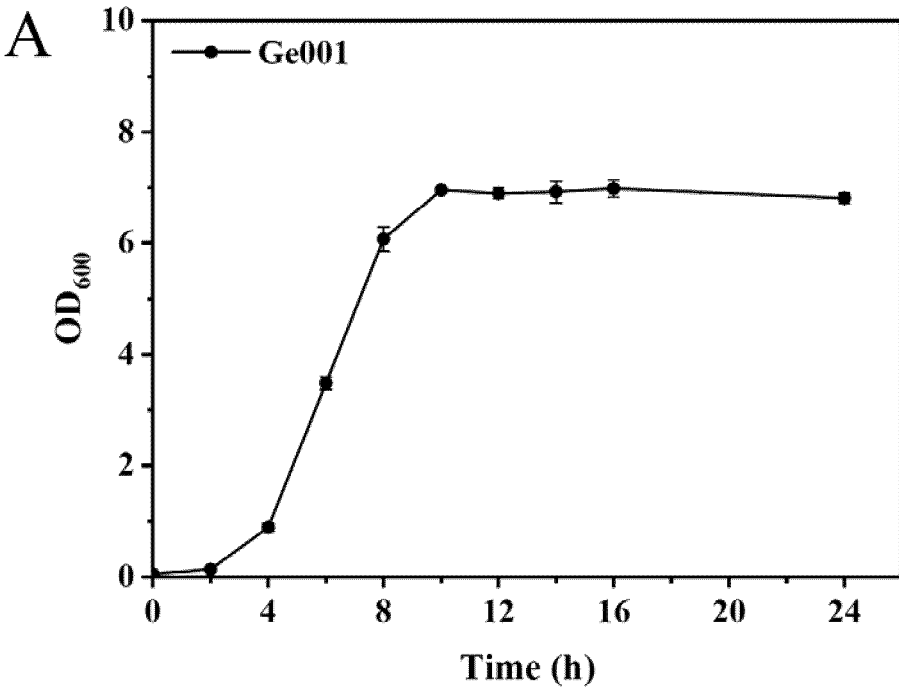
FIG. 10: Performance and nisin production kinetics for Ge001 cultivated in 10% ML 1% YE. (A) Optical density at 600 nm (OD600); (B) pH change; (C) nisin production; (D) lactate and acetoin production. All fermentations were carried out in 25 mL medium using 300 mL shake flasks, two times independently. Error bars indicate standard deviations.
Figure 10:
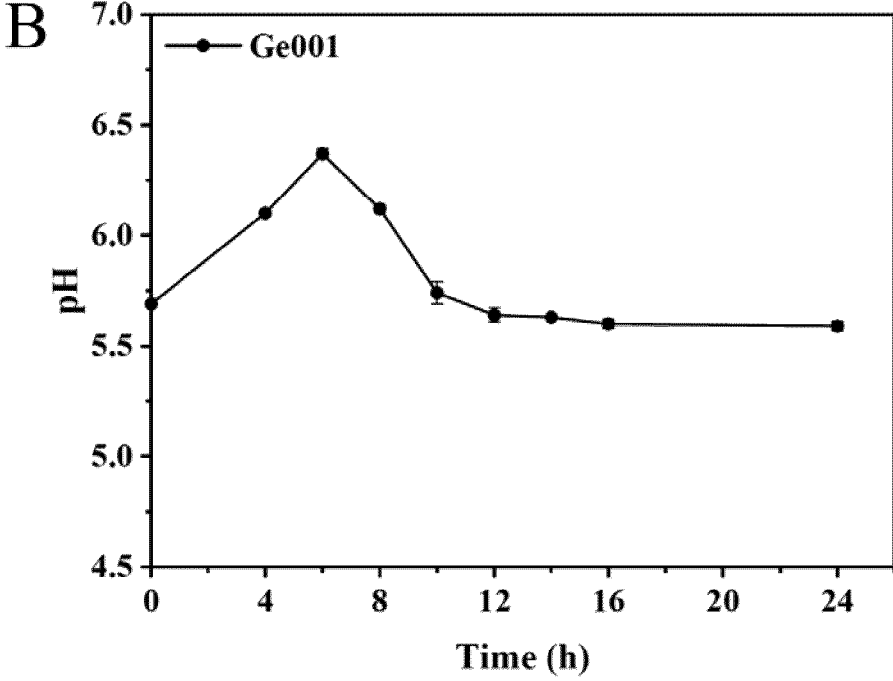
Figure 10:
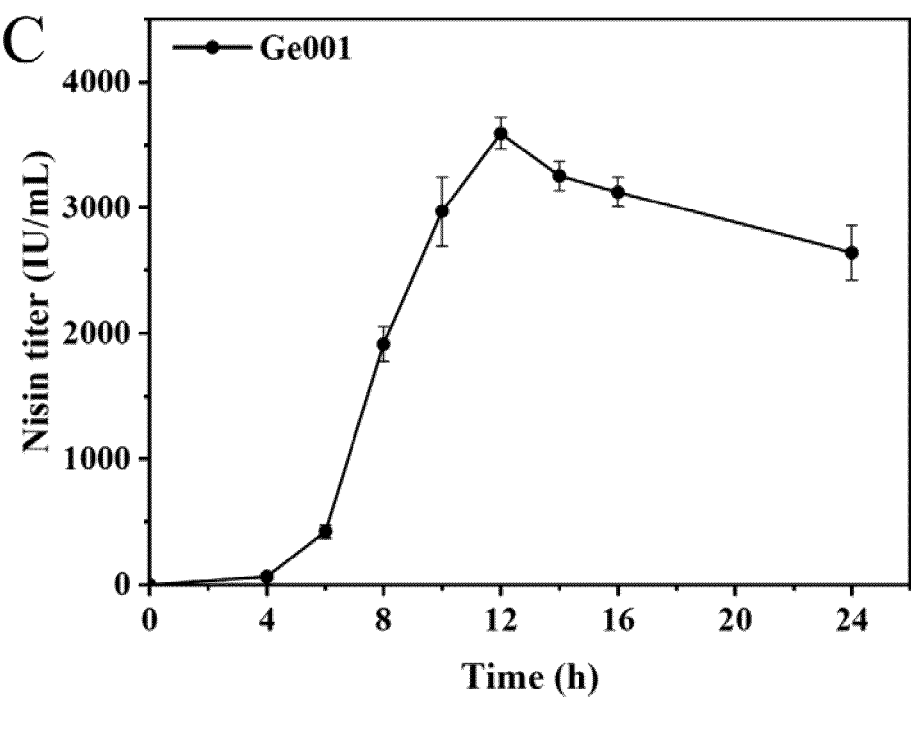
Figure 10:
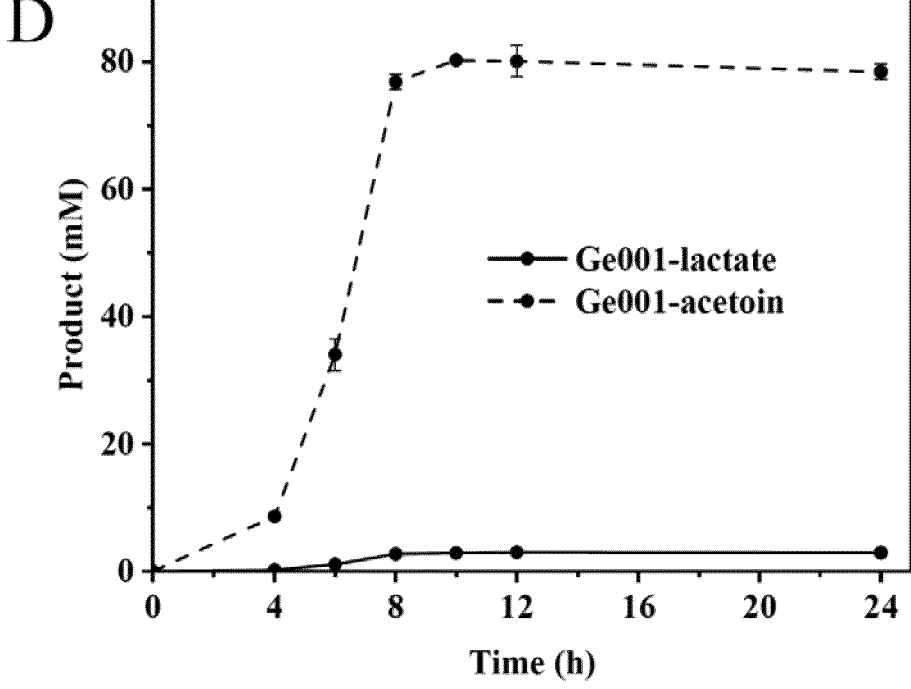

Ge001 grew well and had the ability to produce nisin in ML (FIGS. 10A and 10C). Nisin production by Ge001 was shown to be directly linked to growth, and nisin production ceased after entry into the stationary phase. After 12 hours, the nisin concentration decreased gradually over time, which most likely is due to proteolytic degradation and adsorption of nisin onto producer cells. During fermentation, only a small amount of lactic acid was formed, and the lactose was fully consumed (FIG. 10D). The pH increase observed in the first six hours was due to citrate consumption, however, the pH dropped subsequently to 5.5 to 6.5, which is suitable for growth and nisin production (FIG. 10B).

Further optimization of nisin production was investigated. It was found that both biomass and nisin titer (IU/mL) increased when increasing amounts of yeast extract (YE) were added. The highest nisin activity observed was 5003 IU/mL, when 2% YE was added.

Ge001 needs to be cultured aerobically as oxygen is required by the NADH oxidase NoxE, the function of which is essential for Ge001 to grow efficiently without forming acidic products. One drawback of this is that oxidative stress can arise, which affects the growth of Ge001 negatively. Aerobic growth leads to formation of reactive oxygen species (ROS) with high oxidizing potential, and these can damage various cell constituents. Another drawback is that oxygen can disrupt the structure of nisin, and lead to loss of antimicrobial activity. *L. lactis* is able to respire when heme is added into the growth medium and there are studies that show the protective effect of heme against oxidative stress through elimination of ROS (Kaneko et al 1990). Different concentration of hemin (a chloride of heme) were added into the fermentation medium. The biomass and the nisin titer both increased after adding 0.5 to 2 µg/ml hemin into the fermentation medium. The addition of 1 µg/ml hemin resulted in the highest increase in biomass and nisin production after a 12h cultivation. As such, the highest OD600 achieved in the hemin-stimulated fermentation was 17.6, while the highest nisin titer was 7416 IU/mL.

It was further tested if Mn2+ could have a beneficial effect on nisin production by further decreasing oxidative stress. It was found that Mn2+ can significantly promotes biomass and nisin production: When adding 0.5 or 1 mM Mn2+, the nisin titer could be increased by 21%.

Figure 11:
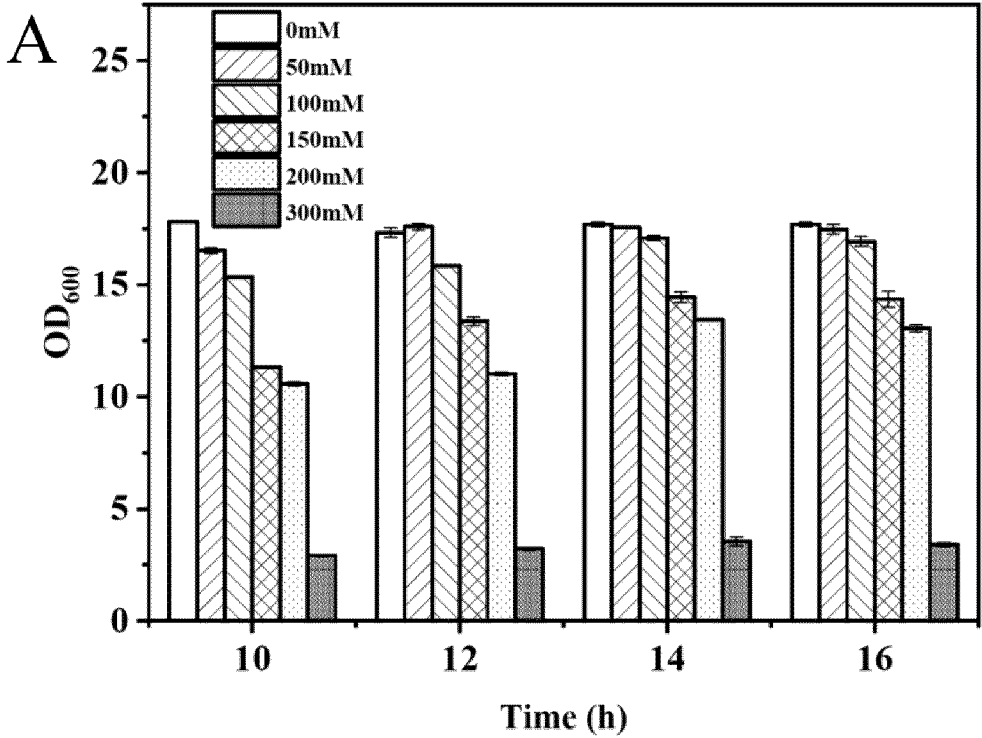
FIG. 11: Effect of Ca2+ concentration (0-300 mM) on the performance of Ge001 using 20% ML, 2% YE containing 1 μg/mL hemin and 1 mM Mn2+. The initial OD600 was 0.05. All fermentations were carried out in 25 mL medium using 300 mL shake flasks and samples were extracted at 12 hours cultivation. (A) Optical density at 600 nm (OD600). (B) Nisin titers. The values are averages of two independent experiments and error bars indicate standard deviations.
Figure 11:
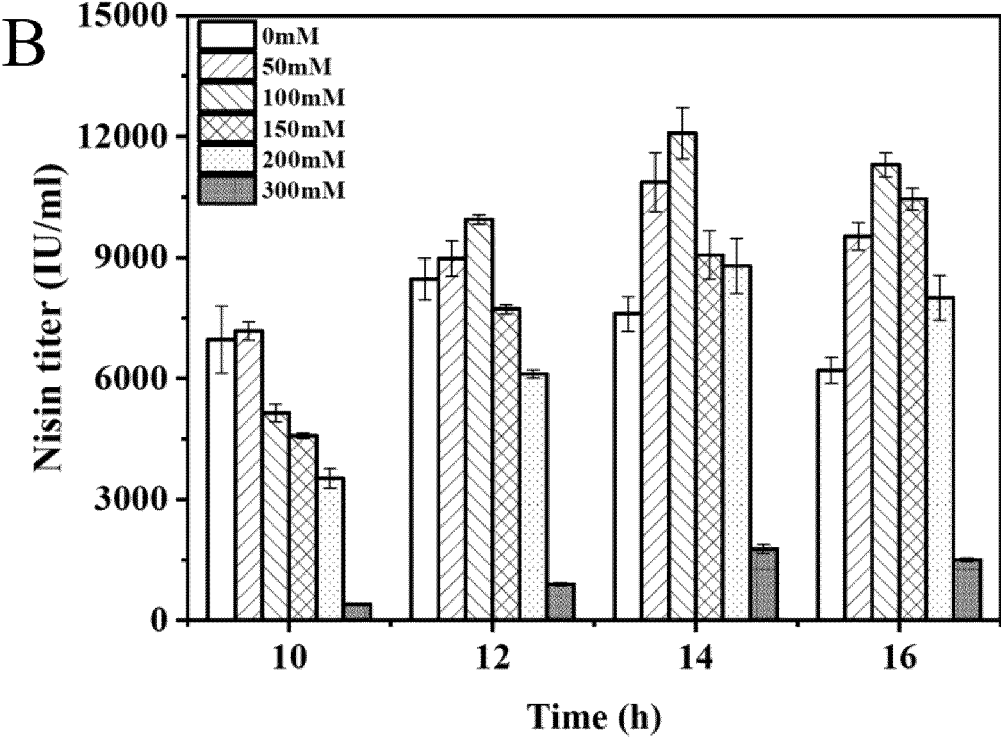

During the fermentation period, nisin were reversibly adsorbed onto the cells due to its positively-charged property. It was found that Ca2+ could displace nisin bound to the cell wall and thereby result in higher nisin titers. As shown in FIG. 11, addition of 0.05-0.2 M $CaCl_2$) led to an increase in biomass and nisin activity, however, when $CaCl_2$ exceeded 0.2 M there was significant growth inhibition. The nisin titer could reach the highest value (12,084 IU/mL) at 12h of cultivation when 100 mM $CaCl_2$) was added.

Example 10: Permeabilization of Microbial Cell Catalysts and Hydrolysis of Lactose in Milk Using the Nisin-Producing Strain Ge001

Figure 12:
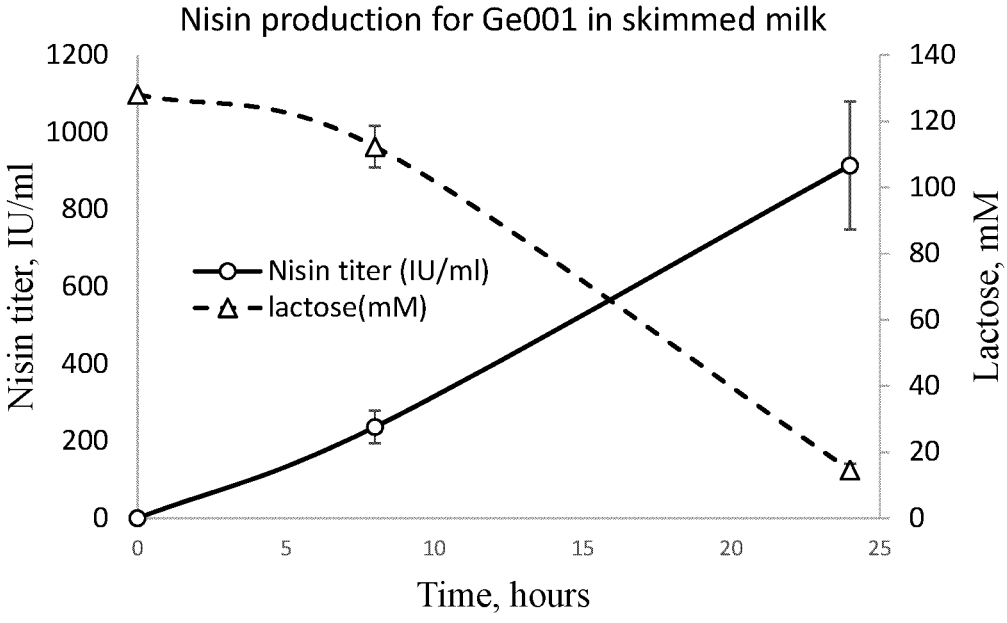
FIG. 12: Nisin production and lactose consumption by Ge001 grown in UHT milk. The fermentations were carried out in 25 mL UHT milk (1.5% fat content) using 300 mL shake flasks. The values are averages of two independent experiments.

Ge001 was grown in 25 mL UHT (ultra high temperature treated) milk (1.5% fat content) using 300 mL shake flasks. Nisin production and lactose concentration was measured over a time course of 24 hours. As seen in FIG. 12, Ge001 is able to grow in UHT milk, utilize lactose, and produce nisin.

*S. thermophilus* ST057-4 was cultivated in LM17 (2% lactose) for 16 hours at 37° C. Cells were harvested by centrifugation at 4° C. and washed in cold POM buffer. Cells were resuspended in 1 ml (OD600 2.5/ca. 0.9 g/L) of (1) POM buffer with 2.5 µg/ml nisin, (2) milk cultured with Ge001 (100%), (3) two times diluted milk cultured with Ge001 (50%), or (4) ten times diluted milk cultured with Ge001 (10%). All dilutions of nisin culture were done using POM buffer. The cells were incubated for 30 min at 30° C. Afterwards, the cells were harvested by centrifugation, resuspended in 1 ml fresh UHT milk (1.5% fat), and incubated at 50° C. Samples were withdrawn regularly (0 h, 0.5 h, 1 h, and 2 h) and analyzed using HPLC. Before HPLC measurement, the milk samples were diluted 10-fold in a 1 M H2SO4 solution (final concentration) to clear the samples. The experiment was carried out using three independent replicates.

Figure 13:
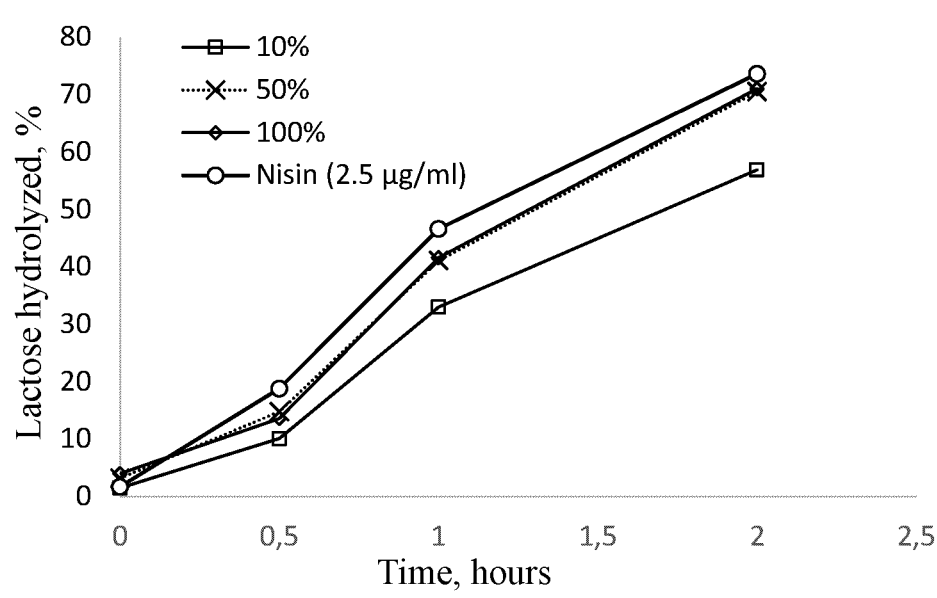
FIG. 13: Hydrolysis of lactose in UHT milk (1.5% fat content) by permeabilized *Streptococcus thermophilus* cells, wherein the cells have been permeabilized by incubating for 30 min at 30° C. with (1) POM buffer with 2.5 μg/ml nisin (commercial), (2) milk cultured with Ge001 (100%), (3) two times diluted milk cultured with Ge001 (50%), (4) ten times diluted milk cultured with Ge001 (10%). All dilutions of nisin culture were done using POM buffer. Harvested permeabilized cells were resuspended in 1 ml fresh UHT milk (1.5% fat), and incubated at 50° C. Samples were withdrawn regularly (0 h, 0.5 h, 1 h, and 2 h) and analyzed using HPLC. The experiment was carried out using three independent replicates.

As can be seen in FIG. 13, the *Streptococcus thermophilus* cells permeabilized using Ge001 culture medium are able to hydrolyze lactose in milk.

REFERENCES

Somkuti, G. A., Dominiecki, M. E., Steinberg, D. H. 1996. Sensitivity of *Streptococcus thermophilus* to Chemical Permeabilization. Current Microbiology 32:101-105.

Somkuti, G. A., Dominiecki, M. E., Steinberg, D. H. 1998. Permeabilization of *Streptococcus thermophilus* and *Lactobacillus delbrueckii* subs p. *bulgaricus* with ethanol. Curr. Microbiol. 36(4):202-6.

Dorau et al 2020. Complete genome sequence of *Lactococcus lactis* subsp. *lactis* by. Diacetylactis SD96. ASM Microbiology resource announcements 9(3) e01140-19. DOI: 10.1128/MRA.01140-19

Broadbent et al 1995. Characteristics of Tn 5307 exchange and intergeneric transfer of genes associated with nisin production. Appl Microbiol Biotechnol 44, p 139-146. Doi:10.1007/BF00164493

Broadbent et al 1991. Genetic construction of nisin-producing *Lactococcus lactis* subsp. *cremoris* an analysis of a rapid method for conjugation. Appl Environ Microbiol 57, p. 517-524.

Zhang et al 2014. Genome shuffling of *L. lactis* subs. *Lactis* YF11 for improving nisin Z production and comparative analysis. J Dairy Sci. Doi:10.3168/jbs.2013-7238.

Liu et al 2005. Effect of nutrient supplements on simultaneous fermentation of nisin and lactic acid from cull potatoes. Appl Biochem Biotechnol Part A Enzyme eng. And biotechnol. Pp 475-483. Doi:10.1007/978-1-59259-991-2_42.

Kaneko et al 1990. Acetoin fermentation by citrate-positive *L. lactis* subsp. *lactis* 302 grown aerobically in the presence of hemin or Cu2+. Appl Environ Mocrobiol 56; 2644-2649. Doi: 10.1128/aem.56.9.2644-2649.1990.

Items of the Invention

1. A method for reducing the amount of a substrate in a sample, said method comprising the steps of:
   I. providing microbial cells comprising at least one intracellular enzyme for catalyzing conversion of said substrate into one or more products,
   II. incubating said microbial cells with nisin,
   III. optionally harvesting permeabilized cells obtained in step (b),
   IV. incubating permeabilized cells obtained in step (b) or harvested cells obtained in step (c) with said sample comprising said substrate;
      wherein said microbial cells are susceptible to nisin-permeabilization, and wherein the substrate can transit through nisin pores of the permeabilized cells.

2. The method according to item 1, wherein said microbial cells provided in step (a) are bacteria selected from *Escherichia, Streptococcus, Lactobacillus, Lactococcus, Lactovum, Pediococcus, Leuconostoc, Fructobacillus, Weissella, Oenococcus, Corynebacterium, Brevibacterium, Bacillus, Sporolactobacillus, Geobacillus, Halobacillus, Halolactibacillus, Tetragenococcus, Acetobacter, Acinetobacter*, Proprionibacterium, and *Bifidobacterium.*

3. The method according to item 1 or 2, wherein nisin is added in the form of a nisin producing microbial cell or a culture medium derived from a nisin producing microbial cell.

4. The method according to item 3, wherein the nisin producing microbial cell is a lactic acid bacterium, such as a *Lactococcus* species.

5. The method according to any one of items 1-4, wherein the sample is a food or beverage.

6. The method according to any one of items 1-5, for reducing the lactose content of a dairy product, said method comprising the steps of:
   I. providing cells of a lactic acid bacterium comprising intracellular beta-galactosidase EC 3.2.1.23. for catalyzing conversion of lactose to galactose and glucose,
   II. incubating said cells of (a) with nisin,
   III. optionally harvesting permeabilized cells obtained in step (b),
   IV. incubating permeabilized cells obtained in step (b) or (c) with said dairy product.

7. The method according to item 6, wherein the lactic acid bacterium is selected from among *Streptococcus thermophilus, Lactobacillus casei, Lactobacillus plantarum, Lactobacillus helveticus, Lactobacillus delbrueckii, Lactobacillus acidophilus*, and *Lactococcus lactis.*

8. The method according to item 6 or 7, wherein the dairy product is a milk product, such as skimmed milk, regular milk, whole milk, yoghurt (and yoghurt like products, e.g. Gaio®, Cultura®), Skyr, Quark, Greek yoghurt, butter milk, cream, whey and butter.

9. The method according to any one of items 6-8, wherein the permeabilized cells are harvested in step (c); wherein the dairy product in step (d) is milk, and wherein said method further comprises the step of:
   e. culturing cells of a yoghurt starter bacterium in the product obtained in step (d).

10. The method according to item 9, wherein the yoghurt starter bacterium is *Streptococcus thermophilus* or *Lactobacillus* delbruckii subsp. *bulgaricus.*

11. The method according to any one of items 6-10, wherein in step (d) said dairy product is additionally incubated with nisin-permeabilized microbial cells comprising (i) xylose isomerase EC 5.3.1.5 for conversion of glucose to fructose. and/or (ii) arabinose isomerase EC 5.3.1.4 for conversion of galactose to tagatose.

12. A whole-cell catalyst comprising nisin-permeabilized microbial cells; wherein the nisin-permeabilized cells comprise at least one intracellular enzyme for catalyzing conversion of a target substrate; and wherein the nisin-permeabilized cells are in a frozen or dried state.

13. A composition comprising (i) nisin-permeabilized microbial cells comprising at least one intracellular enzyme and (ii) substrate(s) and product(s) of a reaction catalyzed by said at least one enzyme.

14. Use of nisin-permeabilized microbial cells comprising at least one intracellular enzyme as whole-cell catalyst in an enzyme reaction, wherein substrate(s) and product(s) of said reaction can transit through nisin pores of the nisin-permeabilized microbial cells.

15. The use according to item 14 wherein said nisin-permeabilized microbial cells are bacteria comprising beta-galactosidase, wherein said substrate is lactose.

The invention claimed is:

1. A method for producing tagatose from isomerization of galactose in a sample, said method comprising the steps of:
   a) providing microbial cells comprising an intracellular arabinose isomerase EC 5.3.1.4 enzyme for catalyzing conversion of said galactose into tagatose,
   b) incubating said microbial cells with nisin as permeabilizing agent, wherein nisin is present in a concentration of 2-250 μg nisin per mg cells,
   c) optionally harvesting permeabilized cells obtained in step (b),
   d) incubating permeabilized cells obtained in step (b) or harvested cells obtained in step (c) with said sample comprising said galactose;
      wherein said microbial cells are susceptible to nisin-permeabilization, and wherein the galactose can transit through nisin pores of the permeabilized cells.

2. The method according to claim 1, wherein the sample is a food or beverage.

3. The method according to claim 1, wherein said microbial cells provided in step (a) are bacteria selected from the group consisting of: Escherichia, Streptococcus, Lactobacillus, Lactococcus, Lactovum, Pediococcus, Leuconostoc, Fructobacillus, Weissella, Oenococcus, Corynebacterium, Brevibacterium, Bacillus, Sporolactobacillus, Geobacillus, Halobacillus, Halolactibacillus, Tetragenococcus, Acetobacter, Acinetobacter, Proprionibacterium, and Bifidobacterium.

4. The method according to claim 1, wherein said microbial cells provided in step (a) are lactic acid bacteria.

5. The method according to claim 1, wherein nisin is added in the form of a nisin producing microbial cell and/or a culture medium derived from a nisin producing microbial cell.

6. The method according to claim 1, further comprising the steps of:
   a') providing cells of a lactic acid bacterium comprising an intracellular beta-galactosidase EC 3.2.1.23 for catalyzing conversion of lactose into glucose and galactose,
   b') incubating said cells of a') with a nisin as a permeabilizing agent, and
   c') optionally harvesting permeabilized cells obtained in step b'),
and wherein in step d) said sample is additionally incubated with cells obtained in step b') or the harvested cells obtained in step c'); and wherein the sample is a dairy sample.

7. The method according to claim 6, wherein the dairy sample is a milk product.

8. The method according to claim 1, wherein the sample is a first dairy sample, wherein the microbial cell comprising an intracellular arabinose isomerase EC 5.3.1.4 is a non-GMO lactic acid bacterium, wherein nisin is added in the form of a nisin producing microbial cell and/or a culture medium derived from a nisin producing microbial cell.

9. The method according to claim 8, wherein the first dairy sample is a milk product selected from the group consisting of: skimmed milk, regular milk, whole milk, yoghurt, Skyr, Quark, Greek yoghurt, butter milk, cream, whey and butter.

10. The method according to claim 8, wherein the nisin producing microbial cell is a non-GMO cell.

11. The method according to claim 5, wherein the nisin producing microbial cell is a lactic acid bacterium.

12. The method according to claim 8, wherein the one or more nisin producing microbial cells are derived from parent strain Lactococcus lactis subsp. lactis bv. diacetylactis SD96 (NCBI accession No. SRX6686433) by virtue of the following genome modifications in the genome when compared to the genome of the parent strain:
   i) a transposon Tn5307 (SEQ ID NO. 4) comprising nisin biosynthesis gene cluster and genes needed for metabolizing sucrose is inserted into the parent genome,
   ii) nucleic acid sequence CCGTCAAG is inserted into the coding sequence region of the parent ldh gene (SEQ ID No. 5) encoding lactate dehydrogenase between nucleotides T464 and C465,
   iii) a parent gene encoding UDP-N-acetylmuramate-L-alanine ligase of SEQ ID No. 8 is modified to encode said amino acid sequence having substitution F68L,
   iv) a parent gene encoding GTP pyrophosphokinase (RelA) of SEQ ID No. 10 is modified to encode said amino acid having substitution V469L,
   v) base pairs 1,823,878-1,897,135 (SEQ ID No. 11) in the parent genome are deleted, and
   vi) a tandem repeat ((A) 6 to (A) 5) upstream of the CodY transcription regulator (SEQ ID No. 12) in the parent genome is deleted.

13. A whole-cell catalyst comprising nisin-permeabilized microbial cells; wherein the nisin-permeabilized cells comprise an intracellular arabinose isomerase EC 5.3.1.4 enzyme for catalyzing conversion of galactose into tagatose; wherein the microbial cells were permeabilized with nisin at a concentration of 2-250 μg nisin per mg cells; and further wherein the nisin-permeabilized cells are in a frozen or dried state.

14. A composition comprising (i) nisin-permeabilised microbial cells comprising an intracellular arabinose isomerase EC 5.3.1.4 enzyme and (ii) galactose and tagatose; wherein the microbial cells were permeabilized with nisin at a concentration of 2-250 μg nisin per mg cells.

15. The method according to claim 11, wherein the nisin producing microbial cell is a Lactococcus species.

16. The method according to claim 7, wherein the milk product is skimmed milk, regular milk, whole milk, yoghurt, Skyr, Quark, Greek yoghurt, butter milk, cream, whey or butter.

* * * * *

SEQUENCE LISTING

<160> NUMBER OF SEQ ID NOS: 12

<210> SEQ ID NO 1
<211> LENGTH: 174
<212> TYPE: DNA
<213> ORGANISM: L. lactis ATCC 11454
<220> FEATURE:

-continued

---

```
<221> NAME/KEY: Nisin
<222> LOCATION: (1)..(174)
<223> OTHER INFORMATION: nisin gene from L. lactis ATCC 11454
<220> FEATURE:
<221> NAME/KEY: CDS
<222> LOCATION: (1)..(174)
<223> OTHER INFORMATION: nisin gene from L. lactis ATCC 11454

<400> SEQUENCE: 1 atg agt aca aaa gat ttt aac ttg gat ttg gta tct gtt tcg aag aaa        48
Met Ser Thr Lys Asp Phe Asn Leu Asp Leu Val Ser Val Ser Lys Lys
1               5                   10                  15 gat tca ggt gca tca cca cgc att aca agt att tcg cta tgt aca ccc        96
Asp Ser Gly Ala Ser Pro Arg Ile Thr Ser Ile Ser Leu Cys Thr Pro
            20                  25                  30 ggt tgt aaa aca gga gct ctg atg ggt tgt aac atg aaa aca gca act       144
Gly Cys Lys Thr Gly Ala Leu Met Gly Cys Asn Met Lys Thr Ala Thr
        35                  40                  45 tgt cat tgt agt att cac gta agc aaa taa                               174
Cys His Cys Ser Ile His Val Ser Lys
    50                  55

<210> SEQ ID NO 2
<211> LENGTH: 57
<212> TYPE: PRT
<213> ORGANISM: L. lactis ATCC 11454

<400> SEQUENCE: 2

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys
    50                  55

<210> SEQ ID NO 3
<211> LENGTH: 13323
<212> TYPE: DNA
<213> ORGANISM: L. lactis ATCC 11454
<220> FEATURE:
<221> NAME/KEY: misc_feature
<222> LOCATION: (1)..(13323)
<223> OTHER INFORMATION: nisin gene cluster from L. lactis ATCC 11454

<400> SEQUENCE: 3
atgagtacaa aagattttaa cttggatttg gtatctgttt cgaagaaaga ttcaggtgca      60
tcaccacgca ttacaagtat ttcgctatgt acacccggtt gtaaaacagg agctctgatg     120
ggttgtaaca tgaaaacagc aacttgtcat tgtagtattc acgtaagcaa ataaccaaat     180
caaaggatag tattttgtta gttcagacat ggatactatc ctattttat aagttattta      240 gggttgctaa atagcttata aaaataaaga gaggaaaaaa catgataaaa agttcattta     300
aagctcaacc gttttagta agaaatacaa ttttatctcc aaacgataaa cggagtttta     360
ctgaatatac tcaagtcatt gagactgtaa gtaaaaataa agtttttttg gaacagttac     420
tactagctaa tcctaaactc tatgatgtta tgcagaaata taatgctggt ctgttaaaga     480
agaaaagggt taaaaaatta tttgaatcta tttacaagta ttataagaga agttatttac     540
gatcaactcc atttggatta tttagtgaaa cttcaattgg tgttttttcg aaaagttcac     600
agtacaagtt aatgggaaag actacaaagg gtataagatt ggatactcag tggttgattc     660
```

-continued

```
gcctagttca taaaatggaa gtagatttct caaaaaagtt atcatttact agaaataatg      720
caaattataa gtttggagat cgagtttttc aagtttatac cataaatagt agtgagcttg      780
aagaagtaaa tattaaatat acgaatgttt atcaaattat ttctgaattt tgtgagaatg      840
actatcaaaa atatgaagat atttgtgaaa ctgtaacgct ttgctatgga gacgaatata      900
gagaactatc ggaacaatat cttggcagtc tgatagttaa tcattatttg atctctaatt      960
tacaaaaaga tttgttgtca gatttttctt ggaacacttt tttgactaaa gttgaagcaa     1020
tagatgaaga taaaaaatat ataattcctc tgaaaaaagt tcaaaagttt attcaagaat     1080
actcagaaat agaaattggt gaaggtattg agaaactgaa agaaatatat caggaaatgt     1140
cacaaattct tgagaatgat aattatattc aaattgattt aattagtgat agtgaaataa     1200
attttgatgt taaacaaaag caacaattag aacatttagc tgagttttta ggaaatacga     1260
caaaatctgt aagaagaaca tatttggatg actataagga taaatttatc gaaaaatatg     1320
gtgtagatca agaagtacaa ataacagaat tatttgattc tacatttggc ataggagctc     1380
catataatta taatcatcct cgaaatgact tttatgagtc cgaaccgagt actctatact     1440
attcagaaga ggagagagaa aagtacctca gcatgtatgt agaagccgtt aaaaatcata     1500
atgtaattaa tcttgacgac ttagagtctc attatcaaaa aatggactta gaaaagaaaa     1560
gtgaacttca agggttagaa ttatttttga atttggcaaa ggagtatgaa aaagatattt     1620 ttatttttagg ggatatcgtt ggaaataata atttgggagg ggcatcaggt agattttctg     1680
cactctctcc ggagttaaca agttatcata gaacgatagt agattctgtc gaaagagaaa     1740
atgagaataa agaaattaca tcgtgtgaaa tagtatttct tccagaaaat atcagacatg     1800
ctaacgttat gcatacatca attatgagga ggaaagtact tccatttttt acaagtacaa     1860
gtcacaatga agttctgtta actaatatct atattggaat agacgaaaaa gaaaaatttt     1920
atgcacgaga catttcaact caagaggtat tgaaattcta cattacaagc atgtacaata     1980
aaacgttatt cagtaatgag ctaagatttc tttacgaaat ttcattagat gacaagtttg     2040
gtaatttacc ttgggaactt atttacagag actttgatta tattccacgt ttagtatttg     2100
acgaaatagt aatatctcct gctaaatgga aaatttgggg aagggatgta aatagtaaga     2160
tgacaataag agaacttatt caaagcaaag aaattcccaa agagtttttat attgtcaatg     2220 gagataataa agtttatttta tcacaggaaa acccattgga tatggaaatt ttagagtcgg     2280
cgataaagaa gagctcaaaa agaaaagatt ttatagagct acaagaatat tttgaagatg     2340
aaaatatcat aaataaagga gaaaaggggga gagttgccga tgttgtagtg ccttttatta     2400
gaacgagagc attaggtaat gaagggagag catttataag agagaaaaga gtttcggttg     2460
aacggcgtga aaaattgccc tttaacgagt ggctttatct aaagttgtac atttctataa     2520
atcgtcaaaa tgaatttta ctgtcgtatc ttccagatat tcagaaaata gtagcaaacc     2580
tgggtggaaa tctattcttc ctaagatata ctgatcctaa accacatatt agattgcgta     2640
taaaatgttc agatttattt ttagcttacg gatctattct tgaaatctta aaaaggagtc     2700
ggaaaaatag gataatgtca acttttgata tttctatttta tgatcaagaa gtagaaagat     2760
atggtggatt tgatactttta gagttatccg aagcaatatt ttgtgccgat tctaaaatta     2820
ttccaaattt gcttacattg ataaaagata ctaataatga ttggaaagtc gatgatgtat     2880
caatcttggt gaattatta tatctgaaat gcttctttga gaatgataac aaaaaagattc     2940 ttaattttttt gaatttagtt agtcctaaaa aggttaaaga aaatgtcaat gaaaagattg     3000
```

-continued

```
aacattatct taagcttctg aaagttaata atctaggtga ccaaattttt tatgacaaga    3060 atttttaaaga attaaagcat gccataaaaa atttattttt aaaaatgata gctcaagatt    3120
ttgaacttca gaaagtttat tcaattattg acagtatcat tcatgtccat aataaccgac    3180
taattggtat tgaacgagat aaagagaaat taatttatta cacacttcaa aggttgtttg    3240
tttcggaaga atacatgaaa tgaggactaa tagatggatg aagtgaaaga attcacatca    3300
aaacaatttt ttaatacttt acttactctt ccaagcacct tgaagttaat tttttcagttg    3360 gaaaaacgtt atgcaattta tttaattgtg ctaaatgcta tcacagcttt tgttccgttg    3420
gctagtcttt ttatttatca agatttaata aactctgtgc taggttcagg gagacatctt    3480
atcaatatta ttatcatcta ttttattgtt caagtgataa caacagttct gggacagctg    3540
gaaagttatg ttagtggaaa atttgatatg cgactttctt acagtatcaa tatgcgcctc    3600
atgaggacta cctcatctct tgaattaagt gattatgagc aggctgatat gtataaatatc    3660 atagaaaaag ttactcaaga cagcacttac aagcctttc agctatttaa tgctatcatt    3720
gttgtgcttt catcgtttat ctcattgtta tctagtctat tttttattgg aacatggaac    3780
attggggtag caattttact ccttattgtt ccagtattat ctttggtact ttttctcaga    3840
gtgggacaat tagagttttt aatccagtgg cagagagcaa gttctgaaag agaaacatgg    3900
tatattgtat atttattgac tcatgatttt tcatttaaag aaatcaagtt aaataatatt    3960
agcaattact tcattcataa atttggaaaa ttaaagaaag gatttatcaa ccaagattta    4020
gctattgctc gtaagaagac atatttcaat attttttcttg atttcatttt gaatttgata    4080
aatattctta cgatatttgc tatgatcctt tcggtaagag caggaaaact tcttataggt    4140
aatttggtaa gtctcataca agctatttct aaaatcaata cttattctca aacaatgatt    4200
caaaatattt acatcatttta taatactagt ttgtttatgg aacaacttttt tgagttttta    4260 aagagagaaa gtgtagttca caaaaaaata gaagatactg aaatatgcaa tcaacatata    4320
ggaactgtta aagtaattaa tttatcatat gtttacccta attcgaatgc ctttgcacta    4380
aagaatatca atttatcctt tgaaaaagga gaattaactg ctattgtagg aaaaaatggt    4440
tcagggaaaa gtacactagt aaagataatt tcaggattat atcaaccaac tatgggaata    4500
atccaatacg acaaaatgag aagtagtttg atgcctgagg agtttatca gaaaaacata    4560 tcggtgctgt tccaagattt tgtgaagtat gagttaacga taagagagaa tataggattg    4620
agtgatttgt cttctcaatg ggaagatgag aaaattatta aagtactaga taatttagga    4680
ctcgattttt tgaaaactaa taatcaatat gtacttgata cgcagttagg aaattggttt    4740
caagaagggc atcaactttc aggaggtcag tggcaaaaaa ttgcattagc aaggacattc    4800
tttaagaaag cttcaatttta tattttagat gaaccaagtg ctgcactcga tcctgtagct    4860
gaaaaagaaa tatttgatta ttttgttgct ctttcggaaa ataatatttc aattttcatt    4920
tctcatagtt tgaatgctgc cagaaaagca aataaaatcg tggttatgaa agatggacag    4980
gtcgaagatg ttggaagtca tgatgtcctt ctgagaagat gtcaatacta tcaagaactt    5040
tattattcag agcaatatga ggataatgat gaataaaaaa aatataaaaa gaaatgttga    5100
aaaaattatt gctcaatggg atgagagaac tagaaaaaat aaagaaaact tcgatttcgg    5160
agagttgact ctctctacag gattgcctgg tataatttta atgttagcgg agttaaaaaa    5220
taaagataac tcaaagatat atcagaaaaa gatagacaat tatattgaat atattgttag    5280
caaactttca acatatgggc ttttaacagg atcactttat tcgggagcag ctggcattgc    5340
attaagtatc ctacatttac gagaagatga cgaaaaatat aagaatcttc ttgatagcct    5400
```

-continued

```
aaatagatat atcgaatatt tcgtcagaga aaaaattgaa ggatttaatt tggaaaacat    5460
tactcctcct gattatgacg tgattgaagg tttatctggg atactttcct atctattatt    5520
aatcaacgac gagcaatatg atgatttgaa aatactcatt atcaattttt tatcaaatct    5580
gactaaagaa aacaaaggac taatatcgct ttacatcaaa tcggagaatc agatgtctca    5640
atcagaaagt gagatgtatc cactaggctg tttgaatatg ggattagcac atggacttgc    5700
tggagtgggc tgtatcttag cttatgccca cataaaagga tatagtaatg aagcctcgtt    5760
gtcagctttg caaaaaatta ttttttattta tgaaaagttt gaacttgaaa ggaaaaaaca    5820
gtttctatgg aaagatggac ttgtagcaga tgaattaaaa aaagagaaag taattaggga    5880
agcaagtttc attagagatg catggtgcta tggaggtcca ggtattagtc tgctatactt    5940
atacggagga ttagcactgg ataatgacta ttttgtagat aaagcagaaa aaatattaga    6000
gtcagctatg caaaggaaac ttggtattga ttcatatatg atttgccatg gctattctgg    6060
tttaatagaa atttgttctt tatttaagcg gctattaaat acaaaaaagt ttgattcata    6120
catggaagaa tttaatgtta atagtgagca aattcttgaa gaatacggag atgaaagtgg    6180
cacgggtttt cttgaaggaa taagtggctg tatactggta ttatcgaaat ttgaatattc    6240
aatcaatttt acttattgga gacaagcact gttacttttt gacgattttt tgaaaggagg    6300
gaagaggaaa tgagaagata tttaatactt attgtggcct taatagggat aacaggttta    6360
tcagggtgtt atcaaacaag tcataaaaag gtgaggtttg acgaaggaag ttatactaat    6420
tttatttatg ataataaatc gtatttcgta actgataagg agattcctca ggagaacgtt    6480
aacaattcca aagtaaaatt ttataagctg ttgattgttg acatgaaaag tgagaaactt    6540
ttatcaagta gcaacaaaaa tagtgtgact ttggtcttaa ataatatttta tgaggcttct    6600 gacaagtcgc tatgtatggg tattaacgac agatactata agatacttcc agaaagtgat    6660 aaggggcgg tcaaagcttt gagattacaa aactttgatg tgacaagcga tatttctgat    6720
gataattttg ttattgataa aaatgattca cgaaaaattg actatatggg aaatatttac    6780
agtatatcgg acaccaccgt atctgatgaa gaattgggag aatatcagga tgttttagct    6840
gaagtacgtg tgtttgattc agttagtggc aaaagtatcc cgaggtctga atggggggaga    6900 attgataagg atggttcaaa ttccaaacag agtaggacgg aatgggatta tggcgaaatc    6960
cattctatta gaggaaaatc tcttactgaa gcatttgccg ttgagataaa tgatgatttt    7020
aagcttgcaa cgaaggtagg aaactagagt gaaaaaaata ctaggtttcc tttttatcgt    7080
ttgttcgttg ggtttatcag caactgtgca tggggagaca acaaattcac aacagttact    7140
ctcaaataat attaatacgg aattaattaa tcataattct aatgcaattt tatcttcaac    7200
agagggatca acgactgatt cgattaatct aggggcgcag tcacctgcag taaaatcgac    7260
aacaaggact gaattggatg taactggtgc tgctaaaact ttattacaga catcagctgt    7320
tcaaaaagaa atgaaagttt cgttgcaaga aactcaagtt agttctgaat tcagtaagag    7380
agatagcgtt acaaataaag aagcagttcc agtatctaag gatgagctac ttgagcaaag    7440
tgaagtagtc gtttcaacat catcgattca aaaaaataaa atcctcgata ataagaagaa    7500
tagagctaac ttcgttactt cctctccgct tattaaggaa aaaccatcaa attctaaaga    7560
tgcatctggt gtaattgata attctgcttc tcctctatct tatcgtaaag ctaaggaagt    7620
ggtatctctt agacaacctt taaaaaatca aaaagtagag gcacaacctc tattgataag    7680
taattcttct gaaaagaaag caagtgttta tacaaattca catgattttt gggattatca    7740
```

-continued

```
gtgggatatg aaatatgtga caaataatgg agaaagctat gcgctctacc agccctcaaa    7800
gaaaatttct gttggaatta ttgattcagg aatcatggaa gaacatcctg atttgtcaaa    7860
tagtttagga aattatttta aaaatcttgt tcctaaggga gggtttgata atgaagaacc    7920
tgatgaaact ggaaatccaa gtgatattgt cgacaaaatg ggacacggga cggaagtcgc    7980
aggtcagatt acagcaaatg gtaatatttt aggagtagca ccagggatta ctgtaaatat    8040
atacagagta tttggtgaaa atctttcgaa atcggaatgg gtagctagag caataagaag    8100
agctgcggat gatgggaaca aggtcatcaa tataagtgct ggacagtatc ttatgatttc    8160
aggatcgtat gatgatggaa caaatgatta tcaagagtat cttaattata agtcagcaat    8220
aaattatgca acagcaaaag gaagtattgt tgtcgcagct cttggtaatg atagtttaaa    8280
catacaagat aaccaaacaa tgataaactt tcttaagcgt ttcagaagta taaaggttcc    8340
tggaaaagtt gtagatgcac cgagtgtatt tgaggatgta atagccgtag gtggaataga    8400
tggttatggt aatatttctg attttagtaa tattggagcg gatgcaattt atgctcctgc    8460
tggcacaacg gccaatttta aaaaatatgg gcaagataaa tttgtcagtc agggttatta    8520
tttgaaagat tggctttttta caactactaa tactggctgg taccaatatg tttatggcaa    8580
ctcatttgct actcctaaag tatctggggc actggcatta gtagttgata aatatggaat    8640
aaagaatcct aaccaactaa aaaggtttct tctaatgaat tctccagaag ttaatgggaa    8700
tagagtattg aatattgttg atttattgaa tgggaaaaat aaagctttta gcttagatac    8760
agataaaggt caggatgatg ctattaacca taaatcgatg gagaatctta agagtctag    8820 ggatacaatg aaacaggaac aagataaaga aattcaaaga aatacaaata acaattttc     8880 tatcaaaaat gattttcata acatttcaaa agaagtaatt tcagttgatt ataatattaa    8940
tcaaaaaatg gctaataatc gaaattcgag aggtgctgtt tctgtacgaa gtcaagaaat    9000
tttacctgtt actggagatg gagaagattt tttaccggct ttaggtatag tgtgtatctc    9060
aatccttggt atattgaaaa gaaagactaa aaattgatag attatatttc ttcagaatga    9120
atggtataat gaagtaatga gtactaaaca atcggaggta aagtggtgta taaaattta    9180 atagttgatg atgatcagga aattttaaaa ttaatgaaga cagcattaga aatgagaaac    9240
tatgaagttg cgatgcatca aaacatttca cttcccttgg atattactga ttttcaggga    9300
tttgatttga tttttgttaga tatcatgatg tcaaatattg aagggacaga aatttgtaaa    9360
aggattcgca gagaaatatc aactccaatt atctttgtta gtgcgaaaga tacagaagag    9420
gatattataa acggcttagg tattggtggg gatgactata ttactaagcc ttttagcctt    9480
aaacagttgg ttgcaaaagt ggaagcaaat ataaagcgag aggaacgcaa taaacatgca    9540
gttcatgttt tttcagagat tcgtagagat ttaggaccaa ttacatttta tttagaagaa    9600
aggcgagtct gtgtcaatgg tcaaacaatt ccactgactt gtcgtgaata cgatattctt    9660
gaattactat cacaacgaac ttctaaagtt tatacgagag aggatattta tgatgacgta    9720
tatgatgaat attctaatgc actttttcgg tcaatctcgg aatatatttta tcagattagg    9780 agtaagtttg caccatacga tattaatccg ataaaaacgg ttcggggact tgggtatcag    9840
tggcatgggt aaaaaatatt caatgcgtcg acggatatgg caagctgtca ttgaaattat    9900
cataggtact tgtctactta tcctgttgtt actgggcttg actttctttc tacgacaaat    9960
tggacaaatc agtggttcag aaactattcg tttatcttta gattcagata atttaactat   10020
ttctgatatc gaacgtgata tgaaacacta cccatatgat tatattattt ttgacaatga   10080
tacaagtaaa attttgggag gacattatgt caagtcggat gtacctagtt ttgtagcttc   10140
```

```
aaaacagtct tcacataata ttacagaagg agaaattact tatacttatt caagcaataa   10200
gcatttttca gttgttttaa gacaaaacag tatgcctgaa tttacaaatc atacgcttcg   10260
ttcaatttct tataatcaat ttacttacct tttctttttt cttggtgaaa taatactcat   10320 tatttttct gtctatcatc tcattagaga attttctaag aattttcaag ccgttcaaaa   10380
gattgcattg aagatggggg aaataactac ttttcctgaa caagaggaat caaaaattat   10440
tgaatttgat caggttctga ataacttata ttcgaaaagt aaggagttag ctttccttat   10500
tgaagcggag cgtcatgaaa aacatgattt atccttccag gttgctgcac tttcacatga   10560
tgttaagaca cctttaacag tattaaaagg aaatattgaa ctgctagaga tgactgaagt   10620
aaatgaacaa caagctgatt ttattgagtc aatgaaaaat agtttgactg tttttgacaa   10680
gtattttaac acaatgatta gttatacaaa acttttgaat gatgaaaatg attacaaagc   10740
gacaatctcc ctggaggatt ttttgataga tttatcagtt gagttggaag agttgtcaac   10800
aacttatcaa gtggattatc agctagttaa aaaaacagat ttaaccactt tttacggaaa   10860
tacattagct ttaagtcgag cacttatcaa tatctttgtt aatgcctgtc agtatgctaa   10920
agagggtgaa aaaatagtca gtttgagtat ttatgatgat gaaaaatatc tctattttga   10980
aatctggaat aatggtcatc ctttttctga acaagcaaaa aaaaatgctg gaaaactatt   11040
tttcacagaa gatactggac gtagtgggaa acactatggg attggactat cttttgctca   11100
aggtgtagct ttaaaacatc aaggaaactt aattctcagt aatcctcaaa aaggtggggc   11160
agaagttatc ctaaaaataa aaaagtaatt tagtaatctc taaggattac ttttttttgtt   11220 tctgaataga ttctgaaaat tgttttatat acttttttta aacataaaat aaagtgagga   11280
aatataatgc aggtaaaaat tcaaaatctt tctaaaacat ataaagaaaa gcaggtgcta   11340
caagatatca gttttgatat taaatctgga acagtctgtg gtttattagg agttaacggt   11400
gcaggaaaat caactttgat gaaaattttg tttggtttaa tttctgcaga tactggaaaa   11460
attttttttg atggacaaga aaagacaaat aatcaacttg gagccttaat cgaggctcca   11520
gcaatatata tgaatttatc tgctttcgat aatcttaaaa ctaaggcttt gcttttttgga   11580 atttcagata agagaattca tgaaactcta gaagtgattg gtttggcaga aacaggaaag   11640
aaaagagcag gaaaattctc tttagggatg aaacaacgtt tgggaattgg tatggctatt   11700
cttacagaac ctcaattttt aattcttgat gaacctacta atggtttgga tcctgatggt   11760
attgcggagt tgttaaactt aatcttaaaa cttaaagcta aaggtgtgac aatcttgatt   11820
tctagtcatc agttgcacga aataagtaaa gtagctagtc aaattattat tttgaacaaa   11880
ggtaagattc gttataatca tgcgaacaat aaagaagacg acattgaaca gttattcttt   11940
aagattgtgc atggaggaat gtgatatgaa aagaataata gcatcagaag caataaaatt   12000
aaaaaaatca ggaactctta gattggtatt aattatccct tttgtgactc tatttatagc   12060
atttcttatg ggtggaatac agattttag tgttttttca atttattggt gggaaactgg   12120
ttttttattc cttttgatga gtttgctttt tctttatgat ataaaatcag aggagcaagc   12180
tggaaatttt caaaatgtga aatggaaaaa gctgagttgg aaaattcatt ggccaaaat   12240 gttgttgatt tggctaagag gtatactagc gagcatagtc ttgattattt tgctttattt   12300
ggttgctttt gtgtttcaag gtattgtagt ggtggatttt atgaaagtaa gtgtggcatt   12360
gattgctata ttactagcag cttcttggaa tttacccttt atatacttga ttttcaagtg   12420
gattaatact tacgtattgt tagctgcgaa taccttgatt tgtttaattg ttgccccttt   12480
```

-continued

```
tgttgcacaa actccagtat ggttcttgct accatacact tatcactata aagttacaga    12540
aagtttgtta aatatcaaac catcaggaga tttgttaaca gggaagataa atttcagtat    12600
ttgggaagtt ttattaccat ttggactttc catagttgta acgataggag tttcgtattt    12660
acttaaagga gtgatagaac atgataagaa gtgaatgtct caaattaaaa aatagcttag    12720
ggttttattt agtttttctc tttactttat tagagctttt aacggttcct atttatttag    12780
cttttggaag aagtcatgtt tcaatgactg atttatcgct catgattttt ttgtttttc     12840 cgttactggt tacaattttg tctattctaa tctttgaaca ggagagtctg gccaatcgtt    12900
tccaagaaat aaatgtaaat aaaaaaagta gcagaatttg gttatcaaag ctaatagtag    12960
tggatttcct tttgttcttt ccatcagcaa tgatctggat aattacggga gtttcacagg    13020
cagtagggca acaaggaatg atgatcgcaa cagctagctg gttgatggca attttttctta    13080 atcattttca tcttttattg acctttataa tcaatcgagg agggagcatg attatcgcga    13140
ttattgaaat attactcatt attttttgcca gtaataaagt tttattagca gcttattggt    13200
gtcccattgc tttacctgtt aatttatga taactgggcg gtgtgcttat ctgatagctg     13260
ccgtagggtg gattgtttta tccacaataa ttcttgtagc attatctaaa aaaaagatta    13320
gat                                                                  13323
```

<210> SEQ ID NO 4
<211> LENGTH: 66040
<212> TYPE: DNA
<213> ORGANISM: L. lactis ATCC 11454
<220> FEATURE:
<221> NAME/KEY: misc_feature
<222> LOCATION: (1)..(66040)
<223> OTHER INFORMATION: Tn5307 transposon from L. lactis ATCC 11454

<400> SEQUENCE: 4

```
ataatggaaa ttttgatac acatataaag tgcgttttaa cctagttttta aaagatttac      60 tgttaataaa aataaaatga accaaagaac taaccaaagc aaaactatac agcatttact     120
ttatccaaaa cctactgtaa aatttatagt aggttttgta atttaaaata ttaaagtaaa     180
tttacaaata actcttaagt gagatagtct aaataaatga attgatgtgc accccaaaag     240
ttagactttt tatccaggta tttattggaa aggttataat aaactagaca caaagttaag     300
agaaatcgtg gaaaggttta ttatgggaag aagaaaattc gataaacaat ttaaaaattc     360
tgcagtaaaa ctcattcttg aagagggtta ctctgttaaa gaagtcagcc aagagcttga     420
ggttcatgcc aatagtcttt atcgctgggt tcaagaagtt gaagaatatg gagaaagtgc     480
ttttccaggc aatgggacag ccctagctga tgcccaacat aagattaaat tgttagagaa     540 agaaatcgt tatcttcagg aggaacttga acttctaaaa aagttccagg tcttcttgaa     600
gcgaagcaag taaaacgttt tgaatttctc ttgaaacatc atgggaagat aaaaattaag     660
catgcagtaa aagttcttaa ggtttctcgc tcaggtttct atgaatacat gcatcgtcgt     720
ccttcaaaac aacaagtgga gagagaaatt ctctcagaga agataaaagc tgtctttcat     780
gagcataagg gacgctatgg tgcggttaga attaccaagg tacttcataa tactggtatt     840
atgaccaaca cgaaacgtgt tgggaaactg atgcacttga tgggacttta tgccaaggga     900
agccgttata aatataaaca ttacaacaga aaaggagctt cgctttcaag acccaattta     960
attaatcaga tctttaaagc aacagctcct aataaagtat ggctgggaga catgacctat    1020
atccctacca aagaaggtac cttatactta gccgtgaatg tcgacgtgtt ttcacgtaag    1080
attgtaggct ggtcaatgtc ttcacggatg caagataaac tggtgaggga ttgcttctta    1140
```

```
caagcttgtg ggaaagaaca tcctcagcct ggcttgattg tccatactga tcaagggagt      1200
caatatacaa gctctcgtta tcaatctact cttcgtcaag tcggtgctca atctagcatg      1260
agtcgtaaag gaaatcccta tgacaatgca atgatggagt cttttttataa gacgctaaag      1320 agggagctta ttaatgatgc tcattttgag acaagagctg aggctactca agaaatattt      1380
aaatacattg agacctatta caatacaaaa aggatgcatt caggtcttga ttacaagtct      1440
ccaaaagact ttgaaaaata taattcttaa attctcttaa ctccgtgtct agttttcgt      1500 tgactttcca ttatgcttgg attttttatt gtttaattcc cttttttgta tacaagctcg      1560
tattcttaac aaataattgg catatcgggt ttaaaaatac tatgtgtttt aaagaatctc      1620
tcatgagttt gacgccaata acttagatta aaatcaccgt caccttattt ttaggcacgt      1680
tcggcagtaa ccttatcaaa ggtatctcgg tcattaagtt tcatgatagt atttactatt      1740
ttgatggttt ttgttattat ccaatcgtta aaatgacaaa aacaaataga taaatagata      1800
aatatttatg gggaggacaa gtgaacttat catgattaat tgtaaacgat tgagttctga      1860
atgtttcaaa ttatgaggaa caacaggagt tggactattc tttaaacgcc tcgacgatac      1920
catcactctt cattagccta aaattaacaa gttaaaatca ttagaataat ctcttttaca      1980
aaaaatattt atttaagtta tagttgacga atatttaata attttattaa tatcttgatt      2040
ttctagttcc tgaataatat agagataggt ttattgagtc ttagacatac ttgaatgacc      2100
tagtcttata actatactga caatagaaac attaacaaat ctaaacagt cttaattcta      2160 tcttgagaaa gtattggtaa taatattatt gtcgataacg cgagcataat aaacggctct      2220
gattaaattc tgaagtttgt tagatacaat gatttcgttc gaaggaacta caaaataaat      2280
tataaggagg cactcaaaat gagtacaaaa gattttaact tggatttggt atctgtttcg      2340
aagaaagatt caggtgcatc accacgcatt acaagtattt cgctatgtac acccggttgt      2400
aaaacaggag ctctgatggg ttgtaacatg aaaacagcaa cttgtcattg tagtattcac      2460
gtaagcaaat aaccaaatca aaggatagta ttttgttagt tcagacatgg atactatcct      2520
atttttataa gttatttagg gttgctaaat agcttataaa aataaagaga ggaaaaaaca      2580
tgataaaaag ttcatttaaa gctcaaccgt ttttagtaag aaatacaatt ttatctccaa      2640
acgataaacg gagtttttact gaatatactc aagtcattga gactgtaagt aaaaataaag      2700
tttttttgga acagttacta ctagctaatc ctaaactcta tgatgttatg cagaaatata      2760
atgctggtct gttaaagaag aaaagggtta aaaaattatt tgaatctatt tacaagtatt      2820
ataagagaag ttatttacga tcaactccat ttggattatt tagtgaaact tcaattggtg      2880
ttttttcgaa aagttcacag tacaagttaa tgggaaagac tacaaagggt ataagattgg      2940
atactcagtg gttgattcgc ctagttcata aaatggaagt agatttctca aaaaagttat      3000
catttactag aaataatgca aattataagt ttggagatcg agttttttcaa gtttatacca      3060 taaatagtag tgagcttgaa gaagtaaata ttaaatatac gaatgtttat caaattattt      3120
ctgaattttg tgagaatgac tatcaaaaat atgaagatat ttgtgaaact gtaacgcttt      3180
gctatggaga cgaatataga gaactatcgg aacaatatct tggcagtctg atagttaatc      3240
attatttgat ctctaattta caaaaagatt tgttgtcaga tttttcttgg aacactttt      3300 tgactaaagt tgaagcaata gatgaagata aaaaatatat aattcctctg aaaaaagttc      3360
aaaagtttat tcaagaatac tcagaaatag aaattggtga aggtattgag aaactgaaag      3420
aaatatatca ggaaatgtca caaattcttg agaatgataa ttatattcaa attgatttaa      3480
```

-continued

```
ttagtgatag tgaaataaat tttgatgtta aacaaaagca acaattagaa catttagctg    3540
agtttttagg aaatacgaca aaatctgtaa gaagaacata tttggatgac tataaggata    3600
aatttatcga aaaatatggt gtagatcaag aagtacaaat aacagaatta tttgattcta    3660
catttggcat aggagctcca tataattata atcatcctcg aaatgacttt tatgagtccg    3720
aaccgagtac tctatactat tcagaagagg agagagaaaa gtacctcagc atgtatgtag    3780
aagccgttaa aaatcataat gtaattaatc ttgacgactt agagtctcat tatcaaaaaa    3840
tggacttaga aaagaaaagt gaacttcaag ggttagaatt attttttgaat ttggcaaagg    3900 agtatgaaaa agatattttt attttagggg atatcgttgg aaataataat ttgggagggg    3960
catcaggtag attttctgca ctctctccgg agttaacaag ttatcataga acgatagtag    4020
attctgtcga aagagaaaat gagaataaag aaattacatc gtgtgaaata gtatttcttc    4080
cagaaaatat cagacatgct aacgttatgc atacatcaat tatgaggagg aaagtacttc    4140 catttttac aagtacaagt cacaatgaag ttctgttaac taatatctat attggaatag    4200 acgaaaaga aaaattttat gcacgagaca tttcaactca agaggtattg aaattctaca    4260
ttacaagcat gtacaataaa acgttattca gtaatgagct aagatttctt tacgaaattt    4320
cattagatga caagtttggt aatttacctt gggaacttat ttacagagac tttgattata    4380
ttccacgttt agtatttgac gaaatagtaa tatctcctgc taaatggaaa atttggggaa    4440
gggatgtaaa tagtaagatg acaataagag aacttattca aagcaaagaa attcccaaag    4500
agttttatat tgtcaatgga gataataaag tttatttatc acaggaaaac ccattggata    4560
tggaaatttt agagtcggcg ataaagaaga gctcaaaaag aaaagatttt atagagctac    4620
aagaatattt tgaagatgaa aatatcataa ataaaggaga aaaggggaga gttgccgatg    4680
ttgtagtgcc tttttattaga acgagagcat taggtaatga agggagagca tttataagag    4740
agaaaagagt ttcggttgaa cggcgtgaaa aattgccctt taacgagtgg ctttatctaa    4800
agttgtacat ttctataaat cgtcaaaatg aatttttact gtcgtatctt ccagatattc    4860
agaaaatagt agcaaacctg ggtggaaatc tattcttcct aagatatact gatcctaaac    4920
cacatattag attgcgtata aaatgttcag atttattttt agcttacgga tctattcttg    4980
aaatcttaaa aaggagtcgg aaaaatagga taatgtcaac ttttgatatt tctatttatg    5040
atcaagaagt agaaagatat ggtggatttg atactttaga gttatccgaa gcaatatttt    5100
gtgccgattc taaaattatt ccaaatttgc ttacattgat aaaagatact aataatgatt    5160
ggaaagtcga tgatgtatca atcttggtga attatttata tctgaaatgc ttctttcaga    5220
atgataacaa aaagattctt aatttttttga atttagttag tactaaaaag gttaaagaaa    5280
atgtcaatga aaagattgaa cattatctta agcttctgaa agttaataat ctaggtgacc    5340 aaattttta tgacaagaat tttaaagaat taaagcatgc cataaaaaat ttattttaa    5400 aaatgatagc tcaagatttt gaacttcaga aagtttattc aattattgac agtatcattc    5460
atgtccataa taaccgacta attggtattg aacgagataa agagaaatta atttattaca    5520
cacttcaaag gttgtttgtt tcggaagaat acatgaaatg aggactaata gatggatgaa    5580
gtgaaagaat tcacatcaaa acaattttt aatactttac ttactcttcc aagcaccttg    5640
aagttaattt ttcagttgga aaaacgttat gcaatttatt taattgtgct aaatgctatc    5700
acagcttttg ttccgttggc tagtctttt atttatcaag atttaataaa ctctgtgcta    5760
ggttcaggga gacatcttat caatattatt atcatctatt ttattgttca agtgataaca    5820
acagttctgg gacagctgga aagttatgtt agtggaaaat ttgatatgcg actttcttac    5880
```

-continued

```
agtatcaata tgcgcctcat gaggactacc tcatctcttg aattaagtga ttatgagcag   5940
gctgatatgt ataatatcat agaaaaagtt actcaagaca gcacttacaa gccttttcag   6000
ctatttaatg ctatcattgt tgtgctttca tcgtttatct cattgttatc tagtctattt   6060
tttattggaa catggaacat tggggtagca attttactcc ttattgttcc agtattatct   6120
ttggtacttt ttctcagagt gggacaatta gagtttttaa tccagtggca gagagcaagt   6180
tctgaaagag aaacatggta tattgtatat ttattgactc atgattttc atttaaagaa   6240 atcaagttaa ataatattag caattacttc attcataaat ttggaaaatt aaagaaagga   6300
tttatcaacc aagatttagc tattgctcgt aagaagacat atttcaatat ttttcttgat   6360
ttcattttga atttgataaa tattcttacg atatttgcta tgatcctttc ggtaagagca   6420
ggaaaacttc ttataggtaa tttggtaagt ctcatacaag ctatttctaa aatcaatact   6480
tattctcaaa caatgattca aaatatttac atcatttata atactagttt gtttatggaa   6540 caacttttg agtttttaaa gagagaaagt gtagttcaca aaaaaataga agatactgaa   6600
atatgcaatc aacatatagg aactgttaaa gtaattaatt tatcatatgt ttaccctaat   6660
tcgaatgcct ttgcactaaa gaatatcaat ttatcctttg aaaaaggaga attaactgct   6720
attgtaggaa aaaatggttc agggaaaagt acactagtaa agataaatttc aggattatat   6780 caaccaacta tgggaataat ccaatacgac aaaatgagaa gtagtttgat gcctgaggag   6840
ttttatcaga aaaacatatc ggtgctgttc caagattttg tgaagtatga gttaacgata   6900
agagagaata taggattgag tgatttgtct tctcaatggg aagatgagaa aattattaaa   6960
gtactagata atttaggact cgattttttg aaaactaata atcaatatgt acttgatacg   7020
cagttaggaa attggtttca agaagggcat caacttctcag gaggtcagtg gcaaaaaatt   7080
gcattagcaa ggacattctt taagaaagct tcaatttata tttttagatga accaagtgct   7140 gcactcgatc ctgtagctga aaaagaaata tttgattatt ttgttgctct ttcggaaaat   7200
aatatttcaa ttttcatttc tcatagtttg aatgctgcca gaaaagcaaa taaaatcgtg   7260
gttatgaaag atggacaggt cgaagatgtt ggaagtcatg atgtccttct gagaagatgt   7320
caatactatc aagaacttta ttattcagag caatatgagg ataatgatga ataaaaaaaa   7380
tataaaaaga aatgttgaaa aaattattgc tcaatgggat gagagaacta gaaaaaataa   7440
agaaaacttc gatttcggag agttgactct ctctacagga ttgcctggta taattttaat   7500
gttagcggag ttaaaaaata aagataactc aaagatatat cagaaaaaga tagacaatta   7560
tattgaatat attgttagca aactttcaac atatgggctt ttaacaggat cactttattc   7620
gggagcagct ggcattgcat taagtatcct acatttacga gaagatgacg aaaaatataa   7680
gaatcttctt gatagcctaa atagatatat cgaatatttc gtcagagaaa aaattgaagg   7740
atttaatttg gaaaacatta ctcctcctga ttatgacgtg attgaaggtt tatctgggat   7800
actttcctat ctattattaa tcaacgacga gcaatatgat gatttgaaaa tactcattat   7860
caatttttta tcaaatctga ctaaagaaaa caatggacta atatcgcttt acatcaaatc   7920
ggagaatcag atgtctcaat cagaaagtga gatgtatcca ctaggctgtt tgaatatggg   7980
attagcacat ggacttgctg gagtgggctg tatcttagct tatgcccaca taaaaggata   8040
tagtaatgaa gcctcgttgt cagctttgca aaaaattatt tttatttatg aaaagtttga   8100
acttgaaagg aaaaaacagt ttctatggaa agatggactt gtagcagatg aattaaaaaa   8160
agagaaagta attagggaag caagtttcat tagagatgca tggtgctatg gaggtccagg   8220
```

-continued

```
tattagtctg ctatacttat acggaggatt agcactggat aatgactatt ttgtagataa    8280
agcagaaaaa atattagagt cagctatgca aaggaaactt ggtattgatt catatatgat    8340
ttgccatggc tattctggtt aatagaaat ttgttcttta tttaagcggc tattaaatac    8400
aaaaaagttt gattcataca tggaagaatt taatgttaat agtgagcaaa ttcttgaaga    8460
atacggagat gaaagtggca cgggttttct tgaaggaata agtggctgta tactggtatt    8520
atcgaaattt gaatattcaa tcaattttac ttattggaga caagcactgt tacttttga    8580 cgattttttg aaaggaggga agaggaaatg agaagatatt taatacttat tgtggcctta    8640 ataggggataa caggtttatc agggtgttat caaacaagtc ataaaaaggt gaggtttgac    8700
gaaggaagtt atactaattt tatttatgat aataaatcgt atttcgtaac tgataaggag    8760
attcctcagg agaacgttaa caattccaaa gtaaaatttt ataagctgtt gattgttgac    8820
atgaaaagtg agaaacttt atcaagtagc aacaaaaata gtgtgacttt ggtcttaaat    8880
aatatttatg aggcttctga caagtcgcta tgtatgggta ttaacgacag atactataag    8940
atacttccag aaagtgataa gggggcggtc aaagctttga gattacaaaa ctttgatgtg    9000
acaagcgata tttctgatga taatttttgtt attgataaaa atgattcacg aaaaattgac    9060
tatatgggaa atatttacag tatatcggac accaccgtat ctgatgaaga attgggagaa    9120
tatcaggatg ttttagctga agtacgtgtg tttgattcag ttagtggcaa aagtatcccg    9180
aggtctgaat gggggagaat tgataaggat ggttcaaatt ccaaacagag taggacggaa    9240
tgggattatg gcgaaatcca ttctattaga ggaaaatctc ttactgaagc atttgccgtt    9300
gagataaatg atgattttaa gcttgcaacg aaggtaggaa actagagtga aaaaaatact    9360
aggtttcctt tttatcgttt gttcgttggg tttatcagca actgtgcatg gggagacaac    9420
aaattcacaa cagttactct caaataatat taatacggaa ttaattaatc ataattctaa    9480
tgcaatttta tcttcaacag agggatcaac gactgattcg attaatctag gggcgcagtc    9540
acctgcagta aaatcgacaa caaggactga attggatgta actggtgctg ctaaaacttt    9600
attacagaca tcagctgttc aaaaagaaat gaaagtttcg ttgcaagaaa ctcaagttag    9660
ttctgaattc agtaagagag atagcgttac aaataaagaa gcagttccag tatctaagga    9720
tgagctactt gagcaaagtg aagtagtcgt ttcaacatca tcgattcaaa aaaataaaat    9780
cctcgataat aagaagaaaa gagctaactt cgttacttcc tctccgctta ttaaggaaaa    9840
accatcaaat tctaaagatg catctggtgt aattgataat tctgcttctc ctctatctta    9900
tcgtaaagct aaggaagtgg tatctcttag acaaccttta aaaaatcaaa aagtagaggc    9960
acaacctcta ttgataagta attcttctga aaagaaagca agtgtttata caaattcaca   10020
tgatttttgg gattatcagt gggatatgaa atatgtgaca aataatggag aaagctatgc   10080
gctctaccag ccctcaaaga aaatttctgt tggaattatt gattcaggaa tcatggaaga   10140
acatcctgat ttgtcaaata gtttaggaaa ttatttttaaa aatcttgttc ctaagggagg   10200
gtttgataat gaagaacctg atgaaactgg aaatccaagt gatattgtcg acaaaatggg   10260
acacgggacg gaagtcgcag gtcagattac agcaaatggt aatatttttag gagtagcacc   10320 agggattact gtaaatatat acagagtatt tggtgaaaat ctttcgaaat cggaatgggt   10380
agctagagca ataagaagag ctgcggatga tgggaacaag gtcatcaata taagtgctgg   10440
acagtatctt atgatttcag gatcgtatga tgatggaaca aatgattatc aagagtatct   10500
taattataag tcagcaataa attatgcaac agcaaaagga agtattgttg tcgcagctct   10560
tggtaatgat agtttaaaca tacaagataa ccaaacaatg ataaactttc ttaagcgttt   10620
```

```
cagaagtata aaggttcctg gaaaagttgt agatgcaccg agtgtatttg aggatgtaat   10680
agccgtaggt ggaatagatg gttatggtaa tatttctgat tttagtaata ttggagcgga   10740
tgcaatttat gctcctgctg gcacaacggc caattttaaa aaatatgggc aagataaatt   10800
tgtcagtcag ggttattatt tgaaagattg gcttttttaca actactaata ctggctggta   10860
ccaatatgtt tatggcaact catttgctac tcctaaagta tctggggcac tggcattagt   10920
agttgataaa tatggaataa agaatcctaa ccaactaaaa aggtttcttc taatgaattc   10980
tccagaagtt aatgggaata gagtattgaa tattgttgat ttattgaatg ggaaaaataa   11040
agcttttagc ttagatacag ataaaggtca ggatgatgct attaaccata aatcgatgga   11100
gaatcttaaa gagtctaggg atacaatgaa acaggaacaa gataaagaaa ttcaaagaaa   11160
tacaaataac aatttttcta tcaaaaatga ttttcataac atttcaaaag aagtaatttc   11220
agttgattat aatattaatc aaaaaatggc taataatcga aattcgagag gtgctgtttc   11280
tgtacgaagt caagaaattt tacctgttac tggagatgga gaagattttt taccggcttt   11340
aggtatagtg tgtatctcaa tccttggtat attgaaaaga aagactaaaa attgatagat   11400
tatatttctt cagaatgaat ggtataatga agtaatgagt actaaacaat cggaggtaaa   11460
gtggtgtata aaattttaat agttgatgat gatcaggaaa ttttaaaatt aatgaagaca   11520
gcattagaaa tgagaaacta tgaagttgcg acgcatcaaa acatttcact tcccttggat   11580
attactgatt ttcagggatt tgatttgatt ttgttagata tcatgatgtc aaatattgaa   11640
gggacagaaa tttgtaaaag gattcgcaga gaaatatcaa ctccaattat ctttgttagt   11700
gcgaaagata cagaagagga tattataaac ggcttaggta ttggtgggga tgactatatt   11760
actaagcctt ttagccttaa acagttggtt gcaaaagtgg aagcaaatat aaagcgagag   11820
gaacgcaata aacatgcagt tcatgttttt tcagagattc gtagagattt aggaccaatt   11880
acattttatt tagaagaaag gcgagtctgt gtcaatggtc aaacaattcc actgacttgt   11940
cgtgaatacg atattcttga attactatca caacgaactt ctaaagttta tacgagagag   12000
gatatttatg atgacgtata tgatgaatat tctaatgcac tttttcggtc aatctcggag   12060
tatatttatc agattaggag taagtttgca ccatacgata ttaatccgat aaaaacggtt   12120 cgggggacttg ggtatcagtg gcatgggtaa aaaatattca atgcgtcgac ggatatggca   12180
agctgtcatt gaaattatca taggtacttg tctacttatc ctgttgttac tgggcttgac   12240 tttcttttcta cgacaaattg gacaaatcag tggttcagaa actattcgtt tatctttaga   12300
ttcagataat ttaactattt ctgatatcga acgtgatatg aaacactacc catatgatta   12360
tattattttt gacaatgata caagtaaaat tttgggagga cattatgtca agtcggatgt   12420
acctagtttt gtagcttcaa aacagtcttc acataatatt acagaaggag aaattactta   12480
tacttattca agcaataagc attttttcagt tgttttaaga caaaacagta tgcctgaatt   12540
tacaaatcat acgcttcgtt caatttctta taatcaattt acttaccttt tctttttttct   12600 tggtgaaata atactcatta tttttttctgt ctatcatctc attagagaat tttctaagaa   12660
ttttcaagcc gttcaaaaga ttgcattgaa gatgggggaa ataactactt ttcctgaaca   12720
agaggaatca aaaattattg aatttgatca ggttctgaat aacttatatt cgaaaagtaa   12780
ggagttagct ttccttattg aagcggagcg tcatgaaaaa catgatttat ccttccaggt   12840
tgctgcactt tcacatgatg ttaagacacc tttaacagta ttaaaaggaa atattgaact   12900
gctagagatg actgaagtaa atgaacaaca agctgatttt attgagtcaa tgaaaaatag   12960
```

-continued

```
tttgactgtt tttgacaagt attttaacac aatgattagt tatacaaaac ttttgaatga    13020
tgaaaatgat tacaaagcga caatctccct ggaggatttt ttgatagatt tatcagttga    13080
gttggaagag ttgtcaacaa cttatcaagt ggattatcag ctagttaaaa aaacagattt    13140
aaccactttt tacggaaata cattagcttt aagtcgagca cttatcaata tctttgttaa    13200
tgcctgtcag tatgctaaag agggtgaaaa aatagtcagt ttgagtattt atgatgatga    13260
aaaatatctc tattttgaaa tctggaataa tggtcatcct ttttctgaac aagcaaaaaa    13320
aaatgctgga aaactatttt tcacagaaga tactggacgt agtgggaaac actatgggat    13380
tggactatct tttgctcaag gtgtagcttt aaaacatcaa ggaaacttaa ttctcagtaa    13440
tcctcaaaaa ggtggggcag aagttatcct aaaaataaaa aagtaattta gtaatctcta    13500
aggattactt ttttttgtttc tgaatagatt ctgaaaattg ttttatatac ttttttttaaa    13560 cataaaataa agtgaggaaa tataatgcag gtaaaaattc aaaatctttc taaaacatat    13620
aaagaaaagc aggtgctaca agatatcagt tttgatatta aatctggaac agtctgtggt    13680
ttattaggag ttaacggtgc aggaaaatca actttgatga aaattttgtt tggtttaatt    13740
tctgcagata ctggaaaaat tttttttgat ggacaagaaa agacaaataa tcaacttgga    13800
gccttaatcg aggctccagc aatatatatg aatttatctg ctttcgataa tcttaaaact    13860
aaggctttgc tttttggaat ttcagataag agaattcatg aaactctaga agtgattggt    13920
ttggcagaaa caggaaagaa aagagcagga aaattctctt tagggatgaa acaacgtttg    13980
ggaattggta tggctattct tacagaacct caatttttaa ttcttgatga acctactaat    14040
ggtttggatc ctgatggtat tgcggagttg ttaaacttaa tcttaaaact taaagctaaa    14100
ggtgtgacaa tcttgatttc tagtcatcag ttgcacgaaa taagtaaagt agctagtcaa    14160
attattattt tgaacaaagg taagattcgt tataatcgtg cgaacaataa agaagacgac    14220
attgaacagt tattctttaa gattgtgcat ggaggaatgt gatatgaaaa gaataatagc    14280
atcagaagca ataaaattaa aaaaatcagg aactcttaga ttggtattaa ttatcccttt    14340
tgtgactcta tttatagcat ttcttatggg tggaatacag attttttagtg ttttttttcaat    14400 ttattggtgg gaaactggtt ttttattcct tttgatgagt ttgctttttc tttatgatat    14460
aaaatcagag gagcaagctg gaaattttca aaatgtgaaa tggaaaaagc tgagttggaa    14520
aattcatttg gccaaaatgt tgttgatttg gctaagaggt atactagcga gcatagtctt    14580
gattattttg ctttatttgg ttgcttttgt gtttcaaggt attgtagtgg tggattttat    14640
gaaagtaagt gtggcattga ttgctatatt actagcagct tcttggaatt taccctttat    14700
atacttgatt ttcaagtgga ttaatactta cgtattgtta gctgcgaata ccttgatttg    14760
tttaattgtt gccccttttg ttgcacaaac tccagtatgg ttcttgctac catcacactta    14820 tcactataaa gttacagaaa gtttgttaaa tatcaaacca tcaggagatt tgttaacagg    14880
gaagataaat ttcagtattt gggaagtttt attaccattt ggactttcca tagttgtaac    14940
gataggagtt tcgtatttac ttaaaggagt gatagaacat gataagaagt gaatgtctca    15000
aattaaaaaa tagcttaggg ttttatttag tttttctctt tactttatta gagctttttaa    15060 cggttcctat ttatttagct tttggaagaa gtcatgtttc aatgactgat ttatcgctca    15120
tgattttttt gtttttttccg ttactggtta caatttttgtc tattctaatc tttgaacagg    15180
agagtctggc caatcgtttc caagaaataa atgtaaataa aaaaagtagc agaatttggt    15240
tatcaaagct aatagtagtg gatttccttt tgttcttttcc atcagcaatg atctggataa    15300
ttacgggagt ttcacaggca gtagggcaac aaggaatgat gatcgcaaca gctagctggt    15360
```

-continued

```
tgatggcaat ttttcttaat cattttcatc ttttattgac ctttataatc aatcgaggag   15420
ggagcatgat tatcgcgatt attgaaatat tactcattat ttttgccagt aataaagttt   15480
tattagcagc ttattggtgt cccattgctt tacctgttaa ttttatgata actgggcggt   15540
gtgcttatct gatagctgcc gtagggtgga ttgttttatc cacaataatt cttgtagcat   15600
tatctaaaaa aaagattaga taaagtattt tttcttatgg taattcgacc taatatgttt   15660
ttgctattta tctcttattt ctgtctatag taatttattc aaagtacctt tagactcata   15720
agtttgaata aaatttccat caatatgtga cagttcttac tctaagaata atgtttccgt   15780
cgttagtttt cttttctcag taatttttta taaagtggtt tcctatcgac ttacactttt   15840
tcttttggag ttattggtgt caagctcatg agagattctt taaagcatat aacattttta   15900
aactgatatg ccagttattt gtgaagaata tgagtttcta tataaagag aaaattaaac    15960 aatgaaaaat ccaagtataa atacttggat ttttcattat ttttgataga catataaagt   16020
gcattttaac ctagaattaa aagatgtatc gttgataata ataaaatgaa ccaaagcaaa   16080
actgacgtta agtcaattta ttagagtcaa aaacgtataa ttttaatgta tttattttaa   16140
gtgatttctt tttcaaattg attaggcgta agataccta aactttgatg gattcgtttt     16200
gaattataaa aggcttcaat ataccagaaa atactctgat aggcttcttc aaagttctta   16260
tatttaaatt gatagaccca ctctcttttt aaatgtccat gccaagattc aagactggca   16320
ttatgataag gatagccctt acgactgaag gagtgagtca ttccagagtt ttttattgtc   16380
tcttcatact catgactcgt atactgactt ccttggtcag aatgaagcat cacagcttct   16440
ggataatttt gtgattccat tgccttattc aaagtccttt gcactaattc tagagtcatt   16500
cgctttccta aatcccaagc aatgactttt ttagtataac gatccataat ggttgagaga   16560
taaacccagc cttgttgagt aggaatataa gtaatatcag ttgcccaaac cttatttatc   16620
tttttaggct cattttgtta ataccatcac ttacggagtg tccgggttta aattttttaa   16680
ggacgacgga cttgagctga agttgtttca taattttttg tacgagcttt atccctactt   16740
tttccccttg attgagtaag aggtgatgaa tcttaggtgc cccatagatt ccccgattcg   16800
ccttgaaaag ttggtcaatc ttcagtgcca agtgttgtct tcttaattga gtttttggatg  16860 ggcgtcgatt gattctctca taataacttg cttcaggaac accaagcagt tggcaactga   16920
gtctgacatt gagtgctaaa gttttaatcg tttgagatat atccgcagca ctcacatctt   16980
tttctcggcg aatatggtca atactttttt aagatgtctc gttcttcctt aactttagcc   17040
agctgtcttt ttaattctag aaaatcatct ttagagactg agctttcatt agacttagaa   17100
tagaggtcga tccatttata aatcgttgca ggagccacgc cgtattcttt agaaagctgt   17160
gtgacggatt gcccagaatg atagaagtcg agaagggtgt ctttaaattc ttgtgagtag   17220 cgttttttgca tgtttttatc ctttgtctaa attatacaat agtgactcta agaattaagg   17280
atagcatcac agtgtctttt tgaagaagta aaatatattt ttaatctata ccataatgta   17340
gctgaacagg aagttgatat gtaatgtcaa tgttatctcc atcaattttt cgtatgatta   17400
aatcaactaa gagttccgct aaatcattta ttggttgctt tatcgttgtt aggttaggat   17460
agtagttttc tataaattca gttccatcaa aacctaccac attaagtgat tttttaaat    17520 ttgaggcgag atcttttact aatatagctg ttaaatcatc tgtacaaaat acaccatcaa   17580
aatcgttgtt ttctagtatt tttttgatct caactttttt gcgaagaaga gtccattgag   17640
aaggaatttt tattatatga gtctttaatt gatttctttc tagctcaagc agatatccat   17700
```

-continued

```
cacgccttaa atatgtagga gaattggtat tatcgttccc agtaaatatg gcgatttttt   17760
tacttccaga gttaatcaaa gctttagtag ctaggattcc tccctcaaaa ttatcagagc   17820
taacaacagt cgtttcaggg gttaataaac ggtcaaaagc aacaataggt gcttcaattg   17880
ctatataatc atgtgctttt aaattatgac tcccataaat aattccatca acttggttag   17940
aaagtaataa ggcaagatag tctcgctctt tttgttcatc atgttctgtt gttgctaaca   18000
tagctttgta acctcgtatg aaaagagctt gctcaatttt ttcaatcaat tctgcataaa   18060
aaatattttt tatagttgga aatactagcc caattaattt taaagacttt ccttgcaaag   18120
aacgtgcggc tgcgtttgga atataatgca agtcttgcat tgcttttttct acttttgata   18180 ttgttgcgtc actcaaatat cctttacgat ttataacacg cgaaactgtc gttacactaa   18240
ccccagcttt atttgcaaca tcttcaagtt taatcacttt tttagctccc ataattttat   18300
ttttatcgga ttttgacttc taatcgaata ctgattctta tttggaaata cacgacctga   18360
taatactttt tcaccatcat taataaaaat ttcaaaaatt gattgatcaa taaatacatt   18420
cattttttct attttaacat gtgccaaacg ttttttcataa tttcttataa gtgtaatagt   18480
attattttct ttatctatct caactttaag tgcactatcc cctttttcat ttgtcattaa   18540
agatagaagt gtagaggttt gctgacgaaa atcgacctca agttcataag agttagatgt   18600
aataatgtta ttatctgcta gtaagagatc ttgttccatt tgtcttaatt ctttcatttt   18660
ttcaactgga tattgataca atttgttgtc ttttattgaa agcttcttaa ccatggacaa   18720
gacaccttga acattgtatt tatcagtggg gtatgatgtc tcaggtaaac ctagccatga   18780
aatggcataa gcagagccat caggtgcatt aaatgactgc gtagcataac agtcaaaacc   18840
ttcatccaaa ttaattagtt gtcctgcatt ttttagctga ttttttgagc cagtagtaaa   18900
gtcatccgca ataacataca cattaggata tatattatca tatttaacaa tcgatttatc   18960
tagtccttgt ggacaaaaaa ctaatactga tctaccattg ataaatataa ggttcgggca   19020
ttcaatcata taacccattt tttcttttga aaaatctaag tttcctaaat ctttccaatc   19080
agttaaatta ttttctattg ctttataaag tttgattata ccattttttt gagagctttg   19140
agcaccaatt aagcaataaa tttgtccttg aaatgaaaaa atttggggat ctcgaaaatg   19200
gtcggttgtt tgagaaaaat caggataaat tagtggttca gtgaatttga ctaattgatt   19260 attttttgtca attttttgctc ccagttgata tggagttcta acccaatctt cgcctctgtg   19320
attacccgta tagattaaaa ataagaagtt ttcaaaagcc aaagcggacc cagaataaac   19380
tccagcatta tcatattttg tatccggata aaggactagc cctgttttct caaagtggac   19440
gagatcatct gagactagat gtacccatga tttttaaacca tgtactggcc caaaaggaaa   19500
atgttggtag aacaaatgcc attttttcatt gaaataagag aatccatttg gatcattaag   19560
aagtccagtt tctggttcaa tatgaaaatt tgatttccaa ggagattttta gtgccagttt   19620 gcgtaaactc tctaaatcac tttcagaata actatcgtag gtacgatatc gttgtttggt   19680
agaccatttc attttttttc ctcatttact aaattatata tatttatgat aaacgttttt   19740
tataaaaaaa tcaatataaa taagtataaa aaaataaaaa ataaaaaaag tgtggcaaac   19800
gcttgacata tatcaaaaaa atgataaaat aacttctgta agcgaaatca ttttatttga   19860
ggagaaaatt atgaatcata agcaggtagc tgaacgcatt ttaaatgcag ttgggcgtga   19920
taacattcaa ggagctgcac attgtgcgac acgactacgt ttagtcctaa aagatactgg   19980
cgttattgat caagaggctc tagataatga cccagatctt aagggggactt ttgaagcagc   20040 tggtcaatat caaattattg tagggccagg tgatgttaac actgtatacg aagaatttat   20100
```

-continued

```
taaacttaca ggaataagtg aggcatcaac tgcagatctc aaagagattg caggaagtca  20160
aaaaaaacaa aatccagtaa tggcacttgt aaagctgctt tctgatattt ttgttccttt  20220
gataccagct cttgtagctg gtggtctgtt aatggctctt aataatgcgc taacagctga  20280
acatcttttc gcgacgaaat cacttgttga aatgtttccg atgtggaaag gatttgctga  20340
tattgttaat actatgagtg ccgcaccatt tacctttatg ccaattttaa taggttattc  20400
tgccacaaaa agatttggcg gaaatccata tttaggtgct gttgtaggta tgattatggt  20460
gatgcctgga cttattaatg gatataatgt tgctgaagca atctctaatc atacaatgac  20520
ttattgggat atttttggtt ttaaagttgc ccaggctgga tatcaaggac aagttcttcc  20580
tgtaattgga gtggctttta tccttgctaa acttgagaga ttctttcata aataccttaa  20640
cgatgctata gacttcacat ttactccgtt actttcagtc atcataactg gatttctcac  20700
attcactatt gtgggaccag cacttcgttt tgtatcaaat ggcttgacag atggtttggt  20760
tggactttat aacacattag gggcactagg aatgcttgtg tttggaggct tctactcggc  20820
aatagtagta actggattac atcagagttt tccggccatt gaaacaatgt taatcacaaa  20880
ctatcaacac agtggtattg gtggagactt tattttttcca gttgcggcct gcgcaaatat  20940
ggctcaagct ggtgcaactt ttgcaatttt atttgttact aaaaacatta agacaaaagc  21000
tcttgcagct ccagctggtg tatctgctat tctaggtatt acagaacctg cgttatttgg  21060
gattaatcta aaactaaaat atccgttctt tattgctctt ggggcttcag caattggttc  21120
attatttatg ggattattcc atgtccttgc ggttagtctg ggatccgcag gattaattgg  21180
ctttatctct attaaagctg ggtataactt acaatttatg atttcgatat ttattagctt  21240
tcttattgct tttgttgtta cctcaatcta tggtcggcgg atggaagcta aatctattac  21300
gaaagaaaaa aataaacaga atgcaacaac tcaataccaa cctgagaaag ttattatcga  21360
tccagttaaa agtgacgaac tccttgctcc gataaatgga tttgtgattc ctctgtctga  21420
tgtaagtgac cctgttttct caaaagaaat tatgggaaaa ggtattgcaa tcaagcctaa  21480
atctggagaa cttttctcac cagccgacgg agaaattatt attgcttatg aaacaggtca  21540
cgcttatggt ataaaaacaa aaaatggagc tgaagttctt ttacatattg gaatagatac  21600
tgtttcaatg aatggtaatg gattcataca aatgttaaa gttggccaga aagtaaaagc  21660
aggggattta ctaggatctt ttgataaaga agaaatcaag aagagtggat tcgatgatac  21720
tgtaattatt gttattacaa attcagcaag ttacaatgag attttgccat tgagtgaaaa  21780
tgttgatatc aaagttggag aaaaaattct attattgaac tagagggagc gaactatgtc  21840
cgtatactat ggatcaattg aggctggtgg tacaaaattt gtacttgcta ttgcagatga  21900
acattttaat attataaaaa aatgcaaatt tgctactact acgccacaag aaactataag  21960
taagacgatt aaatacttta agaaaaccg agtttctgcc attggtttag gatcatttgg  22020
gcctattgat ctaaaccttt caagtaaaac gtatggttac attacttcga cgccaaaagt  22080
tggttggaaa aatataaatt tagttggcca attaaaagaa gcacttgata ttccaatata  22140
ttttactact gatgtaaacg cctcagccta tggtgaaatg aaaaatacag gaataaaaaa  22200
tcttgtttat ttaacaattg gtacaggtat tggagggggga gcaattcaaa atggatattt  22260
tattggtggc attgggcatt cggaaatggg gcaccaaaga ataaatcgtc atagagatga  22320
tcttactttt gaaggaatct gtcccttcca tggtgattgt cttgaaggag ttgcggcggg  22380
gccgagtctt gaagctagaa caggaatact tggggaaaaa atttcttcag atgatcctat  22440
```

```
ctgggatatc ttaagctatt atattgctca agcggctatt aatgcaacat tgacattagc   22500
tcccgagtgt ataattttgg gaggtggtgt aatggaaaaa ccaaatatga tatcacttat   22560
acaaaaacaa ttcatttcta tgcttaataa ttatatagat ctgccttgtt ctgtagaaaa   22620
gtatattcgc ttaccaactg tcaaagaaaa tggttcagca acgttaggaa atttctattt   22680
agcatattct ttatttacaa aagaataata atataaaatc tatatatttc tagcatgtag   22740
ttcaacaaaa tataatggta attgtaaata ttaaggcaat attacaatta taaaaaggtt   22800
tcatttcttt gttatctttt aactttttgc aacataatcg aaagttcttt tagtgatact   22860
aaatacctaa taatttaagt atgagaaaag taaatttcta ggtcttactt tggaaggcag   22920
tatttcacaa attatgtatt atcttattta gaataagaaa agttgaaatg cccaaaatta   22980
tttcaaatat gggaatatta ttggatgcct gtgtagcaat gcattataga aactaaaata   23040
aaatttagtg ggcaaatagt gggtaaaatt taaaatatat aaatcaacta gacattattg   23100
aaagcaatag aaaacttata aaataaagag ccactaaact ttagtgactt tttattttat   23160
gtgttttaat attaagcaaa cgcgttgagc gtttatttca aatatgggaa tattcatgac   23220
tgcctttgta acagtgtatt ataaaaatta aaataaaatt taccgaataa atcgatacta   23280
gaaaaactct taataatttt atatttactt aaaaaacaag tgtaaaatta taaaaataca   23340
aaatagttat aaaaaaagat atatattgta aggagaagag gggattattt aggtcgctct   23400
caaagttaaa ttcaggttct ataagccttt ataaacctgt ttcatagaaa acctcttaaa   23460
ttgaaaaata aaatgggaca aatttgggac aattatggta taaaatcata gctacgattt   23520
aatctcattg aattttgag tttataaagt taaggaacta agcatattat tttggaagat   23580
ttgaacaaaa aataaattaa agagtcatta agaattgaat taatgacttt ttattatgtt   23640
aagtttgttt gatgctttta agctatatgt ttttctcttt ataaactaat aatcagtatt   23700
gagcttaaca aggtgctata cttaatttta tgagatcaca gtctctgttg tggaatagaa   23760
accaaatatg gttatatttt tttgattgat attgtaattt agaattaaag tgatatactt   23820
accttagggt gtggttttgt gaaagcacca cacctccatc attagctact caaatggggt   23880
agcttttttt aaaatatgta attataaaca aaaaaataag ttgataataa ggggaagggg   23940
gcatctaacg aataaaaata aagagaaaaa ggcgattata agcttactgt tttttggatt   24000
tgtagtaagt atattaatta tatacctagt aataacttta ctgatgtgag aaaaaatgct   24060
gttcgggtaa ggtaacacat ttgtaaaata atttacgaac cctaatgtta aattgacttt   24120
acctgatatt agtgttatac ttgcgaagcg ggatggagca gttaggtagc tcgtcgggct   24180
cataacccga aggtcatagg ttcaaatcct attcccgcaa tattttaagg gctttaggga   24240
gtccttattt ttcttataaa aaactcaccc taaagtgaaa tttttttcgtt aaataggcgg   24300 agcctagaat ggaagtgaaa aatgaaaaca ggagataaaa ttacattatc taatggggaa   24360
caagcaattg tcgtttctgg agatattaat ctctataagt atgcactaat tgttgaatta   24420
gaaaaccatg atgtcagggt ggttgataga gaaaccttga cacttgctaa agcaaatcct   24480
catgaaaatc tggggaatca taagaagatc aataagtttt aaatagacca atttgacttt   24540
agtaagaata ggtgttacta ttaagaggta ggttttgtct cgagtttaaa tgtttttagga   24600 atgcactttt tcgcaaaata ggatttacag atgatgcgaa aggatgtatt atatgaataa   24660
aggaacaata aattggttta acgctgacaa aggctatggt tttattatgg cagatgatat   24720
gcaagatgtg tttgcttatc tcttatctat tcagggaaat gattttaaaa aatacgatga   24780
aggtcaaaag gttacttttg atatcaaaat gacgtctcgt ggtcgttatg cttcaaacgt   24840
```

-continued

```
acataaaaga taaatgagtt aaagcatggg gtgtcctttg cttttttatt tattgctatt   24900
gcaaaaacga attaaaatgt tatactgagt gagggaaaga ttagttgctt tccctacagt   24960
tcataaaatc catgtcacta cgatatggat tttattaatc agagagtagc ttgacattga   25020
gtataattag tgttactatg aagaagtaga ttttgtcatg agtaaaatgt tttatagatt   25080
cacttttcgc aaaataagat ttacaatttt gttgaaagga aataaatata ttatggcaaa   25140
tggaacagta aaatggttta acgctactaa aggatttggt tttattacct ctgaagatgg   25200
tcaagatttg ttcgctcact tctcatcaat ccaatctgat ggattcaaat cacttgacga   25260
aggtcaaaaa gttgaatttg atgttgaaga aggtcaacgt ggacctcaag cagttaatat   25320
cacaaaagca taattgtatc tgaaaatcgt gcaaaaactg gagtcatgac ttcagttttt   25380
tttatattca gttgcaatta tgagagagta tgatatactt agccagcaag aggaaactca   25440
cacttcccat tcataaatta ggggcacttt aatatagagt ggtttttttta atgtttatta   25500 attaaaatta atatttaaaa gatttatata aaaaaccatc tatcacagca cataatgata   25560
agcagttttt ggtgcatgtt catagattaa gaagttaata tttaaaacat acaaattaat   25620
aataccatat agatagtctt aaggtcaaaa atagagagat gtgtttaatg gagtacctta   25680
aatataagtg ccagcgaatg tagtgacccc caaaatatag acttttcaaa tctatatttc   25740
ggaggtcttt tcttatggtc aaatattcca tagaattaaa acaacgtgtt attcaagatt   25800
atttatctgg caaaggaggc tctacctatc ttgctaaaat gcacaacata ggttcatcta   25860
gtcaagttag acgctggatt cgcaattatc gagcagaggg acttcctaca gctcactcca   25920
aagtcaataa aaattattct atggaattga aagaaaatgc ggtacaatgt tatttaacaa   25980
ctgatttaac ttatgaagct gtggcaagaa aattcgaaat tactaatttt accttacttg   26040
caagctgggt taatcatttc aaactctatg gagaagtccc aataagcaaa aagagaggac   26100
gacgtaaaaa actagaaagc attgcatcgt ctatgactca gaactcaaat gattctcaac   26160
gaattaaaga acttgaacaa gaattacgtt atgcgcaaat tgaggtagct tatttaaaag   26220
gacttcggag attggagaaa aatgctctaa ataccagccc cgataactca actactggaa   26280
taacgaataa atcaataaat taacaagggt gtattgctac agacaattta aaaatgactt   26340
tgagaatatg aatctcagag tcatttttaa tgtaaaatat tttatgttta ctttaaatca   26400
ttataattat aaatgttata attatgtaga gggccaatta tgaaaaaaat tacttgggaa   26460
caatttgagg cggtaaatga aaataaaact tcatcatttg aaaatatgtg tcgtttacta   26520
tttaataggc aattttttga taacaaaaaa aatttgatat caaagccgaa tcatccagga   26580
gttgaggtct atccagtatt cgaagaaaag tcaggaaaat ggataagttt ccaatcaaag   26640 ttttttttcaa ataatactga ttatgctcaa atcaagaaat cagttgaaaa aacaattaaa   26700
cattactctg atagtttaga cgtttttttat ttgtactgca ataaagatct aaattctgat   26760
tctcggagtt ataaaaaaat tgaagatttg ctaaattcag ctggaattga aattcagtta   26820
attactaatt atgctatcct cgatcaagta attggagact cgagaattgc tgagtttttt   26880
tttaatcacc attctctaaa cgataattgg tttcaagaaa aattggagca aagtcttgac   26940
tcaataggaa ctcgatacaa caatgaattt agtatatcaa ctgaaaccga gaaagaattt   27000
agactttttc taaaaaattc ggaaacattg aaaattattg aagaaaaaaa agacgaaaca   27060
attaacgaac ttaggaattt aagacaacac ctttcaggtg agaacgactt atttgctaaa   27120
tctataatcg tcaaaataca gtctttaaaa atcacggaaa taaacaatat tgagaactgc   27180
```

-continued

```
ctctcttggg aaaatacaat attggaagaa ttttcgtgtg agtttaagag actagaagct   27240
gaaatagaag caaactataa aaagcaagat aaggagaatc agaataaaga gaatggagat   27300
agactttacc aggctaattt gcatggttta ttaaatattt cttcgtattt aaaatttagt   27360
gattttgaga ctaatctgat aaaaagtaag atgcttgtta taaatgggca ggctggaact   27420
gggaaaagtc atcttttatc tgaaaatgcc aataaaattg tcaataatgg tgggcgtgcc   27480
attttattac cagggcatgt gtttgtatcc caagaaccta ttaaaaatca aatagtgtct   27540
tatttaggtc tcgaaattaa ttttcgcgaa cttttggata tccttgaaac ggtaggtgaa   27600
tttactaagg caaatacata tttatttatt gatgcggtga atgagagcaa taataaagag   27660
atctggaaaa atggtttacc aatattactt cgcgaaattg aaaaattgaa tttcgtaaaa   27720
gtcgcaattt cacttcgaag cggatatgaa gatacggttt ttgatgaaaa tatccgtagg   27780
aaaattactg actacgagat tccagagatc acacataatg gattttggaa taatagtatt   27840
gaggcagtaa aagaatttct taattatcat caaattccat tttctccttc atattctttt   27900
caatctgaaa tggcaaatcc tttgttctta actatgttct gcaaagttta tgatggaaat   27960
gattttgatt tatatcaatt acttgaaaaa tttcttgaaa aagcagatag agatgcacaa   28020
agggcgatag gaatacaaga tttttaccg atattaaatg acttagttaa ggaaattgca   28080
gattttcagc ttgaaaatgg gctttatgct gtaggtagga atgatattct aaaaatggag   28140
ttttgggatc ttaatggtct ctcaaataaa aaacttcaat atttatcatc acttggtaaa   28200
tctggagtat ttgtgacttt catgcgtgaa ggggaagaaa agtatagatt tgggtacaat   28260
ctattagaag actttatatg tgccaaagtg atcattaatc gttttcaag cgctcaagag   28320 tgtagagaat atttacgaaa cgatttacta aaaattggca ataaagagag aaaggtatgg   28380
gagaatgctg atgttttcat cgtagccaca aatttatttt tcgagaaatt tggggaagag   28440
tgtattgata ttgctaatga tatcacggat gaatacgacc gaaatcatct acttgatgaa   28500
tatatcaaat cattttcttg gcgaccgtca caaaatattg atcttaaaaa ttttcgcgaa   28560
tttataaatg aaaataagat tgctcgggac actattttca atgtttttgat tgaaaatagt   28620 gtcaagtcca ataacccatt gaatgctgag tttcttcatg aaatactttt taacaaatta   28680
ttgaatgagc gtgattatat gtggaccacc tacattaaca attttgctta tgaagacgat   28740
agattatttc aattgatcag tttatttgat aagggtaaaa agctagagaa ttctagcgaa   28800
aatacttggt tattacttgt attattttct tggctgctga catcgtcgaa tagattgttg   28860
cgagataaag catctaaggc gatgattgag ttgttgaaag atgattttc gttaatttta   28920 ccacttctga aaaaatttga gaatgtgaat gattcctatg ttattcagcg actatacggc   28980
gttgtatttg gggcttgtac gaaaaattta aacatgacag aaccagagtt taaagaattg   29040
gcggaatatg tttacattgc aatatttgat aaagatttag tttatccaga tattctattg   29100
agggattatt caaagctaat cattgagtat ttcttgttta aatttccaga atctaaaacg   29160
attattaacg agataacatt cagaccaccc tataattcta aaccaatacc aatcgcgaaa   29220
aaagcgaaag ataagtatga gggcggacta atatattcg ctcattccat agcaccaaaa   29280
ggtgtggaga gaatgtatgg agatttcggt cgatatgtat ttgattcagc tttgcatcat   29340
ttttccgatg ttgattcagt caatatttat aactattcga tggattttat tgaaaatgaa   29400
cttggttata aaaataaatt atttgccgaa catgatagtc ttcgaaatcg caactcttat   29460
gacaggcata atacgggaaa gattgagaga atcggtaaaa aatatcaatg gattacgatg   29520
tataacattt tggctagggt ttccgaccat tataaacttt ctgatggata tggatggaat   29580
```

-continued

```
aatagcgaag aaccagaaga atttgacggt gcgtggaatc cttatgtacg cgattttgac   29640
ccaacgctaa atcgtaattt tcttgatgat ccgagttgtc cagttttcgt gaaaaaagag   29700
ctaaaagggt tagattttat atcaaaagat gcttcaaagg aagtcgtcaa gaaatgggtt   29760
agcaatgaag acgatgtttt ctttactgca ggaccagatc ttctgctttt ggatgagtcg   29820
caaactgaat gggtggcttt agatgattat atgagtataa aaaatactga tgatgaatta   29880
gaccttatta gtattggaga tagatcgggt aaacagaaaa aatggcttat agcagacggg   29940
tattttatca agaaaagtga attttcggac ttacaaaatg atttgtcaag caaaaatctt   30000
agaaaaatat cattcactga aagttcaaga aacatctatc aactatttaa ccgtgaatat   30060
ggttggtcat cggggtataa gaggtctgta gcagattgtt cttggtcaga ttatgaggtt   30120
gagacaggaa aatttgacac tattgattat ccgagtttta atatctcaat cattgatgat   30180
attgatggtg atgaacttga aactcttgaa tatacggacg aaaagactga aaaatataaa   30240
gtgccaatta aaaaatctct cgcgagagtt atgtcggcaa cagatagttt tttatggaaa   30300
gaacaatatg acgcttcgca agaggaaacg atagcatttg atattccatg tagtcttctt   30360
ataagtgaac tggaattagt gcaacgagaa tatgatggct actattatga taaaaacgga   30420
gaactagtgg cactttatat taaagatagt gaagaatttg atagttcgca cagatttta   30480 atccgaaagg ggcatttaaa taaatttcta gctcaaaatg aattgacttt attctggatt   30540
tgtcggggtg agaaagattt tatggttcaa gaaataagag agcaagaatg gagcgaatgg   30600
ggtggtttac tatatctttc caatgataaa attgtaggtg aaatagtaaa atttgataga   30660
atatagtcaa tacgcttata atgaatcagt aacggtgtat tgctacatag ttttataaaa   30720
aacaagcttc atcgcaatga tgaagcttgt ttttaaattg cgtataataa tatctaactt   30780
aatagttata gtaatgtgca gtatgtttta atatcaggaa tatttgtaat cgtaattgga   30840
aaaacatgca atcatagcag ttattatgat acaatttaaa aaggcatatt tacaagagac   30900
tgaaaggaat gagagtatga cttttttcac tcaaaaggct atggaagttg ctaataaaga   30960
actgggtaaa aaacaattag ctggaattag ccaatataca gtgaataagc tgaattgagg   31020
tgaggcagtg acgataaaaa ctttatcaaa gatttgtaat gctttgcgta gtaggataga   31080
agatattttt gaagtataaa gttttaacga ggaagcttta aattaagtgg aggaacaagt   31140
gtgacaacgt cagaagaaat taaaaaaaga ttgtgggatg gtgccaccga gctacgtggt   31200
tcaatggatg ctagccgata taaggactac atgcttggac taatgttcta taagttttta   31260
agtgataaaa ccttagagac atttagaaat actgcgggct taggcagaat atcagaatca   31320
gatttagttg aagagtacac ccagaatcgt gaagatttag gcgaagaact cgataagatg   31380
attcaacagg tcttgggtta ttttgtagca cctgaatatc tttatcagaa atggataaag   31440
gatatcaata cgggtgattt tgaagtccaa aaagtaaccg atagcttaaa cagttttgag   31500
aagaccatcg cagtaacagg cgagtccgct gattttaaag ggttttttc gagttctact   31560 ttggatttga ccgatacagc tttaggaagc aatctaaacg aacgtagcaa aaacatcaaa   31620
gccttaatca atttgtttgc tgacctcgat atggttgctt tacaaaagag tgatgtgctt   31680
ggtgatgctt atgaatatct gattggccag tttgccatgg aatcgggcaa gaaggcaggg   31740
gaattctaca cgccaagaca ggtttcagaa gttatggcac aaattgtggc aaagacttca   31800
aatatccaat ctatctatga cccaactgta ggttctggtt cgcttttatt aactgttgga   31860
aaacacctga gcaaagaagt gcaaaaagat ttatcttact atggtcaaga aaaaaataca   31920
```

-continued

```
gccacttata acctgacacg tatgaacttg ctcttacatg gggtacgtcc agaaaagatg   31980
acggtaagaa atgcggatac tctatctcat gactggcccg aagatccaag tcgaccaaat   32040
gtgggcgtac agtttgatgc ggttgttatg aacccaccat actcactcaa ggactggaat   32100
aaagctggct taaaaatcag cgaccctcga tttgagattg cagggacatt accgcctgat   32160
tctaagggag actttgcctt cctttttgcat ggccttttcc acttgggaac aaatggtaca   32220
atggcgattg tcttgcctca tggcgtgctc tttagaggtg gttcagaagg tgatattcgt   32280
caaagacttt tagataaaaa tcaaattgat accatcattg gcctgcccag cggaatgttt   32340
accaatacgg ggattccagt gatcgtgatg atttttgaaga aaaatcgtcc agttggagaa   32400
ccagttttag tcattgatgc atctcgtagt tttatcaaag ttgggaagca aaatgttcta   32460
caagaaaaag atattgccaa aatcgtagat acttattcat cacgtcgtga gattgaaggc   32520
tacagctacc tagcgactca taaggaaatt attgctaacg agtggaatat gaacattccc   32580
aggtatgtgg aagctgacaa tgatgagatt gctcaagatg tggatgccca tttatatggt   32640
ggaattccta agtctaatat tgatgagctg cttgtattaa ataagagcgt tcctgaagtg   32700
attcgttcat catttgaggt actacgcgat ggctacctgg tgctaaataa gagcattgaa   32760
caattgacgg aagaagtcaa caatgctcca caagttttgg caaagaatga ggagttgaga   32820
aagattgctg aaagtttcgt tgctaaatat tgggatattc tccgtcaggt caatcttgat   32880
agtgatttgg ctagtctcat gtcagaaatg ctttctgaaa taaaggaaga ggtttctagt   32940
attgaatttg ttgacgcata tagtgcatac caaatcgtgg ctgaaatctg gaaggacaat   33000
cttactaaag atagtgaatt gattgcggca agtgattttt ataccgttgg tcgcacgcgt   33060
gaaccaaata tggtgacaaa aggatcaggc aagaacaaac gccaagagca agatggctgg   33120
attgggacgt ttgttccaaa tggcttgata gcaaaacgtc tttttgcttc agaacaagaa   33180
gaaatcgaag agttgaaaaa taaagctcaa gaaattgaca gcgaattgtc tgagcttgta   33240
gaggctgcca aagttgagga ttctgaagaa tatgaggccc tttacgaatc tatcaagaaa   33300
aatgaggatg acgagccaca ggatactttt gaagctaaaa cgatcaaggc tgaactgaaa   33360
agatcagaaa aaggaacatc tgaatttgag tggctaaaac gtgttgaaaa acttctggcg   33420
gataaaagtt caacgaataa gtccgtcaaa gaaaaagaaa aacaactcaa agaagcggtt   33480
gaatctaaga ttgaaaatct gacaaatgaa gagattgata tgctggtttt tgagaagtgg   33540
tttgcgggta cagtagatgc tcttgtaggg ctagttgaaa agcctttgcg cgcggagctt   33600
tcaacgattg cacttcttga aaagcgttat gctcaaacat tcaatgaaat tgatgcacaa   33660
gtttcagagc tagaaaaagc ttttgaagca cttgcgagtg aattggtggt gaatcaatga   33720
gcaaaaataa aaaattagta ccgaaaagac gtttcaaggc gtttcaaaat gctgacgctt   33780
gggaacagcg tgagttgggg gatctagctg aaattgttag aggagcatca ccaagaccaa   33840
ttcaaaatcc aaaatggttc aaccaaaatt ctgaaatcgg atggttacgg atttcagatg   33900
ttactgaaca aaatggccga atacattttc ttgaacagaa aatatcagaa gctggacaag   33960
gaaaaactcg tgttttgcat tcaagtcact tattacttag tattgctgca acagttggga   34020
aaccagttat taactatgtt ccaaccggcg tacacgatgg attttttaatt ttcctaaatc   34080 caaaatttga cctagaattt atgtttcagt ggttagagat gtttagacct caatggcaaa   34140
aatatggaca accaggaagt caagtaaatc taaattctga tttggtgaaa aatcaaaaaa   34200
tttttatacc atcacttggg gaacaaaaag agattagttc atttttttact aacctcgacc   34260 aaaccatcgc ttttcaacag cgaaagtttg agaagatgaa gtcgatgaaa ttggcttatt   34320
```

-continued

```
tgtcagaaat gtttcctgct gaaggtgagc gtaagccaaa acgccgcttt ccaggcttta   34380
ctgatgattg ggaacagcgt gagctcttaa gtacaataaa atccattgta gattttagag   34440
gacgaactcc taaaaaactt ggcatggatt ggtcagattc aggttatttg gcgttatcag   34500
cgttgaatgt taagaatggc tacattgatt tcaatgaaga tgtccattat gggaatcaag   34560
agctttatga taaatggatg tctggtaaag aactgtataa aggacaagta ctttttacaa   34620
cagaggctcc aatggggaat gtggtacaag tacctgatga taaaggatac attttaagtc   34680
aacggacgat agcctttaat attaacaagg atttgttgac tgatagtttt ctttatgtct   34740
tactgggaag ccttaaggtg tttaaggatt tgtcagcatt atctagtggt ggaacagcaa   34800
agggtgtcag tcagaagtcg ttagaacagt taaaagtttg cattccaaaa gatatagatg   34860
aacagtctaa aataagcgag ttttttatca acctcgacca aactatcgct tttcaacagc   34920
aaaagcttga aaagctgcaa aatatcaaaa aagcatacct caatgagatg tttatttaag   34980
aaaggagcgt aagctgtgag taatgcacct aaagatgcga gtgaaaaagc ctatcaagac   35040
aactttgtag ctgaactggc aaagtttaaa tggcaaacgc ctgacttttt gaatgggaac   35100
aagcaaaaag ttaccgttca aagcctcatt gataactggc gaagtgagct caatcgcttg   35160
aataatgacc agcttgaggg gatttctttg acagatggtg agtttgctca agtgctgtca   35220
aaagttggac agattagcaa ctcctacgag gcagctaaag tgctggcaat ggaggaaggt   35280
aagggtaaaa ttgacggcat ctatcgagat agccatccgc aagtcacccg taagcaaatc   35340
acgctaacca tcttcaaaaa agctgaggta cgtggaggag aatcaagcta tcaggtggca   35400
cgtgaagtgg agacgtctaa tgggaatcgc tttgacatcg tgcttttaat caatggcttg   35460
ccactgataa acattgaaca aaagcggaca gacaagtcga ttgatgaagc ttttggacaa   35520
ttccagcgtt attatcgtga tggcgaatat accaataatt tcatggcctt ttcgcagatg   35580
atggtgataa caactgagat tgaaacgcgc tactttgcca cgccaaaaac aattaatgac   35640
ttcaatcctg cctttgtctt tcactggtca gacagaaaga ataagcgcat caatgactgg   35700
aaaaaggtgg tagaacactt tttgatgatt ccaatggcgc accaaatggt cggtgattac   35760
ttggtcattg atgaagccaa ggaagaagaa aatcgtaggc acatgctcat gcgtccttat   35820
caagtttatg ctcttcaatc catagaaggg gcagcctttg gttgggataa tgacgaaaag   35880
attccgcatg gcggctttgt ttggcatacc actggttcgg ggaaaacaat caccagcttt   35940
aagacggctc tatttctatc tacaagagca ggttttgata aggtcatttt tcttgttgac   36000
agaagagagc tagacagccg tactggggaa aatttcaaag catacgctgc ctacgaacct   36060
gtagatgttg atgatactcg ctccacttat cagctgaaaa agaagctagg gacagtcaaa   36120
aatggtatcg ttgtaacgac tacttttaaa ctaaacaatt tgattgaaga tttgaaaaag   36180
aatgaagact acagtctttc agagaaacgc tttgttttta tcattgatga gcccaccgc   36240 accaccatgg ggcagatgat gggaactatc aaagactatt tcagaaaaaa tggcttgttc   36300
tatggtttta cgggtacacc ccttttttgat gaaaataagg ttaaaggcaa aataaataaa   36360
aagagtgaac tcatcaatac gactgaaaaa ctctttgggc ctgaacttca tcaatatacg   36420
atagaccaag cgatttctga cgggaacgtc cttggtttcc acgtggatta catcaatacg   36480
ggtgaattca gagttatga agatttgcgt gaacaactgc aagataaggc tttaatagag   36540
aatccagatg tcgataagaa agaacttgaa cgtaaatatg cagtgatgtc cgagctggaa   36600
gtggaaaaag aagcagctaa gcaagaaatc ttgatttatc aagatgaaac acatattcca   36660
```

-continued

```
cgggtagtga cagagatttt agagaactgg gaaagtcagt ctcaaaatcg tgagtttaat   36720
gcgatattga ctgttgccta taaaaagcgt gtgatcgact attataaaga gttcaaaaag   36780
caactagctg aacgtgatgg aagtttaaat attgccatga ctttcagctt tggcaatgaa   36840
aatgatccag aaaatccagc acctaaagaa gctgcgatga tgtttaaaga ttatagccaa   36900
tttacaggca ttgaatttat tgctggagac aagaagcacg gtgaagatgc ttattttgaa   36960
gatgtggttg agcgtgcaac acgaggaggt agtggacgaa atcctaagaa tatcgaccta   37020
gtcattgtag ctgatcagct tttaacaggc tatgactcta agcgcttgaa taccctgtat   37080
gtggatcgcc ctttgatgtt gcaaggacta attcaagctt actcaagaac gaatcgagtg   37140
tttggaacag ctaaggagtt cggaacgatt attaactttc aatatcctag gataaccgaa   37200
gcgaccgtca atgttgccct aaaactttat ggcagtggcg gaaaaagtag tcatgcaatc   37260
gttgaccatt atgacattgc agtgagcaaa ctgaatctct tgcttggtga tttggtgtta   37320
accttgccag aaccttcgga gtgggctgat ataaaggatg atgaggataa gaaagaggag   37380
ttcaagcaag ctttctttgc ggcaagcgac caaatgaatt tggtgcaaca atactatgag   37440
tatcagtgga atgatgaaat ctttggtatg actgaacata cttggcttca gtatatcggt   37500
gcttataaaa acctgtttcc aagacaaata ggaccagatg aaccgtctat aataagacag   37560
ctccaaggaa agacaaaact gacgaacatt caagtgattg atgctgctca tattttaagt   37620
ttaatcggtg caaagttgg ttctacgaat ggtattcaga cagtcgatga agaaacaaaa   37680
cgtattattt acgaacaaat tcaagatcta agcaatatgg gggaagccgt aactgctaag   37740
ttacttcgtg aatttgtaga gaacgagtta tttacggggc atctttcttc tagcattgac   37800
tttgatgaga cttttgataa ttggaaaaaa gaaaagttgc aagaaaaaat tgcagaattc   37860 gctgatttt gggggataca ggataaggat actctaatta ggtctattta ttcgtattca   37920
gatagtcagc cagagattgt cccttacatc gaggaaataa ataatagcgt taacatagaa   37980
gcagctcaaa ataaagattt taaaggtcga ctaaagcaca ttatagagtt aggaaaagca   38040
cttcctgact ggatgcaaga agtaaaaagt agactatcat aaaaattcaa ggtaagtagg   38100
tttgatttac accatacaag cacacgaaat acaaagaatt gtgagaataa cagtccctat   38160
aacagaatag aacaatagtt aattgttaag gaggagagat ttcgcaaaat aaaatctgat   38220
tcaaagcgag tcagattttt taatttcatt tgcataatca agtcacttac gtatttttta   38280
tataaaaata aaggcaaata aatatagcca cgctgtgcga aaccgatttc ttttgatata   38340
atcagagata gaatatggtc aaaatgatca catcataaag gagtattgaa attgagcaaa   38400
gtaaaatgtc cgaattgtgg cgctgaaatt gatattgacg atattttggc gcaagatatc   38460
aaggctcagg tagttgctga gagcatgaaa aaacacaaca aagagctcga aaaaattaaa   38520
attcaagctg agaaagcagc caatgatcag ttagccgcta aattagaact gcagagcaa   38580 aagaaaaatc aggaacttga ccttgaacgc gaaaaaatta aggcagaatt tgaaggaaaa   38640
tccaaaaagg aacttcaaga acgtgaactc gccatgaagc aactcaccaa tgatgcggaa   38700
actgaaaaag cggataataa aaagcttcgc gaacaattgt cggaaatgat ggatcaactt   38760
cgcgaagaga aaaatctcg cgaaaatgtc gaactggaag ctaaaaagaa gctttctgag   38820
gaagaagaca aaattcgcga agaagctaag aaaaaggcag atgaagagca tcgcttaaaa   38880
aatcttgaaa tggaaaagaa acttcgcgat acacaggaag ccctcgcgac tgctcaacgt   38940
aaagcagagc aaggttcaca gcagaatcaa ggtgaagttt tagagcttga tctcgaagaa   39000
agtttacgtc aagaatttcc gcttgatgaa attaaggagg tcaaaaaagg agttcgcggt   39060
```

-continued

```
gcggatgtga cgcagattgt taaaaacaat catcttgaac aatgtggcat tatgctctat   39120
gagagtaaaa acgcagcttg gcaaccgaaa tggattgcga aatttaagga agatattagg   39180
gaggcgggcg caagtattgg cgtgttggtt tccaaggaaa ttccggctga ttatggagaa   39240
atgaaaaaca ttgaaggcat ctgggttgta aaaccgaagc tagttttggc acttgcttct   39300
gcgatgcgca atcaaataat ttctgtatgg acagccaatc ataataacga aaacaaagat   39360
gagaaaatgg aaattcttta tcaattcctt acaggcacag agttcaggca ccgtgtggaa   39420
gggattgttg aaaactactc aactttacaa aatgatcttg aacaagaata tcgactcgca   39480
accaatcgtt tccataaacg tcaaaagatg ttacgtggtg taattgataa tacaattggg   39540
atgtatggtg atctgcaggg aattactggt ggtgcgatga gcgagattaa gcaattggaa   39600
gagccagagg aaaattgagt tgatttagaa taaaaagagg attatagaca atgatttcag   39660
acgatataac tacttgggta aatacattac cctattggca aagactcatt tctgacaaaa   39720 ttttttcattc tgttttgatt gatgaagacg ttatgaatga aatttataat gtatttaaga   39780
ttgaaaacaa gttgatgcaa ggtaataatg aaactttgat tttagagcca acgcagtttg   39840
atgatatcca acctgatgaa actgtcctgt ggaaaggcat agaggacgtt aaaggaatta   39900
atgctttatc agataatcag aaaataaata ttggaaatca actaacgatt atttacggga   39960
aaaatggctc agggaaatca ggatatgtaa gaatatttaa taacgccttt gtgtctagag   40020
gagacaagag tctactccct aatatctact cttctagtag tggtaagcaa agtgcaaagt   40080
tattatttga agtaaacgga agcaacaaaa ttgtgaactt tcctaaagac atcaaggtgc   40140
agaactattg tagaagagtt tcagtatttg actcgatgag tgcactagga gatatgacaa   40200
aggaaaatga attatcgctt actccaatag aatttaattt ttttgataag ttggcgaaat   40260
ttactaaaga aataaaggat aaatttgata atgagaaagc cttaaatcaa gttaagaatg   40320
atttttccga atcctttagc gaagaaacga gtgtcaaaaa aacgattgaa tctatcaatg   40380
ggaatactaa gttggaagat atcaaaaagg cgattaaggt ttcagatgat gaagatgaat   40440
tacttaaaaa atatactgta cgaaagaaac agctagatgc gctcaatatc aatgaaagaa   40500
taaaaaaaat taataatttg gtacaagata ttcatcaaat caaagataag ataaaagttt   40560
taagtgataa actctgcgtt gaacgaatac aaaaaatacg taagctaata gataagtata   40620
atcttcaggt ccaactatct tctgaagagg gacttaaaca atttgaaaat gaccaaataa   40680
ataatttggg aactccagaa tggaaatcat ttattgaagc ggccaaatca tattatgatt   40740
ctatcgagaa aggcaatgaa aaacttgatt attgtatttt atgtaaacaa gatatttcaa   40800
agattgattt aattgataaa tactgggcat atcttaaaag cgagtcagag ttacaattag   40860
ctcaagtaaa tagagatatt ataagtctaa taaatgattt tgaaaaattg aaaagcaatg   40920
aaatcattat tcctaaaaca aggctatatg aatatttaga actaaatcac gttaatatct   40980
tgtcagcaat tactcaattc gagggtgaat gtaaaagtca aactaaggat attatcaacg   41040
cactgaggaa aaaagaattt ggaaacgaag ttctatctcc aacctttggt aataaaaattt   41100 tggatgatat tattcaaaat ttgaatgacg aaaaagtaaa actaaattca tatgaaataa   41160
gcaaggaatc tgagactatc caaaaatttt tcaatgaata taatgctaaa ttgattgcag   41220
aaaaactttt gccaaaaata gaagattata ttttaaaaac ttcatggcta atcaaggcag   41280
aaaaatgtcg ggtttctaca caatctatca cagtaaaaca aaatgagtta ttttcaaagt   41340
atgtaacaga agattataaa gaaaagttta agtcagaatg tcaagaatta aaagtgaata   41400
```

```
ttgagattga ttctgttcaa agaggaacga ttggttccac aaagaacaaa ctatctataa    41460
aagggaaaaa cttggataaa attttgagtg aaggggaaca gcgttcagtg gcattagcaa    41520
attttcttgc tgaaacagaa atatctgaag aaaatgtttg tgttattttt gacgaccccg    41580
tttcttcact tgattatgag cgaagggatc gtatagcaaa gagattagtt aagctagcaa    41640
aaagtaagca agtggtagtg cttacccatg atttatcttt tatgcgttcc ctagaggatt    41700
tagctaaaac tgacgaagtt attcttgatt ttcagcatat acaaagactt cctaataaaa    41760
ctataggagt tataaatagt aaaatccctt ggattgggat gaaagtacaa aaacgacttt    41820
cagctttaag gctagatctc caaaacatga ccggcaacta tagaaagtgc gatactccag    41880
aaaaagaaga aaagtatgta aaagatgcaa aagcttggtg tgagaatttg agagagacat    41940
gggaaagagc aattgaagag acgttgttat gcggtgctgt tgagcgttat aagccgtcaa    42000
tcaacacgca aagcttaaaa aaagcgactt tcactaaaga attatatcct gaaatagacg    42060
ctgggatgca tgaatgctca gattgggtgc atgaccgatc attaaatttg ggagagaatg    42120
ttccagaacc agatgatcta aaaagatatt tagatagatg tgaaactttt gttggatcga    42180
acaaggctca ttaagtgtag actgtcataa ggctgaatga tgtgttgtgt tgtaaaccac    42240
ttttcttgta tatctactca aaacttgtat aatgatgggc taataaaaat gtcctagctc    42300
acaaatacga gttgggcaat gtggtgctat taataattaa gacgcttgag atttttcaag    42360
cgtttttgtt tgtatttatt tcgtaaaaac aggcaaccgc acttgggaa atttctcaga    42420 tgagttacta tacttttgac aaaataatag aaagggtgaa aataaacgaa tattcccatt    42480
ccattgataa tactaatttc tagaagtgtt gaaattgtga ttgggagtca taaattaaat    42540
tatcagattt aaaaataaaa tcacgattct aactgaatcg tgatttttgg ggctctttgt    42600
caaatcctgt gggaaaattc ttccccctct aagagtaagt caccgcggtg gcttattttt    42660
gtttcatcaa ttcatcaaaa taatccgctt cttgaagttg ctaaagcggc gaaacccgaa    42720
ggcgacgcgc ttgagcgcct tgattttgtt gttcatgccc tccacgcagc cgttggagta    42780
gggcgtgtgc agtgccaggc ggatagaagt cttttggag gcaagaaatt ggagcttttt    42840
cacaaaggtc tcgggcaata gttcttcttt caattcgtca atgatctcga aaaacttctg    42900
gtcgtcgtgc ttcctgaaag ctgtcagtgc ggcctgcaag acttcccacg cctcgtcgag    42960
cacgggtgta taagctttga gttggagcac caaatcatga ctcgacgtcc actggcgtaa    43020
gctgcgggaa taaaagcgat tttcagagca gtcgtcaaaa ttcttgagca aatagttcca    43080
atagtacttg aggtggcggt actgcgggct gtgcgtgtcg aattgcttca tctcctgaac    43140
tcgcagctgg ttgaacgcgc gggtcagttg ctggacgacg tgaaagcggt ccgtgaccag    43200
ctgagcgttg ggaaaacagc gtttgatgag cgcaccgtaa ttggcattca tatccatgac    43260
gagcattttg actttgagtc gaacttgtct tgggaacttg agaaaataag tcacgaggtg    43320
ctccaaacga cggtcatcca gcaaggaaat cagtttgtgg gtctgtccgt ccatggcgat    43380
aaaagccatt tttcccttgc aatctcctgt ggctttaaac tcatcaatgc aaagcacttc    43440
gggcagaaag ctaaaatgat cttttgtggg catctggttc aaaaggcgat aaaagctata    43500
aggcgagacc ttcaaatctc gcgctgcttc tgagattgac tgcttgcttt tgagtttcaa    43560
aataatttct tttttgagca aaacagaatc tttagtgcct ttggagacca agctttcggg    43620
caactcaggg gtcgacactt tgccgcagaa acaacatttg tagcgctgaa tagcaatgat    43680
caaaaagcaa ggaaagcaca gatattctgt gagctgcacc tttcgaggca tcatgccgtg    43740
cttatgaaat ttgcttttgt gacaatgcgg acaagcttta aaggtggctt tataggtgac    43800
```

-continued

```
cttgagctca tagcacttgc cctttttgag gggcatgagc gtctcgcttt cccaatcctg    43860
agcttgcaaa aacaattctt tcatgataga atcaaacata gcttatctct cctctgtgtg    43920
tagtgatgta cttacagttt agaggtaagt tttttatttt acaagaaaac aaaatcctat    43980
gagaatgatt tcccacagga tttattatag aaccgatttt ccttctaatg gcgaaacaat    44040
cacaaatcgg acaaaagttt tgtttacact agaagaagaa attcgtaagc aataccagct    44100
tttaatcgaa tatggtgaaa ttgaatcaga actttacaat tttattaaga atacaccaaa    44160
tattgcaaat cttcctagcc tagtaaaaaa taaatctgcc tatattactg atgatccaaa    44220
ggctaaaaat attttaaaat tattattttc agatcaagct ggtatgggat atatcaacga    44280
agaactcaag gaggaaaact tagtaaattt gcttcttaaa catgaagtta aagtttcaaa    44340
ttttcataaa tttcagcaag tgaatttaaa agttcttcaa gaaaaaggga ttataaaaga    44400
agatgtagaa acagaaattc tgaaaataaa aaatctcaat cgttttaaaa tttttcaaaa    44460
aatttggagt tacggcgtag tgtgttcccc acatgaagat ataaagcttc agagagaact    44520
aaaaaaaatg gaatctgaaa agttgataag attcagtgag aaactttttg cggaacaaga    44580
gtctgatttt cttaatttcg tcataaataa taaacttttt gataattctt gggcgataag    44640
aaataaatac gaacatggtg caccaattta cgagaataaa aatcaatatg aaatgtagtg    44700
accccccaaa tatagacttt ccactccaaa tgttagattt ttggtctaac ttttgggggt    44760
cacatcaact ttagcgagcg acgttatttt atataatgta taaatgtttg ctaccgttct    44820
taaaacggct acattagacc tgttgacgca ggtctttttt acttgtacat ttattatatc    44880
aaaataattt aatcaaataa aaactatcat ctttaatttt ttgtactaga ttactatttg    44940
tactataatg agtgaaaaag gtttgtgaga taaattagga gataagaatg tcatttggag    45000
tatttttgtt aatagcgttt gttatagtaa ccattgcaag ttttatctgg aaatatagag    45060
gactaatcta ttttgtagga atagtatttt taatttggtt attttttaaa tttttctttg    45120
tagctttaat cgtcatttta gggcttataa tagcttattt tataagaaga gtacaagagg    45180
atgagagaat atcttctgaa gctgacaggg caaaacaagc tcatcaagag gatgttgacg    45240
catggagaaa agagcaagag agaaaatatg gccctaattg gtatcaagca aatagagatg    45300
aacaaaaagc tgaagcaaat aatgctagaa ataatcaagc aactaaatta atagattatg    45360
atagacgttg ggatagtaca gacccttata ttatcttagg agtaagagaa gtttcaactt    45420
tttctgagat aaagaatcaa tataaatttc tttcaaaaaa atatcatcct gacgttgtaa    45480
ctgaagcaaa ttctgatgct attatgaaaa aaataaaattg ggcttgggat gaaattaaaa    45540
aagaacaaga aaactactaa actgttgaag tctagtagtt tttttataag ttcaaataag    45600
aattattgtt gtttctgata atattcattc attactaatt gttctaagac agtattttta    45660
gttgaatggg catattctag ttcgttaatt aattcattca tggataaatt ttttaaaaag    45720
gaaacacaag cgtttttgatc gataacaaat ccacggctta tttttattaa cataattttg    45780
tgttttctaa gttgattatt tttattattg acaagatgtt taatttcaat agtcgtttta    45840
taatcgttat ctctgagctt caaaacaagt tctaatgctt tagaattact taaccctaat    45900
atatgatgta aataatttaa aagtctgcta tgtagtcctt taatactcat accagttata    45960
cttttaattt tgtcaaaaga ataatttcta gttaaaagca tttccagttt tggagttgaa    46020
caaaataaga gtgaagcgat aatattggct tcatcttcaa atggtaaaac gtcatcagaa    46080
tattttcctg aaaattttga agtaaatacc tttttattat cttctaactt atgaaaatat    46140
```

-continued

```
aagtgagtaa gctcatgtaa tatagtgaat ttgattcgag ttaaaggcat tgattgatta   46200
ataaatatca atgttctatc tttttttaggc attgttaaac cagaagttct attcactaaa   46260
ctatcgtcta ggatgataaa atcaggattc tgtacaaggt ctttatagat aatttcattt   46320
ttttgagatt caaaaaatga aaaattaata tcgtaattgg actcaaagta taaaattata   46380
tctttaggaa agatttttga tactggtatt tgactttgag ccgaaatttg attaagtagt   46440
tcattagcta tatttagaca cttattataa acgttagaat caacaactct atattcaact   46500
tttttcatag agtaatatta tttttttccag atagaatcgt cattcaatcg ttctttagca   46560
tatttcatta agtctttaac agcttcattg aattttactt gttcatcagg ggtcatgtct   46620
tcacgttcca tacgaaaagc tccgataagc tcactttctt cttcggataa atcttcctta   46680
tgttttggct catcttgacg tccgagtaag taatctacac tcacatcaaa gtattcagca   46740
atttcattta aacgttttgt tgaaggattt gaacgtttat acgttgttaa agtatttcta   46800
ggataaccca gttctctttc aatttgattt atggattttc cggatttttt aattagtttt   46860
gtgagttgtt cgtagagcat aatttgtttt ctccaaaaaa tatttaaatt ttttttattta   46920 attgttgaca agagtagaat gctatgctac aataaatagt gtagaaaatt attctacata   46980
aaaagaagcg gaagcgcgct gaggcaactc ccactaaaat gttaaattaa taacctaaga   47040
cattattaat tttaacattt ttaaaggaga taagtcaatg caagcactaa gctttaaatc   47100
aaactttata caattgaata gctgtgtgtt atgtcacgtg gcaggtgctt gttccattta   47160
tctaacaagc tagggagag agccgatgaa tgcaccccga taaccgaaag gtcgtattgt   47220
cgtgagacat tctgaatata ccgtttaagg gggagtatgc tgtcaatgag agacactata   47280
ttctctcttt taatttaaat atgaacaaat aaagtttaaa taattgtccg agatgacaaa   47340
aactagtcgc ttaaactgtc agaaatggca gttttttatt gtagaaaaat aatggtttta   47400
gtaaaaatct atcttaataa atttaattcg cttagggact tgttgatact gtccttagga   47460
aatttgattt ataactaaga tagatttttt tatgggaata taatttaata ggctagagta   47520 attacttttta taagtaatgg tactggttca attccagttg ttcccttaat gaaaaaagaa   47580
tggagatttt atgggaagtt tttctgaaag gttaattcat ttaagacaca gcaataattt   47640
aacacgacaa caagtgagag acagtttaaa tattaataat gtatcaactt ataatcgttg   47700
ggaaaatgga agtagaacac ctgataatga aacgattgta agatttgcta attttttttaa   47760 atttactcct atgtatatgc taggattagt caccttagaa atggtgagga atatttacta   47820
gatgttttag aaaatattga atctgatgat actgttgaag ggttgaaagc aaaagctggt   47880
ttagcataat atcgaaaaaa ttacatgtag taatatatgt gttacgttaa tcaagaaata   47940
aagaaacaat gttaatcaac tttaacaaac tgcttgactt gtgatataat aaacttaaat   48000
tagactaaag ataggaatgt atttatgaat aagaatttga atcttttgaa ttggactaaa   48060
aaacagcaaa ttatcggtgg agcagttacg attgttttaa tcggtggtgt tactactgga   48120
gtagtcgcta atgctaatca tcaagcaaaa gaaagaaaaa ttgaagcttt aaaaaataaa   48180
aaaattaaac tttgtaaggc tagagccgaa aaagtaaaac agctttaaaa atctaatgaa   48240
gcagacagta aaaaattact tgatattgct gaaaagactc ctactgacaa aaatattaaa   48300
ctagctgaag attcaattct taaagttaaa aatgctgaag taaaaaaagt gtttgataat   48360
caagtagttg gtattaaaaa tcgtgtgaag tcagaaaatg aagcaaagac agccgttagt   48420
aactatcaaa aagatgctat gaatcaaaat aaatataaaa cggctcaaca agcaatatct   48480
aagctcacaa gctcttattc aaaaggtttg aaagatagct tgaataaaac aacttgcgac   48540
```

-continued

```
ttctaaaaaa caagcagatg acgctacaaa agcacagcaa gctaagagtg agagtgattc   48600
aaaagctaag gcaaccaata ctaataaaga acaatcagct tcaactggaa gtgcaactaa   48660
caataatgct aatgttgatg caggtactga ttcacaaagt acagtaaata atgatgttgc   48720
tagtggttct aattcttacg gtggaggaag tcaaaataac tattctcaag gtggttcaaa   48780
tacttctcaa aacaatacta attcagggtc aagtaatcaa ggtcaaggta atagcggaca   48840
aaataattct aatacaaaca caaatacagg cggtaatggc tcgaatacaa ataataatgg   48900
gtcaaatggt ggcaataaca ataataatca gccacaaaca cgatatgttg gttgggtatc   48960
agttgacgga gtgagaagat attctcaaac tttcaatact ttaggtgaag ctcaaagcta   49020
tgtagatgct acggtaaatt cagctgaagt tattaattta ggatttgaac atagtataag   49080
atatggtgtt gagcctgcat aaaatatttt atttatttaa aaaaatcact ttcttaaatg   49140
agagtgattt ttttctttta gcgaacgaat tagtacggtt gaatggggtt caagtcccca   49200
cgttcgcatt aattgaccga gatgtcgtta aactaataaa gaaaggtgga aatatgatta   49260
aaattccaat taacgcaacg aaactcttag gttcaaaagt tactgtcgat aagaccattg   49320
aaccagtcgc aaaaacatct actgaatcag gttatacgaa atatcgagct acaagtccgt   49380
tacaaccgca aggttttgaa ttacgtgtac caaatggtaa aggggctaaa cctacacgcc   49440
gtcaagaagt tgttttgaca gatgtcacgg ttgcttatgt tcgtaatcgc acaccaaagg   49500
gcaaatattc acaagaatat gttgtttatg ctgaagcgct caaattagcg taattatagg   49560
gggggaatta aatgtcgtta aaattaagta aagttttttga aaaagaaaac aagttgactg   49620
aagaaattgg tgattttgac aaagcattag gtaaagtttt gttcttgcat gctgaaccag   49680
taatggtctt tgaggacgga gaaccaaatg aagaaactgg ggaaatcaaa cgttatccaa   49740
cggacaaagt tgattattat gaggtcaacg tttattctga cgcacaagac aagcaaattg   49800
ttgtaaaaat gcctgctgaa gctgattttt cagggcttga atatgaagat gaaattaaat   49860
tgacgaatcg ctcaattaat ttttggtctg ataaagaact cataccctact ggaaacggac   49920 agttccgaac gaattacttt tcaggtgaaa aatggaatgc tgacgggatt gaaaaattag   49980
gtaaatctaa ttcaaaacct gaacaatctt caaagcctga agctaaaaac aatgaaccga   50040
agaaatgata aatggtaaaa cgtacaataa ataaaggctc tcgtttaaaa cttagagata   50100
agtatgaccg tgaattttttt gtattgatta ctggtttact tgtcgctagt cctgtagggc   50160
tcttttataa aaaatttgaa accttgccat caaaagtact agcaatttat gctgtaggta   50220
ttttgctcat tgcattttcg gtggcttttg gtttattgat tttgctttat cacaagtttc   50280
ttttcttttc aaaaaacaat tataaaagat tgttgctgaa ctatgttgtg aagcatggtt   50340
tagttgaaaa agaaacggtt aaagatgaaa aaggaagtca tgaaaagtta aaactagcgc   50400
ctatttatct gaagcaacct aacacgtatg aattacatac atattttccg attgacggtg   50460
gagttcatca agaaaaattt cttgatttag ctgacggttt agaaacaact tttttttgctg   50520 attatcaaga acaaaatttt attaatgaaa gtaaaattct ttctaaaaaa gcatttgttg   50580
agtatgtttt tgcaattgac ggagaacgta tcgtattcc agttaatgat gttatagttg   50640
ataaaaagct aggtttaaag ttaatgaatg gggtttattg gaattatgaa gctgaccac    50700 atctgcttat tgcaggaggt actgggggcg gaaaaacagt tctttttgatg tcgatttttat   50760 cagcccttgc aaaagtaggt cacgtggata tatgtgaccc taaacgttct gactttgtgg   50820
gaatgagaga tgttccagtt tttgaaaatc gtgtgttctt tgataaagag tctatgattg   50880
```

-continued

```
agtgtttacg ctcaaaaatg caatttatgg acgaacgcta tgattatatg acaaatcacc  50940
ctgactataa ggcaggaaaa cgatattctg attatggttt gacacctgaa tttgttctttt  51000 ttgatgaatg ggctgctttt atttctagtt tagattttag agaatttgat gaagtgattc  51060
aaattttaac tcaaatcgtt ctaaagggac gtcagtcagg ggttttcttg attcttgcca  51120
tgcaacgtcc agacgctgaa tacctcaaat cagctttacg tgataacttt atgaaacggt  51180
tggcggttgg tcgtttgact ggttcaggtt atcgtatggt ctttggtgat gaaaatgaga  51240
aaaaagtttt caaatacatc aagggtaaaa ttggtcgtgg ttatgtcgct aataatggtg  51300
aacttgcacg tgaattttat agtccgtctg tgccatttga taaaggctat gattttcatg  51360
aggaactttc aaaattacca attttagctg atactactga agttcagctt gaagctccac  51420
caatttctaa cgttgaacag gaacgagcag aaagtggggt tttggaagaa aaatcttata  51480 cgattaccctc tttgtctcgt aagttgggtc aaccgtcaaa aactgtgaaa acagccatag  51540
agcgtttaat atgtgacgga tattctatag gtgaaaaatc accttacaat gaagatgatt  51600
ttattgcttt acaaactgtt ttcttaacca aagaaacaga agaatgtact ttgaatgaag  51660
ccattgatac tgtcctagct gatgaatcag agtttgaaaa agaatttgtg acatttgata  51720
aatctgcatg agattttttgc ttataattta tattttgata tactatttta tataggggta  51780
taaataatga gtgatacatg tactatttca ttttttaattg gtaatggttt tgatatagca  51840
atattgaaaa gtttagataa gaattttact acaacgtatg gagaatttta tgattatttg  51900
gcttattttc ttactaataa agaaaatgat atttataagg ctattgataa taaaaagaaa  51960
caattctcaa ataatgaaaa tgaaacatgg aaagattacg aactttttatt aaaagaggtt  52020 gtatgtacga aattaataga attaaaacaa tatactgata atgcattgca ggaaaaagta  52080 ttttttatcat ttttagaaga ttggaaagaa atacaatata catttgctaa cttttttaaat  52140 catgttatta ctccgcaaac attgatggat gtaacagata tggatggtaa aacgacttta  52200
caaaaatttt tgggcgactt gcctatagaa gagtataaaa aaaattgagt ttccccaaaa  52260
aacagataac tatattaaaa ttgattatca tattttttaat tttaattatt ctacattagc  52320
agataattat ttttattggt tatttaatta ccacccatat aatgtttcaa aaaataattc  52380
acatttttat ccgaatccta gtaacatttc aggggggaaag acctcaacta atagtgatac  52440
taactatttt attcgttcaa gtattaattt tcaccaccct cacgggcaac tatcaatacc  52500
agagtcgata ttgtttggaa tgagctataa taaaaaaact tattgtaatt ccaactttga  52560
aggaaaatta tctcaaaagt tagataaagc atattggagt atgcatacag acaaagtaaa  52620
accatttata caaaaaacag atttgttcgt tatttttggt cactctattg gagaatctga  52680
ccaatgctgg tgggaagaaa taatagacca gttaaaacag gggagtgaat taataatata  52740
cgactatgaa gggaaaggtc ttaagaagaa gatactacat tattgtaagg atgatgaaaa  52800
ccttataagt gacaggatat ttgtaattga ctttgatgaa actaagcatt taaagtattc  52860
atttaaattt taagaagcgt aaatttacgc ttttttatttt gattttatat ttctacctgc  52920
aatcggcggt gagtaaatga taggaacttg tttccgtttg tctttagaca acttgccgta  52980
ggcaagtcat tttccacggt cgaattgcct tcgcaaacgg tagtgcgcga tagcggttta  53040
ttcttgaaag aattggagga aaaactttttg gattttatttt taaggctatt gcgtttttaaa  53100 cgtaatgctt ttttttgaaaa agtgcaagaa cgtaagcata gctccgagcg tagcgtaagg  53160
agtgagcgtg tgattgcacg gctgacggct tgcctgaccc cccaaatgct aatgaggggg  53220
ggtacaagtg atacaagtct aactatccta gtcatatcaa ggctttaggt tgtatcacct  53280
```

-continued

```
ctgacttatg tttagaaagt gaggaacgaa cgattgaatt aaaggatata cgctctagcg   53340
caaatgttac tcaacaattc atggctgact tacttggtat atctttagtc tattatcgaa   53400
aaatggaaaa tggcgaccgt ccactctcta aacaatttga agaaaaaatc agaaattctt   53460
ttttcaaaaa aagagagagt tcgacggtct ttgtgggtac aaatgactat acaaatattc   53520
gttttcagac tctaaatgtt cgtgaagtag tttctaagat tttaggttta aacgttgaga   53580
attttcagct caatgagtat aaccgttatc aatacccttt ctatattagt tacggtcaca   53640
ttaacgttta ttatcacgat aaagatataa aagcaggtgt gctaattgaa atgagtggta   53700
aagcgtgccg tgaaatggaa tatgagttta aatatcatca aaaacagcgt acttggtacg   53760
atttttttaa cgattgtttt ctctatgcca ataaaaaagc accagataat gatgattttg   53820
taaaaatcac acgttttgat ttagcacttg atgaacaata taatccgcaa gaaggaaatt   53880
ttgatttgtt caaactttta acttctgccc gtgagggtcg gtggaatggt cgcaaacaaa   53940
actattctgc ggttcttggt ggaagaagga caaagaagg aatgattaat gacggtctaa    54000
ctgtttattt tggatctaaa caaactcatt tattttttcg gttctacgaa aaagattttg   54060
agagagcaag tcaagaaatg acttcggttg aagcgatacg tgaaatgtat ggtttgcgaa   54120
atcgttatga aatttccatg cgaaaagaaa tatcaaccga ctttataaaa agatatatcg   54180
aggaagattt tgatttagcc gatgaagggg tcaaaattat taatgataat ctgacatttt   54240
atgataagga aggaaactta gatagtgaat ggtacgatat gatgggtaga atggatgctt   54300
atcattttac tgttcgtcct gaagtgcctg atttgaaccg aaaatataca tggtttgaac   54360
gtggtgggcc tgtatcaact tatctattgt taaaaaaagc tgaagaactg acaggtgaaa   54420
gtcgtttgga agaaattttt aatgaagcag aactcacaga aagacaagaa aagttcttga   54480
aggaatttag aatgataagg ggtgcaaatg gatagcttat tcaaattgac aggttttcca   54540
gttgatgaaa tagtaattaa agttatcgta gctattattg tatttgtggt tgttattgca   54600
atacttgcgg atatatttga ttgataatta gttaaaggag gagagagggg tgattagacc   54660
taatgtagaa cattttcaaa aaagaatgtt aagagttcca aacaacgtcc gaatgctcca   54720
gtataaaatg agtggatatg aatttaattt gaaaaaattt gagcagggag tttatgacca   54780
gctctttttt tatattccaa atgaaactga agcgttggga ttgcttaatg aaataggctt   54840
gatgtttccg cctgattcaa tgacacgtaa aaaatattat tcactctatc aagataaaaa   54900
aattgcggat ttgcctgaag gctataaaat ggcaatttat tttttaattg ataatgattt   54960
agcacaagtc actttatgat ttttcataaa taaaaacaaa gttatttttc ggataaggaa   55020
aggcaaattt tgtggtggga aataaaaaaa gaaaagagat aaaatatgcc aactttaaaa   55080
acagaactta accaaattac aactgattta aatgaaattg aagctgttat caatgcagaa   55140
aatgcctttc aagatgctgc tcaaaagctc aaaggaaaag ggaaagcgct ccgtattgta   55200
gaaaatgata cttctatttc agatgataca gtcgaagtta ttgcgaaccg tacaaatgac   55260
ttgattagaa atcttgtcaa ggcttcatca tcatacaatt tcacaaagaa atcatttaat   55320
gaattaaaag aaaactgga agaagcgcaa gcgcaagcac gtagtagcgc taaataaata   55380
gtccacgtaa atctttgaaa taagggtagg gtttgccttt ccttatctga aaagtaacaa   55440
tgttaaaagc ctcactcatg gtaaggcaag agaaaggata ctcaccatga gtgagaaata   55500
gaaatatgac agtaacaaat atgagcaaag cacaaccaca gattgatttt tcacttcaca   55560
aagcaccata taaagatttg tatgatatac aaattctttt tcctgacggt acaaatcaat   55620
```

-continued

```
tttggtctgg aattaatgaa aacaaagtaa tgtggctgtg tgagaaatac aatcctatct   55680
caactccgct gtcaattgcg attgctccta gattttttacc aaaatctaat attcaaaaac   55740
ctaactggga aattagaaag ggttagaaat gaaaaaagat gattctttat taaaaattat   55800
aatagtgttt ttgctttcgt ttttgtgtct tcctagacag attataacac actcatttgt   55860
gtctactttt atagtatagc tccaaaaatg aaaaaaacaa aatataaatc aagaactccg   55920
ccaaattatt ttggtgagat attattttaa attgaaaaaa gaggtgaaaa tgtacgttgt   55980
aaaaatgcgt ggtggctatc tttgtgccaa tggtggagcg actaaacact taaaatttgc   56040
tactactttt gatactaaga ggaaagctga agaagtggct gaaaaatggt taagaagtga   56100
tgtatctttt aaagctgttg aaaaagaaag tgaggaatat gagcaaaatt aaaatttatg   56160
aattagctga caagttaggg gttgagcgaa aagagttact ctctaaggct caagaatttg   56220
gaatttcagc taaatcaaca tcaaaatctt tgagtgacgc tgaagtatta aaactagaaa   56280
atttctataa aaaatcagat actcaagaag ttgttggcga agaagaatct gaagtggaaa   56340
caattgatgt tcctaaaaaa aaggaatcga agttttctct ccttgcaggt agaaagcctg   56400
aaaagaataa gccaaaaatg ttaaggaagt tgcccaatga aacaccgcct aagcttaaaa   56460
ggatttcagc taaacaggta ggggctttgg ttgtgggtgg ggtcggtttc ttaatattgt   56520
caaacgtggt cttgtttggt ttgatggcaa gtggatacag accaacacag aaaattattt   56580
atcaagaagt gagtgctacg caaaaagctt caggtaatgg acttgattta caagcgaaaa   56640
attatcttga tggatttgtt caaacttatt tcactttccc tgaagatgaa aaagaccaag   56700
aacaagcagt taaagatatt aatgcttact ttgttcaaaa tctaccagtg attagtcaag   56760
gcattcaacg tacaccttct aaatttgagg gtgcggtcat gatgagtttg acggataatg   56820
aagcgactta taaagtgact tatagtgcag gtgaagtcac aacaaaagaa gtcaaaaagg   56880
ggaaagatac aacaaaacaa aatgtggtga aatatcatga tgaaacaact ttgtttacga   56940
ttccttacca aaaagtaggt tcagcttact atatttcaga tgaaccttat ttttcaagtg   57000
ttcctgattt acaggcaaat gaaaatcaag tacctactaa aacatggtca ggtactgata   57060
acaatagtgc ttcagtcaaa aaagatttag acaagttcac aaaatcattg tttactgctt   57120
atacaactga cggtgataca ttgaaactaa tttcaaaagg gctttcgctt aataaggggc   57180
aagagtttaa atccttagac caagccactt atgaatcaaa aggtgacaat aaatatcatg   57240
cggtagttca agtcaccatg aaaaatgcac tcggaacaca cgtagaaaat tatcaattta   57300
caattgaaaa acaaaagcag tcatattttg cgactgactt taaacacact ttacctgaag   57360
gtaagaaaga ataggagaaa tcaaattgaa agagatacta attaatcata tcagcgtaac   57420
ttatggtgcg attggattga caggcttttg gaactttttc caagaaaatg caaaatatgt   57480 cattttttgca ggagggattt attttgcagg taaagaatgg caaaagaagg caacaggtaa   57540
aatgataatg atgattgttg ttgcagcagt tttgtttgtt ctcacactag accctcaaac   57600
ggttttacaa ccactcggtc aaaaactatt tgaaatgatt ggtgctaaat aaaaaggagt   57660
tatgattgtc aaaagaaaat aaaaaaggac tgaaatattc taataaaagt tcactttctc   57720
aaccattaag aatccaaaaa cttttttgaag gatggtcgct aggtaaggct tggcggttgt   57780 cctttttttat ttactttgga ttgattggtt ttgctttgtg gaaactttta ttttcaaaat   57840
ttactgtttt tcctgttggt tttcgattaa tggtgctagg gataatttgc tataaaagtg   57900 cattattat ctctgaaatt cgtcctgacg ataagacacc acctgtttat tttaaagata   57960
tgattgtatt tttatttaac tttggattta caggaaaaag catacataag ggatggattc   58020
```

-continued

```
atccattaag aaaaggaaaa gaggaattag aagaaaaatg aagaaaaaag caatatggga   58080
aaatcacgta ttatcggtgc atgataattt agttttaaaa gatgatggca cagtatttgc   58140
aatgtttgaa gtgcctgcgt ctattatatc aatgatggat aataaaggaa aagaggcaca   58200
caaacaagcg acacaagcag tcattaccag tttatacgaa aatttaggct ttgaaatttt   58260
agtgaagcca cttttcaaaag atttacttaa atcatatgaa gtattattaa aagattgcga   58320
ccctagaact cgtgaatttg gagagtatct attagagcag tcttattcag aattaatgaa   58380
tgaattagga aacttacatc attataaatt cttttttaact gttcctttga gtgatttctc   58440
attttcaggt gatttaagaa aaatgatgaa agaaggctgg caacgtttcg gaaaatctgt   58500
tgtaaatttg attcgtagag aattagaatt caatcttaat tggtatgaat cctataaaca   58560
aacggcttca gatttagaaa tgaatttaaa tttacttcag gctcgccctt tgaagagaga   58620
agaaacgctc ctttataatt cacttaatta tatacgtggt attgaagtca ataaagatga   58680
agtgttagct gatgttaaaa atgccattga aaatatggat gatacaacga tagatgttcg   58740
ctccgatgga ctattagaaa ttcatcatcc acaaggaagt agcctattaa aattcttacc   58800
attggctgat tatccagaag tggttaataa tattcatctt atcgaacact tgcaaacttt   58860
accatttcca gttgaatttc gtatcaaggc tcgatttaga aaaaataaag gggctttagg   58920
aatggaagct accgcagaga gaaatcgaga tagaattggt acggaacttt cagaagcaga   58980
tgaaaaagga aatgtgacaa aatcttcatc tgttggtgcg tatatgattc ttgaagatat   59040
tatttctggg gtagataatg gggaatattt cctagacttc ttacctgttt ttgcgattac   59100
tggttcaact cctgaagaaa ttaattatta taagaagatg ttaatgactg ccatggaagg   59160
tttaggagtt aaaattgttc ctagtcaatg ggatcagcct tatcttttt ataaaatgcg   59220 ttcaactgaa gaattgacac gttcagacag atattgggtt caaaatatga aagtgtctgc   59280
ttttgttgaa aacttgtttt ttgtcagtca aaaagtgggt tcagatattg gattttactt   59340
tggacgtgtt gaccatacca ctttaaattg ggcaggaaac tatgaaaagg caattgcaag   59400
ttcatctact ccgttttct ggaatatgtt tcaagccaat aaagaagata ttgaagggaa   59460
attaggagat agtcctcatg tgggtatttt tggtgataca ggttcaggta aatcttcctt   59520
cgcaaaactt gcatttgttt atcattccat cttaaaaggg ttgagccttt atattgaccc   59580
taaagatgag atgaaatcac agtttttata tgtgagggat aaattagaat cttatttgcc   59640
agaaatggaa gaaaaaatag cggatttagt cgctcttatt gaagatgatg aaattttgga   59700
acgaagaatt agaaatctag agtttgctta tcataagcct ttgattgatt atattaatca   59760
tattcatttt gtcagtctaa atacaaaaga taaaaagaat attggggcat tagaccctat   59820
tgtatttttg gaaagtgaac aagcaaaaga actttctaca caagttactg aagggctgat   59880
tggtacaaaa ttgactgaag atgatagatt tgaaaactca tttaactatc atttacaaca   59940
agtcattgaa agaagagcaa aaggtgaaac tgttggattg cttaatgttt ttaaagaaat   60000
ggcaaaatca aaagaagaac ttattaaaga ccgttcggaa aatatccttt caaaaatatc   60060
aggtacaatg ctagaacttg tcttttcaga aggtaaaaat ccgtcagtta gtatggacga   60120
ccacatcacc gttttaggag ttacaggact taatctagct aaatctggtg aagtaaaaac   60180
agctcaaaat aaaaatgtcag atattatcat gtatgcgtta ggtgattttt gtcgattctt   60240
tggtgcaaga aatcgagacc aagaaacggt tattttcctt gatgaaggtt ggttctttaa   60300
tacaacggat attggaaaag gtatttaat gcggatgaaa cgtgttggac gttcggaaaa   60360
```

```
taatttcttg gctttgatta ctcaaagtgt aaaagatggt tcgtctgatg aagatgatac    60420
agcttttgga acaattttttg cttttaaaga aactggaaat acaaaggcag ttcttcaagc   60480
atttggttta cctgatgatg acgaagatgt gataacttgg tatgaaaatc aaactaaagg    60540 tcaagcccctt gctaaagacc cttttcggtcg gattggtcgt gttgtaattc atggtcaaaa   60600
ttcagcattg aatgaatgct ttaaaacaac gtttagtgaa atggaatcag caaaggcggt    60660
ggcatagtga aaaagaaaat gttgttattt gtagggctat tagcattttt tatgccttca    60720
gccctgcata cttttgcgga tacaggcttt actccgccct ctactcctga tttttcagtt    60780
tcaggtgata agaatacttc caaaaatgat tcaaaggata aaacagattc atcttctaat    60840
tcatcaataa ctgacggaac gattaaacca ccaattgata atttagatga ttttggctcg    60900
gatgattctc caagtaaagt catgactgaa gcggaaagaa aaaaggcaag agcaaattta    60960
gataattata cttcttatat gtattttgat gatggaaaat ttctaacagg ttcaatgaat    61020
gcaggaatgc aaactttttt cattcgttct caatttttttg ttacaaaaac aatttatcgt    61080
tttgtgaatg cggtcaatga aaagttaaat agtgattcat taatcactcg atggacagcc    61140
caattgttcg tgacagttca aaatatttat aatcaatttt ctaaccctca acttatccca    61200
attattgcga tagctgttat tagtagtctt ttattttact ggtttaaacg tcgctttttt    61260
gaaggggtca gaaaattggc gcttgtgatg atactggtag gtctatttat taatggtggt    61320
caaaagttaa ctgaacaagt taatactgct ttaaatgatg ttacaactac tttgatgtca    61380
acggttaagg tggcaggtgt ttctgcgaaa aattctaatg atttaaaaac gacaatggtt    61440
gaagttccct ttcttttacct taattttgac aatgtgaaaa taaatgcgga tggttcatct   61500
aatatctctg aagataacat tgtcaatctt ctaacttcag gggatgataa tgacaagata    61560
aaagcgattc aatctgattt aaaagattca catttgacct cgaaaaaaat gggtgaaaaa    61620
gtattaactg ctctagcaag tattttcaat gcaatattag tcggttttat ttacctagct    61680
tttgcgataa tggctttttgt aatgagaatg tttttcttaa ttctcttact tttactgcca    61740 tttgtggggga ttctttcctt atttcctgtc tttgacgtag tgattttaag atgggcaaaa    61800
gcaacaggtg gggcattgat tatttctaat gtagtcgtta ttggtacagc tttaattagt    61860
gttttagata gtattgtttc ttctacagta acctcaatga ttgggagtga ttatttcttt    61920 atcacccttta taaaattcat tgtatatatt atcttattta agaaacgtca aaaaatctta    61980
gatattttca aagcaggaca tcttagtaat agtggtttttg caggtcgtat ggatggctta    62040
ctttcaaatg ttcgcagaaa aggctcaaat atgattaaag ctccactttt ggcaggttct    62100
tcagcaggac tggtcgcagg tttaactgct ggtcaaatgg caactggtaa ggcgaaagaa    62160
atagctaaac aacgatttac aggtggaact ggtagtttgt ggcatggtgg cttgagtaaa    62220
aaagcagacc gtaccatgaa taaaacagat aaagcaaatc ctgatactaa aaaaggtcaa    62280
aaactacagg ctaaagaaga aaaaatcaaa caacgtttgg aaaaacgcaa acagaaattt    62340
gaaaatccta atctgctaaa acgaaaagta gctgactatc gcaaacagta tcaacaacga    62400
aaaactatga ataacccaaa tcttgctcaa aagatggaac aaaaaaataa agaaaaaaat    62460
gcttcgattc aagctcttta tgataaaaat aaaactcaac ttcaagcaag agcaattgag    62520
cgtagaatgc gtgaagctgt tcctgaccaa gaaaaatcta atctatcaga attagctaaa    62580
aataagcaaa aagctttagc taaagaaaag ttagatgaaa gagcaatgaa acaatcagca    62640
ggtagaatgg ctgaaagatt tgaaaaggaa aaagtcagtc atagtagttt taaacgtaaa    62700
ccaaactatc cttgggataa taatgatacc aatcaaaaac ttaacaatcc atttgtgatt    62760
```

-continued

```
gatgaaaaat agggggtgaa aatgaaaaaa gcaattaagc ggaaggttat attagttagc   62820
cttccttttt tgttgctttt attgccaata ttagctttct tttcattatt tgttggttca   62880
aattcttctt cagatacaga tattaatatt aatacaccac agcaacaaac tgcaaaagtg   62940
atttgggata gagttctaaa agaaggtgga acgaaagaag gggcggctgc tttacttggt   63000
aataatcaag cagaaagtga acttcaacct tcaattattc aatctaatgc aacctataat   63060
gaagcaaaag caatggatac cactttaggc ggttatgctt tcggcttggc tcaatgggat   63120
agtggcaggc gagtaaactt gctaaactat gcgaaaagcc agaaaaaatc ttggacagat   63180
actaatcttc aagttgagtt catgattgag caagacggta cagattcaac gttacttaaa   63240
aaattagtca aaggaactaa tgttaagcaa acgactgaag atattatgcg aaagtgggaa   63300
cgtgcagggg cggttgatag ccttccaaaa cgtcaaggtt ttgcggaata ttggtacacg   63360
ttcatgacga ctggtggtga tagtggaact ggtggtggtt caggaattac tccagatata   63420
ccttctggtt ggactttaga taaaccaatt aatacaagtg gttatcttgc gacaagttat   63480
gagtataaac aatgtacgtg gttcacatgg aatcgagcga aagatttcgg tattaccttt   63540
ggaatgtata tgggaaatgg tgctgattgg caaaaacaag caggatatac tgtaacgaca   63600
actccgacac tccatagtgc ggttagcttt agcggtggtc aaacagtagg cggtcaatgg   63660
aacgcagacc ctgtttacgg tcacgtggct ttcgtggagg gaatacattc agacggttca   63720
gtcttgattt cacagtcagg aactggtttt agtacggttt atactttcca agtcttaact   63780
aaagcacaag ctagtcaatt acattatgtg ataggaaaat aaaaaatagt caattaatgt   63840
tcggtattaa cttagttttc acgttgaaaa ttctaaagtt tttaaagtta tttccgaaca   63900
atagaagata gaaaagagaa aaaatggaaa caccaaaaat ttttgtagta aatttaaata   63960
gttataacaa tggaagaaca agaggtaagt ggtatgaatt acctgttgac tttacaagga   64020
tacagtcaga tttactttta gatgtggcgc atggagaaga atatgcaatt catgattttg   64080
aaaactttta tggttataaa gtaggcgagt attcatcaat tcaagaactt aatgagtatg   64140
cggaaaaatt ggaggcaatt tctgacatag atcatttaaa agattttctt gaaatttata   64200
gcattgatga tattatcggc aataaagatg acttggattt tgtggaagcc gaaaatgatg   64260
aagatttggc acaagaatta attgaacaaa tgggcggttt agaagtttta agtgtagaaa   64320
cgttacaaag gtattttaac tttggtgctt acggtcgtga tttagcgatt ggtgattatt   64380
caaaaacaag tcatggatat attagagata tttaaagttt aagtaaagag caagaaaaat   64440
cttgctctat ttttttgttgg aggaaaaaaa tggaagaaaa ttataaagat aaacggggaa   64500
tttcagaatt atttgatgta cctataaaaa cacttaataa tgatttaact gaaatgagac   64560
ggactgaatt taatgtttat atattacgac caagtcataa acgtgtttat ataaatgtcc   64620
agggttataa atcttttctt gaatataagc aaaaaataag agaaagtaca atttagaaaa   64680
aagataaaag taatatgcag atatgatata atataagtgc tgtatagctt tcttttatct   64740
ttggtaaaag gaggaaatat gttttataag caacttgata gtggaaaata tagatacttt   64800
gaaaaatact ttgatgaaaa gagaaataaa tggcgacaag taacggtcac attaaaatca   64860
aaatcaaggg ttgctcaatc agaagctaaa aatagattag caagaaaaat agagcaatca   64920
aaaaaagtac caactgctaa cgagattcag gaacaaatcg ttcaaaataa gacggtacaa   64980
gaaatttatg aagaatgggt tgtaattaga aaacaagatg ttaagccagc aagttttgta   65040
gcggagcaaa tttctttaaa aggatttatc gaaaaatttt caaaatataa agtctcagaa   65100
```

-continued

```
gtgacgaccg cagatataca aagttattta atggaattag atattgcgaa ttcaacaaga  65160
aaaaatcgca gaatttacat tagaattttg ttcaagtatg ctgaaaacat cgggtatatt  65220
gattcaaatc cagctgacaa agtagtatta cctaaagtaa ggttagaaat tgaaacatta  65280
gaacgagcaa atgaaaaatt tttaagtaaa gaagaaatga gttctgtttt gatattttgc  65340
aaatcttata aaaaaaatat aagatacact ttagctatgg aatttatttt cctaacagga  65400
tgtagattcg gtgaatttgc ttctattcgt tatcaagatg ttgatttcaa aaataagtta  65460
ctaagaattg accacacttt agaatatcgt gttgcaaaat atgatgatcg agttattcaa  65520
acacctaaaa cggtaggttc gattcgtaca attagtttaa gtaatcgttg cttggaaatt  65580
attgattatt tccaaaaaaa ctgtttagat gataagtttg tttttgtaaa tgcggttggt  65640
ggaattttca gacaacctgt attttataag tttatttgtg ataattgtca aaaagtatta  65700
ggaaatgaaa gaaaatacgg tatccattta ttgagacatt ctcatgtatc attacttgtg  65760
gaacttggag taccaattaa agcaattatg gaacgagttg gtcatagaga tgagtcaatc  65820
actctgagga tttattctca tataagtggt acaattaaaa atgaaattag tcaaaaattg  65880
aaccaaatta atctctaaaa taactaacca agagactaac caagaattaa ccaaagcaaa  65940
aagaatcatg aggaagatta gggaatatca atttttgaaa ttcttctaaa aactattgtt  66000
agagactttt gaggaagaat aaggaagtat aaataaaaat                        66040
```

```
<210> SEQ ID NO 5
<211> LENGTH: 978
<212> TYPE: DNA
<213> ORGANISM: Lactococcus lactis subsp. lactis bv. diacetylactis SD96
<220> FEATURE:
<221> NAME/KEY: CDS
<222> LOCATION: (1)..(978)
<223> OTHER INFORMATION: lactate dehydrogenase (ldh) from Lactococcus
      lactis subsp. lactis bv. diacetylactis SD96

<400> SEQUENCE: 5 atg gct gat aaa caa cgt aaa aaa gtt atc ctt gta ggt gac ggt gct        48
Met Ala Asp Lys Gln Arg Lys Lys Val Ile Leu Val Gly Asp Gly Ala
1               5                   10                  15 gta ggt tca tca tac gct ttt gct ctt gta aac caa ggg att gca caa        96
Val Gly Ser Ser Tyr Ala Phe Ala Leu Val Asn Gln Gly Ile Ala Gln
                20                  25                  30 gaa tta gga att gtt gac ctt ttt aaa gaa aaa act caa gga gat gca       144
Glu Leu Gly Ile Val Asp Leu Phe Lys Glu Lys Thr Gln Gly Asp Ala
            35                  40                  45 gaa gac ctt tct cat gcc ttg gca ttt act tca cct aaa aag att tac       192
Glu Asp Leu Ser His Ala Leu Ala Phe Thr Ser Pro Lys Lys Ile Tyr
        50                  55                  60 tct gca gac tac tct gat gca agc gac gct gac ctc gta gtc ttg act       240
Ser Ala Asp Tyr Ser Asp Ala Ser Asp Ala Asp Leu Val Val Leu Thr
65                  70                  75                  80 tct ggt gct cca caa aaa cca ggt gaa act cgt ctt gac ctt gtt gaa       288
Ser Gly Ala Pro Gln Lys Pro Gly Glu Thr Arg Leu Asp Leu Val Glu
                85                  90                  95 aaa aat ctt cgt atc act aaa gat gtt gtc act aaa att gtt gct tca       336
Lys Asn Leu Arg Ile Thr Lys Asp Val Val Thr Lys Ile Val Ala Ser
                100                 105                 110 ggt ttc aaa gga atc ttc ctt gtt gct gct aac cca gtt gat atc ttg       384
Gly Phe Lys Gly Ile Phe Leu Val Ala Ala Asn Pro Val Asp Ile Leu
            115                 120                 125 aca tac gct act tgg aaa ttc tca ggt ttc cct aaa aac cgc gtt gta       432
Thr Tyr Ala Thr Trp Lys Phe Ser Gly Phe Pro Lys Asn Arg Val Val
```

-continued

```
              130               135                140 ggt tca ggt act tca ctt gat act gca cgt ttc cgt caa gca ttg gca      480
Gly Ser Gly Thr Ser Leu Asp Thr Ala Arg Phe Arg Gln Ala Leu Ala
145                 150                 155                 160 gaa aaa gtt gat gtt gac gct cgt tca atc cac gca tac atc atg ggt      528
Glu Lys Val Asp Val Asp Ala Arg Ser Ile His Ala Tyr Ile Met Gly
                165                 170                 175 gaa cac ggt gac tca gaa ttt gcc gtt tgg tca cac gct aac gtt gct      576
Glu His Gly Asp Ser Glu Phe Ala Val Trp Ser His Ala Asn Val Ala
            180                 185                 190 ggt gtt aaa ttg gaa caa tgg ttc caa gaa aat gac tac ctt aac gaa      624
Gly Val Lys Leu Glu Gln Trp Phe Gln Glu Asn Asp Tyr Leu Asn Glu
            195                 200                 205 gct gaa atc gtt gaa ttg ttt gaa tct gta cgt gat gct gct tac tca      672
Ala Glu Ile Val Glu Leu Phe Glu Ser Val Arg Asp Ala Ala Tyr Ser
        210                 215                 220 atc atc gct aaa aaa ggt gca aca ttc tat ggt gtc gct gta gct ctt      720
Ile Ile Ala Lys Lys Gly Ala Thr Phe Tyr Gly Val Ala Val Ala Leu
225                 230                 235                 240 gct cgt att act aaa gca att ctt gat gat gaa cat gca gta ctt cca      768
Ala Arg Ile Thr Lys Ala Ile Leu Asp Asp Glu His Ala Val Leu Pro
                245                 250                 255 gta tca gta ttc caa gat gga caa tat ggc gta agc gac tgc tac ctt      816
Val Ser Val Phe Gln Asp Gly Gln Tyr Gly Val Ser Asp Cys Tyr Leu
                260                 265                 270 ggt caa cca gct gta gtt ggt gct gaa ggt gtt gtt aac cca atc cac      864
Gly Gln Pro Ala Val Val Gly Ala Glu Gly Val Val Asn Pro Ile His
            275                 280                 285 att cca ttg aat gat gct gaa atg caa aaa atg gaa gct tct ggt gct      912
Ile Pro Leu Asn Asp Ala Glu Met Gln Lys Met Glu Ala Ser Gly Ala
        290                 295                 300 caa ttg aaa gca atc att gac gaa gct ttt gct aaa gaa gaa ttt gct      960
Gln Leu Lys Ala Ile Ile Asp Glu Ala Phe Ala Lys Glu Glu Phe Ala
305                 310                 315                 320 tct gca gtt aaa aac taa                                              978
Ser Ala Val Lys Asn
                325
```

```
<210> SEQ ID NO 6
<211> LENGTH: 325
<212> TYPE: PRT
<213> ORGANISM: Lactococcus lactis subsp. lactis bv. diacetylactis SD96

<400> SEQUENCE: 6

Met Ala Asp Lys Gln Arg Lys Lys Val Ile Leu Val Gly Asp Gly Ala
1               5                   10                  15

Val Gly Ser Ser Tyr Ala Phe Ala Leu Val Asn Gln Gly Ile Ala Gln
                20                  25                  30

Glu Leu Gly Ile Val Asp Leu Phe Lys Glu Lys Thr Gln Gly Asp Ala
            35                  40                  45

Glu Asp Leu Ser His Ala Leu Ala Phe Thr Ser Pro Lys Lys Ile Tyr
        50                  55                  60

Ser Ala Asp Tyr Ser Asp Ala Ser Asp Ala Asp Leu Val Val Leu Thr
65                  70                  75                  80

Ser Gly Ala Pro Gln Lys Pro Gly Glu Thr Arg Leu Asp Leu Val Glu
                85                  90                  95

Lys Asn Leu Arg Ile Thr Lys Asp Val Val Thr Lys Ile Val Ala Ser
                100                 105                 110
```

```
Gly Phe Lys Gly Ile Phe Leu Val Ala Ala Asn Pro Val Asp Ile Leu
        115                 120                 125

Thr Tyr Ala Thr Trp Lys Phe Ser Gly Phe Pro Lys Asn Arg Val Val
        130                 135                 140

Gly Ser Gly Thr Ser Leu Asp Thr Ala Arg Phe Arg Gln Ala Leu Ala
145                 150                 155                 160

Glu Lys Val Asp Val Asp Ala Arg Ser Ile His Ala Tyr Ile Met Gly
                165                 170                 175

Glu His Gly Asp Ser Glu Phe Ala Val Trp Ser His Ala Asn Val Ala
                180                 185                 190

Gly Val Lys Leu Glu Gln Trp Phe Gln Glu Asn Asp Tyr Leu Asn Glu
                195                 200                 205

Ala Glu Ile Val Glu Leu Phe Glu Ser Val Arg Asp Ala Ala Tyr Ser
        210                 215                 220

Ile Ile Ala Lys Lys Gly Ala Thr Phe Tyr Gly Val Ala Val Ala Leu
225                 230                 235                 240

Ala Arg Ile Thr Lys Ala Ile Leu Asp Asp Glu His Ala Val Leu Pro
                245                 250                 255

Val Ser Val Phe Gln Asp Gly Gln Tyr Gly Val Ser Asp Cys Tyr Leu
                260                 265                 270

Gly Gln Pro Ala Val Val Gly Ala Glu Gly Val Val Asn Pro Ile His
                275                 280                 285

Ile Pro Leu Asn Asp Ala Glu Met Gln Lys Met Glu Ala Ser Gly Ala
        290                 295                 300

Gln Leu Lys Ala Ile Ile Asp Glu Ala Phe Ala Lys Glu Glu Phe Ala
305                 310                 315                 320

Ser Ala Val Lys Asn
                325
```

```
<210> SEQ ID NO 7
<211> LENGTH: 1374
<212> TYPE: DNA
<213> ORGANISM: Lactococcus lactis subsp. lactis bv. diacetylactis SD96
<220> FEATURE:
<221> NAME/KEY: CDS
<222> LOCATION: (1)..(1374)
<223> OTHER INFORMATION: UDP-N-acetylmuramate-L-alanine ligase from
      Lactococcus lactis subsp. lactis bv. diacetylactis SD96

<400> SEQUENCE: 7 gtg att gat aaa gaa ata gaa tta ctg aca gaa aat ttt atc atg gaa      48
Val Ile Asp Lys Glu Ile Glu Leu Leu Thr Glu Asn Phe Ile Met Glu
1               5                   10                  15 aaa aca tat cat ttt acc ggt att aaa ggt tca ggc atg agt gca ctt      96
Lys Thr Tyr His Phe Thr Gly Ile Lys Gly Ser Gly Met Ser Ala Leu
                20                  25                  30 gcg cta atg tta cat caa atg gga aag aaa gtt caa ggt tcg gac tca     144
Ala Leu Met Leu His Gln Met Gly Lys Lys Val Gln Gly Ser Asp Ser
        35                  40                  45 aca gat tac ttt ttc aca caa cgt ggt ctt gaa caa gct gac gta cca     192
Thr Asp Tyr Phe Phe Thr Gln Arg Gly Leu Glu Gln Ala Asp Val Pro
        50                  55                  60 ctt ttg cct ttt gac gaa aaa aat att aag ccc gaa ttt gaa ttg att     240
Leu Leu Pro Phe Asp Glu Lys Asn Ile Lys Pro Glu Phe Glu Leu Ile
65                  70                  75                  80 gct gga aat gct ttt cgc gat gat aac aat gtt gaa att gca ttt gcc     288
Ala Gly Asn Ala Phe Arg Asp Asp Asn Asn Val Glu Ile Ala Phe Ala
                85                  90                  95
```

```
cat aaa aat gga ttt cca ttc aaa cgt tat cat gaa ttt ttg gga cat      336
His Lys Asn Gly Phe Pro Phe Lys Arg Tyr His Glu Phe Leu Gly His
            100             105                 110 ttc atg gaa gat ttt act agc atc ggg gtt gca ggt gca cat ggt aaa      384
Phe Met Glu Asp Phe Thr Ser Ile Gly Val Ala Gly Ala His Gly Lys
        115             120             125 act tca aca act gga atg tta gct cac gtg atg tct aat atc gtg gac      432
Thr Ser Thr Thr Gly Met Leu Ala His Val Met Ser Asn Ile Val Asp
    130             135             140 act tct tac ttg att ggt gac gga act ggt cgt ggg att gag gga agt      480
Thr Ser Tyr Leu Ile Gly Asp Gly Thr Gly Arg Gly Ile Glu Gly Ser
145             150             155             160 gaa tat ttt gtc ttt gaa tct gat gaa tat gaa cgt cat ttc atg cct      528
Glu Tyr Phe Val Phe Glu Ser Asp Glu Tyr Glu Arg His Phe Met Pro
                165             170             175 tat cat cct gaa tat aca att atg aca aat att gac ttt gac cat cct      576
Tyr His Pro Glu Tyr Thr Ile Met Thr Asn Ile Asp Phe Asp His Pro
            180             185             190 gac tac ttt gaa gga att gaa gat gtc acc tca gct ttc caa gat tat      624
Asp Tyr Phe Glu Gly Ile Glu Asp Val Thr Ser Ala Phe Gln Asp Tyr
        195             200             205 gca aat aat att aaa aaa ggt att ttt gct tac ggg gaa gat gtt aac      672
Ala Asn Asn Ile Lys Lys Gly Ile Phe Ala Tyr Gly Glu Asp Val Asn
    210             215             220 tta cgt aaa ttg act gcc aaa gca cct att tac tat tat ggt ttt gag      720
Leu Arg Lys Leu Thr Ala Lys Ala Pro Ile Tyr Tyr Tyr Gly Phe Glu
225             230             235             240 gct aat gac gat tat cgt gcc gaa aat ttg gtc aga agt aca cgt ggc      768
Ala Asn Asp Asp Tyr Arg Ala Glu Asn Leu Val Arg Ser Thr Arg Gly
                245             250             255 tca tct ttt gat gct tat ttc cgc ggt gaa aaa att ggt cat ttt gtc      816
Ser Ser Phe Asp Ala Tyr Phe Arg Gly Glu Lys Ile Gly His Phe Val
            260             265             270 gtt cca gct tat ggt aaa cac aat gta ttg aat gcc ttg tca gtt gta      864
Val Pro Ala Tyr Gly Lys His Asn Val Leu Asn Ala Leu Ser Val Val
        275             280             285 gcc gtt tgt cat aat ctt ggg ttg gat atg acg gaa gtt gca gac cac      912
Ala Val Cys His Asn Leu Gly Leu Asp Met Thr Glu Val Ala Asp His
    290             295             300 tta ttg act ttc cgt gga gtg aaa cgt cgt ttc act gag aaa aaa gta      960
Leu Leu Thr Phe Arg Gly Val Lys Arg Arg Phe Thr Glu Lys Lys Val
305             310             315             320 ggt gag aca gtc att att gat gat ttt gct cat cat cca act gaa atc     1008
Gly Glu Thr Val Ile Ile Asp Asp Phe Ala His His Pro Thr Glu Ile
                325             330             335 gaa gca aca ttg gat gct gca cgt caa aaa tat cct gat cgt gaa atc     1056
Glu Ala Thr Leu Asp Ala Ala Arg Gln Lys Tyr Pro Asp Arg Glu Ile
            340             345             350 gtt gct gtt ttc caa cct cat act ttt act aga aca att gca ttt gct     1104
Val Ala Val Phe Gln Pro His Thr Phe Thr Arg Thr Ile Ala Phe Ala
        355             360             365 gac gaa ttt gca gag gtg ctt gac cat gcg gat acc gtt tac ctt gct     1152
Asp Glu Phe Ala Glu Val Leu Asp His Ala Asp Thr Val Tyr Leu Ala
    370             375             380 caa att tac ggt tca gca cgt gaa gta gac cat cat gaa att acg gca     1200
Gln Ile Tyr Gly Ser Ala Arg Glu Val Asp His His Glu Ile Thr Ala
385             390             395             400 caa gat tta gct gac aaa gtt cgt aaa cca gcc aaa gta att gat ctt     1248
Gln Asp Leu Ala Asp Lys Val Arg Lys Pro Ala Lys Val Ile Asp Leu
                405             410             415
```

```
gac aat gtt tcg cca ttg ttg gat cat gac cgt ggg gtt tac gtc ttt          1296
Asp Asn Val Ser Pro Leu Leu Asp His Asp Arg Gly Val Tyr Val Phe
            420             425             430 atg gga gca gga aat att caa aaa tat gaa ctt gct ttt gaa aag tta          1344
Met Gly Ala Gly Asn Ile Gln Lys Tyr Glu Leu Ala Phe Glu Lys Leu
            435             440             445 ctt agc caa gtc tca act aac tta caa taa                                  1374
Leu Ser Gln Val Ser Thr Asn Leu Gln
        450             455
```

<210> SEQ ID NO 8
<211> LENGTH: 457
<212> TYPE: PRT
<213> ORGANISM: Lactococcus lactis subsp. lactis bv. diacetylactis SD96

<400> SEQUENCE: 8

```
Val Ile Asp Lys Glu Ile Glu Leu Leu Thr Glu Asn Phe Ile Met Glu
1               5               10              15

Lys Thr Tyr His Phe Thr Gly Ile Lys Gly Ser Gly Met Ser Ala Leu
            20              25              30

Ala Leu Met Leu His Gln Met Gly Lys Lys Val Gln Gly Ser Asp Ser
        35              40              45

Thr Asp Tyr Phe Phe Thr Gln Arg Gly Leu Glu Gln Ala Asp Val Pro
    50              55              60

Leu Leu Pro Phe Asp Glu Lys Asn Ile Lys Pro Glu Phe Glu Leu Ile
65              70              75              80

Ala Gly Asn Ala Phe Arg Asp Asp Asn Asn Val Glu Ile Ala Phe Ala
            85              90              95

His Lys Asn Gly Phe Pro Phe Lys Arg Tyr His Glu Phe Leu Gly His
            100             105             110

Phe Met Glu Asp Phe Thr Ser Ile Gly Val Ala Gly Ala His Gly Lys
        115             120             125

Thr Ser Thr Thr Gly Met Leu Ala His Val Met Ser Asn Ile Val Asp
        130             135             140

Thr Ser Tyr Leu Ile Gly Asp Gly Thr Gly Arg Gly Ile Glu Gly Ser
145             150             155             160

Glu Tyr Phe Val Phe Glu Ser Asp Glu Tyr Glu Arg His Phe Met Pro
            165             170             175

Tyr His Pro Glu Tyr Thr Ile Met Thr Asn Ile Asp Phe Asp His Pro
            180             185             190

Asp Tyr Phe Glu Gly Ile Glu Asp Val Thr Ser Ala Phe Gln Asp Tyr
            195             200             205

Ala Asn Asn Ile Lys Lys Gly Ile Phe Ala Tyr Gly Glu Asp Val Asn
        210             215             220

Leu Arg Lys Leu Thr Ala Lys Ala Pro Ile Tyr Tyr Tyr Gly Phe Glu
225             230             235             240

Ala Asn Asp Asp Tyr Arg Ala Glu Asn Leu Val Arg Ser Thr Arg Gly
            245             250             255

Ser Ser Phe Asp Ala Tyr Phe Arg Gly Glu Lys Ile Gly His Phe Val
            260             265             270

Val Pro Ala Tyr Gly Lys His Asn Val Leu Asn Ala Leu Ser Val Val
            275             280             285

Ala Val Cys His Asn Leu Gly Leu Asp Met Thr Glu Val Ala Asp His
        290             295             300

Leu Leu Thr Phe Arg Gly Val Lys Arg Arg Phe Thr Glu Lys Lys Val
```

-continued

```
305              310              315              320

Gly Glu Thr Val Ile Ile Asp Asp Phe Ala His His Pro Thr Glu Ile
             325              330              335

Glu Ala Thr Leu Asp Ala Ala Arg Gln Lys Tyr Pro Asp Arg Glu Ile
             340              345              350

Val Ala Val Phe Gln Pro His Thr Phe Thr Arg Thr Ile Ala Phe Ala
             355              360              365

Asp Glu Phe Ala Glu Val Leu Asp His Ala Asp Thr Val Tyr Leu Ala
             370              375              380

Gln Ile Tyr Gly Ser Ala Arg Glu Val Asp His His Glu Ile Thr Ala
385              390              395              400

Gln Asp Leu Ala Asp Lys Val Arg Lys Pro Ala Lys Val Ile Asp Leu
                 405              410              415

Asp Asn Val Ser Pro Leu Leu Asp His Asp Arg Gly Val Tyr Val Phe
             420              425              430

Met Gly Ala Gly Asn Ile Gln Lys Tyr Glu Leu Ala Phe Glu Lys Leu
             435              440              445

Leu Ser Gln Val Ser Thr Asn Leu Gln
    450              455
```

```
<210> SEQ ID NO 9
<211> LENGTH: 2223
<212> TYPE: DNA
<213> ORGANISM: L. lactis subsp. lactis by diacetylactis SD96
<220> FEATURE:
<221> NAME/KEY: CDS
<222> LOCATION: (1)..(2223)
<223> OTHER INFORMATION: GTP pyrophosphokinase from Lactococcus lactis
      subsp. lactis bv. diacetylactis SD96

<400> SEQUENCE: 9 atg cct aaa gaa cca gat tta acc gga gca gag gtt gtc aat atc tgt        48
Met Pro Lys Glu Pro Asp Leu Thr Gly Ala Glu Val Val Asn Ile Cys
1               5               10              15 tct gac tac atg aat gaa aca gac att tta ctc gta gaa aaa gca ctt        96
Ser Asp Tyr Met Asn Glu Thr Asp Ile Leu Leu Val Glu Lys Ala Leu
            20              25              30 gct tgt gct tca ctt gcc cat gca gac caa tat cgt gca tca gga gaa       144
Ala Cys Ala Ser Leu Ala His Ala Asp Gln Tyr Arg Ala Ser Gly Glu
        35              40              45 gct tac ttt gtc cac cct acc caa gtt gca gga att tta gcc aaa tta       192
Ala Tyr Phe Val His Pro Thr Gln Val Ala Gly Ile Leu Ala Lys Leu
    50              55              60 aaa ctg gat gcc gtt acc gtt tcc tgt ggt ttt ttg cat gat gtt gtt       240
Lys Leu Asp Ala Val Thr Val Ser Cys Gly Phe Leu His Asp Val Val
65              70              75              80 gaa gat acc aat ttt acc caa ggt gat ttg caa gaa tta ttt ggc gac       288
Glu Asp Thr Asn Phe Thr Gln Gly Asp Leu Gln Glu Leu Phe Gly Asp
                85              90              95 gaa att gct gaa att gtt gat gga gtt act aag tta ggt aaa gtt gag       336
Glu Ile Ala Glu Ile Val Asp Gly Val Thr Lys Leu Gly Lys Val Glu
            100             105             110 tat aag tca cac gaa gaa caa ttg gct gaa aac cac cgt aag atg ctt       384
Tyr Lys Ser His Glu Glu Gln Leu Ala Glu Asn His Arg Lys Met Leu
        115             120             125 atg gct atg tcc aaa gac att cgt gtt att ttg gtc aaa ttg gct gac       432
Met Ala Met Ser Lys Asp Ile Arg Val Ile Leu Val Lys Leu Ala Asp
    130             135             140 cgc ttg cac aat atg cgc acg ctt aaa cat ctc aga cca gat aaa caa       480
```

-continued

```
Arg Leu His Asn Met Arg Thr Leu Lys His Leu Arg Pro Asp Lys Gln
145             150             155             160 aag cgg att tca cgt gaa acc atg gaa att tat gcc cct ctt gct cat      528
Lys Arg Ile Ser Arg Glu Thr Met Glu Ile Tyr Ala Pro Leu Ala His
                165             170             175 cgc ttg ggg att gcc agt atc aaa tgg gaa tta gaa gat tta tca ttc      576
Arg Leu Gly Ile Ala Ser Ile Lys Trp Glu Leu Glu Asp Leu Ser Phe
            180             185             190 cgt tat ctt gaa gaa gca gaa ttt tat cgc att cgt ggt ctc atg aat      624
Arg Tyr Leu Glu Glu Ala Glu Phe Tyr Arg Ile Arg Gly Leu Met Asn
            195             200             205 gaa aaa aga aca gct cgt gaa gcg ctt gtt gct gaa gta att ggt aaa      672
Glu Lys Arg Thr Ala Arg Glu Ala Leu Val Ala Glu Val Ile Gly Lys
    210             215             220 tta caa gaa cga gtc gaa aaa gct ggt gtt gac gca gaa att tat ggt      720
Leu Gln Glu Arg Val Glu Lys Ala Gly Val Asp Ala Glu Ile Tyr Gly
225             230             235             240 cgt cca aaa cat att tat tct att tat cgt aaa atg cac gat aag aag      768
Arg Pro Lys His Ile Tyr Ser Ile Tyr Arg Lys Met His Asp Lys Lys
                245             250             255 aaa cgt ttt gat gag att tat gac ctg att gcc att cgt tgt atc aca      816
Lys Arg Phe Asp Glu Ile Tyr Asp Leu Ile Ala Ile Arg Cys Ile Thr
            260             265             270 gaa aca aca agt gac gtt tac acg act tta ggt tat att cat gac ctt      864
Glu Thr Thr Ser Asp Val Tyr Thr Thr Leu Gly Tyr Ile His Asp Leu
            275             280             285 tgg aaa cca atg ccg ggt cgt ttt aaa gat tac att gcc aat cca aaa      912
Trp Lys Pro Met Pro Gly Arg Phe Lys Asp Tyr Ile Ala Asn Pro Lys
    290             295             300 gcc aat ggt tat caa tct gtc cat aca acc gtt tat ggt ccc aaa ggc      960
Ala Asn Gly Tyr Gln Ser Val His Thr Thr Val Tyr Gly Pro Lys Gly
305             310             315             320 cca atg gaa ttc caa att aga aca cga gaa atg cac caa atc gct gaa     1008
Pro Met Glu Phe Gln Ile Arg Thr Arg Glu Met His Gln Ile Ala Glu
                325             330             335 ttt ggg gtt gcc gct cac tgg gct tac aaa caa ggg att aaa gca aaa     1056
Phe Gly Val Ala Ala His Trp Ala Tyr Lys Gln Gly Ile Lys Ala Lys
            340             345             350 gtt gat gtt cat gaa att tct gaa acc ttg aat tgg att cat gaa ctt     1104
Val Asp Val His Glu Ile Ser Glu Thr Leu Asn Trp Ile His Glu Leu
            355             360             365 gtg gaa ttg cgt gaa gaa gct ggt gat tca gca gaa gat ttt gtc aaa     1152
Val Glu Leu Arg Glu Glu Ala Gly Asp Ser Ala Glu Asp Phe Val Lys
    370             375             380 gcc gtt caa gaa gat att tta tca gat aag att tat gtc ttc act cca     1200
Ala Val Gln Glu Asp Ile Leu Ser Asp Lys Ile Tyr Val Phe Thr Pro
385             390             395             400 aat ggt gaa gtc caa gaa tta cca aga ggt tca ggt cct att gac ttt     1248
Asn Gly Glu Val Gln Glu Leu Pro Arg Gly Ser Gly Pro Ile Asp Phe
                405             410             415 gct tat gct atc cat aca aaa gtt ggt gac cat gcg act gga gcg aaa     1296
Ala Tyr Ala Ile His Thr Lys Val Gly Asp His Ala Thr Gly Ala Lys
            420             425             430 gta aat gga cga atg aaa cca tta tct gtt caa cta aaa aca ggt gat     1344
Val Asn Gly Arg Met Lys Pro Leu Ser Val Gln Leu Lys Thr Gly Asp
            435             440             445 cgg gtt gaa att att acc agc tca agc tct ttt gga cca agc cgt gat     1392
Arg Val Glu Ile Ile Thr Ser Ser Ser Ser Phe Gly Pro Ser Arg Asp
    450             455             460
```

```
tgg att aat cta gtt aaa act aat aaa gcc aga aac aaa atc aaa caa      1440
Trp Ile Asn Leu Val Lys Thr Asn Lys Ala Arg Asn Lys Ile Lys Gln
465                 470                 475                 480 ttc ttt aag aac caa gat aaa gaa ttg tcg gtc aat aaa ggc cgt gaa      1488
Phe Phe Lys Asn Gln Asp Lys Glu Leu Ser Val Asn Lys Gly Arg Glu
                    485                 490                 495 atg tta caa gaa gct ttg gaa gaa ggt ggc ttt gta cca aat cag tat      1536
Met Leu Gln Glu Ala Leu Glu Glu Gly Gly Phe Val Pro Asn Gln Tyr
                500                 505                 510 tta gat aag aaa cat cta gat gaa gtc ttc aat aag att agc tac cgt      1584
Leu Asp Lys Lys His Leu Asp Glu Val Phe Asn Lys Ile Ser Tyr Arg
            515                 520                 525 aat gcg gaa gct ttg tat gca gca att gga ttt ggt gag ctt tca gca      1632
Asn Ala Glu Ala Leu Tyr Ala Ala Ile Gly Phe Gly Glu Leu Ser Ala
        530                 535                 540 aca aca att gcc aat cgt tta act gaa aat gaa cgt cgt gaa gtt gag      1680
Thr Thr Ile Ala Asn Arg Leu Thr Glu Asn Glu Arg Arg Glu Val Glu
545                 550                 555                 560 aga gcc aaa caa aaa gcc gaa gcc gaa gag ctg atg aag ggt gaa gtt      1728
Arg Ala Lys Gln Lys Ala Glu Ala Glu Glu Leu Met Lys Gly Glu Val
                565                 570                 575 aaa cgc gaa tca agt aaa aac att atg aag att cgt cac gat ggt gga      1776
Lys Arg Glu Ser Ser Lys Asn Ile Met Lys Ile Arg His Asp Gly Gly
                580                 585                 590 gtc agt gtt tct ggt att gat agc cta ctt gtt cgt atc gcc aaa tgt      1824
Val Ser Val Ser Gly Ile Asp Ser Leu Leu Val Arg Ile Ala Lys Cys
            595                 600                 605 tgt aat cct gtt cca ggg gac cca att gtg ggg tat att aca aaa ggg      1872
Cys Asn Pro Val Pro Gly Asp Pro Ile Val Gly Tyr Ile Thr Lys Gly
        610                 615                 620 cgt ggt gtt tca gtt cat aga gct gat tgt caa aat gtg cga agt atg      1920
Arg Gly Val Ser Val His Arg Ala Asp Cys Gln Asn Val Arg Ser Met
625                 630                 635                 640 gaa gac ttt gaa caa aga ctt gtt gaa gtt gaa tgg gat gat tca gaa      1968
Glu Asp Phe Glu Gln Arg Leu Val Glu Val Glu Trp Asp Asp Ser Glu
                645                 650                 655 aac tta gtg aaa gaa tat gtc gct aat att gat gtc tat ggc ttt aat      2016
Asn Leu Val Lys Glu Tyr Val Ala Asn Ile Asp Val Tyr Gly Phe Asn
                660                 665                 670 cgt cct gga tta ctc aac gat gtg atg caa gtt tta tca aat tct act      2064
Arg Pro Gly Leu Leu Asn Asp Val Met Gln Val Leu Ser Asn Ser Thr
                675                 680                 685 aaa aat ttg att tca att aat gct caa ccc act aaa gat aaa aaa atg      2112
Lys Asn Leu Ile Ser Ile Asn Ala Gln Pro Thr Lys Asp Lys Lys Met
        690                 695                 700 gcg aat att cac atc gct tta ggc att aaa aat cta tca gat ttg act      2160
Ala Asn Ile His Ile Ala Leu Gly Ile Lys Asn Leu Ser Asp Leu Thr
705                 710                 715                 720 ttg att gtt gat aaa atc aaa atg acc cca gat gtt tat tct gta aaa      2208
Leu Ile Val Asp Lys Ile Lys Met Thr Pro Asp Val Tyr Ser Val Lys
                725                 730                 735 cgg aca aat gct taa                                                  2223
Arg Thr Asn Ala
                740
```

<210> SEQ ID NO 10
<211> LENGTH: 740
<212> TYPE: PRT
<213> ORGANISM: L. lactis subsp. lactis by diacetylactis SD96

<400> SEQUENCE: 10

```
Met Pro Lys Glu Pro Asp Leu Thr Gly Ala Glu Val Val Asn Ile Cys
1               5                   10                  15

Ser Asp Tyr Met Asn Glu Thr Asp Ile Leu Leu Val Glu Lys Ala Leu
            20                  25                  30

Ala Cys Ala Ser Leu Ala His Ala Asp Gln Tyr Arg Ala Ser Gly Glu
        35                  40                  45

Ala Tyr Phe Val His Pro Thr Gln Val Ala Gly Ile Leu Ala Lys Leu
    50                  55                  60

Lys Leu Asp Ala Val Thr Val Ser Cys Gly Phe Leu His Asp Val Val
65              70                  75                  80

Glu Asp Thr Asn Phe Thr Gln Gly Asp Leu Gln Glu Leu Phe Gly Asp
                85                  90                  95

Glu Ile Ala Glu Ile Val Asp Gly Val Thr Lys Leu Gly Lys Val Glu
            100                 105                 110

Tyr Lys Ser His Glu Glu Gln Leu Ala Glu Asn His Arg Lys Met Leu
        115                 120                 125

Met Ala Met Ser Lys Asp Ile Arg Val Ile Leu Val Lys Leu Ala Asp
    130                 135                 140

Arg Leu His Asn Met Arg Thr Leu Lys His Leu Arg Pro Asp Lys Gln
145                 150                 155                 160

Lys Arg Ile Ser Arg Glu Thr Met Glu Ile Tyr Ala Pro Leu Ala His
            165                 170                 175

Arg Leu Gly Ile Ala Ser Ile Lys Trp Glu Leu Glu Asp Leu Ser Phe
            180                 185                 190

Arg Tyr Leu Glu Glu Ala Glu Phe Tyr Arg Ile Arg Gly Leu Met Asn
            195                 200                 205

Glu Lys Arg Thr Ala Arg Glu Ala Leu Val Ala Glu Val Ile Gly Lys
    210                 215                 220

Leu Gln Glu Arg Val Glu Lys Ala Gly Val Asp Ala Glu Ile Tyr Gly
225                 230                 235                 240

Arg Pro Lys His Ile Tyr Ser Ile Tyr Arg Lys Met His Asp Lys Lys
            245                 250                 255

Lys Arg Phe Asp Glu Ile Tyr Asp Leu Ile Ala Ile Arg Cys Ile Thr
            260                 265                 270

Glu Thr Thr Ser Asp Val Tyr Thr Thr Leu Gly Tyr Ile His Asp Leu
    275                 280                 285

Trp Lys Pro Met Pro Gly Arg Phe Lys Asp Tyr Ile Ala Asn Pro Lys
    290                 295                 300

Ala Asn Gly Tyr Gln Ser Val His Thr Thr Val Tyr Gly Pro Lys Gly
305                 310                 315                 320

Pro Met Glu Phe Gln Ile Arg Thr Arg Glu Met His Gln Ile Ala Glu
            325                 330                 335

Phe Gly Val Ala Ala His Trp Ala Tyr Lys Gln Gly Ile Lys Ala Lys
            340                 345                 350

Val Asp Val His Glu Ile Ser Glu Thr Leu Asn Trp Ile His Glu Leu
    355                 360                 365

Val Glu Leu Arg Glu Glu Ala Gly Asp Ser Ala Glu Asp Phe Val Lys
    370                 375                 380

Ala Val Gln Glu Asp Ile Leu Ser Asp Lys Ile Tyr Val Phe Thr Pro
385                 390                 395                 400

Asn Gly Glu Val Gln Glu Leu Pro Arg Gly Ser Gly Pro Ile Asp Phe
            405                 410                 415
```

-continued

```
Ala Tyr Ala Ile His Thr Lys Val Gly Asp His Ala Thr Gly Ala Lys
            420             425             430

Val Asn Gly Arg Met Lys Pro Leu Ser Val Gln Leu Lys Thr Gly Asp
            435             440             445

Arg Val Glu Ile Ile Thr Ser Ser Ser Phe Gly Pro Ser Arg Asp
            450             455             460

Trp Ile Asn Leu Val Lys Thr Asn Lys Ala Arg Asn Lys Ile Lys Gln
465             470             475             480

Phe Phe Lys Asn Gln Asp Lys Glu Leu Ser Val Asn Lys Gly Arg Glu
                485             490             495

Met Leu Gln Glu Ala Leu Glu Glu Gly Gly Phe Val Pro Asn Gln Tyr
            500             505             510

Leu Asp Lys Lys His Leu Asp Glu Val Phe Asn Lys Ile Ser Tyr Arg
            515             520             525

Asn Ala Glu Ala Leu Tyr Ala Ala Ile Gly Phe Gly Glu Leu Ser Ala
            530             535             540

Thr Thr Ile Ala Asn Arg Leu Thr Glu Asn Glu Arg Arg Glu Val Glu
545             550             555             560

Arg Ala Lys Gln Lys Ala Glu Ala Glu Glu Leu Met Lys Gly Glu Val
                565             570             575

Lys Arg Glu Ser Ser Lys Asn Ile Met Lys Ile Arg His Asp Gly Gly
            580             585             590

Val Ser Val Ser Gly Ile Asp Ser Leu Leu Val Arg Ile Ala Lys Cys
            595             600             605

Cys Asn Pro Val Pro Gly Asp Pro Ile Val Gly Tyr Ile Thr Lys Gly
            610             615             620

Arg Gly Val Ser Val His Arg Ala Asp Cys Gln Asn Val Arg Ser Met
625             630             635             640

Glu Asp Phe Glu Gln Arg Leu Val Glu Val Glu Trp Asp Asp Ser Glu
                645             650             655

Asn Leu Val Lys Glu Tyr Val Ala Asn Ile Asp Val Tyr Gly Phe Asn
            660             665             670

Arg Pro Gly Leu Leu Asn Asp Val Met Gln Val Leu Ser Asn Ser Thr
            675             680             685

Lys Asn Leu Ile Ser Ile Asn Ala Gln Pro Thr Lys Asp Lys Lys Met
            690             695             700

Ala Asn Ile His Ile Ala Leu Gly Ile Lys Asn Leu Ser Asp Leu Thr
705             710             715             720

Leu Ile Val Asp Lys Ile Lys Met Thr Pro Asp Val Tyr Ser Val Lys
                725             730             735

Arg Thr Asn Ala
            740
```

```
<210> SEQ ID NO 11
<211> LENGTH: 73258
<212> TYPE: DNA
<213> ORGANISM: Lactococcus lactis subsp. lactis bv. diacetylactis SD96
<220> FEATURE:
<221> NAME/KEY: misc_feature
<222> LOCATION: (1)..(73258)
<223> OTHER INFORMATION: deleted base pairs 1,823,878?1,897,135

<400> SEQUENCE: 11
tttatatcgt tggtatataa ggtttttttg tttatctttt tttatttacc cctctttttg      60
ccccattatt tattgtttta attaatctct aagaattaat tatattaaat ttcatttaat     120
```

-continued

```
taacaaataa attacatttc aagctcttta tttatctttt tcttttaaac tcaataaaca      180
caagatattg agtgtgttta cataatttaa tctatatatt gtgtcatctt gtattatctg      240
ctaaaatagg tgtagaccat tgagtaggaa acttcataag ttttgaaggg agttggtgcc      300
ttggattatt gtttatttaa aaggttattc ccttatatga aagtaaatct caataatgat      360
tgaaaagatt atttgcttaa ttgagcttat tcatctttta cttgatatct ataaacttt       420 taaatagagt ataatagtta tcaaaaaaag tcgttaactc cccagtaaac gacttcattg      480
ctatgttgca accataatac tatgaaactt accaatggtt ttaaagaact tgtacacgca      540
agttcttttt ttactttgtc taaatgttgc cagtagatac tctcttaata ataaatatat      600
tagcttattt gttagcgtat ttgttagctt atttgttagc caatctataa atattttata      660 aacttttgt aaataattta gtaagtattt cagtaacact tttagtaaat gttttagtat        720
attctatggt gtaattattg tataagtaaa ttatagtata tatagatact tctgtcaatg      780
agaaaaaaaa gggggtctta tcaaatggct ttatttatcc tttatttatc ctttataaat      840
tagttaaaaa tatttaacta atagctaact aaataccta ccaaataccc aaccaaatac        900
ccaaccaaat acctaaccaa atacctaacc aaatacctaa ccaaataacct aaccaaatac      960 ttaaccaaat atttaaccaa atacttaacc aaatatttaa ccaaatattt aaccaaatat      1020
ttaaccaaat atttaaccaa acttttttat aattttctaa ttgcttcaaa acctgcatct     1080
ctcttttcag ataacaaatg acgataggtt ttttcaaatt gtagtacagt atgacctaga     1140
acttttgcgc aaatatccac aggtattcct gaatgaataa gataactagc tcttgtgtgt     1200
cttaatccat aaaccgataa gttatagggt cttattttcg tatcctccaa aatctttctt     1260
aaagctttgt tgcttgatac tgtacttggt acatcatgtg ataagccgta atgctgaaac     1320
actaaattgt atttattttt gattctaat tcggcgttac tcaactcctg aactttcttt      1380 aaaccttta aaacctttat atcattttcg tttaatggaa tatctcggat tgaaatatta       1440
gtttttggag caacaaattt ccaaattttt ggcgaggtgt taaatcttcg atatgtatga     1500
attatttcat cttcaaaatt aatgtcattc cacgtaagag caatcatttc gccatatctc     1560
ataccagtag agagtaaaaa ataaagtaca taagggacaa ctgattttt ataatttaat       1620 ctttgtctta attccccttg tagtttcata atatctgatg tactatgaag atatttatcc     1680
tcaatcagtt ttgacttctt ttgagtattt aaatctactc ctagtgtaaa gtcatcaaca     1740
agcactttat cacttttcgc caactgtata gacttatgaa taacactatt tattctttgt     1800
aaaacatcgt aactaacttt ttctcccaat tcattcattt tttgttgata ctgacttgtc     1860
ttaatatttt ttattggaat atcaaagttt tcttgaatca cattttata ataagagtat       1920 tttctaaaag ttgctatttc taaattttta ctattaattt tcacatcaag ccagtaagca     1980
tataagttag gcagagtcat ttctggattt aacttacttc cattttgaat ttcttgaaaa     2040
ataggacttc caactagttg agccattctt tttgttttaa aaccaccttg ataagctaaa     2100
ctttttcctg attcatctct aatttcatag tgccaaagtt tttttactcc acgttgccta     2160
tatcttattg ttgccattat gctacttctc caatccctat aatttcacaa ataaatttaa     2220
atggtgcaaa attttgctta ccattataaa aggtaaagcc tgctgaaact gcttttttct     2280
ttgcatcatg taccaccctt ttagcctgag ttggtggaat acctaattgt tctaaatctt     2340
cacttgtaat tattggtttg tttattagtt tttgattcat taaatttatt ctcctttatc     2400
attttcgtat aacgcaaaaa aatagagcaa gattcctctt gctctttac ttaaccttta       2460 aatatctctg atatatccat gacttgtttt tgaataatca ccaattgcta aatctcgacc     2520
```

-continued

```
ataagcacca aagttaaaat atctttgtaa cgtttctacg cttagaactt ctaaaccgcc   2580
catttgctcg attaattctt gtgccaaatc ttcatcattt tcagcttcca caaagtccaa   2640
atcatcttta ttattgataa tatcatcaat actataaatt tcaagaaaat cttttaaatg   2700
atctctgtca gaaatttctt ctaatttttc cgcatactca ttaagttcct gaattgacga   2760
atactcgcct actttataac cataaaaatt ttcaaagtca tgtattgcat attcttcccc   2820
atgctctaca tctaaaaata agtctgattt aattcttgaa aaatcaacag gtaattcata   2880
ccacttaccc cttgtttttc cattattata actgtttaaa tttacaacat aaatttttgg   2940
tgtttccata ttcttctctt ttctgttttt ttattttcct atcacataat gtaattgact   3000
agcttgtgct tttgttaata cttggaaagt ataaactgta ctaaaaccag ttcctgactg   3060
tgaaatcaag actgaaccgt ctgaatgtat tccttccaca aaggccacgt gaccgtattg   3120
tgggtcagca gtccattgac cgcctactgt ttgacctcca ctaaagctaa ccgcactatg   3180
aagtgttgga gtagtcgtta cagtatatcc tgcttgatgt tgccaatcag caccatttcc   3240
catatacatt ccaaaagtaa taccgaaatc ttgggctcga ttccatgtaa accacgtaca   3300
ttgtttatac tcataacttg tcgcaagata accacttgta ttaattggtt tatctaaagt   3360
ccaacctgaa ggtatatctg gagtaattcc tgaaccacca ccagttccac tatcaccacc   3420
agtcgtcatg aacgtgtacc aatattccgc aaaaccttga cgttttggaa ggctatcaac   3480 cgccctgca cgttcccact ttcgcataat atcttcagtc gtttgcttaa cattagttcc   3540
tttgattaat tgtttaagta acgttgaatc tgtaccgtct tgctcaaaca tgaactcaac   3600
ttgaagatta gtatctgtcc aagatttttt ctgacttttc gcatagttta gcaagtttac   3660
tctcctgcca ctatcccatt gagccaaacc gaaagcataa ccgcctaaag tggtatccat   3720
tgcttttgct tcattatagg ttgcattaga ttgaataatt gaaggttgaa gttcactttc   3780
tgcttgatta ttaccaagta aagcagctgc cccttctttc gttccacctt cttttagaac   3840
tctatcccaa atcactttgg cagtttgttg ctgtggtgta ttggtattaa tatctgtatc   3900
tgaagataaa tcacttgaac ctacaaatag agcaaagaaa gctagaattg gcaataaaag   3960
caataaaaaa ggaaggctaa ataatataac cttccgttta atcacctttt tcattttca   4020 cctctctatt acttaatcac aaatggatta tctggtattt tttgattaaa tggattgtca   4080
ttatccttct cccacggctc ttttttcttt tgctgtgttt tttttatccc ttcaggcata   4140
tttttaccat gtaaaacctt tggttttcct gcattttcag caattattgg tgatgcacta   4200
gaattattct tattgccttc attaatcaca tttttattaa ttgacggttt aatggtgtca   4260
gctgattttg atttattttt tatcattggg tcaactttat ccaatgtttc acttttgat   4320 tttttatcat tggttgaatt aggtttattt ttaaggaatt cctctgctct agcattagtt   4380
gcatcataca tattttttat tccttcacgt ttaccattgc gtttattttg aagattatta   4440
tatgcttcag tattttttacg caaacgttgt ttatcaaacg cttcacggaa tttagaacgc   4500
tttgtatttt ctgactgatt gaatttacct tgacgtttat tcatttttc tctcaacttt   4560 tgctcgcgtt gattaagttt ttgacccttt tcagaatcag aacccttttt ttgcaattta   4620
tctaaggttt tattgtagcg ttggttatcc caaccatgtc taagcgaacc agtacccgct   4680
gtaactttat ctttcgcaaa tttacctgca agcatacctg cggttactcc accagttacc   4740
cctgccaaaa caggagcttt caatgttccc attgctttag attttatatt tgacaacata   4800
ttatccatac gaccagtaaa tttcccttgc cccatgtgat gagcagaaaa tatgccaatt   4860
```

-continued

```
atagtcttac gtttaacata aacaaagata taaagtccaa tctttactag tgttatgaaa      4920
aagtagttac tccctaatag agaacttaga gctaggctaa caattccgtc aaatagacca      4980
atgagagccg ttccaaatac ccctaaacct gatagaatta atacaccaaa acttgtttta      5040
ccccattgaa tgattgtctt ttcaaaattt ggaaaaaatg atgcaatcgc tgcaaatggt      5100
aatataaaca ctagaataat gaaaaagaaa tccataaaga atgagaaaat agaaaagaat      5160
aaataaattg ccccaagcaa caaagcatta aatatacttg ctagtgctgt taaaaattta      5220
tcccctagtt tttaaaggt taaatgttta tcttttaaat cttcttgtat tttcttaatc       5280
gaatcgttat catcatctga agtaagcaaa cggtcaatat cactctgctt aatatttatt      5340
tttccgtcct tatcaatctt gacattatca aaattaaggt aaaggaaagg aattttaacc      5400
attgtggtaa ataagtcgtt tttatcagtt cctgaaacac ctgctaccga aatggtttta      5460
acaacacttg ttgtaacatc attcattgca tcatgaactt tagtcactag gctatttccc      5520
ccataaacaa aaaacgtact taaagcaatg attaaaagaa cttttctaat tccctgcatc      5580
atttgcttat gtaaaaaata atatagaagt gtcaaaaaca gccccatagc gactatcgga      5640
agtaactctg gactcataaa cttaccgtaa atagtttgag cagtttggaa aacagatgtc      5700
ctccaatcac taagtattga attaccattt aatccttgat tgacaaaatt tacaaactga      5760
taaatggttt ttgtcacgaa aaattgtgac cgtataaaca ccatttgaat acctgcggta      5820
aatgaaggaa gtatcacgac tttatcactt gcatacatat aagaggtata gttatctaaa      5880
tcttttctag cttcctcatt tttggcttca tctactactg tactcggaga attagcatct      5940
ccatagtcat tcatattatc agcaattggt ggattgatta aaccactatt tcctgtatta      6000
gaggaaactt ttttattaga tgtatcattt gagctattct ttgaatcatc ttttgaatta      6060
tttttattgt ctgaaacaga aaaatcaggg gttgacggag gagtaaagcc tgaactatct      6120
gcataagtat gtagggctaa aacacttaaa aatgcgaata gccccacaaa taacaatatt      6180 ttcttttttca ctatgccacc acctttgtat ttttcatttt agtttctaca gtatcaaata     6240
aaactgtgac ttctggtaat tggaaatcaa ccgtaattct agctgtccgt ccaaatggat      6300
cacgcatgat acattgtcct ttagtcatat tgtcatacca tgcctgcgtt gtttcctcaa      6360
ctggaagttt aaagtatta aggactttat ctgtttcagt cggttcacga aaagcaaaaa       6420
ttgtaccaaa agccgttgaa tcatcttctg tttccacatc tgaaatagat tgtgtaatca      6480
atcctaagaa attgtttga gaacgtccga cacgtttcat tgacattaaa atagatgctc       6540
cgatttctgt cttattaaag aaccacgctt catcaacaaa tattatggtt tcttgtgttc      6600
ggtcacgttc cccaaattca cgacaaaatt cgcctaaagc atacataata attaatgact      6660
ctttatggtc gcttgtgatt ttttcatctg ctttaggaag atttaaacca gtaacaccca      6720
atactgtaat gcgtgcgtcc atatcaacgg ctgaattttt accatgagaa aagacaagtt      6780
ccatttgaga attttttaatt tttcttaaag ccaaattagc acgtgtagaa atcatttcat      6840
ctgttgaatc taataatctt tcaaaaacat ttaataaacc aacttttttt cctttttctc      6900
gttcactcat tactgcatct aaagattcaa gaaaggcaat ttcaaactta tcttcttttg      6960 tatattttc accaagcaat tcttcagtaa ctttaacaga aattttctta caagcatcac       7020
catgtaaaaa tactagaggg tctaatgctc catgattgtt ttcttctttt gcatctaagc      7080
tgacaaagtg aatgttatta atataatcaa caactggttt ataatactta tattcaatcc      7140
ctcgaattac ccagtaaagc tgttcttcat cttcaattgc ttcacgtgct tgttcaattt      7200
caaactccat ttttggaaaa tcggcttcat attttgcttt gattttcata tattgagcct      7260
```

-continued

```
tcatttcatt tttagggtca atataaagcg tcagagcttt aagaagtgag tggcaaagga    7320
atagtccttt agttaggaat gatttacctt caccagtttg tcctacaatg gcaaaagctg    7380
gattgtctgt aattttttcct gcaatccctt gcttattagc ttgaaacagg ttaagaaata    7440
cagcattggt agaactagca agtgctttt tatagtcacc tgcccaagat tcgactgcat    7500
ggtcgattcg cccaatagga aaaccgatat ctgaaccaat tttttgacta gtaaaaaaca    7560
gattttcaca ggctgatgaa agtttcatag cttgaataca atatttgtct ttttcttcca    7620
attgttcgat aaatcgattt ttatagaaga aataaagttg gtctgacatg ccagaaacaa    7680
cttgaactcc aatatctttc atatcagatt gaataatttt tttataataa ttaacctctc    7740
tcatactttg acctgcaact acaaaagtcg ctaggtaatt gacaaagagt tcacgattat    7800
ctacaccgtc agtcatttca tcaagaataa tacgagcagt tgcaagtgac ccttttttgat    7860 ttgaaccatt ttcataggct tcaatttggt tctccttgat tcggtctgat gcacgttccc    7920
cttttgatgc taaagaaaaa gcccctttca ttttagagaa atggaacttc caatgtaatt    7980
caataggaaa cggtaatttt tgagcatgtt ctactaaatg aatattattt acaacgtttg    8040
gcatattagc aataggtaac gcttttacta aacttttttcc gtagctattt ttcaatccaa    8100
ttacaccatt tgataatggt tcaataactg tatcatcaat attttgtacg ctactttcaa    8160
ttgatgctat ttcttcatca cgattataat taagacctcg taaataatct actcgttgat    8220
aaaagcctgt ttcttttttt gttgtttttc gaccttgaat taatgaaaga tttaactcta    8280
aatctccatt cgccttgtca taggcttcat accagttcat ctcaaattca agtgtttgac    8340
gaacgacagc aactgctttt tctttaaagc gcccccacgc atcttttaac atttgtttaa    8400
tatcacctga aacttcaaac gattttaaag ggatagtcat aaagaactta tagttaatca    8460
gttgaccaat tgaaccatat aaatcttcat ttgtttttttc caagaaataa agcgccatat    8520
cataagtatc atctgcgcaa tcctccaaca gcgccccaaa gcgttcttct aaattaatcg    8580
gaactggtaa cattccaata tcaaacgata aattaggtgc taaactagca aataccgctt    8640
cagttctttt tttaaatttt atctttcctt ctacgtccat acttgaaata atagacgcag    8700
gcacttcata cattgcaatg actgaaccgt catctcttag tgctaagtta tcatgaacag    8760
aaataactct attctcaaaa tcgactttat tcactttta ttcttcctcc ataaattctt    8820
ctacacttcg caattttact ttttcatatt tttgaccctt atatatttca attgctttca    8880
aaccataccc aaattgataa acgataaagt cccacaaaaa tactggtggt aatttatcat    8940
ctgggcgcaa atcagatact ttaaccgaaa tttgccatga agcaaaaagc gtaagcgcta    9000
ctttcacttg ccattgaaaa tatggaatca attttccaac tgtaaaatat agcaaaatga    9060
atactaagaa aaaataagca aataaggaaa gacggactgc ctttctcaac gcaaaattat    9120
ctgtcagttg ctgtatccaa aaaggttggt ctaatgacaa tttataggaa aacttaggca    9180
cttcttcttt ttttgctttt tcagacattc cgccttcctt tctagcctaa accgagaact    9240
tttttcacta aattaccaac tggtgtaagc aaaccacctg gattattgac gagtagagcc    9300
aataatgaac caaaaacaat aacaactatc attttttccat actttcgacc gaaaaattct    9360
tttcctgcaa gataaccaag agctatccaa actacgattt gtccttgttg ttgaaaccaa    9420
gaccaacctc cagtcaaccc aatatcgcca aagataacat tgttaattaa tatatttcgt    9480
aacatttttt ctcctattct ttttttacctt caggtaaagt gtgtttaaag tcagtcgcaa    9540
aatatgactg cttttgtttt tcaatcgtaa attgataatt ttctacatgt gtaccgagtg    9600
```

-continued

```
cattttttcat tgtgatttga actaccgcat gatatttatc tcccccttttt gcttcatagg   9660 tcgcttggtc taaagattta aattcttgac ccttattaag agataaccct tttgaaatca   9720
atttcaacgt atcaccgtca gttgtataag cggtaaacaa tgattttgtg aacttatcca   9780 aatcttttttt tacaaaatca ctcgttttttc ctgaatcaga ccacgtttta gtgggcactt   9840
gattttcagt tgcttgtaaa tcaggaacac ttgaaaaata aggttcatct gaaatatagt   9900
aagctgaacc tacttttttgg taaggaatcg taaacaaagt tgtttcatca tgatatttca   9960 ccacatttttg tttcgttgta tcttttccct ttttgacttc ttttgttgtg acttcaccag  10020
cactataagt cactttataa gtcgcttcat tatccgtcaa acttatcatg accgcaccct  10080
caaatttgga aggtgtacgt tgaatacctt gactaatcac tggcagattt tgaacaaagt  10140
aagcattaat atctttaact gctgtttctt gttcttttttc atcttcaggg aatgtgaaat  10200
aagtttgaac aaagccgtca agataatttt tcgcttgcaa atcaagccca ttacctgatg  10260 cttttttgcgt agcactcact tcttcacgaa tgattttatg agtgggttta tatccacttg  10320
ccactagact aactaaagta acatttgcaa taaataaaaa aacaacccct cccacgacca  10380
aagcccctgc ctgtttagca gacatctttt ttagttttggg tggtttttca ttcggctgct  10440
tctttaacat tttgggttta ttcttttcag gttttcgact tgaaagaagg gaaaatttcg  10500 attcctttttt ttcaggaatt ttagttgttt ctgaaacttt catttcagat tcacattctt  10560
ctttttcaat aacttctgaa atatctgatt ttttatagat attttctagt tttaatactt  10620
cagcgtcact caaagatttt gatgttgatt tagctgaaat tccaaattct tgagccttag  10680
agagtaactc atttcgctca acccctaact tgtcagctaa ttcataaatt ttaattttgc  10740
tcatattcct cactttcttg ttcaacagct ttaaaagata catcacttct taaccatttt  10800
tcagccactt cttcagcttt cttttttagta tcaaaagtag aagcaaattt taagtgttta  10860
gtcgctccac cattggcaca aagatagcta ccacgcgttt ttacaacgta catttttcacc  10920 tctttttttca atttaaaata atatctcacc aaaataattt ggcggagttc ttgatttata  10980
ttttgttttt ttcattttcg cctaaaataa aaagcagaca attaaatctg ctattttcta  11040
aacaatatca tgttcataag tttgctcatt ttcatcacaa aaaataatca catcttcatc  11100
aaattccaca atctcaaagt tttctctaat aaaatcatgg agtttaactt catttgtttc  11160
gcctgtttgt ctttcttgta atttcagaaa gaattgacga gcctgtcttt caagtattcg  11220
ccacgctttt tcataagtca atttattcac cttcttcttt agctgatttt ttcttttcgc  11280 aactcttttta atctttcagc aaatacactc ataattcaac ctccaaagaa tttcattaat  11340
aaataagtta gtccaaaaat tgctaagaaa atatcaaaat aaatagcaat tttaaatatt  11400
tgtttctatc cattttctaa cccttttctaa tttcccaatt aggctttttga atatttgatt  11460 ttggtaaaaa tcgaggagca atcgctattg acagcggagt tgaaatagga ttatatttct  11520
cacacagcca catgactttg tttttcattaa ttccagacca aaattgattt gtaccgtcag  11580
gaaaaagaat ttgtatatca tacaaatctt tatatggtgc tttgtgaagt gaaaaatcaa  11640
tctgtggttg tgctttgctc atatttgtta ctgtcatatt tttatttctc actcatggtg  11700
agtatccttt ctcttgcctt accatgagtg aggcttttaa cattgttatt tttcagataa  11760
ggaaaggcaa accctacccct tatttcaaag atttcgtgga ctatttattt agcgccacta  11820
cgtgcttgct cttgtgcttc ttccagtttt ccttttaatt cattaaatga tttctttgtg  11880
aaattgtatg atgatgaagc cttgacaaga tttttaatca agtcatttgt acggtttgca  11940
ataacttcga ctgtatcatc tgaaatagaa gtatcatttt ctacagtacg aagtgctttc  12000
```

-continued

```
cctttcctt tgagcttttg agcagcatct tgaaaggcat ttcctacatt aattacggct   12060
tcaatttcat ttaaatcagt tgcaatttgg ttaagttctg tttttaaagt tggcatattt   12120
catctctttt cttctttatt ttccctccac taaatttgcc ttcccttatc tgaaaaataa   12180
ctttgttttt atttatgaaa attcataaag ttgcttgtgc taaatcatta tcaattaaaa   12240
agtaaattgc cattttatag ccttcaggca aatccgccat tctttttttct tgatagagtg   12300 aataatattt tttacgtgtc attgaatcag gcggaaacat caagcctatt tcattaagca   12360
atcctaatgc ttcagtttca tttggaatat aaaaaaaaag ctggtcataa actccttgct   12420
caaatttttt caaattaaat tcatatccac tcattttata ctggagcatt cggacgttgt   12480
ttggaactct caacattctt ttttgaaaat gttctacatt aggtataatc acctctccct   12540
ttcctccttt aactaattat caatcaaata tatccgcaag tattgcaata acaaccacaa   12600
atacaataat agctacgata actttagtta ctatttcatc aactggaaaa cctgccaatt   12660
tgaataagct atccatttgc accccttatc attctaaatt ccttcaagaa ttttttcttgt   12720 ctttctgtaa gttctgcttc attaaaaatt tcttccaaac gactttcacc tgtcagttct   12780 tcagctttt ttaacaatag ataagttgat acaggaccac cacgttcaaa ccatgtatat   12840
tttcggttca aatcaggcac ttcaggacga acagtaaaat gataggcatc cattcgaccc   12900
atcatatcgt accattcagt atctaagttt ccttccttat cataaaatgt cagattatca   12960
ttaataattt tgaccccttc atcagctaaa tcaaaatctt gctcaatata tctctttata   13020
aagtcggttg atatttcttt tcgcatggaa atttcataac gatttcgcag accatacatt   13080
tcacgtatcg cttcaaccga agtcatttct tgacttgctc gctcataatc tttttcgtaa   13140
aaccgaaaaa ataaatgagt ttgtttagat ccaaaataaa cggttagacc gtcattaatc   13200
attccttctt ttgtccttct tccaccaaga accgcagaat agtttgtttt acgaccattc   13260
caccgaccct cacgggcaga agttaaaagt ttgaacaagt caaaatttcc ttcttgcggg   13320
ttatattgtt catcaagtgc taaatcaaaa cgtgtgattt ttacaaaatc atcattttct   13380 ggtgctttt tattggcata aagaaaacaa tcattaaaaa aatcgtacca agtacgctgt   13440
ttttgatgat attcaaactc atattccatt tcacggcacg cttgaccgct catttcaatc   13500
agcacaccgg cttttatatc tttatcatga taataaacat tgatgtgacc gtaactaata   13560
aaaaaagggt attgataacg gttatactca ttgagttgaa aattctcaac gtttaaacct   13620
aaaatcttag aaacaacttc acgaacattt aaagtctgaa agcgaatatt tgtatagtca   13680
tttgtaccaa caaaaaccgt tgaactctct cttttttttga aaaaggagtg tcttattttt   13740
tcttccattt cagaagtaac agcacgttcg ccttttttcca tttttcggta atagctcaaa   13800
gatatcccta agaggtcaca cataaactgt tgagtaacat tcgcactaga gcgtatatcc   13860
tttaaatcaa tcggtcgttc ctcactttct aaattaaaaa ctacaatatt tgttttaaa   13920 ataaaaaaga tacttaagtt taagcatctt taatcttttg tttcttcctc atctagagct   13980
ctctgaatac tttgttgtct tattttgttg atgtaattta ataccataat tacaagtcct   14040
cccaaaatag aagagctaat aaataaaact actaaaactg caataaaata tcccatacca   14100
tctctttgat acatttcaga ataagcaata taattttag tgccttgaat aatcgttaca   14160
agcattccca caaaaaacat taccgtaaaa gtatttattt ttccttgtgt tccttccaaa   14220
ttgattcctg caataatact tctaattata gtgtaaatag ctattccaac aacacaaaaa   14280
agttctactg catactgctt aaatggtgca tcaaaaaata tttgttgaac gattaccgat   14340
```

-continued

```
gaaaatagga caacactaat tataatatag gcttctccct gaatgcgatt catctgagta   14400
ataactctca tcacgtatta tttttattctt tttcatcatg ttcctcccaa aaaatatcgt   14460
tcaatgtttt tttttaaaact ctacaaatat ctatgcatag ccttaaggac ggattaaact   14520
ttccagattc aataagtcca attgtttgtc gagtcacacc tacttcatca gctaaatctg   14580
cttgactcat ttcagcctca attcgagcca tttttcatttt cttgtttttc accgttcctc   14640
cttccttagt tatagtatac catatatttt gcaaaaagca atatatatat tgctttaata   14700
ttaacaattt aaaaatgcca tgagataaaa tactcctaaa tagaagaaca attgaatatt   14760 tattttttata ggtactagaa atttacgtat ttcatttttt cataagagaa cacgcttaaa   14820
ctcttgaata acattagtcc tgaagtgtcc cctttaaaat caattgagcg ttccttactt   14880
tgtaaaatgt aaaagaggtg acacaagcta tactgttggt atgactagga tagttagact   14940
tgtgtcactt gtacccccc tcattagcat ttggggggt caagtccaag ctgacggcaa    15000
gccgtcagcc gtgcaatcac acgctcactc cttacgctac gctcggagct atgcttacgt   15060
tcttgcactt tttcaaaaaa agcattacgt tttaaacgca ataaccttaa aacaaaaccc   15120
aaaattttct ctccaattct ttcaagagta aaccgctgtc gcgcactacc gtttgcgagg   15180
gcaattcgac cgtggaaaat ggcttgcctg cggcaagttg tctaaagaca aacggaaaca   15240
agttcctatc atttactcac cgccgattgc atgatgttta ataaaataaa aagcatagga   15300
tatcctatgc ttctcgttgg tcaactaatt ttattatttg agaataatca ttcaatgaac   15360
tcttatattt atcaaagaac gccacttcta cattaagaat ttctgctaac atttccttag   15420
aaatacgcat tgaataagtt aaactttgga catctgttaa attatttgaa agaacaacat   15480
ctaacatact caaaatttt ccaggcttat atactggtat ttctcggtca agaggttcaa    15540 atatttttata atttttttttg tgtatttgac gataaaaata actattttgt gccggagtaa   15600
gatatcctaa cttaaatgcc ttatattcta aagcttgtat tgaaacatta aaatattgtt   15660
tcaacggaat ataacgatct ggttggctaa ctttagtacc taccaatttt tcaaaagtct   15720
tcttaaattc attttcaggt aataataaac ttgaagcaaa ttcattagct tcttgctctt   15780
ttaaatcatg ttcattaata tctaaaagtt caaaatctac agccctatgg agtagtaaat   15840
gacctaattc atgtgccaaa tcaaaatttc ttcgagcgta agatttacca attgccaaga   15900
ccaaatacgg aacattatcg ttggtccaaa ggctataagc atcagcgcta cttccttcag   15960
gcataaacct tgatagcaca ttaattcctg acatttctat tctgtaaagt aaatcatcat   16020
tatgtatcga aatgtctaag tgtttacgcg ctaataaagc aatttcagaa ataagtcttt   16080
tatcgagttt cttcccttga agttttcttt caactacttc aaccaatgaa tatatggttt   16140
taggagccga tgtcaaataa ctttctaaat cctcaattag agcatgtgcc gcattgacat   16200
atacttcttg catttggatt gttttcttcg aagccaaatc tccatttcta aaagcaatgc   16260
ttcctctatt tacatgagaa accaatgggt ttgcttcaaa aaatttaata tttactttaa   16320
ataattttgc aagagttaaa acagtgggtg aaagctttgg atttacctta ttcgtttcaa   16380
attgccaaac agcttgctcc gttacatcga gttttttctgc aagctctgcc ctactcatgc   16440
cataaagtaa tcttaattct tgtagctttt ctcctttaaa catttaatcc tcttctaaga   16500
ctaggattcg cccttacctt cttgttcacg aacttggaat tggtagttat tatgctctgg   16560
catacgttct ttcccaactt ccccatcatc aacagtataa gcttgacgaa tacagtcact   16620
aaaatcttgt aattctattg cacctttttt ggagtctaaa gtatatattc caagataagt   16680
aatttgtcct gaaacttgtt caaaatcata acataaagct aaaaaagcct ttgttttttc   16740
```

-continued

```
tggttttgct agaggaagac tattatcttt tttctcaagt aattccataa aatcaatagt   16800
ttcaataggt ttctcagtag ataacgagtt ctttctggca taatccacta aatgaaccgc   16860
tctatcttcc tcaaaaccat taataagtgt acttcttctc tttacaatta aaacactctg   16920
accatagata gtttccccag tatgttcaaa gtacttatta ccaaaaccat tatccttagt   16980
attggtagtg cattcaaaag aaattaaacc tttttgaata tcagatttaa tagaacaatc   17040
aataaagtct cttctagttt ttttcaaatt actatctagc tcaagtgttg cttgagtaaa   17100
tcgtttagta tttaaaaaat ttttatttcc tctcactaca ctattagcat attcctgtag   17160
taactcctgc ggtagttctt catttaccat agttcacctt tttctttttag ttattttata   17220 caattatatc atataactaa agaaaaaggt acattttttcg tgtttttatt aaagtgtcta   17280
acatgtttta caatgattta ttgtatcatt tttttataaa aatataaagt tttttttataa   17340 attaagcaac atcttctttg tgaaaagtca caaattcttt ttcaaactct gcttcatcag   17400
ctaggacagt atcaatggct tcattcaaag tacattcttc tgtttcttta gttaagaaaa   17460
cagtttgtaa agcaataaaa tcatcttcat tgtaaggtga ttttttcactt atagaatatc   17520 cgccacttgt taaacgctct atggctgttt tcacagtttt tgaaggttga cccaacttac   17580
gagataaaga ggtaatctta taagatttttt cttccaaaac cccactttct gctcgttcct   17640
gttcaacgtt agaaattggt ggagcttcaa gctgaacttc agtagtatca gccaaaactg   17700
gtaattttga aagttcctca tgaaaatcat aacccttatc aaatggtaca gaagggctat   17760
aaaattcacg tgcaagttcg ccattattgg caacataacc acgaccaatt ttacccttga   17820
tgtatttgaa aactttttttc tcattttcat ctccaaatac catacgataa cctgaaccag   17880
tcaaacgacc aaccgccaac cgtttcataa agttatcacg taaagctgat ttaagatact   17940
cagcgtctgg acgttgcatg gcaagaatta agaaaacccc tgactgacgc ccctttaaaa   18000
cgatttgagt taaaatttga atcacttcat caaattctct aaaatctaaa ctagaaataa   18060
aagcagccca ttcatcaaaa agaacaaatt caggtgtcaa accataatca gaatatcgtt   18120
ttcctgcctt atagtcaggg tgatttgtca tataatcata gcgttcgtcc ataaattgca   18180
tttttgaacg taaacactca atcatagact ctttatcaaa gaacacacga ttttcaaaaa   18240
ctggaacatc tctcattccc acaaagtctg aacgtttagg gtcacatata tccacgtgac   18300
ctacttttgc aagggctgat aaaatagaca tcaaaagaac tgttttttccg cccccagtac   18360 ctcctgcaat aagcagatgt gggtcagctt cataattcca gtaaacccca ttcattaact   18420
ttaaacctag ctttttatca actataacat tattaactgg aatacgatta cgttctccgt   18480
caattgcaaa aacatactca acaaatgtct ttttagaaag aattttattt tcattgataa   18540
aattttgttc ttgataatca gcaaaaaaag ttgtttctaa accgtcagct aaatcaagaa   18600
atttttcttg atgaactcca ccgtcaattg gaaaataagt atgaagttca taagtattag   18660
gttgtttcag ataaataggc gctattttta acttttcatg acttcctttt tcatctttga   18720
ctgtttcttt ttcaactaaa ttatgcttca caacatagtt cagtaacaat cttttataat   18780
tattttttga aaagaaaagg aacttgtgat aaagcaaaat caataaacca aaagccaccg   18840
aaaatgcaat gagcaaaata cctacagcat aaattgctag cacttttggt ggcaaggttt   18900
caaaattttt ataaaagaac cctacaggac tagcgacaaa taaaccagta atcaatacaa   18960
aaaattcacg gtcatactta tctctaagct ttaaacgaga gcctttactt attgtacgtt   19020 ttgccatttta tcatttcttc ggttcattgt ttttagcttc aggctttgga gattgttcag   19080
```

-continued

```
gttttgaatt agatttacct actttttcaa tcccttcagc attccatttt tcacctgaaa    19140
agtaattggt tctgaactgt ccgtttccag taggtacgag ttctttatca gaccaaaaat    19200
taattgagcg attcgtcaat ttaatttcat cttcatattc aagccctgaa aaatcagctt    19260
cagcaggcat ttttacaaca atttgcttgt cttgtgcgtc agaataaata ttgacctcat    19320
aataatcaac tttatccgtt ggataacgtt taatttcacc agtttcttca tttggttctc    19380
cgtcctcaaa gaccattact gattcagcat gcaagaacaa aactttacct aatgctttgt    19440
caaaatcacc gatttcttca gtcaacttgt tttctttttc aaaaacttta cttaatttta    19500
acgacattta atttcccccct ataattacgc taatttgagc gcttcagcat aaacaacata    19560
ttcttgtgaa tatttgccct ttggtgtgcg attacgaaca taagcaaccg tgacatctgt    19620
caaaacaact tcttgacggc gagtaggttt agccccttta ccatttggca cacgtaattc    19680
aaaaccttga ggttgtaacg gacttgtagc tcgatatttc gtataacctg attcagtaga    19740 tgttttgcg actggttcaa tggtcttatc gacagtaact tttgaaccta agagtttcgt    19800
tgcgttaatt ggaattttaa tcatgtttcc acctttcttt attagtttaa tgacatctcg    19860
gtcaatttat gcgaacgcag ggacttgaac cccattcaac cgtgtaactt cgttcgctta    19920
aagaaaaaaa accaccctca tttaagaaag tgatttttta tatataattt tattttttaa    19980
acttcaaccg tatcaagacc ataaccaata ctatggtcaa gccctaaatt aattacttca    20040
gcagaattta ctgtagaatc tacataactt tgagcttcag caaccgtatc acacattttt    20100
gtatattttc gtacaccatc tacagatacc caacctaaat attttgtagt atgtgttggt    20160
tgacctgagt tccccccca ttagaaccat tattatttgt attagaacca ttcccacctg    20220
tgtttgaatt agaattagaa ttattttgtc cactattacc ttgaccttga ttacttgaac    20280
ctgaaatagt attgttttga gaagtatttg aactaccttg tgaatagtta ttttgacttc    20340
ctccaccgta agaattagaa ccactagcaa catcattatt tactgtgcta tgtgaatcag    20400
cacctgtatt agaattgtta ctattattag ttgaatttga ttcttgttta ttagtgtcag    20460 cagttttttgc ttttgaatca ctcgcactct tagattattg tgcctttgta gcgtcatcag    20520
cttgtttctt agaagtcgca agttgtttat tcaagctatc tttcaaacct tttgaataag    20580
agcttgtgag cttagatatt gcttgttgag ccgtttttata tttattttga ttcatagcat    20640
ctttttgata gttactaatg gctgtctttg cttcatttttc tgacttcaca cgatttttaa    20700
taccaactac ttgattatca aacgcttttt ttacttcagc atttttaact ttaagcattg    20760
aatcttcagc tagtttaata ttttttgtcag taggagtttt ttcagcaata tcaagtaatt    20820
tcttactgtc tgcttcatta gattttttcaa gctgttttac tttttcggct ctagccttac    20880
aaagtttaat ttttttattt tttaaagctt caatttttct ttcttttgct tgatgattag    20940
cattagcgac tactccagta gtaacaccac cgattaaaac aatcgtaact gctccaccga    21000
taatttgctg tttttttagtc caattcaaag ggtttaaatt cttattcata aatacattcc    21060
tatctttact ctaatttaag tttattatat cacaaaccat ttggtttgtt aaagttaatt    21120
aacattgttt cttgattcac tttttttttagt aacatattta ttacgctgtg aattctttttc    21180 tatattcttc taaagcatat tttactttag ttccttcagg gtcaccagtc aactcaatat    21240
tttctaaaac atctaataaa aattcatctc cattcataag gtgactgatt ccaagcatat    21300
acattggaga aactttgaag aaaattagcaa actttactat agtttcatta ctaggtgtcc    21360
ttgctcctct ttcgtagcga ttataatttg agcgcacaag ccctaaagca tcacttactt    21420 cttttttgtgt taaattgtga ctgtgtctta aatgaatcaa acgttctgaa aaactttcca    21480
```

-continued

```
taaaaaaact ccattctttt tataagggaa caactggaat cgaaccaata tcaccactta   21540
taaaagtggt tactctagcc tattaagcta tattcccata aaaaaatcta tcctcaaatt   21600
aagtctgaca gatagtatca acacatctga tagatactta tttcataaga tagattttta   21660
ctaaaaccat tattttttcta aaataaaaaa ctgccatttc ggacagttta aacgactagt   21720
tttttgtcat ttcggacgat tttttaaaat ttatattttc aataatttgt tattgtcttt   21780
acgcaggcag taacctttta gaccagaacc ctcttcctct cgctttggtc ttgatttata   21840
tagcgccctt actcaaaatc ctcctgctct gcggtatgta tcttccccct caggcacgct   21900
tgttatttca aagtttgttt taagctttgt gcttgcattg aaaatctcct tctgaaatgc   21960
tataataata attgctacgt tatttatata acatttctgt gggagttgcc aaagcgcgct   22020
tccgcttatt tttcttgtag tttttaacgt tctacgttaa ctacatatat gattttaacc   22080
tattacgtta aaaatgtcaa ctattaaatg cattttttc gatttttttt ggagatgata   22140
caaatatgtt ctacgaacgc ttgaaattgc ttgctaaaga aaagaaaaaa tctttcaatg   22200
aaattgaatc tgaactagga tattcaaaaa attctatgta tcactataaa aaagttaaac   22260
caagtagtga taaattatct aaattagccg aatattttgg cgtaagctct gattatcttt   22320
tgggcaatac agatttaaga gaacccaaaa aagaaccagt tgaccttgaa gaattaactt   22380
ctgatgacgg tatcaactgg gacgaatggc tttctttgg cggtaaacca atttctgaac   22440
atgataaaaa taaaatcaag gaaattttg gagatcgctt gaaagattaa tttatgaata   22500
aagatgaact tattgaacta atcttactta atatagaaag attaggaatt gtcatggcac   22560
cgacaaaatt agaacagttt gctattataa actgtgaaaa atttattgga gtttatgacc   22620
cttcaagcgt gacccctttt attcttgctc atgaattgat acatgccaag tatggtgata   22680
aactgcgcca ttgcgataat gatattttaa gttgtgaaga aaagagagca aataaagaag   22740
caattattct tttgtgggaa atatacaaag aacaaggtgg taatgcatct tattttttcaa   22800 attttattga aatagctggt tgcccttttg aagaatctat cactattcta agagaaatag   22860
aaatgaatga tgaaaatatt gaagagatta ctccatgttt tgaaggaaat ctaagagaat   22920
gtgctattca ttatatttct ggctttgatg tattaaattc aatcaaagta tatgattttc   22980
ttgaattata taatttatct tatgatttat atgatgaagc agttaaagaa tttcagcaac   23040
ttttagacca acaaaattta gcctattaaa aaaacttgta agatttccta caagtttttt   23100
atttataata aatatatgaa ctattttcat ttccgattct ttgaaccatt ttcacttcca   23160
ctcgagcagg tttaaaataa tcttttgtat ctctcatacc agatattaag tatctttcta   23220
agtccctcgc ttcatactca ttatcaaaat ctctttcttc ataatcaaaa taatttgttg   23280
catatctaat tactcgccac tttattttag aatattttg ttcaaattca attttttttgt   23340 tttttttgaag ttcatcttta gttgttgaat ctgaattatt actccttata ggtataatat   23400
tatctgattt tgggtcataa ttttcaagcc cccccattac cattaaaata aaaacagcta   23460
caatcactag taaaactact ataaataccc gaattgctag ttgattattt agccatgact   23520 tgataccga tagaatagct taaagtctct ggttccagtg atttagctga ttttaacaat   23580
aaagaatacg ctaaaagtat catctctaat ttcaattgaa aaccttgagg cgaacgactt   23640
ttacaacgct cagctcctag atttgtcaaa aaagagaaaa ctcgctcatc actttttctac   23700 gttttgaaaa attagggaac agggtggttg atagagaaac cctgacactt gctaaagcaa   23760
atcctcatga aaatctgggg aatcacaaga aaatcaataa gttttaaata gaccaatttg   23820
```

-continued

```
actttggtaa gaataggtgt tactattaag aggtaggttt tgtctcgagt ttaaatgttt   23880
taggaatgca ctttttcgca aaataggatt tacagatgat gcgaaaggat gtattatatg   23940
aataaaggaa caataaattg gtttaacgct gacaaaggct atggttttat tatggcagat   24000
gatatgcaag atgtgtttgc ttatctctta tctattcagg gaaatgattt taaaaaatac   24060
gatgaaggtc aaaaggttac ttttgatatc aaaatgacgt ctcgtggtcg ttatgcttca   24120
aacgtacata aaagataaat gagttaaagc atggggtgtc ctttgctttt ttatttattg   24180
ctattgcaaa aatgaattaa aatgttatac tgagtgaggg aaagattagt tgctttccct   24240
acagttcata aaatccatgt cattacgata tggattttat taatggagag tagtttgaca   24300
ttgactataa ttagtgttat tatgaagaag taaattttgt catgagtaaa atgttttata   24360
gattcacttt tcgcaaaatg agatttacaa ttttgtcgaa aggaaataaa tattatggca   24420
aatggaacag taaaatggtt taacgcagat aaaggatttg gctttatcac ttcagaagaa   24480
ggcaaagatt tgttcgctca cttctcagca atccaatctg atggattcaa aacacttgat   24540
gaaggtcaaa aagttgaatt tgatgttgaa gaaggtcaac gtggacctca agcagttaat   24600
atcacaaaag cataattgta tctgaaaatc gtgcaaaagc tggagtcatg acttcagttt   24660
ttttatattc agttgcaatg atgagagagt atgatatact tagccagcaa gaggaaactc   24720
acacttccca tgcataaatt agggccactc taatatagag tggttttttt aatgtttatt   24780
aattaaaatt aatatttaaa acatacaaat taataatacc atatacccga attgctagtt   24840
aattatcaag tcatggctaa ataatcaact agcaattcgg gtattaatat atctataaat   24900
tgttgttcta gaaactcccc aagaatccgc aatcgattta atttgtgttc cactttctat   24960
caatgtttta agaagcttaa cgtctttatt cctccattga tactattgta ccataacttg   25020
aaagcactta tataaatgaa catagaataa attacgggtt aatgaacaat aaatgcaaat   25080
gattttaata atcttaataa gaaaagaaga gtgttcagaa aatgaccatt ttctgaacac   25140
aatataaaaa aagaaaaaca attattaacg ctttttcttt ttatgtctaa ttatttgata   25200
atagtccaat aatgttgaag cccactttaa taaccatact aaatagatta aaattctacg   25260
tttgttactc taaaaactag acttaacgtc acttggcatg atgattttct cctaacatta   25320
aaatctgtaa ttacataaac tgatgacgac agaaaaattt aactattatc gacccacatc   25380
tcgcattggc caattacggt agctactgca tcatccatgc ctttaggtgg atatttgtac   25440
tttttaagaa gtctcttaac catacgcctc atcccagctc ttgcagattc tttcttctgc   25500
caatccactg ttctactctt gcgtaacaag tcagttaatt catgagccaa cgaaacgagt   25560
tcatcattct cataaaaatc cttaactgct tctggctttg taatagcgtc ataaaaagct   25620
aattcttctg cagttagtcc caagtcgtta ccttcttgac tggcattagc catatctttc   25680
gccatcttca tcagttcttg aatgacttcc tcattcgaga gcataccgtt aagataagct   25740
ttcatagcac gagaaagcat gtcagagaat ttttctgatt tcactaggtt ggtacgttta   25800
tacagtgaga cttgctcagt aattagtttc tttagtaatt ccactgcaag attcttttcc   25860
ttcattttag aaatttcatc caaaaactta ggatcaaaca aggagaagcc cgtgtctata   25920
tctgagaata aattgattac tccctcactc ttgatactag acttcaacag ttcgttgata   25980
cgctgattga tttccttcaa agataaaggt tttctatcac ctgtgatgcg tgtcaacaaa   26040
gtacgaactg cttcaaagaa tgcagcctcg aatcgctgtt ctggtgttaa taaagaacga   26100
cataatgaga gggcttggcg aagcaaaagt gcttgtttga tatattcctc tttatccttt   26160
tctttattaa ccgcagaaag gaagttaaca cctctactaa tcgttttagc acgggtcaaa   26220
```

```
tctgtggcag aatcgtccat gaatttggag tagtcaaagc catggaacat atctcgacaa   26280
acttctagtt tttcgataaa ttttggcaga gctgtctcag caatatttgg gtctccaaag   26340
ttccccttat ctcgtttcgt ataatcattc atggcttgtt tcaacgcact agcaattccc   26400
acgtagtcaa caactaaacc accttcttta tctttataga cacgatttac acgagcaata   26460
gcctgcatca gattatgacc actcataggt ttgtaaacat acatagttgc caaactagga   26520
acatcaaatc cagttagcca catatctacc acaatagcta atttgaatgg gtcatcatca   26580
tttttaaatt tctttgccat ttcgtcttta tggctcttgt ttccaatgat gtcatgccat   26640
tcttcggggt cattatttcc agaagtcatg accactccaa ctttttcagt ccagtttgat   26700
cgcttttcaa gaatcttatg gtaaatcttc atcgcaattg ggcgagagta ggcaacaatc   26760
atagcctttc cagttagttc ctgcgcacga ttgttttcat agtggtcaat gatatcgtca   26820
actaatgcat tcagtgtctg ctccgcacca agaattgagt ccatgcgtcc cagttctttt   26880
ttgcttcttt caattacatg gtactctgcc gtttcctcca tgaccatata ttcattatca   26940
atggcttcaa gaacagactc atctagtttc aaatgaatga cacggctctc ataataaact   27000
gggcgagttg ctccatcttc taccgcttga gtcatatcat aaacatcaat ataattgcca   27060
aacacttcag tagttgattt gtccttatta gaaattggtg taccagtaaa tccgatataa   27120
gtagcgtttg gtaagctatc tcggattttt cttgccgttc cgattttcac ttggccagtt   27180
gttgcatcga ctttctcctc tagcccatac tgtccccgat gcgcttcgtc agccatgaca   27240
ataatatttc tacgttcaga aagaggttca tctgactctt caaatttttg catggtagtg   27300
aaaataattc catttgcttc tctaccatca agcagttctt ttaaatttgc acggtcagaa   27360
gcctggattg gtgtctgacg aagaaacttc tcacatttcg caaactgtcc aaaaagctgg   27420
tcatcaaggt catttctatc tgtaagtaca acaaaggttg gagaatttaa tgcttgttgc   27480
aataaatgag tgtaaaagac catcgacaag gatttaccac ttccttgagt atgccaaaac   27540
actccgccac ggccatctgt ttctgtcgct tttttggtcg agttaatcgc ttttctcact   27600
gcaaaatact gatgataggc agctaaaatc tttgcatcgt tagagaaaca gataaagttt   27660
tgaaggatgt caaggaatcg cttttttgtca aacattcctt cgatgaaggt gtcaaaagtt   27720
gcgtactgcg tattttcata actaccgtca atggttttcc attccataaa gcggtcttca   27780
ccagcagtaa ttgtgccagc ctttgaagtc gccaggtcac tcatgacaca gaacgcattg   27840
tatgtaaaaa gacttgggat ttccttttga taggttctaa gctgtaaaaa ggcatccgaa   27900
gcatccgttt cctcacgaga aggactcttc aattcaaaaa ccaccacagg taaaccattc   27960
acaaacacaa taacatctgg ccgtttattg ctatattcaa taatcgtcca ctggttaatg   28020
acagtaaatg aattattctc gatgttctca aaatcaacaa tcttaactat gcccgcaaga   28080
tgctcaccat catgaaaata agacacttca atcccatttt gcagataatt catgaagact   28140
tcgttctttt gcagaatcga tccattctca aaatgtttta gcttattcaa tgcctcttga   28200
atagcccctt ctggtaaaag gggattaatc cgagttaaag ctggctccag ctcatcaaga   28260
tataacggct ctgtgtaatc acgttctaca tctggaccat attgtatatga gtagcctaat   28320 tcatcttgaa aaagctgaat aatcgctttt tcgtagttat cttctgcaaa agccatgact   28380
tatgcctcct tatgcataat attgttaaat tcctagttca tcataaactg actgcttata   28440
atgataagca cccgttttttc cgtctttacg ataacttgca tctgacgtgg gacaattttc   28500
taaagcatat tgcattatct tacttccaaa tggaataaag atgcttaact tatcatctaa   28560
```

-continued

```
actctttgga caaagggtat ctttactctt ctttccattt aaatttacaa agataattgg   28620
taattctttc tttatcgcta gttcaatttc ccacttaaca aattttgtta aatttttcgt   28680
actttctcca attagaagta caaatacttt actgtttgcc attcgttctc ttagttggcg   28740
tttgataggt tcttcttgac ttgaatctct ggcagtattt aaatcgtggg catcatagaa   28800
attaaaatct gttttatcac tctgtttcta tgccttcatc agatgataat atctaatgtc   28860
tttatctcca tcaaaagcaa catatgtttt gtttcggtat gccatattat tcattctcct   28920
ttagttcata taaatttact tttttaaca aatcctcgtg tatgattatc tgaagtttag   28980
caggataagt aaactttatc ttgctgactt taaatgtcca gaccatgatt tgaagtaatt   29040
cattgatgtc tatatcctca aagccatttc taaatctagt tatacctgct ccaaaaacag   29100
gaactgatac cgttctctgt gcatatagcc tattaatctc attccaaaaa gccaaaagaa   29160
agttgatata ttcctgcatc gttagttctg ctttattatc atcatcaaat cggctaaaag   29220
cagtaagaat aaattcatca tcaattaaga cagaactccc aagcttatat cttttctttt   29280
tcccgacttc tcgattcatc tcttcaatca agcctttttc aagactttta tcgctctcaa   29340
tctgcttatc caatccttga atatctggaa aatatttttc aatcacctgt ccatttaaag   29400
acctcttagc aataatcaca tcatccactt gtgtgtcaaa gtactcatta aaagcaatag   29460
ctttcaatcc atcctgttta aataaatctc ccgattttat ttgaactgtt gtcgctccta   29520
tacttattga aatatcgttt aaggtattag ctctgttcca agtcaaaaaa taaatagcaa   29580
ccaaaaccaa gagaacaaca ccaccagcaa ttagtcttaa attcactgga atatcaacaa   29640
atattagtac ggcagacaaa atggcgaata atgttgcaga gcgactgcca aattgcatta   29700
taacttgctt atcaaaaagt ggaacttttt tagttttcaa aatgattaac tttttctttt   29760
cagtatttga taaatcatca tttagcggcg taataacata cttttatttc gcctgacatt   29820
aatttcggta acaaactatc tctgagggat attagagatt cagtttcttt aatgacaacc   29880
ttcattcttt caaataacgg ttctactaga gagttaaact ccttgaaaat tttttcacta   29940
ctagggatag ctaatttgta atttggaaca gcttttttac ttaaatgaag aacggtcgta   30000
ccgttaacaa agcccaaaca atattgtttg aaaagttcat tctttgtcat caagagcagt   30060
gtgtaattac ttattcctga tattttagaa ttgattttga ctaagtccat tgaagcaacg   30120
attgcatcgt agccgaaatc attaagaagt atttctgaat ttccaataat atctgcattt   30180
tgtgttaagt cagtatgagc aatcaaaatt tcatttatag acacaaaatg agtcggcttt   30240
atcttgtcac ttggcactag ctctttgaaa ccatttgatt taaaaccacc gtttctatca   30300
aaatttttga ttgtagccat tgcagtagaa gattctttaa gttctttccc tttatatgaa   30360
taaccattgc tgatttcagc aatttctgaa agtgaaacaa ctttccagct tgagggaatc   30420
atgccaatct cagtttcaac aaaatctgtt gagttctcgt aatcaatgaa ccacgacttg   30480
aaaatcgcct cgcgccatcaa ttctaaatga tgatttatct tcctattatt ctcgatcttg   30540
tcatctaatg agccaaggat ttttgctatc tcatgttgtt tctctttatt agacggaact   30600
gtaacatcga tagctttac agttttacca gaaacctcct taaaggtagt tccactaccc   30660
atattttcaa ttttatcttt attgaacttg agcaaataat ataaaaacaa ataatctgtg   30720
tcatcattgg gaacaatgga cttaaaaccc tgattagttg aaacctcatt ttcagctata   30780
gccacatacc caataggtgc tctagaactc aacaaaatgg tatttttagg cattaatctg   30840
gctgaactac ccttcaatcc ctcttcagta atatttcgtt ttccatgttt aatgaatctc   30900
cctgaaaagg tagataaatc ttttggagta atccaagcaa tatctcctcc ataatactca   30960
```

-continued

```
ggctttttgg tagaaggtgt tccaccacca acgacttcac ctaaatctcc caaagtacaa   31020
tttttccatt cggacatcta atctctcctt atcctataaa cttccgatgc gaattcttca   31080
cattcgcttg attgaccatc gcataatgca tagtcgtatc tatctttaca tgcccgagca   31140
ggtgttgcac ctgctctatt ggcattcctt tatctattgc tcgtgttgcc aaggttcttc   31200
taaacttatg aggatgaact ttttgcaaat caaccctttt tccgatttct cgaagtctcg   31260
tctccacgcc accaatttgt aatcgctcat gcggtttttcc taatgtaaca aacaatgcaa   31320
gattgctatc cgttcgactt tccaagtaag tcatcaagtg tattttcgtt ctggcatcaa   31380
aataaaccaa acgttcacta ccacctttac caaataccac acattctcgt tcatggaaat   31440
tgatgtctgc ttggtctaat ccaaccagct caccaacacg cattcctgtt gaagccaata   31500
agtctatcat tgccaaatca cgaatttctg tgcaagaatc acgtaataat tccaaagatt   31560
catccgatag cgtttccttg ataggtttat ccgtctttat cttatgaatt cttcgaacag   31620
gacttttcaa gatataatcc tcatcttcta gccaaccaaa gaaactactg aaaatgcgac   31680
gcatattatc aatcgttacc ttgcttgatt tgcgttcttt ttgataatct gacaaatacc   31740
cacgaagatt atcagtatca atctcacgta ttggtatatc tgattttgta agaagcatct   31800
gaatagttga ttcatagtac ttgagcgact tatcagaaca cccctcaact ctctttgctg   31860
acaaaaacat tttgagcagc cctacgttat ctatactttc ttgaatagtg ttgtccgttc   31920
tttttacgac ttcaacgctt tgaaaaacag ccgacagtac ttgcgttagt tctgttaatt   31980
gcacttgact caacacccct gacatcctca tttgtatttc tgtaataacc ttatctttca   32040
tctcttcctc caaaaaacag ttttcctcta ttttatcaag gaatgatgag aaacttgtgt   32100
actaaatcat catttagctg agattgccaa aagcattttc gacagctact ttattgattt   32160
agagccgtat ggtgggaatg taccagttga ttggcaatca tcaaacctaa caggtattgc   32220
aaactatctt aacggcttgg ctatgcagaa ataccgccct caaagtaatg aacaaggctt   32280
gcctgtctta aaaattaaag aactccgcca aggtttttact gattcaacaa gtgacttatg   32340
ctcttcaagt attcggaaag actatattat tcatgatgga gatgtgattt tctcctggag   32400
tggtagtcta cttgtcgatt tttggactgg aggaggctgt ggtctcaacc agcacttatt   32460
taaagtgacg tctggcactt atgataaatg gttctattat gcttggacaa aacatcatct   32520
tgaccgattt attaagatgg cagctgaccg tgcaacaacg atggggcata tcaaacgtga   32580
tgcacttgaa aaagctgaag ttctaattcc aagcgataag gactatgacg aaatcggtaa   32640
tatgcttaag ccgatttatg accagataat taataaccgc attgaatcca gaaagctagt   32700
cgctttgaga gactccttgc ttccgaaact catgtcggga gaaatctcgg tcaattaagc   32760
cactaaatga tgatttatct tcttgttttc agcaattcta tcatccaaag aacgaagtat   32820
agaaccaatt tcttttttgtt cgttaatcgg tgggactggg atttctaatc ttctaaagtc   32880
agttttatta aatttaggtt gagcacttcc agatactata gatttgagca tgtgttgccc   32940
aaatctactt ttcatccagt aatagtaaaa atcattatct cctttaggta taaacataat   33000
cgagtttggt cctaaagaca ttggtttaga tagactcgga gctttgaaca ccgtaccaac   33060
attagctcca acatttgaaa taattatctc attcccaaat aatttacttt tttttcaaaaa   33120 atcatatgaa tgtcggctta gatatacaaa gttcccatca aattcattgt taaagtcaac   33180
taatctaatt aagattgcat aatccggttc gttcttatat tgcacatttt ctttaaggga   33240
agcaaagctg ccatttgcaa cataatcagt cactaatttg gaattttcaa gaatcgttcc   33300
```

-continued

```
gactcccaa tgttcaggaa tctttccaaa cggagtttct ttataattca aatccaatcg   33360
cccccaatct ttctttgatt tctttctcca attcatgaga acgtgcaaac atttctgaaa   33420
gctctgaggt tagtcgttcc atcttttctt caaatggttc atcgtcttcc tcttgttctt   33480
caattccaac atagcgtcct ggagtcaaga tataatcctg tttctcgata tcttttgttt   33540
ctacaaccgc acaaaagcct ttaacatctt ctaactcacc attttgaaag gcttcaaagg   33600
tatctgcaat tttcttgatg tcatcatcac taaagtcacg gtgcttgcgg tcaaccattt   33660
cacccatctt gcgagcatca ataaagatag tcttgccttt ttgtttctta tcacgagaaa   33720
taaaccaaag gctaacagga atcgtaacac tataaaagag gttagatggt aatgcgacta   33780
ttccttctac caagtccgct tcaatgatgt tttttcgaat ctctccctca ccactggtcg   33840
tagttgaaag tgacccattt gccaaaacca atccaatctt tcctttcggt gctagatgag   33900
aaatcatatg ctgcatccat gcatagttag catttccagt cggtggaaca ccgtacttcc   33960
atctcacatc atcggtaaga cgttcgccac cccaatctga aatattgaat ggaggatttg   34020
ccatgacaaa atcagccttt aatgttgggt gcaaatcatt atggaaagtg tctgcttggt   34080
gagctccaaa gtttgcctca agtccacgca gagccatgtt catctttgcc attttccaag   34140
tgtcaggatt tgcttcttga ccatagatag acaaatcatt gatatttccg ctatgttctc   34200
ttacaaattt tgcagattgt acgaacatcc caccagaacc gcatgcggga tcgtacactc   34260
tgcccttgaa gggcttaagg attgcaacga ttgttttttac aatactggat ggtgtataaa   34320
attctccacc attcttccct tccaaagcgg caaatttctc gatgaaatac tcataggcac   34380
ggcctaacaa atcttgctct tcattttcac tgtgcaattc aatatttgta aagatatcta   34440
ctacattgcc tagaactcgt ttgtcaatat ctgggcttgc ataaatgata ggaagtacat   34500
ttttcaaaga tttattttct ttttcgattg cacgcatcgc ttcatcaagt tttacaccga   34560
tttctggcgt gtgagcacta cttgaaatca cgctccaacg tgctgtttct gggacaaaga   34620
atacattttt ctcaatataa gcatctctat cttcttcgtc tccctcatag taatcctcag   34680
cgtttaacaa ctcttgatat ctgaaatcaa aagcatctga gacatacttt aagaaaatca   34740
atccaactac gattttttcga tagtctgaag ctgatacatt tccccgcata gcatctgctg   34800
ccgcccataa ttcattttca aaaccaattt ttgcatttgt ctgtttttgcc attctatatt   34860 ttctcctact tgcttatttt ttctctggaa taatctcaaa agcatctgat actggcaact   34920
tctgataaaa cgctctcttt atattatatt ccttttgtcg taatttctct aactctgctt   34980
gtacttcttc taaaccgatt tgatattctt gtttagccag tttttgctcc tcaagagtca   35040
actctgggat agggaagttc ttcaagtcct gaaggctgat ttgccgaatg gttgtccctc   35100
gtgaaatcct ttctagcaga acttttgcca taggactttc tagataaatt tttaaccatt   35160
cagggtctgt agttctattt gctctaattc tgattaggtt ggcattgaac agcagcgaat   35220
catcatcttt atctaccatt ccgattttat ttgttgtacc acgaatactt aagagtaaat   35280
cgcctttctc tacccgataa tcatcaacat tctttacatc tgatgtaacc ctgactgatt   35340
catcataatt gattccatct tctgtgatgt ctgatattct aatgacttgg tactttccgt   35400
tttcactttc agtggcacga gtattattaa agcctctact taaacttgct acttcactca   35460
gttttagagt tttaattcta tctagcttat tgaaatctgc tttgacctca aggccatcga   35520
aatgataact atcctgaaca acgtatgaat ctactacaag gtcaccgtta tggatatcat   35580
ttagattaac agtctccgaa aatcctttaa ttgattcttt gtttccataa acagtagaga   35640
ttttggaaat caattcattt gacaaaaccc gttcacggcg attgacaacc gtcaccatat   35700
```

-continued

```
cttcggtcac tttgatgaac tgaactcgat tttttgcatt ctccttctta ttggtgttta   35760
gcactaatat tactgttgga atcatcgtgt tattaaacat accattaggt aaagaaatga   35820
cggtttcaat aaaatcaaag ttaagaatag attggcggat gattcgatct ggcccacctc   35880
taaacaatgc tccatttgga acaacaatca cagcttttcc attatcgggt ttaagtgctg   35940
ataaggcgtt gctaacaaaa gcccaatccc ctgcagaacg tgataagggg ccaaatttga   36000
aacggtcatc atttgataaa tcagcctcta ctttcacccc aaatggaggg acttgaacga   36060
ctttgtcaaa tttaccatat ttgggatact caggattttg caacgtatct cctgataaga   36120
taacagactt ttcagcacca ttcacaatta aattaatggc agcaaacgta cttaattctg   36180
cgttaatttc ttgaccgact aagagtgatg gctgatgttt gatagcctca acaagagttc   36240
cagctgtgcc tgctgttgca tccaaaacca tatctccagt ctggatattg gctaaggaaa   36300
caatcagttt attcaaactc tccgagttaa tatgctcttg atttctcatt gcctcaaatc   36360
cagaatttat taacatctta ggactgtagt cgttaatcag tttcagtatt tctcgatact   36420
tgccatcagg gagttttttca attaattctt ttgttctact tagaaacact tttagctgtg   36480
ggatattgtc ttcttgcata atctcatgtt ccaatgaatc caagaaggcc attttatatt   36540
gaagcattag agtcttaaaa atgtcgttat ttttgtattt caaatatgca cttgcaacta   36600
acatattcgg tatatcaaca gaactcatag tgccacgcca ttcatttgtt aagtttaatt   36660
caattgcttg tgtcatgttt tggacctcca ccttttactt taacttagta tttgaaatac   36720
taagttttgt atcttaaaaa aatatagccc ttttctagcc gaagaataaa ctgatatttt   36780
cttgattaaa taaattatat cataatattg atttgatgtc aaataaaaaa catgtatact   36840
taaaattagt attgctaata ctaattagtg tttaaccata aaatatcctc actttagttt   36900
tcgcaattct aaagtcacag aagttcaaat ttatgatttg agcttctttt attaaaaaag   36960
gagtttgata tgacaaggat tcaagatgat ttattcgcta ctgttaatgc tgaatggtta   37020
gaaaatgcag aaattcctgc tgataaacca agaatttcag cttttgatga attagtacta   37080
aaaaatgaga aaaatttggc taaagattta gctgagttat cacaaaacct acctactgat   37140
aatccagaat tgcttgaagc aatcaaattt tataataaag caggagattg gcaagcagga   37200
gaaaaagcgg attttttatgc cgtaaaaaat gaacttgcta aagttgaaac tttaaatact   37260
tttgaagatt ttaaaaataa tttgactggt tctgttgcaa agtttgaaaa tcaaacgcac   37320
ccgctctgaa ctccaaatat cttaggctgg tattcccatt aataccttga tttcagtaga   37380
caccgaaaag ccgaagagcg ttccatttct tcggttcttt ttatatattc ctcgaagggt   37440
ctccatgccc ttaatcgtgg aagaggctgt acggagactt tgataaaatt tattccgtcg   37500
tttaataggt cgatggtctt gttctattaa attgttaaga tacttcacag ttcggtgctc   37560
tgtcttagta tataaaccca cactctgtaa ctttctaaag gcggagccaa gagaaggtgc   37620
tttatcggtc acaattgctt tcggctcacc aaactgttta tggagtcgtt ttaagaaagc   37680
ataggctgct tgcgtatccc gtttctttcg taaccagata tctaaggtta agccgtccgc   37740
atcaattgca cgataaagat aatgccaacg tcccttaatt ttgatatagg tttcgtccat   37800
tttccatgaa tagaaggatt gtctatttttt cttcttccaa agataataga ggactttgct   37860
gtactcttgc acccaacgat aaatcgtagt atgacaaaca tttattccac gatcatataa   37920
caattcctga acttcacgat agcttagatt gtaacgcagg tagtaaccaa cagcgacaat   37980
aatgacgtct tttttgaatt gtttgccttt aaaatgattc attactctgt cgtctctgtc   38040
```

-continued

```
tttttttctca attttacact aaaatagatt ttttggaaaa ctttgcaaca gaaccacttt   38100
gagcaagttg gtgcttagct ttaagcgttt cactaaaatg cagtacgccc cataggtaac   38160
aagcgatagc taagcaatct gatgttgcga gatggacgtt ctttcggttt tgaacctcaa   38220
ggggaacact cgtttgataa agcgtctcaa tggttgtcag taaataaaca aaaacttttg   38280
gaagtgtgct attataagtc atataagtcg tgcgctttct aatgcttagt ggtttaagat   38340
taggatagca agacttattt attttccaat gaaattaact agcaattcgg gtataatgta   38400
gaatagagct atggagcttt aaaattcctg aaatgattta ttaagttaat cgagatataa   38460
tgtgtctaaa tgttcgttct gttcgctcct gatgagcatg ataatatgtt tcggtaattc   38520
gggttttttt ggaaagtgag aactaaaaat gactaaagta aataattttg aagaattgat   38580
tgagaaatct ttcgcaagtt tattacaagg aaaaacaaaa tatatttttt tcttgaaagg   38640
ttttaattat tggatcaaaa attttgatct aaatttctta cttgagagta attctgctgg   38700
aagcaatgag gagatttcgg tcgaaaaaat agttagtaaa ctttctggaa atgataaatc   38760
atactttgca tggtatgaag acattatttt attacaagaa aataaattgg aaggaattct   38820
gaatagctta caatataagt gtataataat agaaaatgat ttcttttaa gatattatcc   38880 ttattttaaa ggtcaatatg aagatgttta cacaaaagta gaatcttct cagagaacat   38940 ttatcaaact tactataatg aatttcaaaa tattaataat cagtcatata tttcttatgg   39000
gggtgtgaaa gattttaaat gcagatatac taaattttcg gacttaattt ctcaaaacga   39060
atttgagtta gtgctaaatg atgcatccat agaaatttca tcagaattgg aaattgttgt   39120
ttcagattat atacttaaag tacttaatat cctgccacaa agaatatttt tatctagaga   39180
acttaagaag aataaagtta attttgaatt gctgagggaa ttaggcatta atatagatat   39240 tatgacgaa tcagaagata gtgatcaaat atctagaatt aaagaatatg aaaagatact   39300
aaagagaaag aacaaaaatt atgaattcaa aaatattccg atttatgaaa acccattcga   39360
aaataatatt ttaaaatctg taaatcagtc tgtcattatt aatgaattag ttcaaaattc   39420
tgagaatgca caagcctcaa ctacttttaa agatgttttt gtaacagctc ccactggtgc   39480
aggaaaatct gttatgtttc agataccggc gatttatctt gctgaaaatt tgaatttagt   39540
gactcttatt attactccat taattggttt gatgaatgat caagtggcaa atattgaatc   39600
tatgacagat tctgcagtaa caattaattc ggactatact cccattgaga agcaagagac   39660
tttagaaaaa ataaaaagtg gggaaaaatc aattctctat ttatcaccag aaactcttct   39720
ctcaaatagc gatttaacaa atcttattgg tgacagaaaa ataggattat tagttgttga   39780
tgaagcccat attgtagcaa cttggggaaa aagctttcgt ccagattatt ggtacctagg   39840
agattttatc aatcgactaa gaaatgggaa gaaatcttct caacatttttc caatagctac   39900 atttacagcc actgctacat ttggcggaga cgaagacatg tatgaagata tagttggatc   39960
attaaaaatg aacccaactc gtttcttagg aaatgtaaaa agagatgata ttcactttga   40020
tattcggttg aaggaaaaac agctagctta tcgagaagaa aaattagaaa ccgttgtaaa   40080
tacagtaaat gagtcaatca ataataatat aaaaacactc acatatactc cctatacaag   40140
gcaaattcaa gaaattattg aaaaagtatc tgatagaact aaagtgagtg gttatcatgg   40200
gaaagttaat ccatctaaaa aaaatgagag cttaaagaaa tttaaatctg gtgaacttga   40260
agcaataatt gctacaaaag ctttttgggat gggtattgat attgatgata ttaagcaagt   40320
ttatcacttt gcacctactg gaaatattgc tgactatgtc caagagatag gacgtgcagc   40380
gcgtaatcca gaaatgaatg gtatcgcaag tatggatttc tataaagagg atttcagata   40440
```

-continued

```
tattaagcaa cttttttggta tgtcatcgat taaaaacttt caaattgttg gtgtttttgcg   40500 caatattaat gaattgttta agaaaaataa gacacgtaat tttttagtat ctcctgagga   40560
tttctcgtat attttttccag aagaaacgat tgaaaatatg gatacaaaac tgaaaaccac   40620
tgtgctcatg attcagaaag attttgaaat ggatccaagg aatggatttg taccattaat   40680 tttttaaacca aggagtatgt ttactgaagg atatgtatgc ataaatgacg atttttttaga   40740 taatatcaaa ttgtttggtg cagaaaagta tttttctaaa atttcattgc ctcgaaaagt   40800
ggataagatt gataaaagtg gaaagatata tacatcagaa tttactggag atacttataa   40860
attaaattat aaattgttgt gggaagaaaa gtataaagat atgtcatttg gggctttttaa   40920 aagggctttc caaatgaacg aactcaagga taattactcc gtagggacta agattcttaa   40980
tagagtaatt attgagatcg atggaggaga aaataatttt aaattaataa aatcgaaatt   41040
taattacgtt ctggattctt tgattacaat cttttgacgag ttaaaacagg caaacaaaca   41100
tttttcagtt gatgaattaa agaaaaaaat agtagaaaaa ggattttttgg atcaaaatca   41160 tcaagcagaa cctcttgctg cttcaatcat acatctatta aatagagttc cagtacagca   41220
attcagtggt aagagattca cagagtttaa tagtcaaaca aataagtttt caatcaaaaa   41280
ttcaacatat gaaaaaagga tcaatgaatt gaaaaagcat tgtagaccaa tgttaggaat   41340
tgatgcgaat acaaaaacaa ttatctatac ttcaactttg aaagatagca tggaaattct   41400
tgtgggacaa attctgaaag tattagaatt ggctgaggta aaaatctctg gaggaaataa   41460
gcccgagtac tttgtccgtg taaacagtcc ttatgcgatt gaaagaataa taaatgacga   41520
aaactaccac agtgagatgt taaaaattgt ttatgcaaga catcaaaagt ctattgaact   41580
catggaaaag tttttttacag agttgaattc tgatgaagag cgttgggaat ttattgagaa   41640
atattttctg ggacaaattt aattgtaaaa agaaaaatat gataaactat attaaaatca   41700
agaataaagt atgatattgt ttttaaaaat tattcaattt ttaattcatt atcccattat   41760
agattcattc aagatgagat tattctttgg tacactttca aatattctta agctttaaaa   41820
tgcggggaat aataggtaat taaatgttca acctgcatta ttggtattgg gtagatgata   41880
gtttgtctgg atgtaattta ggaaaagttt caaaaaggat tatatatcaa taattatgta   41940
atgaatatct gcgttcaagt tattagaaaa ctattgagga gaaactgacg ttaagtcaag   42000 ttttttagagt aacaaacgta gaattttaat ctatttattt taagcactta cctttttcaaa   42060 ttgattaggt gtaaaatacc ctaaactttg atggattcgt tttgaattat aaaaggcttc   42120
gatgtaccag aaaatactct gataggcttc ttcaaagttc ttatatttaa attgatacac   42180
ccactctctt tttaaatgtc catgccaaga ttcaagactg gcattatgat aagggtatct   42240
ttaaattctt ttgagtagcg tttttttcatg tttttgtcct ttgtctaaat tatacaaatag   42300 tgactctaag atttaaggat aacatcacct ctggcgaaga atagaaaatt aaaaagcctt   42360
ttaggctttt ttataaacgc tcgaagagcg tttcttctta tcttgattgt ttgcctttaa   42420
aatgattcat tactctgtcc tctctgtctt tttttctcaat tttacacaaa aatagatttt   42480
ttggaaaact ttgcaacaga accatatttt tttataattg agttagacta tcaactattt   42540
ttttagttaa ttcttttttgt tggggttgcag ttagtttact tgaggttcta attacacatg   42600
taccacaaac ttcatgagac ccagagttga ataatcctgc cccatcgaat gctgataaat   42660
aagtattgcg tttttttgcgct tcttcaggtg atttgtacac ttcaatttgt cccccctgcat   42720 cagtacctttt agcaataata tctgatccat ctatttgatc ttgtacttca gagtccgtaa   42780
```

```
aataaatagc agaggtgtac cccccaggtt tattcaatga tccattggga tcattgcttt      42840
cggttactgc ttcaactcct gtaatggtag gtatcgattt taattttttt attacaaaat      42900
ctgaagatgg attagtcacc aacttatttt tattgattga ttctttaaaa ttagataaag      42960
ccaatttcaa ttctttttgg ttatcactat agtcaactgt ttttggcaaa tcctttattg      43020
atttgttaat atcagaagtt ttagtgggga ttttgggaac tatgaccata tcattctggg      43080
attgctttaa aacattgtca aggttcgcct tagttgaatt gtccagtggt aattcgttag      43140
tttttagact tttttctgcc tcttgaataa ttttatccaa agatttattt ttttctttga      43200
taggtttata agcactatta aaattatcaa ccgcttcctg atgtggtttt gcaattccaa      43260
agtagtatcc taatcctata ccgacaaaaa caactatcat agaaaatata gtaattcttt      43320
ttttcatttg tatctcctca aatataatta tactccatac attagctatt atatcactaa      43380
aacaaaaaac aacccctatt atctaagagt tagataatag gggttgtttt catttgattt      43440
cttaggggtt attatataat tatagtccct acacaaacat cttttgtaaa aagccttttt      43500
tctgttcttt caacaaatct aacttacgtt gatgaagaga gataataaag agctcaaaac      43560
ttaacagttg tgagctcttt ttttgtgtgt taaaattaaa ggagaaagaa cggctcgtaa      43620
cttagggtta ttaatagagg tcaaaatatg aaaattgggg atgcacgtgt cagtactttt      43680
gaacagaaat tagaatctca aattgaagtt ctgaaagaag caggagcaga agaagttttc      43740
caagaaaaat ttacggggac tacagttgaa cgtccacaat ttaatttagt gctcaaaaag      43800
ttaacaaatg gcgatacttt aattgtgaca aagttagatc gattagccag gaacactaaa      43860
gaagttttag aaattgttca atcgttattt aatagaggaa ttaaggttta tatattaaat      43920
attggactta tcgataatac accgacaggt caacttattt ttaccatctt cagtgctttt      43980
gcgcagtttg aacgagacct tattgtaacc aggactcagg aaggaaaaaa ctttgctaaa      44040
atccatgatc cgaactttaa agaaggacgt cctcagaaat ttactgaaga acaaattcaa      44100
tttgcttatg aattaaagca gcaaggtatg acttacaaga tgattgagcg aaaaactggt      44160
atcagtattg cgactcaaaa aagaagattt atgaagatcg caaaaaataa atctattgac      44220
aaagactatt gaaatgatat aattaacata acgaatgatt gtgggagtat tatctcacag      44280
agagtcggga cacgtcgaaa aggtctcggc tttttttata aaaaaacact cactccgtcg      44340
aaaagtgagt gatgtggaat tagtggcgct ttttatgtcg gtgttttaac cagtccttga      44400
aaagttcaag gacaactcct accacaatgg aagcgacagc tgtaacgaat gactgcagaa      44460
gcatagatct caccccctcc ctaaggcatt tctgcattgg tcaggtgcgc caatttatat      44520
tgtagcatat caggaaggat taggctatgt caaataaaaa atcaaaatat tgaaatacaa      44580
atattagtaa atttctatat tttaaaagtg gttaagtttc cccgcatcat cactggattt      44640
gtaaagcctc acacgttaaa tctgttaagg atctcgaaaa tagagaaggc cgtaagataa      44700
tcactaacta acaattaata aagaattatg aatcagtagt agtgataaat caaactgacg      44760
gaaagaaaaa cagttacccc atagctaacg cttgcaatgg agaagttagt atttcagaag      44820
aaaaaaataa tacaagaaaa acctaagaac tggaatgttt ttaggttttt cattctctac      44880
tgaaattaat attttgatgg ggatacaagc ataatcaaaa tataagttta agaatttgat      44940
actctttttg aaaacgttgc aacagaaacg tcggagggga ttttaaagac ctttctgttt      45000
gatgatttaa tctttttataa attatatgat gcatactata ggatttaatg ataacatcac      45060
cattcagagt accccgacaa tccggaaatt tatggtaaca cttccttaag gaacctataa      45120
atattcatct tgggtcaaga ttttcaattc tgggatgatc gttactacaa taccattatc      45180
```

-continued

```
tagatctgcc ttatcatcaa acaatatgcc catttttcca tctcgttcaa tcagtaaaca   45240
gtttggagta aatctatttt ttgactgcga tgacactgaa ttgagcaata tattttcaat   45300 cttttttttga atttcaactc tattttgaag aaaataggta taggcatttt cttggttctc   45360
agttatacct tcatcctcaa aatatgattt cgcgtttacg actaaaaaaa atactgtccc   45420
caaaaattca aattctaaat ttgtcttcca accataatca aactggacat caccaaaaac   45480 tttatttttcc attatttacc tccttcacta ttttcaagag ctctcatcat cgaaacacct   45540
ccactatgtc tgatattact gtgaacttca cttggtaatt tttgcatcgt ttgtccatct   45600
ctacattcgt gccaagtata gccgttatct ttcctccatt ttgaaacttc ttcaggagta   45660
tatccagtat tccttgcttg agcaatatca gcttttgcaa aattatcagg tcgactgctt   45720
gacatttcag aaattttaac atctccttta ctaattggtg aaaagtcagg ctcaccttca   45780
ctaaaattaa tgccgtcaat tccatatttg ggtaaaattt ctccgaatgt ttttccttca   45840
gaattcgcaa tcttaggaac cgcatctgaa tctggaataa atttcgattc gcctcgttcc   45900
ccctcccaat gcccgctcga accttcaatg ggattgtgag aatatttatt ttcgaatggc   45960
ttgtcatatt ctgtcattgg tttatcaaaa tccttacctt ctacagattt acctaaaggg   46020
ctctcagaaa tgttgttttt tgaaatttct gacacttcct tcatcatcat cggattcatc   46080
tggcgtcacc ccctttcccg tgtatactca atccattgtt ggtaaatctt ttctctgact   46140
tctgtttcat cttttccttt actaaagtcc tttatcatac aatgacaaag cgccaatcgg   46200
acatttctag atgcttccgg aataacttca ctagataatt tcaaaagtcc aatagtcaat   46260
tcctcatcat cccgggcagt caaaatattg ttctctactc gaccacgaat acccagaata   46320
ctaatcagtc tccgggataa ctgactaaaa tcaccatccc atgaattacc gaactccgga   46380
ttttcaatat aatctgcaat ctgatcaaga atatagagcc gatcaactga gctgagtcgc   46440
aatatatcaa tattattcac gattttagaa gcattgaaat ctaaatgctc cccaactctc   46500
agatgcagga gaaattttac tacttgattc ctaatatttt gctcagttag aactttttga   46560
gtttccgagt attgaaaaga tgtttcgtca actgtcgctt tatgcacttt gactaaaaca   46620
ggattaaccc agttattttg ataaaccgcg gcaacaccat tgtcaagctt tgcaagttct   46680
ttaatctgtt catcattcaa attcgcagct tttcccacta attctcgatc actctgggca   46740
ggcaatctca aaataatttt ggtattcgta ttacgaataa ccgccatatc cagcaactct   46800
ggagactgat ccgcaataat aaagccttcg ccataagttc gcatttcggc aatcgagttg   46860
gtcaacattt ctacagattt tccaagcaga ttggctccat cagccgattg ttccgtcgag   46920
gttcgcttga gcaggttatg agcttcctcg agaacagtaa tgtgggacaa gggactgttt   46980
gactttccag aagtcatccg atactcatta agcttcatca ccagcaagcc catgattaaa   47040
gctttagttt caactgaccc tactcgactc aaatccacaa taaccttgct gtcaaatagt   47100
gccttatcag ataagtcatt gacagtaaaa atctgtccat tcagcccatt ggtcaatgaa   47160
cggactcgcg tcatcaaggc accgatataa tcccctttac tgtcagcaga atacctagag   47220
ttttcaataa cctgctcaat tttgtccaaa acatctgcaa agttcgggta tttttcacca   47280
tttggattct cagatgtttc caggtcccat cctactgact tgtaagcata ctccatcgct   47340
tcttttaata ttgcaggcat cgcagcatac atcggccagc aagcattaaa gagttctacc   47400
aaacggtcaa ggtgctctag gatatgaata tcagcaggga atcggaatgg attaatccgt   47460
agcaagggca ttttcttagg attggtacca tatacagcaa catcccttct atttccaaac   47520
```

-continued

```
gcatttttgt attccccttt tgcaggttca accactaaaa atggaatatt aaaaagtttt   47580
tctgtcttat caaggatctc ataaatcgta ttacttttcc cagcccctgt cgaaccgtc    47640 acaaatgtgt gcatagtaag cgaatcaagc tcaatttcaa ctctggtctt cccttcaatt   47700
cccatagaat agatttcccc aagcgaaaat gaccgttttg aatcatccgc gttataacac   47760
acaacttctt tcccaaattc tgcgtgatcg acgacaggga agccagttac tgattttcta   47820
ggcaacccca tatgaagagc catttcatta ccactaacca gtgatgctgg agttacttgg   47880
agcgtagcta aaggagattc ataactaaac actgggtgaa tgaaatttgt aatatattcc   47940
ttcagacgtt tgtgattttc ttggtcatct ttcccccaag agttgatagc tgaaacttct   48000
acgccggttt tttcaccccg cattagggaa ttataggttc cagccgccat ttctgccgtt   48060
tgttgactat cagacaaaaa gtaggttgca cattcccaca ttccaagact ttcacactca   48120
tccattcgtt tgagctgtgt gtcgattcgt tccaacgtat taatcagcgt tttgttctga   48180
atcgtgagtt gcaaattatt tgacgttcca ttcgaaacgc tgttagtttt tgttgctgat   48240
tcattgacac tatcattttc cccttcagtt cttccctctg tattgccaac acttgaagaa   48300
tcagaatctc ccattgttgt agtgtctttg aagagtgtag ctccaattcc tgaaactcct   48360
gcgactatca tagcacctcc tacaggagca cctactccag tagtagccaa agccacccca   48420
ctaacaactc cagcaactgc tccaattcct cccagcaact tacttgccat attatccttg   48480
gatacagatt ttgaagtact ggtacttata ttttcagatt ttgttttga aaaagaacta    48540 cttgtccctt tgctagatcc tttagaaaac gcatctgaaa cactgagtgc catattttgt   48600
ccatagctca tttgcagatt tgcaaaggga gagagttgcg tgtagattgt ttcataagcg   48660
ttgcgagtct ctgaaagttc ttctggatca acactttac ccaaaacaat tcccgtatat    48720
tttttccctt gcattgccaa agcaaacttt tcaagacctt ggataaagtg gagattatcc   48780
ttggagtttt cgtctttgct ttttgcaacc actgacacac tagtaatgtg ctcgcttgga   48840
agtctcttca gaagtccttc cgccgggtca ttcaataagt tttcagtctt tacgcctgga   48900
aattgacctt taagtgaatt ttccagcata gatttcaaag tgctagttgt ccgtttgtca   48960
tcaagtgaac gaacacccat atagaattcc gtcttttctc catcactatc tacgacaata   49020
aatacaccgc aattcagatt ttgcagaaca tcaaaaacgg cagaaaattt atgagtagaa   49080
tattcatcgg tttgataaac catttccgtg attttgaaaa gttggatgtc attaatttga   49140
atctccgggt tttcaagagg tagcacttcc agctctgata atcgtgttaa ataatgtttg   49200
agaaccacgc catccaccaa ctgattcgct tctgcaagtt tctgtttcaa cccgtcaata   49260
ggtattacat tagattgttg cttagttagg tctgaaattt tcttggcatc agtcattatt   49320
tttcaccatt agtcgctacc gcagtaacaa ctcctccaac aacggctcca gctgcggctc   49380
ctaaaataat tgatgatcct gatgctgcgg caactgcagc acctactacc gcaataacca   49440
cagctccacc tgcaactttt acttctctaa ttggccctct tttcttgtca cgcttctttt   49500
gctcgtgata actccaagat tctgatgtct aaacgtagt ttttggccga tctgttgctg    49560
ttggactttt caaagtcgtt tctgggcgta attttttcac aacctcttta agatgcgaaa   49620
tcctctcatg ggaaaaatta cgagtgactt gagccaataa tatattcatg tagtcttcgt   49680
cccaagacct ggaatcttct tttaacactt tttcatcgtg cttatcgtaa agtccattca   49740
cagttgaagc cagacgatcc atctcgtcga attccttaaa acttgggtca acaagaagac   49800
tatccttcat catgatgcgg attttactga cattatttc ttcaactgct tgtctaaaat    49860
tattaccaat cttcattttg attgtttttc tctttcttga acttagcggc aatttttta    49920
```

```
attgcttcaa ttttgcttgg attttttttcc agtcgtatct ctaactgctt aagatcttta   49980 ttttttttgtt gctgataact ttttcttgag ctaccttttg tacttacaac tttgtcccta   50040
tatcttttag aatttggaac ttccatggga tagatttttt tcacgatctg cttgatgtgc   50100
ctgattctct cccgtgagaa attgcggagc agctgcacca tcagtaaatc taaatattga   50160
ctgtcccata gactctcgtc tgcacgaagt tcacgattat caaaatcgtc atacagtcct   50220
tcaatttgag aggccagagt gttcatttta ttgaaagttt ttagacttgg atcaacaatc   50280
aagctgtctt tcatcataat ccgaaccaag ctaatgtttt tattttttgac ggcttcttca   50340 aaagcttttg taatcatccg ttttcctcag atttccaaaa ttgactctac tttttggtta   50400
attgcttcta accaagcaag tttctttttgc gattctttca tccgttcctt agccagattt   50460
ccactcttag cataatcgtc tagctttgtt aacttatcaa ccaggaccgt atccaaagat   50520 ttgattttttt tcttaaaatc ggcgacaact ttagttgact gttccttagc atagattgtt   50580
gcttcagtag cattcgtatt taggttctct tgaacagggg tcaagaattc ttgagcaaac   50640
tcacttccgc taattttttg aacagttttg tattttgttt tataataacc ttgctcttgc   50700
agccaagtcc atggtttgta ccaagccttg ttgtaatttt ttacatattc ttgtccatcc   50760
tcctcttcag tatcataaat taaatcttca acatttactc tattatcagt tatgctggct   50820
tccattaatt tcaaaggttc aattttaata ccatcagcca catgaatttc cgtaaacgca   50880
gctaacttgt ttcggtattc ttcaagaagt gtttcgcttg tgcttcgcaa gctgttaatc   50940
accactttat ctagttcaac ctctaattct ggttgaagat ttcgtgaaaa ggtttcaagt   51000
tttgctgctt cagcttctgc ttgatctata tcaatctctt gacctctaaa ctgatcaatt   51060
tgttttgtaa tttgcctctg gaatttagca atcacattat cgacagcatc ctcagcatct   51120
cgacctactt tgatcatttg gtcatccact ttatcaataa acttcttcgc ttcattacca   51180
tcagaaattt tagtttggag ttcttttatt tgatgactaa ttctttcact ttcttcatga   51240
gcggctgcca gctctttttt cgcattttca aaagccccga cttcttcaag attgtggctg   51300
aaggtatcca caatgttttt tatcttggct gttttcgcat acttttcaac atactgttga   51360
atcgctgcct cgattgaagg gattccagaa tgaatcaagg cttctttcgg attgtttaat   51420 ttttttccctc cgctttcctt aagttggaca accgaactta aattatctga aattttttctt   51480 ttaatacttg ctggcaaagt tgcaaattga tcaaagtaaa gttcttcatt tcggttcaac   51540
tttttgacct tagtttcagt ttcatctata acatcttcgt cttttctcttc tccgctttca   51600 agaagtctga tattaagtgc cgtcagtgct gaggcaggaa atagatttgg attttcaatt   51660
ccgtgatttt gaagatattt ttttgtatcc tcaagaaacg tttctaagga accatcatct   51720
tttgtccgac catctaactt attaacgaca aagataaatc ggtctttgga ttgtttcccc   51780
ttaactttca tactttctga tacccggcgg agcagcaaat tgtcatcatc cgttcctcgc   51840
tcacctgtca tgatataaag caccaaagct tttgaggatt cactcagcat ctccacttga   51900 cgcttttttgt gctgtgggtc tcgagaatta ttcggccctg gtgtatctac aatcacaaga   51960
gcagcatctt ctgcgataac aaatggaata tctcctaaaa tggtaatttc agacactttt   52020
tcatcactat tgagtctgac catatcggca taagacaata ttggcagttc ttcaatgagc   52080
tcatgctcat catcatagac tttagcctga taagtctcac tgtctgtgtc tttgattcgc   52140
gtgataattg ctgtgcaagc ttcttgtttt gatggcatca gcttggtttg cagcagtgcg   52200
ttaatcaacg ttgatttccc agcactcatt gttgcgacga catcaacttc aaactcatta   52260
```

-continued

```
ttttttcgctt gttcaaaggc cttttttcaac gcaggggctt tgagttcttc aaatggcccc   52320
tcttgaattt cttttgaaaac ctctgaaatg agttttttcct tatcctttgt ttcttttttgca   52380 ggtttgtgat ttaatctacg aatcgtcaaa tctgacgatt caaaaacttc cttcatgtct   52440
tcgaaatcta attgtgtccc gaagaattca acgtcaaaat ttaaatcatt gcattcttca   52500
acgagaattt taggtaaatc ttcaatccac tcttgaagac gtatatctga tttcaacaaa   52560
ttgctatccg cttttggaag cttattgtca attttgattt cagtttcgag cttatagggga   52620 ttgtattttta ttgcaatatt cttcataaga tctctctatt ttctagatat ttttctaaag   52680
ctgtcagtcc actattggca taggacgcat taacttcgac cttatcgaag ttaaggttat   52740
aggattcctt ttttagcttt ttagtaagtc ggtaatattc atccttatcg tcttcatcag   52800
ataggccttc atactcattt tgcttcgcta gaaaagcata ataagccgat attggaaaga   52860
cctttggatt cttgtaaccc agttcgatca aatcctttat cacctgttca aggctctcag   52920
gtatcgaatc ttcatttttga ttgaatcggt caaacttatt gacgacaaaa acgactttat   52980
ctttcgggac gtttttttgat aaccagagca agtgattttg agcatcctct acacctagat   53040
ttgtcgcgtc taaaacgcaa atcacctcat catagtcttc ttcaagcaat gctctcttcg   53100
taatcttttg gtggtctcga ttcgttgctg agtttacacc aggtgaatca ataatgcaca   53160
aacgagaatt tttttttcgaa cttttttctaa aataggatga aataattagg cttttatctc   53220
gctcagctgc tttcaaattc gtaaggctta tatcgaagtc cagattatca gtctcaactg   53280
caatcttgtc atcttcaaat ggtttattaa acaagtagtt aatgtgacta gtgcaggcaa   53340
cttgcgaaat gttcattaga ggttttccaa tcaaggcatt aattagcgtt gattttccgg   53400
cactcatcgt tgctgtgatg aatattgttc gcaacggttt tttttgaaac tcgatgtttt   53460
tcctgatctg aagtatctgc tctttttaggt aagaaaattt ttcttcaact tctttattac   53520
tttctattat ttggatcact tcactaagtt gatcgaattg tttttttatta agcttctcac   53580 gccattttga catagcttga ccaaaatcgc tttttttgagt tatcaaaatc agatataggt   53640
cgcaaagcaa aatgaatctc atttttttttcc tccagagaac attccaatag cctaatactt   53700
tctgattttc agttattaca gagtctgata ggccaagtat cttccaatat tgttccaata   53760
ttccttgtgc gtactttgtt cttgtaacat ggttcacaag caaacttaaa gactgaaaat   53820 attttttcttt tgtttgtgat ttacagtgca acatcggatg gttatctaaa tctaacgctg   53880
tgctattctc aaaattcatg gttttccttt ccctatcatc ctcatagtaa cccaataaca   53940
ccatttaatt ctttctcttt tcaaaacggg gagatgacgg aattaaacac tactcaaaag   54000
ttatttgata ctaaaatatc tttgtcttgc attatcatat ccgtctgcaa ttattattac   54060
atttgattct gcagatgctc ctaggaatga ccattccaat gcggaccta ctctaaattc   54120 tttttcctgt acactgcgac tatattcgtt gaacaatttt tcgctgaaaa ggaagtgtaa   54180
cagcaaaaaa taaaaaagta taattttaat tacccaaact atctaagcaa gataacacat   54240
cttcaatatc ttgatttaaa aattcttcca tttcttaaaa atcaaattct tgaaaaacct   54300
ctgattggtt tttgaacttt ttcattttca tatcaaatta tccaaaatct aatcacaatc   54360
ttattatctt attttatgat aataaaatca aatatcatta ggatagatat atcatactaa   54420
tcagaccttt ttgagataat ccatctgtct accctcatac tctttttcttt acattttacg   54480 ataaaccagg agttatagga aactttgcaa gagaaccact ttacctaata tattaggttg   54540
ggtaaacact tctctttcgt catctaaatc attcaaatct gataatattt cttcaatatc   54600
ttgatttaat aagtcttcta tagaatcaaa atcaatgtct tcaaatccat ctcgtatttc   54660
```

-continued

```
attttttacaa tctatcacat tttttttgaaa actagtctttt attttttcatc ttctatctttt   54720 gtttcagact attctaacag tttgactgca tctccttgac ttctcaacca catcataagc   54780
ccttctccaa aagcttctgc tcgaatgatc cactcccctt tggcaacttc ctgttcgatt   54840
tttgctgtgg gtattctatc tagtaaggcc tccaaaactc ctgtgtattt gaatcggata   54900
tgctgaagct ctccggtgtt catgaatagt attctttttgt aaaattccga ttcactaaac   54960
ttctctgaat atggaattgt aaattttttct ccatctgata acagattttt tactcgatct   55020
actctgtaaa ttgttggtcc atcattatta gcatctagat ggtaagctaa taaataaaag   55080
taaaactcag aaaaaacaat actaacgggc ttaacgtgat gtttttttttc tgtgccatct   55140 tgacgttgat actcaaagga aattaagttt tgattcctaa cagatgtggc aatttcccag   55200
attctattta ttaaatctttt tccatgttta agttctatat agtggagtct ttgatttcct   55260
ataagctttg aaacttctttt ggattctttg atattgcatt gtctcaataa tttatctatt   55320
aaagcgttaa attcatagtg gttgaatgca cgactttcaa ttaatatttt acaaagtgca   55380
taaacttcct tcttagtgaa cctttttgggt tctgatagaa gataataagc gtttaaagtt   55440
ttatcataga caattttctc atctgtttca aaataaaatt cacgtaaaaa cttaatatcc   55500
cgatcaaatg ttttactagg aatatcaaac tcttttttttta tttcttgctt tctaagatac   55560 tccccccttgt ttagtcgttc gttcatcctt aaaactcttg aagtcttatc attttttaata   55620 aacattttttc ctctttaata ttatacaact ctatcataga caatttttgg gtatataaaa   55680
attataccag ttttaaaagt taaaagctta aatggaaaga attccttaaa ttatgacacc   55740
ctaaacgtat tacccatatt ttgacccacc tatagtgcta ttgttataga caggagatta   55800
aattatgaca caaaaatcgt attgtaataa ttgtggttca tcaaatactc tagaagactc   55860 atttttgctca gagtgtggag cgccactaaa tcaggggaag ccgacaacag gcgaggctaa   55920
aactataaca aatagaagag tgaatcattc taaaccgatt aaaaaaatca ttggaagtat   55980
ttgtgttggt ctgttagtgg ttgctgctgg ggtcacagca gttgtaatct atcataatga   56040
acagactcaa agcaaaaaaa ctaccgcaca cgagaaattc ctatccagcc aggcatctca   56100
agaaaaaaag caaagttcat cctcattatc tgattataaa aagcttcaaa atcttgcaat   56160
agattctgtt gataaagcct ataatactaa aagtagcgct gacatttcct ctgctcaaga   56220
tgtgataagc aaattaaaaa agtcagacca agcagcctta tcacaacgat tgaaaaattt   56280
aacagatcaa atttctaaag aaaatgaaac gacatcatct tcctcgtcta gttctaaaac   56340
aaacccacaa acctcttcat tattatctgg ttatagcgat gatcaaattg aatttgcacg   56400
tgtaactgaa gcaattgttg tttattataa atatacttat caacctatttt cgattagtgt   56460 aactaaaaat gaagcaaatc accaagtgtt accatttgat agttccatag tcattcctca   56520
agaatcagtt actttatcgt ttagttctga taatacaatg gctggaacaa ctactattac   56580
ttatacttct aatcacaatg gttctattaa tttctatcat gaacccaatc attatcaaga   56640
tgacagatat ttaagtgatc ctgattgggt taggcaacaa tctcaagaaa tattaaacga   56700
tatgacaacc atagtcattc ctacatcagt cgatgataaa gcctccttaa tcattttccaa   56760 aatacaaatt aactagaaaa ggaataaaac ttaacatgaa aaaaaatata atttgcccac   56820
agtgtggcgc tagtaatacg tcagaaaata tattttgttc agagtgtgga acaccactaa   56880
aacaagagag cgctccaaaa ggtgagccta aaactgtaac taatagaaga gtgaatcatt   56940
ctaaaccaat aaaaaaaaatc attggaagta tttgtgttgg tcttttagta gttgctgggg   57000
```

-continued

```
gagttacagc agtcgtaatc tatcataatg aacagattca aaatcaaaaa actgctgaac    57060
accaaaaatt actatctatc caggcatcta aagaaaaaga gcaaagttct tcctcattat    57120
ctgagtataa aaaacttcaa aatgttgcga tatcttccgt tgataaagca tataatacta    57180
aaagtagtga tgacatttcc tctgctcaag atgcgatcag taaacttaaa aagtcggacc    57240
aatcgtcctt atctgaacga ttgaaaaatt taacagatca aatttctaaa gaaaatgaaa    57300
cgacatcaaa atcatcttcc gaggataata caaccacgtc ttctcaagaa caaataaatc    57360
aaccaccaat tttaaagaaa gaatataaag cctcaggtaa tattctacgt ttttatccga    57420
accctgtggg gcaagcagat ggtgtataca gaattgatac agctaatgat gatggaacag    57480
caaatatggg gatgtggaga gcttataaac aagtaggaaa tattatttat gattctactg    57540
atggaaaccc aatttctgcg ggagatatta atggcgggga acaaaatgca gtatttcaaa    57600
cagacggtcc atcggctcga tataatataa caattgaccc tcaatcagga aacatacaaa    57660
taggtggtgc aactttttgta ccaactaact aaggagaaaa aatgaaaagt tattgtgaaa    57720
aatgtggaaa tgaacttaaa gaaggttcca aattctgtgt caaatgtggg aatccgacca    57780
gtacaaaaaa agaacaaaat atttctcctg attcaataga aaccgaacta atccaagccg    57840
atgaaacaat tatggagttt tgtacaaatt gtggggaaga aatgacccct gaagctgatt    57900
tctgcatcaa atgtggagta tccaaaaata aaatccataa gtattgtata cattgcggtt    57960
caactgtaac agcagaacaa gatttttgta ttaaatgcgg aactaaaatt tcctcaaact    58020
ttagtatcgg gaacatcaaa atatcagatg gaacacaaga acaagtggat aaattcgcta    58080
aaactacagt cggaagagcc tatattaact actggttgaa gtggaacaat tatacagaaa    58140
aagcaactag accagatttt tggtatgcgt tgcttgtttg tgccattgtt tattttgttc    58200
tttttatcat tactgctatt ttatcggtaa taccattagt cggaaccatt gtatctatca    58260
tttttgtggt atttattctt ataaatcttg ccccggttat tgccctctat atcagacgct    58320
caaatgatgc tggtctcaat tggaaatggt tcattttagc cactgtttta tcggcaaacc    58380 tattttttagc tattttacca agtaaagaat aaaaaataaa acaatttagt aaataaggtt    58440
ctgttgcaaa gttctaaaat tggtaccaag aattttagtt taacaccttta attatgctga    58500 tatcctccgt aaaccttaaa tttcaagcaa taccgaaaaa ccgaagagct ttccatttct    58560
tcggttcttt ttgtatatgc ctcgaatagt ctccatgccc tttatcgtgg ttgaggcagt    58620
acgtagactt cgataaaatt tattgcgtcg tttgattggt cgatggtctt gctctattag    58680
attgttaagg tatttcacgg ttcgatgctc tgtcttagta tataattcat tactctgtaa    58740
ttttctaaag gcagagccaa tagacggagc tttatccgtg acaattactc taggttcaac    58800
aaactgctta tgtagtcgtt tcaagaatgc ataagccgct tgagtatccc gtttctttcg    58860
taaccagata tctaaagtca atccaaactg gagctatact ataaaagtgg acagaaaaat    58920
gtgtgttata atctgtctat taagacacaa aaatgaaagg acttttatgt caggttttaa    58980
acgttacgac gaggatttca aacaatcgct cgttaatctc tatcaaactg gtaaaacaca    59040
aactgaactc tgtaaagatt atggggtatc ttcttctgca cttgcaaaat ggattaagca    59100
gtactctcaa gtgcgtcttg aagataatac ggtgttgact gctaaacaga ttcaagaatt    59160
acaaaaaagg aatgcccaac tagaggaaga aaatctgatc ttaaaaaaag cgagtgccat    59220
attcatgcaa aactccaagt aagattgaaa gccatcttag actccgattt gaacacacga    59280
cagtcatgct ctgtcgtgtt ttacatgtca atcgttccat caactataac tttataaaca    59340
agaggccttc gaagcgtgaa gtaaaaaatc aacgcttgtg aaaacacctc cttgagattt    59400
```

-continued

```
atatgaaagc caagaaaaga attggaacga gagcttttaa aatcattctt ctgcgtgatt   59460
atggcgttaa tatttctgaa ggctgtatct taagacttct caagtctatg acactcccta   59520
aaatgtcaac cataaaacct cgtttttaaat caaataaatc tcctgtattt tcttctgata   59580
atctgcttaa acaagaattt aacccgaatt ccccaaatca agtttggaca acagatttca   59640
cttatatctc tataggagct aagcgacatg tttatctctg tgctattctt gacctctact   59700
caaggaaatg tattgcgtga aaagtaagtg ataggattga tgccaaactc gcctgtgata   59760
ccttagaaat agctataact aagaggaagc ctaaggaacc aattatcttt cattcggatc   59820
aaggaagcca atttaaatca gcttccttta gaaagttatt agatgagcat caattgcttg   59880
cttcttactc caagcctgga tatccctatg ataatgccgt cactgatgtc tttttcaagt   59940
atcttaaaca acgagaaatt aatcgcagaa cttatcactc cattcaagaa gttcaactct   60000
cttgctttga atacatcgaa caattttata acaattataa tcctcattcc gccaacaatg   60060
gtttaactcc aaattagaaa gaagaaaatt attttaagaa aatatagctc attttgtgtc   60120
taaatatttg acattagtcc acctaggatt aaattaaaaa aaggaacacc gatattttca   60180
acttttttaa aaccaaatct gataacttta ttgaaatgaa ccaagccaaa gcctgtcctg   60240
taaaagacat ttgattcatt ctctgatagg ctcgccttaa gtatttatcc ttttttttctc   60300 ctcgttcact ttcaaatgat aatatgctta actctattat aacaataaca ttttatcagt   60360
tttaatgttt ttttttattgt ttttcactct aaaaaaagat ataatatcag taaaactgat   60420
atttttgatt taggaggaac aatggaacaa ttaaaattaa atcaatactt tgactattcc   60480
cttgagccac gtcgtgccat cctctttcaa gatgtcaagt ctaattatgc ttcaattgaa   60540
tgcgttcagc gaaatttaaa tcctctgacc acttctcttt gtgtcatgag tcgagcagat   60600
cattctaaag ggttaacgct tgcctctagt ccaacctttta aaaaagtttt tggtatgaaa   60660
aatgtcagtc gtgccagcga tttacctttt cttatagaat cacgaaagtt caattatccg   60720
caatggtatc gaacacatac agacattcat ggacagcgaa ctgaaccaac tttgcaatat   60780
gtcgctttca ttgaatcttg ggcgaaacgc acgtggattg ttcctccaca aatgcagctc   60840
tatgtggact ataaaataga agttacggat attctaacca attatacatc aattgatgaa   60900
attcattctt actcgattga tgagtcgttt cttgacgtaa cagaatcact caatttctttt   60960 tatcctgaga ttaaaaatcg ttatgaacaa atgaatcgaa ttgctttaga cttgcaacgt   61020
gagattcgag ataaactcgg actatatgtg actgtgggca tgggagacaa tcccttgctt   61080
gccaaacttg caatggataa ctatgccaag cacaatgata atatgagagc gttaatccgt   61140
tatgaagatg tccctagtaa actatggacg atccctaaga tgacggactt ctggggaatc   61200
ggaaaacgaa ctgagaaacg attaaacaaa cttggaatca cttctatcaa agagcttgcg   61260
aatgctgacc ctttttttgct gaagcaaaaa ttaggaataa ttggacttca acatttttttc   61320 catgctaacg gaatcgatga aagcaacgta agagaaaaat atactccaaa atctactagc   61380
ttcagcaatt ctcaaattct gccacgtgac tatcataagc aaagagaaat cgaacttgtg   61440
attaaagaaa tggctgagaa cttagcgata agattgagaa agggcggaaa actagcaagc   61500
aatctttcac tttatgcagg agctgcttct acttctgaat actcatctat taaggtttct   61560
cgcaatatcg aagcaacgca aaacacaaag gaattgcaag acctcgcaat ctctttattt   61620
cgtgaaaagt accaaggggg agcgattaga caaataggga taagcgggaa tcaactttct   61680
gatagttctg ttaaacaact gtctttattt gaaagtgttc aagaaaatca aactaataaa   61740
```

-continued

```
aagcaagaat cactccaaaa agctattgat gagattagag aaacattcga ttttctatct   61800
atacaaaaag caagtagttt atccgaggga tcacgtgtca tttatcggaa caaactcatt   61860
ggaggtcatg cagcaagtca agacaaggag gaaaaagatg tcagttgacc gttcatatag   61920
tccctacgag gttattagga tgtatcacga tagaggaatg atgaaatggg gggcatttgc   61980 gactgggaa ttaactgaag cccaaaatac ttttgaaaaa gaaaaaaaag aagataagat    62040
aattcaagca ttaccacatc atctcgtgct tcatcttctt aaccagtcct tttctaatca   62100
ggtgcaaatt aaaattcaat atcaagccaa agataaatta actgaagtct atggtaatgt   62160
atcagaattt atcaataatc aagtaagagt taaatcaacg gataaaatct atctcatatc   62220
cattaagcaa atcgtaaata tatcataaaa aaagctatcc ttgttgtata ttactacaac   62280
aacttggata gccttttata tgacgttaag tcaagttttt agagtaacaa acgtagaatt   62340
ttaatctatt tattttaagc acttaccttt tcaaattgat taggtgtaag ataccctaaa   62400
ctttgatgga ttcgttttga attataaaag gctcataagt ggaggagaa aatcatgaaa    62460 tatggatatg ctagagtaag tacaatagac caaaaactag aatctcaaat cgaacaatta   62520
aagaatgctg gtgcagaaga aattttccaa gaaaaattta ctggaacaac aaatagtcgc   62580
ccagccttta taaatttatt aaatacattg gaatcaggag atactttaat cattacaaag   62640
ctagatcgct tcgcaagaaa tactagagaa gcattagcaa ctattcaaga actttttgac   62700
gcaaattgta aaatgaagtt agccaccttg agtcaagcaa aaaacatctg aatctcttat   62760
actagaagtt cgaccaaata gtataaaaag gaaattcaga tgcaagacta ttctatcaca   62820
agccagagca aagggaaaca cctgaccaat caagaccgtt taaacattga acgttggcac   62880
aataaagaag gactgagcaa ccgtgagatt gcgcgcttat tgaataaagc tcatgggacg   62940
attgacagag agatgaagcg aggggaaatc cagctcaagc ggaaggtaaa atactctgct   63000
aaaaaggctc aagaaaatta tgaaggattg agggctcaca gtgttcgtcc gagtaaactc   63060
acgactgaga ttgattgtta tgtgagtaca cgtcttaaag aagacaagga ctctttggaa   63120
gtcattcatc aggctctaaa aggagtttct ctgagcagcc tctacaattg ggtcaactgg   63180
ggctggttag aagccaagcg tcatcatctt ttctatccgc agtataaggc ggcaaagaaa   63240
atcaaacctc gtgcgccaaa gcatcctttt ggcaagtcta ttgaagaacg gcctgagttc   63300
attaacaatc gcttagaagt gggggcattac gagattgaca cggtcattct tacgagagct   63360
aagaacaagg tgctttttgac gctcacagag cgaaaatacc gcacggagat cattcgcttg   63420
attgatggga aaacagcaca ggcggtcaat gatgagctgg tggaacttca aaaaagttat   63480
gacttcaaat ccattacccc tgacaatggc catgaatttg caaggctctc tgaggtcgta   63540
agctgtccag tttactatgc acacgcctac gcgagctttg agcgagggac gaatgaaaac   63600
cataaccgaa tgattcgtag gcatctgcca aaaggcacaa caaagacgac ccctgaagaa   63660
gtcgccgcta tcgagtattg gatgaaccat tatccaagaa aaatgttcaa ctataagagt   63720
tcatatgaga tgagcttggc tggctaactt ggacttgcaa tttgcgaaga acttttgat    63780 aaggatataa aaataaatat tttaaatatg ggagtgatag ataataccgc aactggaaaa   63840
ttaatcttta ctatttttag tgcctttgct caatttgaaa gagatatgat tgttagcaga   63900
acacaagagg gaaaagaata ttcaagaaaa aataatccaa actttaaaga gggtagaccc   63960 aataaatttta cagaagaaca aattcaatta gcttatgaat taaaacaaca aagaatgaca   64020
cacaagatga tcgaacgaaa aactggcatt agtgtttcta ctcaaaaaag aagatttaat   64080
aaaatagttt agtttttat ttattagata aataaataat taaataatta aataaacaaa    64140
```

-continued

```
ttgtttattt ttttaattat ttgtgttata atagatatag gaaggtggta gtacattgaa   64200
aatcattaca tttacagcca ttaaaggcgg agttggtaaa acaacactaa cactaaatta   64260
tagcgattgg ttggtaaaaa aaggaaagaa agttttatta attgatttag atcatcaatg   64320
caatttaaca acaatttttc aaccaacacg aagaaataat actattgcag aagcatttaa   64380
agatagtgag gaagcacaag aagttatcat tgataacatt aaagagaatt tagacttagt   64440
agctggtttt attgatttag atgaactagg aagcaaatta gaaacaaca gcaataaaga   64500 aatgttatta tttctttggt taaaaaataa ttttgaaaaa ctaaatattg gaagctatga   64560
ctatatttta attgatacac accctgattt ttctacaata acaaaaaatg cagtagcaat   64620
aagtaattat ttagttagtc caattacacc tagtgaacat ggatattcag caaaatttga   64680
tttagaagct cgtttagaaa aattcagaaa atctttgttt gattataaaa ctggagaaac   64740
ttatgttgac gcacaattat tttttgtagc taatatgatt aaacataaca ccagcacatc   64800
acatgaattg ttaagccaca taaaagatga tgaaactgtt atttctacta tttctgaaag   64860
agaaattttt aataaagcaa ctactaaaca cttatctatt tttgattttg ctaaaaccca   64920
agataaaaaa gacgataaag ttttaaataa tattaatgat agtttttcaa aaatatataa   64980
tcatacaaaa taaaggagtt taaattatga gttttgatac atttaacaaa gataaagatg   65040
aaattgttaa acagaattta aaagaaacaa ttgatcctga accaaaaaag gaagatgaaa   65100
ttcacagcgt aattagttct attttgaagt ctaatgatat gaaaagtgaa aaaagaaaat   65160
cagtcacttt ttcattgact gaaagtcaaa taaagaaaat tgaagaacaa gcacaaaaac   65220
acggttttaa aacaaaatct aaactgttag cttatctcat agatcaaatg taactttaaa   65280
caattaatta aataatttgt ttatttaata attaaataat ttgtttagtt gaaggaggtt   65340
ctcatgaaaa aaatcatgga cttatggctt tacttttata taagttgtat ctactttttg   65400
ccattaattg ctctcatgcg ttctagcaat aaaagtagca atttcttatt aagaagatta   65460
ctatttccct ttgaatattt aattcaaaga agacttgaaa aaacaacaaa ttataatcgt   65520
ggatcaattc gtgtcgttca tattttcatt tggtttttct gtattttag cttaatgttt   65580 gcgacagcac cgctaatttt tttccacgaa ccacttgaaa atcacaccac attattatta   65640
tttattactt actactgtat gttagcccca ttctgttttt ggtttcaacc aagaaatcta   65700
aaacaataaa aaggagaact ttatgtttat agcaactgac aatcaattta cagcaagagg   65760
aagattagta gacagtcctc aaattaatat ttcagaaaaa acaggaaatg ctattgtttc   65820
aatcacacta gcacaagaac accctttaa aaaaaatgaa gctggggaaa gagaatctgt   65880
ttttattaaa tacaccgcaa ttgatacaaa aaacaacccc attgccagtc gcattgcaga   65940
atatgtgaca aaaggatcat tagttagtct tattggttat catgacagtt actttaaaga   66000
aaactcagag ggtaaaaaag aatattttga agtgaaaaga atttcaactt ttagaaatga   66060
agaatcaaaa gaaaaaacat tggagcgtag aactaaagca taataattaa taaaggaaag   66120
tgatttttat ggaaaaacac aaagtggact tttacaatat accgatcgta gactacttac   66180
tttcaattgg agaacccctt gaaagtgttg gtcataacta ctatcaacat aaacatcatg   66240
atagtttaaa aattaatcaa aggaaaaact attttgtttg gaatagtcgt tcatctgaaa   66300
aaaattcacg aggtggagtt gttcagtata tgcagatcat gcataattta tctttacaag   66360
aaacactctc aaaattaagt gaagatttag acggtaaagt tcttccagcg atccctaaaa   66420
aaagctatcc taaaaaattt aattacccga attgctagtt gattatttag ccatgacttg   66480
```

-continued

```
atacccgata gaatatctta aagtctctgg ttccagtgat ttagctgatt ttaacagtaa   66540
agaatacgct aaaagtatca tctctaattt caattgaaaa ccttgaggcg aacgactttt   66600
acaacgctca gctcctagat ttgtcaaaaa agagaaaact cgctcaatca cttttctacg   66660
ttttgaaaaa ttagggaaaa ggattttctt ttgcttcatg ttcttcctga caggtgtaat   66720
tagatcaatt cctttttaatt ccagcctatc atgcagtgac tgacctaaat atcccatatc   66780
tccaaggact gttggtgtcc caaattgact caacacttcc tcggtcattg aactatcagc   66840
cattgaagca ggagtaattg tgtagtctat gacatagcct gattcactga ctaaagcatg   66900
acatttaaat ccatagaagt actgtccctt tgtagcattg tagccaacat ttgcataatc   66960
tccaagaact ttgcttctga aattacgaat cgactgacac aaaggaatgg ggaagctgtc   67020
aataatggat acactcattc cttcaacctc tttaaagacg agtgcttggc gaatgacttg   67080
gatactcggt aagagggcat tacaacggcg gacaaagcga gaatattcta ggaaattagg   67140
aaataaactt tgagccaatt ggtgcttagc tttaagcgtt tcactaaaat gcagtacgcc   67200
ccatagataa caagcgataa ctaagcaatc tgatgttgcg agatggacgt tctttcggtt   67260
ttgaacctca agggaaacac tcgtttgata aagcgtctca atggttgtca gtaaataaac   67320
aaaaactttt ggaagtgtgc tattataagt catataagtc gtgcgctttc taatgcttag   67380
tgggttaaga ttaggatagc acgacttatt tattttccaa tgaaattaac tagcaattcg   67440
ggtaaaaata taatgatgat tgaaccccgt gaaaccctct tgatatatac tataatataa   67500
aaatgaatgt aaaaaaacaa atttttaaag gcacgctcta tgcagttgtt gccggttgta   67560 tgtgggggaat ttctggcatt tttggtcagc ttttttttccg tgattatcat ggtagcccac   67620
tttggattac atcaacacgt ttaacgattg ctggtattat tttactggtc atgtcttatt   67680
cgcgagacca taagcgtttt tttgatgtct ggaaatcaaa aaagaacatg ccaacgctct   67740
ttttgtatgt ttttggtgga gttttctctg ttcagtattt ttattatgtt gccattcaat   67800
tgtctaacag tgccacggcg acaattttac aatatacagc acccgttttt attatgcttt   67860
atttattcat tttccaaaga caagtgccaa aacctaaatc ggtcttattt gttattttag   67920
caatgatagg tgtttttttta ttgattacaa atggaaacat caaacatctt tcaattagtc   67980
cacttgccct tgtgacaggc cttcttgcgg gtgttgcggt cgtaatctat tctatcattc   68040
cacgtccttt attggataag tatggggcgc tcaatatgac tggatgggga atgatgcttg   68100
cgggaattgc ttgtaatatc ttttatccgg tttggcggat taatttccga attgaacctc   68160
tttcaatttt ttacgtttttg acgatttcta tagtgggaac agcattggct ttttttgttgc   68220 ttttaagagc attccagcta atatcacctc ttgttgtttc ggttgcaacg gccactgaac   68280
cactaacctc tgtcttttta agtattccct tatttggctt aaaattaaca ctactagaaa   68340 tggtgggggat tgttatggtt attgtttcag ttattctttt atcaaaatca gaacaagctt   68400
aaaagaaacc agtaggtttc ttttttcttat atacaagatt ttgactttt tcagaatatt   68460 ctatgatata ataaatgcaa agatagcatt taacatcaaa aataaaatga attgaggaaa   68520
atttatgatt gagattagag aattaacaaa gatgtatggc aagcagtatg ctctaaatca   68580
tctaagttta acaattccag aaggtcaaat attcggtttt ttagggcata atggggcagg   68640
gaaatccaca acaataaaat gtctgacgag tattattgaa ccgacaagtg gacaagtttt   68700
agttgatggt ttaaatcttg ctgaacatca ttcagaaatc aaaaaaagaa ttggctatgt   68760
tcctgatact ccggatatct ttttacaatt atctcctaaa gaatattgga atttaattgc   68820
ctcagctttt gcacttgaaa cctctgaaaa ggaaagacaa ctagaaactc ttacacgact   68880
```

-continued

```
tttcgatatt gaagggaaag aatatcaaac aattgaaagt ttttctcatg gaatgcgtca   68940
aaaagtaatt gtcattgggg ctctcttatc gactcccgat atttggatac ttgacgaacc   69000
cttgcaagga ttggaccctc aagcagcttt tgatttaaaa aatctgatga aagcacacgc   69060
tgcccaagga aaaacggtta ttttttctac acatgcttta gaagtagcgc aacagctatg   69120
tgatcaacta gccattttaa aagctggcga actaatttat tcgggaacag ttgatgcttt   69180
attagattca gcagaagatc aatctttgga gtcggtttat ctcaaaatgg taggtcgtca   69240
gcaagaagag ctaaatagag gagacgatga tgaatcttca acaaattaaa agtcttttta   69300
gtgtcaacct cctttatgcc aatcctcaag ctacccaacg tcaaagagaa aaaggtaaaa   69360
ccaaaaattt aaccaaatca cttttgattc aatatgggct tgtctcgctc atcatgttgc   69420
catttttcgg actgatgatg ttagcaattg actttccaaa atatccggga tttttttactt   69480 tttattgtgc tctgtttgcc ctgatgactt tttctcaagc cttgtcagca attttaaata   69540
ttttttatga gagcaaagac tttcgagatt atctgcctct cccttttgaa aatgttaata   69600
tttttgctgc taaatttta gtcgtaattt ttgttatctt accttattta atgcctcttt   69660
tggtgctttt tggaataaca ggttttaggg caaacggagt gattggcctc tttctcggat   69720
tagttggatt ttttctgttt gctctattat tcttactgct tagtacatgg ttgattactt   69780
ttttggttca atctaaaata tttcaacgct ataaaaaagt ttcccagacc atactattat   69840
tgatttcaat ggttggaatt tttgctggga ttatgtatct aaataatgct caaacgacga   69900
ttagtgcgac aggtaagttg ttggatagag gaacttttct gccatttta ccttttttgga   69960 aatggttagt aaatccgttc tctttctata gtttatttag ttttctcttt tttataatct   70020
tattgattgc tctttactat gtttttacac ttctagtggt tccaaaaatg tttaaaaattc   70080 tcttggaaga gtcaaaagaa acgagaattg ttcaaaaaag aaaaataaga agaacgagaa   70140
attttacctc acaattaaga atttataatc taggactaat taaaaatcct accttatgga   70200
ttcaaatgct gacaggatcc tttattttc cgcttgctat gctgcccggt cttttatcta   70260
gtggtctaaa tttgtcaaaa ttggatttga aattttttgc tattttttcct atcatcggaa   70320 ttagtttagc ttttctgacc attaacaata gctctcttcc ttcaatgatt atctcacttg   70380
atcgggaaaa ttttaattat tttaaaagct tacccatgaa gttgaatttc tatctcagag   70440
tgaaatttca ttttgccttt tttattcaac tagttcttga cttaatctta tctttagtga   70500
ttggtatttt actgaaagtc cctgttacct tgctctttgg gctgttaatt gggaatgtta   70560
ttggggtata tctgatttca cttcattatt ttgtcagaga ttggcatctc ttaaatttaa   70620
attggactgc gttgactcaa cttttttacaa gaggttctgg gggatttcgg gtttttatca   70680
ttttctttgc tacgcttttg ggagcaggag cactcattgg agcaattatt gccctgatta   70740
tctttattcc atatcctttta gttgttaacc ttgccctagt cctcctttta ggattttcgg   70800
taggagtgat acttcatttt tatcagaaaa attttttggaa taatctctga taaaaattaa   70860
caataaaatt actctgcttt aggagtaatt tttttataaa aaaaattaag aaaacccgaa   70920
ttgctagtta atttcattgg aaaataaata agtcgtgcta tcctaatctt aacccactaa   70980
gcattagaaa gcgcacgact tatatgactt ataatagcac acttccaaaa gtttttgttt   71040
atttactgac aaccattgag acgctttatc aaacgagtgt tcccttgag gttcaaaacc   71100 gaaagaacgt ccatctcgca acatcagatt gcttagttat cgcttgttac ctatggggcg   71160
tactgcattt tagtgaaaca cttaaagcta agcaccaatt ggctcaaagt ttatttccta   71220
```

-continued

```
atttcctaga atattctcgc tttgtccgcc gttgtaatgc cctcttaccg agtatccaag   71280
tcattcgcca agcactcgtc tttaaagagg ttgaaggaat gagtgtatcc attattgaca   71340
gcttccccat tcctttgtgt cagtcgattc gtaatttcag aagcaaagtt cttggagatt   71400
atgcaaatgt tggctacaat gctacaaagg gacagtactt ctatggattt aaatgtcatg   71460
ctttagtcag tgaatcaggc tatgtcatag actacacaat tactcctgct tcaatggctg   71520
atagttcaat gaccgaggaa gtgttgagtc aatttgggac accaacagtc cttggagata   71580
tgggatattt aggtcagtca ctgcatgata ggctggaatt aaaaggaatt gatctaatga   71640
cacctgtcag gaagaacatg aagcaaaaga aaatcctttt ccctaatttt tcaaaacgta   71700
gaaaagtgat tgagcgagtt ttctcttttt tgacaaatct aggagctgag cgttgtaaaa   71760
gtcgttcgcc tcaaggtttt caattgaaat tagagatgat acttttagcg tattctttac   71820
tgttaaaatc agctaaatca ctggaaccag agactttaag atattctatc gggtatcaag   71880
tcatggctaa ataatcaact agcaattcgg gtctataaat ataatcatat aaaactccta   71940
aatttttgct aatctttttt aattttaaag ttatctacat gtatttttc gcaatcaata   72000 tcaaatttat tctccaatat aattttattt atgtttcctt tatcattttg ggaataatag   72060
ctaaataaat attttgcttc aggggcgcat ctgactagtt ctttaaaata aacccagtct   72120
atcttattat atgaatgacc taagattatt acttcatgaa tatttttatt tttaacaaaa   72180
gactcaattg agtcttttaa aagatttact ggtttataaa atcttcctat attttcatca   72240
taaaacttat tagaattaag ctttctagaa ccctgttctg caaacattct ttgtgtttcc   72300
ttaaattcct tcgtaaaact tgtttctaac cctggtaatt tgtcgtctat ttctggcgaa   72360
tgaaatccta atactacatc ttctagattt tttacagaac catgtaaatg tagtacatct   72420
ttttgttgat aaacatcttc catagtattt gtatagttaa aggaaattac agacgaatct   72480
tcatctattt catagatatt tttcgtattt tttaaaataa tcgtttgtat ccattcttga   72540
aaactaatat ataaatatgg aacccatata tatagttccc ttaccttatt gttaaaatac   72600
tttaaggcat actcttgaat ttcattatga tatatatcag tatcgaatgt actatcttgt   72660
ttttttatta acttttaaa acaatcaata aatttatgcc tctcacctcc aatatctaat   72720
ttgcagctcc attcttcttc aaagattata attttcccct ctgatatttc tgatattatt   72780
ttctcagtct gttcttcaaa atcgctccat aaatcatttg gttgacaata tctttcaaaa   72840
tttcgtaaaa tatctccttt tgatattatt aaatcttcat ctgtatatac ttcatcccta   72900
tgttccaata aatataatct aaactctgta tatgatgttt tcagattgtg tgataaatca   72960
aagccattac caactatata taatttcatt gtatctccca ctaacttaac tcaataacta   73020
taactataaa tataaatata attatataat aatcaaaaca gaaaatctcg aaaaaatatg   73080
caaatagaaa aacactaatt caaaaaaata attttttta gttacatatt tgaatactct   73140
taacttgaaa tgcccccaat ttgccccatt ttatttttca ctttaagagc ttttctatag   73200
tgaacacttt gagagcttta tagagcctgt atttaacttt gaaaactatc taaacaat     73258
```

```
<210> SEQ ID NO 12
<211> LENGTH: 82
<212> TYPE: DNA
<213> ORGANISM: Lactococcus lactis subsp. lactis bv. diacetylactis SD96
<220> FEATURE:
```

-continued

```
<221> NAME/KEY: misc_feature
<222> LOCATION: (1)..(82)
<223> OTHER INFORMATION: deleted tandem repeat ((A)6 to (A)5) upstream
      of the CodY

<400> SEQUENCE: 12
tttgttctcc tattttttta tattcttgtt tttatacaaa atttttcata atcagtataa      60
cataaaaaag catgaaaaac aa                                              82
```